(12) United States Patent
Gee et al.

(10) Patent No.: US 12,343,063 B2
(45) Date of Patent: Jul. 1, 2025

(54) MULTI-LAYER CLAMP ARM PAD FOR ENHANCED VERSATILITY AND PERFORMANCE OF A SURGICAL DEVICE

(71) Applicant: Cilag GmbH International, Zug (CH)

(72) Inventors: Jacob S. Gee, Cincinnati, OH (US); Michael A. Keenan, Cincinnati, OH (US); Joshua D. Raker, Waynesville, OH (US); Jeffrey D. Messerly, Cincinnati, OH (US); Frederick E. Shelton, IV, Hillsboro, OH (US); Geoffrey S. Strobl, Williamsburg, OH (US); Joseph S. Salguero, North Plainfield, NJ (US); Wei Guo, Mason, OH (US)

(73) Assignee: Cilag GmbH International, Zug (CH)

( * ) Notice: Subject to any disclaimer, the term of this patent is extended or adjusted under 35 U.S.C. 154(b) by 1122 days.

(21) Appl. No.: 16/951,259

(22) Filed: Nov. 18, 2020

(65) Prior Publication Data
US 2021/0196353 A1 Jul. 1, 2021

Related U.S. Application Data

(60) Provisional application No. 62/955,292, filed on Dec. 30, 2019.

(51) Int. Cl.
*A61B 18/00* (2006.01)
*A61B 18/14* (2006.01)

(52) U.S. Cl.
CPC ............ *A61B 18/1442* (2013.01); *A61B 2018/00077* (2013.01); *A61B 2018/00083* (2013.01);

(Continued)

(58) Field of Classification Search
CPC .... A61B 17/320068; A61B 17/320092; A61B 2018/1455; A61B 2018/1405;
(Continued)

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| CA | 2535467 A1 | 4/1993 |
| CN | 2460047 Y | 11/2001 |

(Continued)

OTHER PUBLICATIONS

Covidien Brochure, [Value Analysis Brief], LigaSure Advance™ Pistol Grip, dated Rev. Apr. 2010 (7 pages).

(Continued)

*Primary Examiner* — Majid Jamialahmadi

(57) ABSTRACT

An end-effector configured to grasp tissue is disclosed herein. The end-effector includes an ultrasonic blade configured to transfer ultrasonic energy to the tissue and a clamp arm. The clamp arm includes a clamp arm pad including an electrically conductive material and an electrically non-conductive material. The clamp arm pad is configured as an electrode of a radiofrequency energy circuit, wherein the electrode is configured to transfer radiofrequency energy through the tissue to a return electrode of the radiofrequency energy circuit, and wherein the electrically non-conductive material is configured to reduce the possibility of an electrical short between the electrically conductive material and the ultrasonic blade as the clamp arm pad degrades throughout the usable life of the end effector.

20 Claims, 87 Drawing Sheets

(52) U.S. Cl.
CPC ................ *A61B 2018/0013* (2013.01); *A61B 2018/00136* (2013.01); *A61B 2018/00148* (2013.01); *A61B 2018/00601* (2013.01); *A61B 2018/0063* (2013.01); *A61B 2018/00994* (2013.01); *A61B 2018/1455* (2013.01)

(58) Field of Classification Search
CPC .. A61B 2018/00077; A61B 2017/2926; A61B 2017/320095; A61B 2017/320069; A61B 2017/320093; A61B 2017/320094
See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,739,759 A | 4/1988 | Rexroth et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |

(56) References Cited

U.S. PATENT DOCUMENTS

| | | |
|---|---|---|
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,003,693 A | 4/1991 | Atkinson et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |

(56) References Cited

U.S. PATENT DOCUMENTS

| | | |
|---|---|---|
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,536,267 A | 7/1996 | Edwards et al. |
| 5,540,681 A | 7/1996 | Strul et al. |
| 5,540,684 A | 7/1996 | Hassler, Jr. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knopfler |
| 5,630,420 A | 5/1997 | Vaitekunas |
| 5,632,432 A | 5/1997 | Schulze et al. |
| 5,632,717 A | 5/1997 | Yoon |
| 5,638,827 A | 6/1997 | Palmer et al. |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,759,183 A | 6/1998 | VanDusseldorp |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |

(56) References Cited

U.S. PATENT DOCUMENTS

| | | |
|---|---|---|
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,011,416 A | 1/2000 | Mizuno et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,102,909 A | 8/2000 | Chen et al. |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,238,384 B1 | 5/2001 | Peer |

(56) References Cited

U.S. PATENT DOCUMENTS

| | | |
|---|---|---|
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,261,286 B1 | 7/2001 | Goble et al. |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,417,969 B1 | 7/2002 | DeLuca et al. |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,436,129 B1 | 8/2002 | Sharkey et al. |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,558,380 B2 | 5/2003 | Lingenfelder et al. |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |

(56) References Cited

U.S. PATENT DOCUMENTS

| | | |
|---|---|---|
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,988,649 B2 | 1/2006 | Shelton, IV et al. |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |

(56) References Cited

U.S. PATENT DOCUMENTS

| | | |
|---|---|---|
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |

(56) References Cited

U.S. PATENT DOCUMENTS

| | | |
|---|---|---|
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,685,608 B2 | 3/2010 | O'Shaughnessy et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |

(56) References Cited

U.S. PATENT DOCUMENTS

| | | |
|---|---|---|
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,151 B2 | 9/2010 | Whitman |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,954,682 B2 | 6/2011 | Giordano et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,048,074 B2 | 11/2011 | Masuda |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |

(56) References Cited

U.S. PATENT DOCUMENTS

| | | |
|---|---|---|
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,216,223 B2 | 7/2012 | Wham et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,308,721 B2 | 11/2012 | Shibata et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,398,674 B2 | 3/2013 | Prestel |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,036 B2 | 5/2013 | Shelton, IV |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |

(56) References Cited

U.S. PATENT DOCUMENTS

| | | |
|---|---|---|
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,517,239 B2 | 8/2013 | Scheib et al. |
| 8,518,067 B2 | 8/2013 | Masuda et al. |
| 8,521,331 B2 | 8/2013 | Itkowitz |
| 8,523,043 B2 | 9/2013 | Ullrich et al. |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,040 B2 | 1/2014 | Artsyukhovich et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,702 B1 | 4/2014 | Edwards et al. |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |

(56) References Cited

U.S. PATENT DOCUMENTS

| | | |
|---|---|---|
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,831,779 B2 | 9/2014 | Ortmaier et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,370 B2 | 4/2015 | Reschke et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,692 B2 | 5/2015 | Behnke, II et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,230 B2 | 6/2015 | Morgan et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,083 B2 | 6/2015 | Yates et al. |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,333 B2 | 8/2015 | Konesky et al. |
| 9,095,362 B2 | 8/2015 | Dachs, II et al. |
| 9,095,367 B2 | 8/2015 | Olson et al. |
| 9,099,863 B2 | 8/2015 | Smith et al. |

(56) References Cited

U.S. PATENT DOCUMENTS

| | | |
|---|---|---|
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,266,310 B2 | 2/2016 | Krogdahl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,283,054 B2 | 3/2016 | Morgan et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,767 B2 | 5/2016 | Koch, Jr. et al. |
| 9,326,787 B2 | 5/2016 | Sanai et al. |
| 9,326,788 B2 | 5/2016 | Batross et al. |
| 9,332,987 B2 | 5/2016 | Leimbach et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,727 B2 | 5/2016 | Leimbach et al. |
| 9,351,754 B2 | 5/2016 | Vakharia et al. |
| 9,352,173 B2 | 5/2016 | Yamada et al. |
| 9,358,003 B2 | 6/2016 | Hall et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,206 B2 | 6/2016 | Vidal et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,014 B2 | 8/2016 | Ingmanson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,438 B2 | 10/2016 | Baber et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |

(56) References Cited

U.S. PATENT DOCUMENTS

| | | |
|---|---|---|
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,465 B1 | 1/2017 | Liu et al. |
| 9,554,794 B2 | 1/2017 | Baber et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,056 B2 | 3/2017 | Mozdzierz et al. |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,629,623 B2 | 4/2017 | Lytle, IV et al. |
| 9,629,629 B2 | 4/2017 | Leimbach et al. |
| 9,632,573 B2 | 4/2017 | Ogawa et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,128 B2 | 9/2017 | Baber et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,826,977 B2 | 11/2017 | Leimbach et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,877,782 B2 | 1/2018 | Voegele et al. |
| 9,878,184 B2 | 1/2018 | Beaupre |
| 9,883,860 B2 | 2/2018 | Leimbach et al. |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,895,160 B2 | 2/2018 | Fan et al. |
| 9,901,321 B2 | 2/2018 | Harks et al. |
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |
| 9,925,003 B2 | 3/2018 | Parihar et al. |
| 9,931,118 B2 | 4/2018 | Shelton, IV et al. |
| 9,937,001 B2 | 4/2018 | Nakamura |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |
| 9,993,248 B2 | 6/2018 | Shelton, IV et al. |
| 9,993,258 B2 | 6/2018 | Shelton, IV et al. |
| 9,993,289 B2 | 6/2018 | Sobajima et al. |
| 10,004,497 B2 | 6/2018 | Overmyer et al. |
| 10,004,501 B2 | 6/2018 | Shelton, IV et al. |
| 10,004,526 B2 | 6/2018 | Dycus et al. |
| 10,004,527 B2 | 6/2018 | Gee et al. |

(56) References Cited

U.S. PATENT DOCUMENTS

| | | |
|---|---|---|
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |
| 10,052,102 B2 | 8/2018 | Baxter, III et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,347 B2 | 10/2018 | Weisshaupt et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |
| 10,117,649 B2 | 11/2018 | Baxter, III et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,206,676 B2 | 2/2019 | Shelton, IV |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,097 B2 | 4/2019 | Honda et al. |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |
| 10,258,505 B2 | 4/2019 | Ovchinnikov |
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, III et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,602 B2 | 7/2019 | Strobl et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |
| 10,398,466 B2 | 9/2019 | Stulen et al. |
| 10,398,497 B2 | 9/2019 | Batross et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,413,352 B2 | 9/2019 | Thomas et al. |
| 10,413,353 B2 | 9/2019 | Kerr et al. |
| 10,420,552 B2 | 9/2019 | Shelton, IV et al. |
| 10,420,579 B2 | 9/2019 | Wiener et al. |
| 10,420,607 B2 | 9/2019 | Woloszko et al. |
| D865,175 S | 10/2019 | Widenhouse et al. |
| 10,426,471 B2 | 10/2019 | Shelton, IV et al. |
| 10,426,507 B2 | 10/2019 | Wiener et al. |
| 10,426,546 B2 | 10/2019 | Graham et al. |
| 10,426,978 B2 | 10/2019 | Akagane |
| 10,433,837 B2 | 10/2019 | Worthington et al. |
| 10,433,849 B2 | 10/2019 | Shelton, IV et al. |
| 10,433,865 B2 | 10/2019 | Witt et al. |
| 10,433,866 B2 | 10/2019 | Witt et al. |

(56) References Cited

U.S. PATENT DOCUMENTS

| | | |
|---|---|---|
| 10,433,900 B2 | 10/2019 | Harris et al. |
| 10,441,279 B2 | 10/2019 | Shelton, IV et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,448,986 B2 | 10/2019 | Zikorus et al. |
| 10,456,140 B2 | 10/2019 | Shelton, IV et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| 10,485,607 B2 | 11/2019 | Strobl et al. |
| D869,655 S | 12/2019 | Shelton, IV et al. |
| 10,492,785 B2 | 12/2019 | Overmyer et al. |
| 10,492,849 B2 | 12/2019 | Juergens et al. |
| 10,499,914 B2 | 12/2019 | Huang et al. |
| 10,507,033 B2 | 12/2019 | Dickerson et al. |
| 10,512,795 B2 | 12/2019 | Voegele et al. |
| 10,517,595 B2 | 12/2019 | Hunter et al. |
| 10,517,596 B2 | 12/2019 | Hunter et al. |
| 10,517,627 B2 | 12/2019 | Timm et al. |
| 10,524,787 B2 | 1/2020 | Shelton, IV et al. |
| 10,524,789 B2 | 1/2020 | Swayze et al. |
| 10,524,854 B2 | 1/2020 | Woodruff et al. |
| 10,524,872 B2 | 1/2020 | Stewart et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,543,008 B2 | 1/2020 | Vakharia et al. |
| 10,548,504 B2 | 2/2020 | Shelton, IV et al. |
| 10,548,655 B2 | 2/2020 | Scheib et al. |
| 10,555,769 B2 | 2/2020 | Worrell et al. |
| 10,561,560 B2 | 2/2020 | Boutoussov et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,892 B2 | 3/2020 | Danziger et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,929 B2 | 3/2020 | Boudreaux et al. |
| 10,595,930 B2 | 3/2020 | Scheib et al. |
| 10,603,036 B2 | 3/2020 | Hunter et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,420 B2 | 4/2020 | Shelton, IV et al. |
| 10,617,464 B2 | 4/2020 | Duppuis |
| 10,624,635 B2 | 4/2020 | Harris et al. |
| 10,624,691 B2 | 4/2020 | Wiener et al. |
| 10,624,692 B2 | 4/2020 | Akagane et al. |
| 10,631,858 B2 | 4/2020 | Burbank |
| 10,631,859 B2 | 4/2020 | Shelton, IV et al. |
| 10,631,928 B2 | 4/2020 | Basu et al. |
| 10,632,630 B2 | 4/2020 | Cao et al. |
| RE47,996 E | 5/2020 | Turner et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,646,292 B2 | 5/2020 | Solomon et al. |
| 10,653,413 B2 | 5/2020 | Worthington et al. |
| 10,660,692 B2 | 5/2020 | Lesko et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,677,764 B2 | 6/2020 | Ross et al. |
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,688,321 B2 | 6/2020 | Wiener et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,119 B2 | 6/2020 | Smith |
| 10,702,270 B2 | 7/2020 | Shelton, IV et al. |
| 10,702,329 B2 | 7/2020 | Strobl et al. |
| 10,709,446 B2 | 7/2020 | Harris et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,233 B2 | 7/2020 | Wellman |
| D893,717 S | 8/2020 | Messerly et al. |
| 10,729,458 B2 | 8/2020 | Stoddard et al. |
| 10,729,494 B2 | 8/2020 | Parihar et al. |
| 10,736,629 B2 | 8/2020 | Shelton, IV et al. |
| 10,736,685 B2 | 8/2020 | Wiener et al. |
| 10,751,108 B2 | 8/2020 | Yates et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,294 B2 | 9/2020 | Jones |
| 10,765,427 B2 | 9/2020 | Shelton, IV et al. |
| 10,765,470 B2 | 9/2020 | Yates et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,786,253 B2 | 9/2020 | Shelton, IV et al. |
| 10,786,276 B2 | 9/2020 | Hirai et al. |
| 10,806,454 B2 | 10/2020 | Kopp |
| 10,813,638 B2 | 10/2020 | Shelton, IV et al. |
| 10,820,938 B2 | 11/2020 | Fischer et al. |
| 10,828,032 B2 | 11/2020 | Leimbach et al. |
| 10,828,058 B2 | 11/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,307 B2 | 11/2020 | Shelton, IV et al. |
| 10,842,492 B2 | 11/2020 | Shelton, IV et al. |
| 10,842,523 B2 | 11/2020 | Shelton, IV et al. |
| 10,842,563 B2 | 11/2020 | Gilbert et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| D908,216 S | 1/2021 | Messerly et al. |
| 10,881,399 B2 | 1/2021 | Shelton, IV et al. |

(56) References Cited

U.S. PATENT DOCUMENTS

| | | |
|---|---|---|
| 10,881,401 B2 | 1/2021 | Baber et al. |
| 10,881,409 B2 | 1/2021 | Cabrera |
| 10,881,449 B2 | 1/2021 | Boudreaux et al. |
| 10,888,322 B2 | 1/2021 | Morgan et al. |
| 10,888,347 B2 | 1/2021 | Witt et al. |
| 10,893,863 B2 | 1/2021 | Shelton, IV et al. |
| 10,893,864 B2 | 1/2021 | Harris et al. |
| 10,893,883 B2 | 1/2021 | Dannaher |
| 10,898,186 B2 | 1/2021 | Bakos et al. |
| 10,898,256 B2 | 1/2021 | Yates et al. |
| 10,912,559 B2 | 2/2021 | Harris et al. |
| 10,912,580 B2 | 2/2021 | Green et al. |
| 10,912,603 B2 | 2/2021 | Boudreaux et al. |
| 10,918,385 B2 | 2/2021 | Overmyer et al. |
| 10,925,659 B2 | 2/2021 | Shelton, IV et al. |
| 10,926,022 B2 | 2/2021 | Hickey et al. |
| D914,878 S | 3/2021 | Shelton, IV et al. |
| 10,932,766 B2 | 3/2021 | Tesar et al. |
| 10,932,847 B2 | 3/2021 | Yates et al. |
| 10,945,727 B2 | 3/2021 | Shelton, IV et al. |
| 10,952,788 B2 | 3/2021 | Asher et al. |
| 10,959,727 B2 | 3/2021 | Hunter et al. |
| 10,966,741 B2 | 4/2021 | Illizaliturri-Sanchez et al. |
| 10,966,747 B2 | 4/2021 | Worrell et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,987,105 B2 | 4/2021 | Cappola et al. |
| 10,987,123 B2 | 4/2021 | Weir et al. |
| 10,987,156 B2 | 4/2021 | Trees et al. |
| 10,993,715 B2 | 5/2021 | Shelton, IV et al. |
| 10,993,716 B2 | 5/2021 | Shelton, IV et al. |
| 10,993,763 B2 | 5/2021 | Batross et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,020,140 B2 | 6/2021 | Gee et al. |
| 11,033,322 B2 | 6/2021 | Wiener et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,275 B2 | 6/2021 | Boudreaux et al. |
| 11,051,840 B2 | 7/2021 | Shelton, IV et al. |
| 11,051,873 B2 | 7/2021 | Wiener et al. |
| 11,058,424 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,064,997 B2 | 7/2021 | Shelton, IV et al. |
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,090,104 B2 | 8/2021 | Wiener et al. |
| 11,096,688 B2 | 8/2021 | Shelton, IV et al. |
| 11,096,752 B2 | 8/2021 | Stulen et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,129,669 B2 | 9/2021 | Stulen et al. |
| 11,129,670 B2 | 9/2021 | Shelton, IV et al. |
| 11,134,942 B2 | 10/2021 | Harris et al. |
| 11,134,978 B2 | 10/2021 | Shelton, IV et al. |
| 11,141,154 B2 | 10/2021 | Shelton, IV et al. |
| 11,141,213 B2 | 10/2021 | Yates et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,179,173 B2 | 11/2021 | Price et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,670 B2 | 12/2021 | Worrell et al. |
| 11,207,065 B2 | 12/2021 | Harris et al. |
| 11,207,067 B2 | 12/2021 | Shelton, IV et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,430 B2 | 3/2022 | Clauda et al. |
| 11,272,931 B2 | 3/2022 | Boudreaux et al. |
| 11,278,280 B2 | 3/2022 | Shelton, IV et al. |
| 11,284,890 B2 | 3/2022 | Nalagatla et al. |
| 11,291,440 B2 | 4/2022 | Harris et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,451 B2 | 4/2022 | Shelton, IV |
| 11,298,127 B2 | 4/2022 | Shelton, IV |
| 11,298,129 B2 | 4/2022 | Bakos et al. |
| 11,298,130 B2 | 4/2022 | Bakos et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,306 B2 | 4/2022 | Shelton, IV et al. |
| 11,311,326 B2 | 4/2022 | Boudreaux |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,324,503 B2 | 5/2022 | Shelton, IV et al. |
| 11,324,527 B2 | 5/2022 | Aldridge et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,747 B2 | 5/2022 | Voegele et al. |
| 11,344,362 B2 | 5/2022 | Yates et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,369,377 B2 | 6/2022 | Boudreaux et al. |
| 11,376,098 B2 | 7/2022 | Shelton, IV et al. |
| 11,382,642 B2 | 7/2022 | Robertson et al. |
| 11,389,161 B2 | 7/2022 | Shelton, IV et al. |
| 11,389,164 B2 | 7/2022 | Yates et al. |
| 11,399,837 B2 | 8/2022 | Shelton, IV et al. |
| 11,399,855 B2 | 8/2022 | Boudreaux et al. |
| 11,406,382 B2 | 8/2022 | Shelton, IV et al. |
| 11,406,386 B2 | 8/2022 | Baber et al. |
| 11,413,060 B2 | 8/2022 | Faller et al. |
| 11,419,606 B2 | 8/2022 | Overmyer et al. |
| 11,419,626 B2 | 8/2022 | Timm et al. |
| 11,419,667 B2 | 8/2022 | Messerly et al. |
| 11,424,027 B2 | 8/2022 | Shelton, IV |
| 11,426,167 B2 | 8/2022 | Shelton, IV et al. |
| 11,426,191 B2 | 8/2022 | Vakharia et al. |
| D964,564 S | 9/2022 | Boudreaux |
| 11,446,029 B2 | 9/2022 | Shelton, IV et al. |
| 11,452,525 B2 | 9/2022 | Shelton, IV et al. |
| 11,452,560 B2 | 9/2022 | Kase |
| 11,464,511 B2 | 10/2022 | Timm et al. |
| 11,464,512 B2 | 10/2022 | Shelton, IV et al. |
| 11,464,601 B2 | 10/2022 | Shelton, IV et al. |

(56) References Cited

U.S. PATENT DOCUMENTS

| | | |
|---|---|---|
| 11,471,155 B2 | 10/2022 | Shelton, IV et al. |
| 11,471,156 B2 | 10/2022 | Shelton, IV et al. |
| 11,471,206 B2 | 10/2022 | Henderson et al. |
| 11,471,209 B2 | 10/2022 | Yates et al. |
| 11,478,242 B2 | 10/2022 | Shelton, IV et al. |
| 11,484,310 B2 | 11/2022 | Shelton, IV et al. |
| 11,497,546 B2 | 11/2022 | Nott et al. |
| 11,497,547 B2 | 11/2022 | McKenna et al. |
| 11,504,122 B2 | 11/2022 | Shelton, IV et al. |
| 11,517,309 B2 | 12/2022 | Bakos et al. |
| 11,529,137 B2 | 12/2022 | Shelton, IV et al. |
| 11,529,139 B2 | 12/2022 | Shelton, IV et al. |
| 11,553,971 B2 | 1/2023 | Shelton, IV et al. |
| 11,559,304 B2 | 1/2023 | Boudreaux et al. |
| 11,559,307 B2 | 1/2023 | Shelton, IV et al. |
| 11,559,308 B2 | 1/2023 | Yates et al. |
| 11,559,347 B2 | 1/2023 | Wiener et al. |
| 11,571,210 B2 | 2/2023 | Shelton, IV et al. |
| 11,576,672 B2 | 2/2023 | Shelton, IV et al. |
| 11,576,677 B2 | 2/2023 | Shelton, IV et al. |
| 11,638,604 B2 | 5/2023 | Kobayashi et al. |
| 11,653,920 B2 | 5/2023 | Shelton, IV et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0032452 A1 | 3/2002 | Tierney et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0123749 A1 | 9/2002 | Jain |
| 2002/0133152 A1 | 9/2002 | Strul |
| 2002/0151884 A1 | 10/2002 | Hoey et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177373 A1 | 11/2002 | Shibata et al. |
| 2002/0177862 A1 | 11/2002 | Aranyi et al. |
| 2003/0009164 A1 | 1/2003 | Woloszko et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0073981 A1 | 4/2003 | Whitman et al. |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0176778 A1 | 9/2003 | Messing et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0094597 A1 | 5/2004 | Whitman et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0143263 A1 | 7/2004 | Schechter et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0181242 A1 | 9/2004 | Stack et al. |
| 2004/0193150 A1 | 9/2004 | Sharkey et al. |
| 2004/0193153 A1 | 9/2004 | Sartor et al. |
| 2004/0193212 A1 | 9/2004 | Taniguchi et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0171533 A1 | 8/2005 | Latterell et al. |
| 2005/0177184 A1 | 8/2005 | Easley |
| 2005/0182339 A1 | 8/2005 | Lee et al. |
| 2005/0187576 A1 | 8/2005 | Whitman et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |

(56) References Cited

U.S. PATENT DOCUMENTS

| | | |
|---|---|---|
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0142656 A1 | 6/2006 | Malackowski et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217700 A1 | 9/2006 | Garito et al. |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0259102 A1 | 11/2006 | Slatkine |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0129726 A1 | 6/2007 | Eder et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015473 A1 | 1/2008 | Shimizu |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0046122 A1 | 2/2008 | Manzo et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0161809 A1 | 7/2008 | Schmitz et al. |
| 2008/0167670 A1 | 7/2008 | Shelton et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0036913 A1 | 2/2009 | Wiener et al. |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088745 A1 | 4/2009 | Hushka et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0105750 A1 | 4/2009 | Price et al. |
| 2009/0112206 A1 | 4/2009 | Dumbauld et al. |
| 2009/0118751 A1 | 5/2009 | Wiener et al. |
| 2009/0131885 A1 | 5/2009 | Akahoshi |
| 2009/0131934 A1 | 5/2009 | Odom et al. |
| 2009/0138025 A1 | 5/2009 | Stahler et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0182333 A1 | 7/2009 | Eder et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0248022 A1 | 10/2009 | Falkenstein et al. |

(56) References Cited

U.S. PATENT DOCUMENTS

| | | |
|---|---|---|
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0036373 A1 | 2/2010 | Ward |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0145335 A1 | 6/2010 | Johnson et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0193566 A1 | 8/2010 | Scheib et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0225209 A1 | 9/2010 | Goldberg et al. |
| 2010/0228249 A1 | 9/2010 | Mohr et al. |
| 2010/0228250 A1 | 9/2010 | Brogna |
| 2010/0234906 A1 | 9/2010 | Koh |
| 2010/0256635 A1 | 10/2010 | McKenna et al. |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0305564 A1 | 12/2010 | Livneh |
| 2010/0331742 A1 | 12/2010 | Masuda |
| 2010/0331871 A1 | 12/2010 | Nield et al. |
| 2011/0004233 A1 | 1/2011 | Muir et al. |
| 2011/0015632 A1 | 1/2011 | Artale |
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022528 A1 | 1/2012 | White et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101493 A1 | 4/2012 | Masuda et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |
| 2012/0143182 A1 | 6/2012 | Ullrich et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0211542 A1 | 8/2012 | Racenet |
| 2012/0226266 A1 | 9/2012 | Ghosal et al. |
| 2012/0234893 A1 | 9/2012 | Schuckmann et al. |
| 2012/0253328 A1 | 10/2012 | Cunningham et al. |
| 2012/0253329 A1 | 10/2012 | Zemlok et al. |
| 2012/0265241 A1 | 10/2012 | Hart et al. |
| 2012/0296239 A1 | 11/2012 | Chernov et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0071282 A1 | 3/2013 | Fry |
| 2013/0085510 A1 | 4/2013 | Stefanchik et al. |
| 2013/0103031 A1 | 4/2013 | Garrison |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0190760 A1 | 7/2013 | Allen, IV et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0264369 A1 | 10/2013 | Whitman |
| 2013/0267874 A1 | 10/2013 | Marcotte et al. |
| 2013/0277410 A1 | 10/2013 | Fernandez et al. |
| 2013/0296843 A1 | 11/2013 | Boudreaux et al. |
| 2013/0321425 A1 | 12/2013 | Greene et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0107538 A1 | 4/2014 | Wiener et al. |
| 2014/0121569 A1 | 5/2014 | Schafer et al. |
| 2014/0135804 A1 | 5/2014 | Weisenburgh, II et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0180310 A1 | 6/2014 | Blumenkranz et al. |
| 2014/0194868 A1 | 7/2014 | Sanai et al. |
| 2014/0194874 A1 | 7/2014 | Dietz et al. |

(56) References Cited

U.S. PATENT DOCUMENTS

| | | |
|---|---|---|
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0236152 A1 | 8/2014 | Walberg et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0276768 A1 | 9/2014 | Juergens et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0303605 A1 | 10/2014 | Boyden et al. |
| 2014/0303612 A1 | 10/2014 | Williams |
| 2014/0357984 A1 | 12/2014 | Wallace et al. |
| 2014/0373003 A1 | 12/2014 | Grez et al. |
| 2015/0014392 A1 | 1/2015 | Williams et al. |
| 2015/0025528 A1 | 1/2015 | Arts |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0080889 A1 | 3/2015 | Cunningham et al. |
| 2015/0088122 A1 | 3/2015 | Jensen |
| 2015/0100056 A1 | 4/2015 | Nakamura |
| 2015/0112335 A1 | 4/2015 | Boudreaux et al. |
| 2015/0119901 A1 | 4/2015 | Steege |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0230796 A1 | 8/2015 | Calderoni |
| 2015/0238260 A1 | 8/2015 | Nau, Jr. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272657 A1 | 10/2015 | Yates et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0351857 A1 | 12/2015 | Vander Poorten et al. |
| 2015/0374430 A1 | 12/2015 | Weiler et al. |
| 2015/0374457 A1 | 12/2015 | Colby |
| 2016/0000437 A1 | 1/2016 | Giordano et al. |
| 2016/0038228 A1 | 2/2016 | Daniel et al. |
| 2016/0044841 A1 | 2/2016 | Chamberlain |
| 2016/0045248 A1 | 2/2016 | Unger et al. |
| 2016/0051314 A1 | 2/2016 | Batchelor et al. |
| 2016/0051316 A1 | 2/2016 | Boudreaux |
| 2016/0066913 A1 | 3/2016 | Swayze et al. |
| 2016/0120601 A1 | 5/2016 | Boudreaux et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0228171 A1 | 8/2016 | Boudreaux |
| 2016/0249910 A1 | 9/2016 | Shelton, IV et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0317216 A1 | 11/2016 | Hermes et al. |
| 2016/0331455 A1 | 11/2016 | Hancock et al. |
| 2016/0358849 A1 | 12/2016 | Jur et al. |
| 2017/0020614 A1 | 1/2017 | Jackson et al. |
| 2017/0065331 A1 | 3/2017 | Mayer et al. |
| 2017/0086909 A1 | 3/2017 | Yates et al. |
| 2017/0105754 A1* | 4/2017 | Boudreaux ............ A61B 90/03 |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164997 A1 | 6/2017 | Johnson et al. |
| 2017/0189095 A1 | 7/2017 | Danziger et al. |
| 2017/0202595 A1 | 7/2017 | Shelton, IV |
| 2017/0209145 A1 | 7/2017 | Swayze et al. |
| 2017/0224332 A1 | 8/2017 | Hunter et al. |
| 2017/0224405 A1 | 8/2017 | Takashino et al. |
| 2017/0231628 A1 | 8/2017 | Shelton, IV et al. |
| 2017/0281186 A1 | 10/2017 | Shelton, IV et al. |
| 2017/0296169 A1 | 10/2017 | Yates et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348043 A1 | 12/2017 | Wang et al. |
| 2017/0348044 A1 | 12/2017 | Wang et al. |
| 2017/0367772 A1 | 12/2017 | Gunn et al. |
| 2018/0014872 A1 | 1/2018 | Dickerson |
| 2018/0085157 A1 | 3/2018 | Batchelor et al. |
| 2018/0132850 A1 | 5/2018 | Leimbach et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0206904 A1 | 7/2018 | Felder et al. |
| 2018/0221045 A1 | 8/2018 | Zimmerman et al. |
| 2018/0250066 A1 | 9/2018 | Ding et al. |
| 2018/0271578 A1 | 9/2018 | Coulombe |
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0333179 A1 | 11/2018 | Weisenburgh, II et al. |
| 2018/0353245 A1 | 12/2018 | Mccloud et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000475 A1 | 1/2019 | Shelton, IV et al. |
| 2019/0000477 A1 | 1/2019 | Shelton, IV et al. |
| 2019/0029746 A1 | 1/2019 | Dudhedia et al. |
| 2019/0038283 A1 | 2/2019 | Shelton, IV et al. |
| 2019/0053818 A1 | 2/2019 | Nelson et al. |
| 2019/0069949 A1* | 3/2019 | Vrba .................... A61B 18/06 |
| 2019/0104919 A1 | 4/2019 | Shelton, IV et al. |
| 2019/0117293 A1 | 4/2019 | Kano et al. |
| 2019/0125361 A1 | 5/2019 | Shelton, IV et al. |
| 2019/0125384 A1 | 5/2019 | Scheib et al. |
| 2019/0125390 A1 | 5/2019 | Shelton, IV et al. |
| 2019/0175258 A1 | 6/2019 | Tsuruta |
| 2019/0183504 A1 | 6/2019 | Shelton, IV et al. |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201048 A1 | 7/2019 | Stulen et al. |
| 2019/0201104 A1 | 7/2019 | Shelton, IV et al. |
| 2019/0201136 A1 | 7/2019 | Shelton, IV et al. |
| 2019/0201594 A1 | 7/2019 | Shelton, IV et al. |
| 2019/0206564 A1 | 7/2019 | Shelton, IV et al. |

(56) References Cited

U.S. PATENT DOCUMENTS

| | | |
|---|---|---|
| 2019/0206569 A1 | 7/2019 | Shelton, IV et al. |
| 2019/0209201 A1 | 7/2019 | Boudreaux et al. |
| 2019/0223941 A1 | 7/2019 | Kitamura et al. |
| 2019/0269455 A1 | 9/2019 | Mensch et al. |
| 2019/0290265 A1 | 9/2019 | Shelton, IV et al. |
| 2019/0298350 A1 | 10/2019 | Shelton, IV et al. |
| 2019/0298353 A1 | 10/2019 | Shelton, IV et al. |
| 2019/0366562 A1 | 12/2019 | Zhang et al. |
| 2019/0388091 A1 | 12/2019 | Eschbach et al. |
| 2020/0054321 A1 | 2/2020 | Harris et al. |
| 2020/0078076 A1 | 3/2020 | Henderson et al. |
| 2020/0078085 A1 | 3/2020 | Yates et al. |
| 2020/0078609 A1 | 3/2020 | Messerly et al. |
| 2020/0100825 A1 | 4/2020 | Henderson et al. |
| 2020/0100830 A1 | 4/2020 | Henderson et al. |
| 2020/0113622 A1 | 4/2020 | Honegger |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0229834 A1 | 7/2020 | Olson et al. |
| 2020/0237434 A1 | 7/2020 | Scheib et al. |
| 2020/0261086 A1 | 8/2020 | Zeiner et al. |
| 2020/0268430 A1 | 8/2020 | Takei et al. |
| 2020/0268433 A1 | 8/2020 | Wiener et al. |
| 2020/0305870 A1 | 10/2020 | Shelton, IV |
| 2020/0315623 A1 | 10/2020 | Eisinger et al. |
| 2020/0315712 A1 | 10/2020 | Jasperson et al. |
| 2020/0338370 A1 | 10/2020 | Wiener et al. |
| 2020/0405296 A1 | 12/2020 | Shelton, IV et al. |
| 2020/0405302 A1 | 12/2020 | Shelton, IV et al. |
| 2020/0405316 A1 | 12/2020 | Shelton, IV et al. |
| 2020/0405410 A1 | 12/2020 | Shelton, IV |
| 2020/0405439 A1 | 12/2020 | Shelton, IV et al. |
| 2020/0410177 A1 | 12/2020 | Shelton, IV |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0153927 A1 | 5/2021 | Ross et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186499 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196360 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0212754 A1 | 7/2021 | Olson |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |
| 2022/0039891 A1 | 2/2022 | Stulen et al. |
| 2022/0071655 A1 | 3/2022 | Price et al. |
| 2022/0167982 A1 | 6/2022 | Shelton, IV et al. |
| 2022/0168005 A1 | 6/2022 | Aldridge et al. |
| 2022/0168039 A1 | 6/2022 | Worrell et al. |
| 2022/0226014 A1 | 7/2022 | Clauda, IV et al. |
| 2022/0304736 A1 | 9/2022 | Boudreaux |
| 2022/0313297 A1 | 10/2022 | Aldridge et al. |
| 2022/0346863 A1 | 11/2022 | Yates et al. |
| 2022/0387067 A1 | 12/2022 | Faller et al. |
| 2022/0406452 A1 | 12/2022 | Shelton, IV |
| 2023/0038162 A1 | 2/2023 | Timm et al. |
| 2023/0048996 A1 | 2/2023 | Vakharia et al. |
| 2023/0270486 A1 | 8/2023 | Wiener et al. |
| 2023/0277205 A1 | 9/2023 | Olson et al. |
| 2023/0372743 A1 | 11/2023 | Wiener et al. |
| 2023/0380880 A1 | 11/2023 | Wiener et al. |
| 2023/0397909 A1 | 12/2023 | Shelton, IV et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 201029899 Y | 3/2008 |
| CN | 101474081 A | 7/2009 |
| CN | 101516285 A | 8/2009 |
| CN | 101522112 A | 9/2009 |
| CN | 102100582 A | 6/2011 |
| CN | 102149312 A | 8/2011 |
| CN | 202027624 U | 11/2011 |
| CN | 102792181 A | 11/2012 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |
| CN | 104434298 A | 3/2015 |
| CN | 107374752 A | 11/2017 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0468194 A2 | 1/1992 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |

(56) References Cited

FOREIGN PATENT DOCUMENTS

| | | |
|---|---|---|
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| EP | 3476302 A2 | 5/2019 |
| EP | 3476331 A1 | 5/2019 |
| EP | 3694298 A1 | 8/2020 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0576482 A | 3/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | H11169381 A | 6/1999 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 2008017876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012223582 A | 11/2012 |
| JP | 2012235658 A | 11/2012 |
| JP | 2012235824 A | 12/2012 |
| JP | 2013126430 A | 6/2013 |
| KR | 100789356 B1 | 12/2007 |
| KR | 101298237 B1 | 8/2013 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9712557 A1 | 4/1997 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-02080793 A1 | 10/2002 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2006091494 A1 | 8/2006 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2011092464 A1 | 8/2011 |
| WO | WO-2012044606 A2 | 4/2012 |
| WO | WO-2012061722 A2 | 5/2012 |
| WO | WO-2012088535 A1 | 6/2012 |
| WO | WO-2012150567 A1 | 11/2012 |
| WO | WO-2016130844 A1 | 8/2016 |
| WO | WO-2019130090 A1 | 7/2019 |
| WO | WO-2019130113 A1 | 7/2019 |

OTHER PUBLICATIONS

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

(56) References Cited

OTHER PUBLICATIONS

Jang, J. et al. "Neuro-fuzzy and Soft Computing." Prentice Hall, 1997, pp. 13-89, 199-293, 335-393, 453-496, 535-549.

Sullivan, "Optimal Choice for Number of Strands in a Litz-Wire Transformer Winding," IEEE Transactions on Power Electronics, vol. 14, No. 2, Mar. 1999, pp. 283-291.

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Wall et al., "Thermal modification of collagen," J Shoulder Elbow Surg, No. 8, pp. 339-344 (Jul./Aug. 1999).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

National Semiconductors Temperature Sensor Handbook—http://www.national.com/appinfo/tempsensors/files/temphb.pdf; accessed online: Apr. 1, 2011.

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Douglas, S.C. "Introduction to Adaptive Filter". Digital Signal Processing Handbook. Ed. Vijay K. Madisetti and Douglas B. Williams. Boca Raton: CRC Press LLC, 1999.

Chen et al., "Heat-induced changes in the mechanics of a collagenous tissue: pseudoelastic behavior at 37° C.," Journal of Biomechanics, 31, pp. 211-216 (1998).

Technology Overview, printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in Physical Properties of Tissue (1990).

http://www.apicalinstr.com/generators.htm.

http://www.dotmed.com/listing/electrosurical-unit/ethicon/ultracision-g110-/1466724.

http://www.ethicon.com/gb-en/healthcare-professionals/products/energy-devices/capital//ge . . . .

http://www.medicalexpo.com/medical-manufacturer/electrosurgical-generator-6951.html.

http://www.megadyne.com/es_generator.php.

http://www.valleylab.com/product/es/generators/index.html.

Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desinger, K., "The longitudinal vibration response of a curved fiber used for laser ultrasound surgical therapy," Journal of the Acoustical Society of America 102, 1191-1199 (1997).

Walsh, S. J., White, R. G., "Vibrational Power Transmission in Curved Beams," Journal of Sound and Vibration, 233(3), 455-488 (2000).

Covidien 501(k) Summary Sonicision, dated Feb. 24, 2011 (7 pages).

Morley, L. S. D., "Elastic Waves in a Naturally Curved Rod," Quarterly Journal of Mechanics and Applied Mathematics, 14: 155-172 (1961).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Fowler, K.R., "A Programmable, Arbitrary Waveform Electrosurgical Device," IEEE Engineering in Medicine and Biology Society 10th Annual International Conference, pp. 1324, 1325 (1988).

LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

Campbell et al, "Thermal Imaging in Surgery," p. 19-3, in Medical Infrared Imaging, N. A. Diakides and J. D. Bronzino, Eds. (2008).

Gerhard, Glen C., "Surgical Electrotechnology: Quo Vadis?," IEEE Transactions on Biomedical Engineering, vol. BME-31, No. 12, pp. 787-792, Dec. 1984.

http://www.4-traders.com/JOHNSON-JOHNSON-4832/news/Johnson-Johnson-Ethicon-E . . . .

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Kurt Gieck & Reiner Gieck, *Engineering Formulas* § Z.7 (7th ed. 1997).

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

(56) References Cited

OTHER PUBLICATIONS

Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe, Integrated Circuit Engineering, Addison-Wesley Publishing, Reading, MA (1979). (book—not attached).
Erbe Electrosurgery VIO® 200 S, (2012), p. 7, 12 pages, accessed Mar. 31, 2014 at http://www.erbe-med.com/erbe/media/Marketing materialien/85140170 Erbe En VIO 200 S D027541.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Missinne, et al. "Stretchable Optical Waveguides," vol. 22, No. 4, Feb. 18, 2014, pp. 4168-4179 (12 pages).

\* cited by examiner

SECTION 43-43: UNDEFLECTED

SECTION 43-43: DEFLECTED

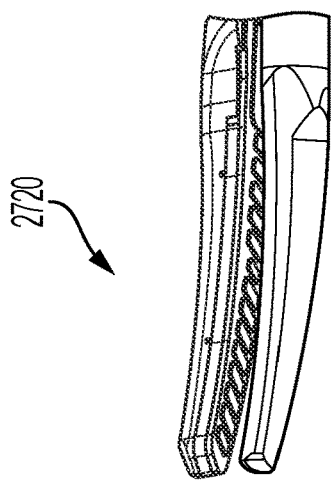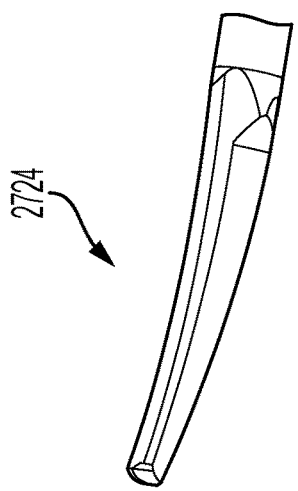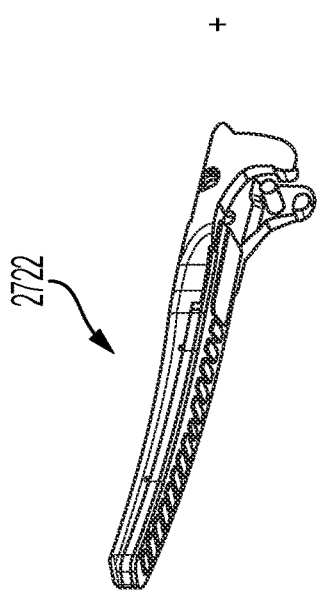
FIG. 52

MULTI-LAYER CLAMP ARM PAD FOR ENHANCED VERSATILITY AND PERFORMANCE OF A SURGICAL DEVICE

CROSS-REFERENCE TO RELATED APPLICATION

The present application claims priority under 35 U.S.C. § 119(e) to U.S. Provisional Patent Application Ser. No. 62/955,292, titled COMBINATION ENERGY MODALITY END-EFFECTOR, filed Dec. 30, 2019, the disclosure of which is herein incorporated by reference in its entirety.

TECHNICAL FIELD

The present disclosure generally relates to end-effectors adapted and configured to operate with multiple energy modalities to enable tissue sealing and cutting employing simultaneously, independently, or sequentially applied energy modalities. More particularly, the present disclosure relates to end-effectors adapted and configured to operate with surgical instruments that employ combined ultrasonic and electrosurgical systems, such as monopolar or bipolar radio frequency (RF), to enable tissue sealing and cutting employing simultaneously, independently, or sequentially applied ultrasonic and electrosurgical energy modalities. The energy modalities may be applied based on tissue parameters or other algorithms. The end-effectors may be adapted and configured to couple to hand held or robotic surgical systems.

BACKGROUND

Ultrasonic surgical instruments employing ultrasonic energy modalities are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and hemostasis by coagulation, desirably minimizing patient trauma. The cutting action is typically realized by an end-effector, ultrasonic blade, or ultrasonic blade tip, at the distal end of the instrument, which transmits ultrasonic energy to tissue brought into contact with the end-effector. An ultrasonic end-effector may comprise an ultrasonic blade, a clamp arm, and a pad, among other components.

Some surgical instruments utilize ultrasonic energy for both precise cutting and controlled coagulation. Ultrasonic energy cuts and coagulates by vibrating a blade in contact with tissue. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

Electrosurgical instruments for applying electrical energy modalities to tissue to treat, seal, cut, and/or destroy tissue also are finding increasingly widespread applications in surgical procedures. An electrosurgical instrument typically includes an instrument having a distally-mounted end-effector comprising one or more than one electrode. The end-effector can be positioned against the tissue such that electrical current is introduced into the tissue. Electrosurgical instruments can be configured for bipolar or monopolar operation. During bipolar operation, current is introduced though a first electrode (e.g., active electrode) into the tissue and returned from the tissue through a second electrode (e.g., return electrode). During monopolar operation, current is introduced into the tissue by an active electrode of the end-effector and returned through a return electrode such as a grounding pad, for example, separately coupled to the body of a patient. Heat generated by the current flowing through the tissue may form hemostatic seals within the tissue and/or between tissues and thus may be particularly useful for sealing blood vessels, for example. The end-effector of an electrosurgical instrument also may include a cutting member that is movable relative to the tissue and the electrodes to transect the tissue. Electrosurgical end-effectors may be adapted and configured to couple to hand held instruments as well as robotic instruments.

Electrical energy applied by an electrosurgical instrument can be transmitted to the instrument by a generator in communication with the hand piece. The electrical energy may be in the form of radio frequency ("RF") energy. RF energy is a form of electrical energy that may be in the frequency range of 200 kilohertz (kHz) to 1 megahertz (MHz). In application, an electrosurgical instrument can transmit low frequency RF energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy is useful for removing, shrinking, or sculpting soft tissue while simultaneously sealing blood vessels. RF energy works particularly well on connective tissue, which is primarily comprised of collagen and shrinks when contacted by heat.

The RF energy may be in a frequency range described in EN 60601-2-2:2009+A11:2011, Definition 201.3.218— HIGH FREQUENCY. For example, the frequency in monopolar RF applications may be typically restricted to less than 5 MHz. However, in bipolar RF energy applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications. It is generally recognized that 10 mA is the lower threshold of thermal effects on tissue.

Ultrasonic surgical instruments and electrosurgical instruments of the nature described herein can be configured for open surgical procedures, minimally invasive surgical procedures, or non-invasive surgical procedures. Minimally invasive surgical procedures involve the use of a camera and instruments inserted through small incisions in order to visualize and treat conditions within joints or body cavities. Minimally invasive procedures may be performed entirely within the body or, in some circumstances, can be used together with a smaller open approach. These combined approaches, known as "arthroscopic, laparoscopic or thoracoscopic-assisted surgery," for example. The surgical instruments described herein also can be used in non-invasive procedures such as endoscopic surgical procedures, for example. The instruments may be controlled by a surgeon using a hand held instrument or a robot.

A challenge of utilizing these surgical instruments is the inability to control and customize single or multiple energy modalities depending on the type of tissue being treated. It would be desirable to provide end-effectors that overcome some of the deficiencies of current surgical instruments and improve the quality of tissue treatment, sealing, or cutting or combinations thereof. The combination energy modality end-effectors described herein overcome those deficiencies and improve the quality of tissue treatment, sealing, or cutting or combinations thereof.

SUMMARY

In one aspect, an apparatus is provided for dissecting and coagulating tissue. The apparatus comprises a surgical instrument comprising an end-effector adapted and configured to deliver a plurality of energy modalities to tissue at a distal end thereof. The energy modalities may be applied simultaneously, independently, or sequentially. A generator is electrically coupled to the surgical instrument and is configured to supply a plurality of energy modalities to the end-effector. In one aspect, the generator is configured to supply electrosurgical energy (e.g., monopolar or bipolar radio frequency (RF) energy) and ultrasonic energy to the end-effector to allow the end-effector to interact with the tissue. The energy modalities may be supplied to the end-effector by a single generator or multiple generators.

In various aspects, the present disclosure provides a surgical instrument configured to deliver at least two energy types (e.g., ultrasonic, monopolar RF, bipolar RF, microwave, or irreversible electroporation [IRE]) to tissue. The surgical instrument includes a first activation button for activating energy, a second button for selecting an energy mode for the activation button. The second button is connected to a circuit that uses at least one input parameter to define the energy mode. The input parameter can be modified remotely through connection to a generator or through a software update.

In one aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the at least one electrode acts a deflectable support with respect to an opposing ultrasonic blade. The at least one electrode crosses over the ultrasonic blade and is configured to be deflectable with respect to the clamp arm having features to change the mechanical properties of the tissue compression under the at least one electrode. The at least one electrode includes a feature to prevent inadvertent contact between the electrode and the ultrasonic blade.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the movable clamp jaw comprises at least one non-biased deflectable electrode to minimize contact between the ultrasonic blade and the RF electrode. The ultrasonic blade pad contains a feature for securing the electrode to the pad. As the pad height wears or is cut through, the height of the electrode with respect to the clamp jaw is progressively adjusted. Once the clamp jaw is moved away from the ultrasonic blade, the electrode remains in its new position.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the at least one bipolar RF electrode is deflectable and has a higher distal bias than proximal bias. The bipolar RF electrode is deflectable with respect to the clamp jaw. The end-effector is configured to change the mechanical properties of the tissue compression proximal to distal end to create a more uniform or differing pattern of pressure than due to the clamping alone.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the bipolar RF electrode is deflectable and the end-effector provides variable compression/bias along the length of the deflectable electrode. The end-effector is configured to change the mechanical properties of the tissue compression under the electrodes based on clamp jaw closure or clamping amount.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. The one aspect, the pad includes asymmetric segments to provide support for the ultrasonic blade support and the electrode is movable. The asymmetric segmented pad is configured for cooperative engagement with the movable bipolar RF electrode. The segmented ultrasonic support pad extends at least partially through the bipolar RF electrode. At least one pad element is significantly taller than a second pad element. The first pad element extends entirely through the bipolar RF electrode and the second pad element extends partially through the bipolar RF electrode. The first pad element and the second pad element are made of dissimilar materials.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, variations in the physical parameters of the electrode in combination with a deflectable electrode are employed to change the energy density delivered to the tissue and the tissue interactions. The physical aspects of the electrode vary along its length in order to change the contact area and/or the energy density of the electrode to tissue as the electrode also deflects.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, an ultrasonic transducer control algorithm is provided to reduce the power delivered by the ultrasonic or RF generator when a short circuit of contact between the ultrasonic blade and the electrode is detected to prevent damage to the ultrasonic blade. The ultrasonic blade control algorithm monitors for electrical shorting or ultrasonic blade to electrode contact. This detection is used to adjust the power/amplitude level of the ultrasonic transducer when the electrical threshold minimum is exceeded and adjusts the transducer power/amplitude threshold to a level below the minimum threshold that would cause damage to the ultrasonic blade, ultrasonic generator, bipolar RF electrode, or bipolar RF generator. The monitored electrical parameter could be tissue impedance (Z) or electrical continuity. The power adjustment could be to shut off the ultrasonic generator, bipolar RF generator, of the surgical device or it could be a proportionate response to either the electrical parameter, pressure, or time or any combination of these parameters.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, the clamp jaw features or aspects are provided in the clamp ram to minimize tissue sticking and improve tissue control. The clamp arm tissue path or clamp area includes features configured to adjust the tissue path relative to the clamp arm/ultrasonic blade to create a predefined location of contact to reduce tissue sticking and charring.

In another aspect, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In one aspect, a partially conductive clamp arm pad is provided to enable electrode wear through and minimize electrical shorting between the ultrasonic blade and the bipolar RF electrode. The clamp arm pad includes electrically conductive and non-conductive portions allowing it to act as one of the bipolar RF electrodes while also acting as the wearable support structure for the ultrasonic blade. The electrically conductive portions of the clamp ram pad are positioned around the perimeter of the pad and not positioned directly below the ultrasonic blade contact area. The electrically conductive portion is configured to degrade or wear to prevent any contact with the ultrasonic blade from interrupting the electrical conductivity of the remaining electrically conductive pad.

In another aspect, the present disclosure provides an end-effector configured to grasp tissue. The end-effector includes an ultrasonic blade configured to be coupled to an ultrasonic transducer and a clamp arm, including a clamp arm pad. The ultrasonic blade is configured to transfer ultrasonic energy to the tissue. The clamp arm pad includes an electrically conductive material, and an electrically non-conductive material. The clamp arm pad is configured as an electrode of a radiofrequency energy circuit. The electrode is configured to transfer radiofrequency energy through the tissue to a return electrode of the radiofrequency energy circuit. The electrically non-conductive material is configured to reduce the possibility of an electrical short between the electrically conductive material and the ultrasonic blade as the clamp arm pad degrades throughout the usable life of the end effector.

In another aspect, the present disclosure provides a clamp arm configured to grasp tissue in conjunction with an ultrasonic blade. The clamp arm includes a clamp arm pad including an electrically conductive layer defining a channel and an electrically non-conductive layer. The electrically non-conductive layer is positioned adjacent the electrically conductive layer such that at least a portion of the electrically non-conductive layer is positioned through the channel. The clamp arm pad is configured as an electrode of a radiofrequency energy circuit. The electrically non-conductive material is configured to reduce the possibility of an electrical short between the electrically conductive material and the ultrasonic blade.

In another aspect, the present disclosure provides an end-effector configured to grasp tissue. The end-effector includes an ultrasonic blade and a clamp arm including a clamp arm pad. The clamp arm pad includes an electrically conductive material and an electrically non-conductive material. The electrically non-conductive material is configured to prevent the electrically conductive material from being positioned a predetermined distance away from the ultrasonic blade as the clamp arm pad degrades throughout the usable life of the end effector.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

Further, it is understood that any one or more of the following-described forms, expressions of forms, examples, can be combined with any one or more of the other following-described forms, expressions of forms, and examples.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the described forms are set forth with particularity in the appended claims. The described forms, however, both as to organization and methods of operation, may be best understood by reference to the following description, taken in conjunction with the accompanying drawings in which:

FIG. 10 is a side view of an end-effector comprising a shortened clamp arm, an ultrasonic blade, an electrode, and a clamp arm pad, according to at least one aspect of the present disclosure;

FIG. 11 is a top view of the end-effector, according to at least one aspect of the present disclosure; and FIG. 12 illustrates a clamp arm comprising a clamp jaw, an electrode, and a clamp arm pad, according to at least one aspect of the present disclosure.

FIG. 19 illustrates the clamp arm open and tissue of non-uniform thickness ($T_{1a}$, $T_{2a}$, $T_{3a}$) is disposed over the flexible electrode;

Figure 20:
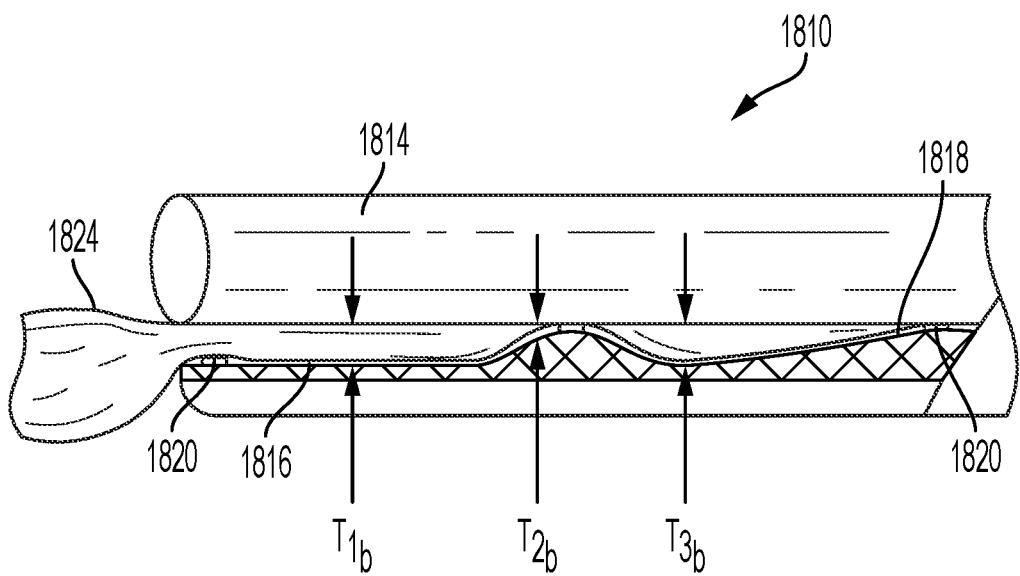

FIG. 20 the clamp arm is closed to compress the tissue; and

Figure 19:
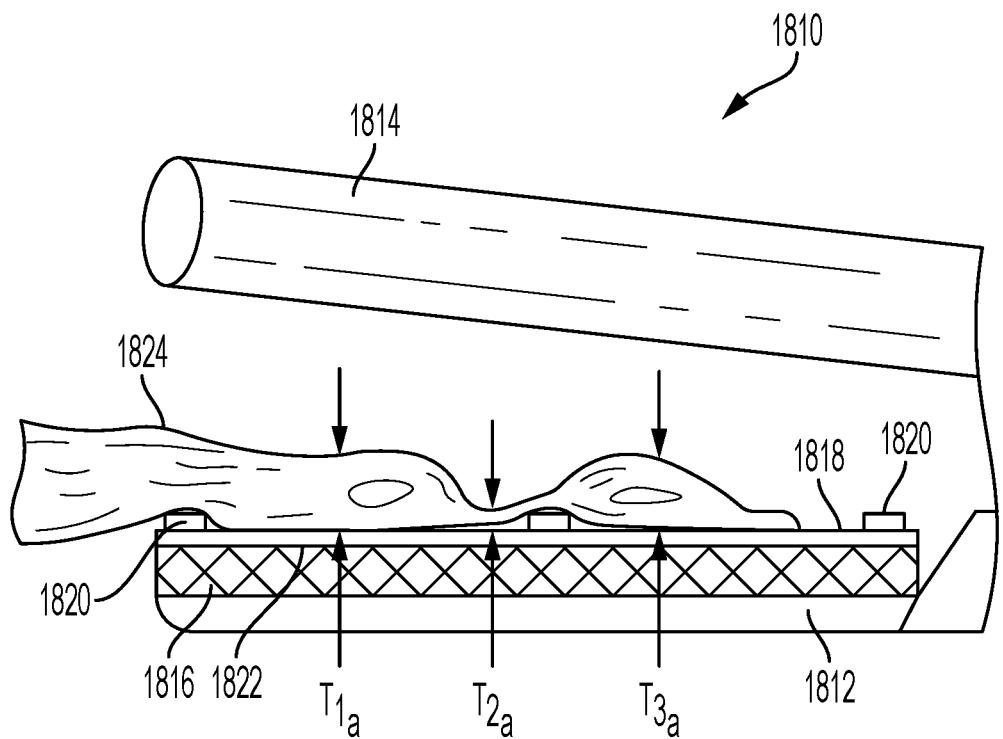
FIGS. 19-21 illustrate an end-effector comprising a clamp arm, an ultrasonic blade, a lattice cushion, a flexible electrode disposed above the lattice cushion, and a plurality of hard spacers to set a gap between the flexible electrode and the ultrasonic blade, according to at least one aspect of the present disclosure, where.
Figure 21:
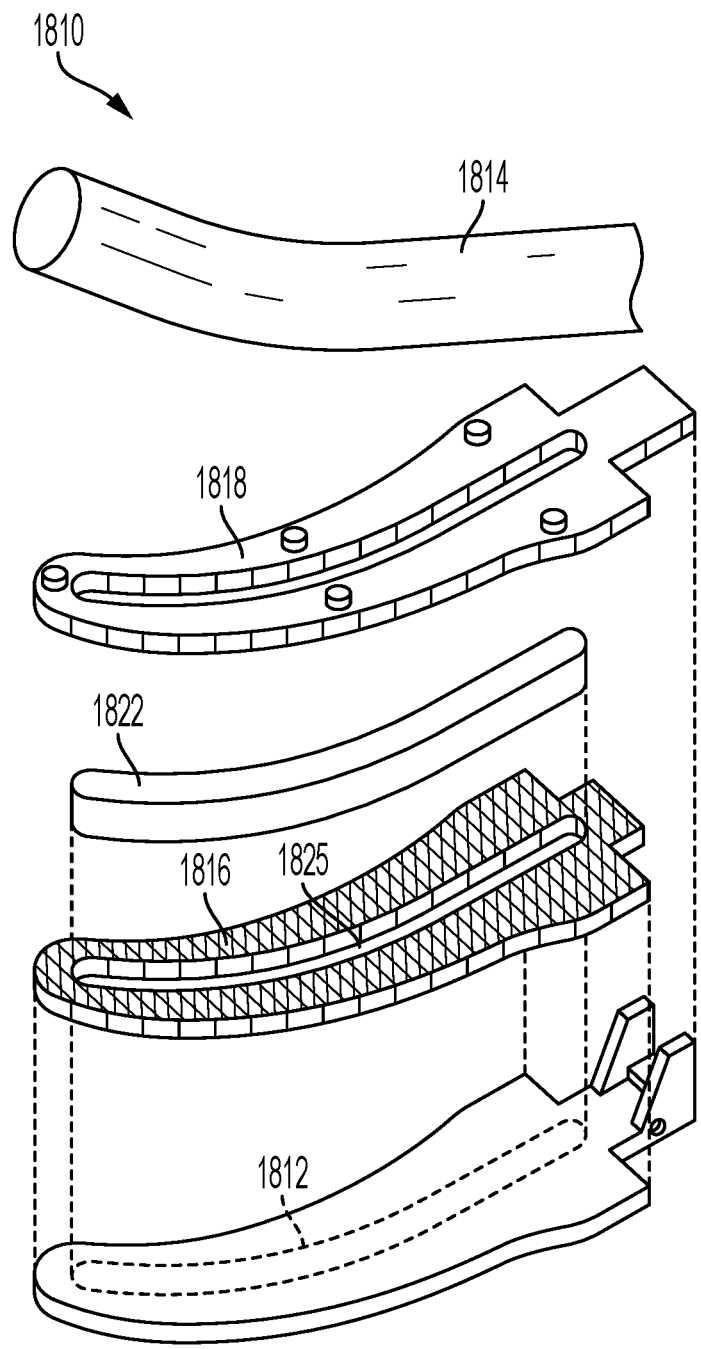

FIG. 21 is an exploded view of the end-effector shown in FIGS. 19-20.

Figure 22:
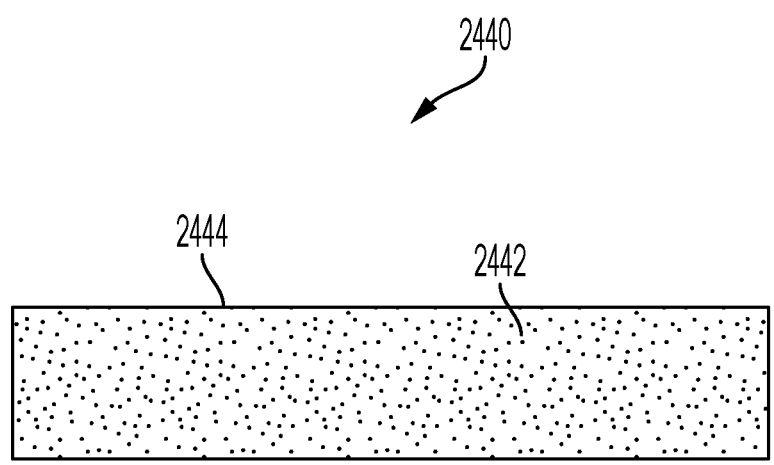

FIG. 22 is a section view of a conductive polymer clamp arm pad, according to at least one aspect of the present disclosure.

Figure 23:
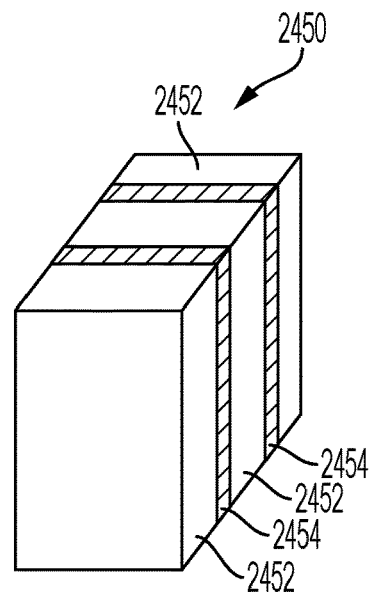

FIG. 23 is a perspective view of a clamp arm pad configured to replace a conventional electrode, according to at least one aspect of the present disclosure.

Figure 24:
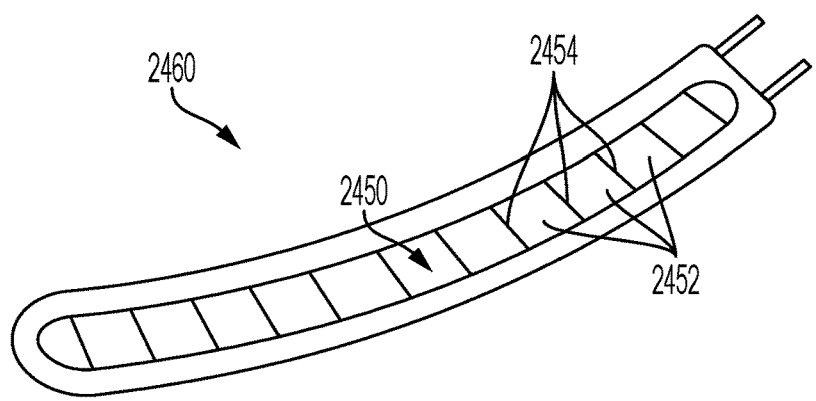

FIG. 24 illustrates a clamp arm comprising the clamp arm pad described in FIG. 23, according to at least one aspect of the present disclosure.

Figure 25:
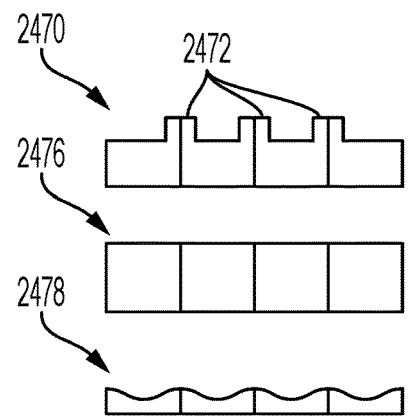

FIG. 25 illustrates clamp arm pads configured as described in FIGS. 23-24, according to at least one aspect of the present disclosure.

Figure 26:
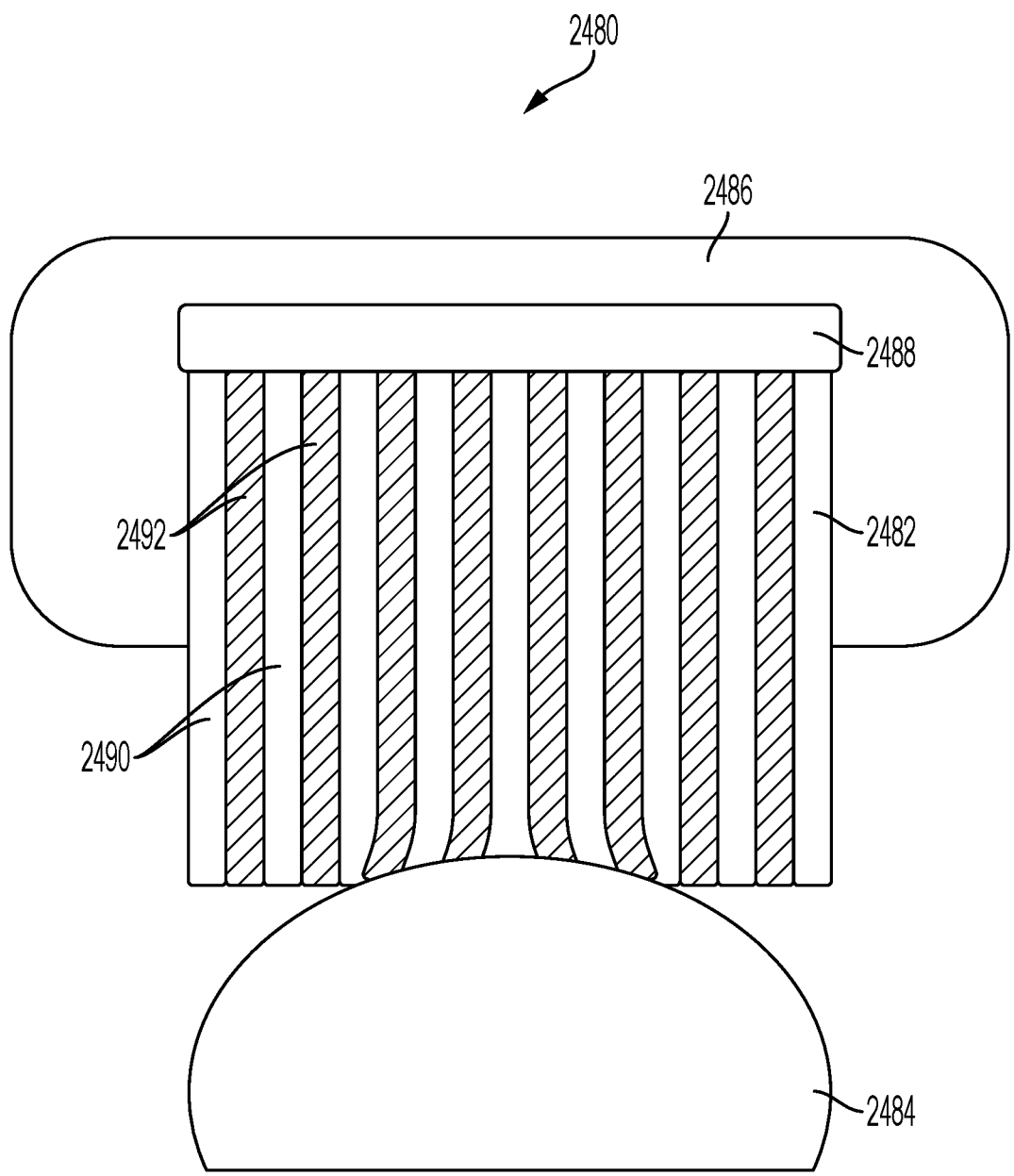

FIG. 26 is a section view of a clamp arm comprising a composite clamp arm pad in contact with tissue, according to at least one aspect of the present disclosure.

Figure 27:
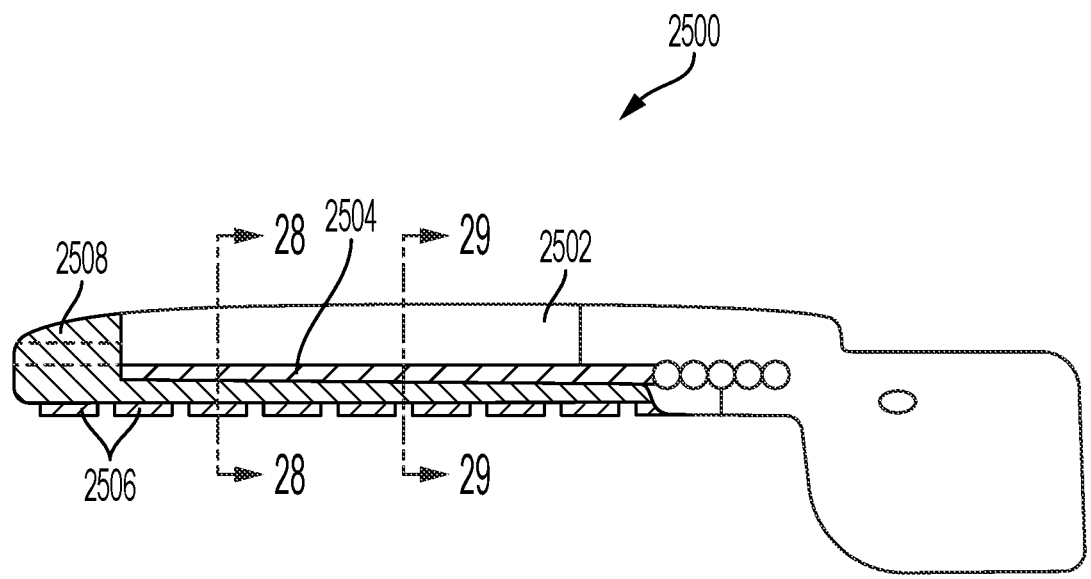

FIG. 27 illustrates a clamp arm comprising a clamp jaw to support a carrier or stamping attached to the clamp jaw and a clamp arm pad, according to at least one aspect of the present disclosure.

Figures 28, 29:
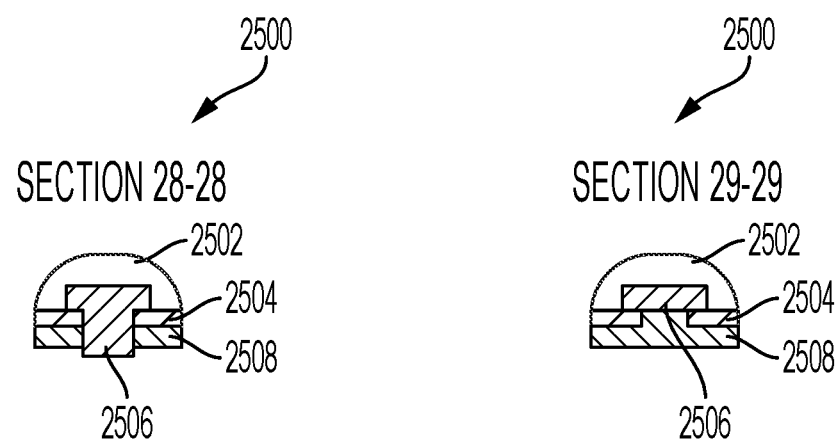

FIG. 28 is a section view taken at section 28-28 in FIG. 27.

FIG. 29 is a section view taken at section 29-29 in FIG. 27.

Figure 30:
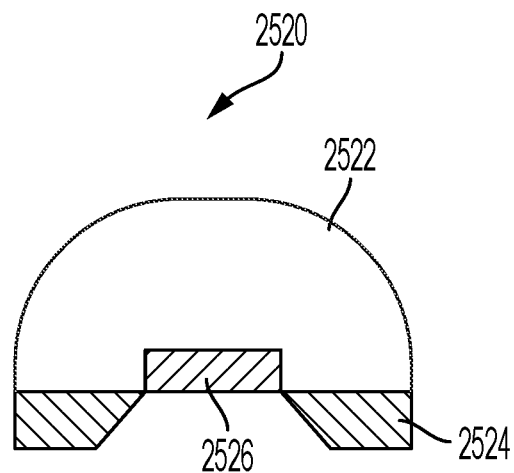

FIG. 30 is a section view of an alternative implementation of a clamp arm comprising a clamp jaw, an electrically conductive pad, and an electrically non-conductive pad, according to at least one aspect of the present disclosure.

Figure 31:
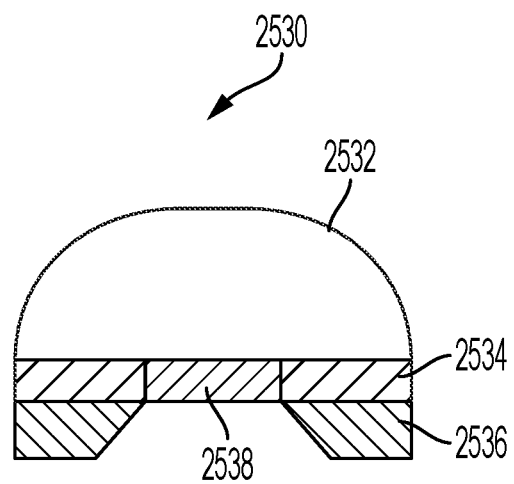

FIG. 31 is a section view of an alternative implementation of a clamp arm comprising a clamp jaw, a carrier or stamping welded to the clamp jaw, an electrically conductive pad, and an electrically non-conductive pad, according to at least one aspect of the present disclosure.

Figure 32:
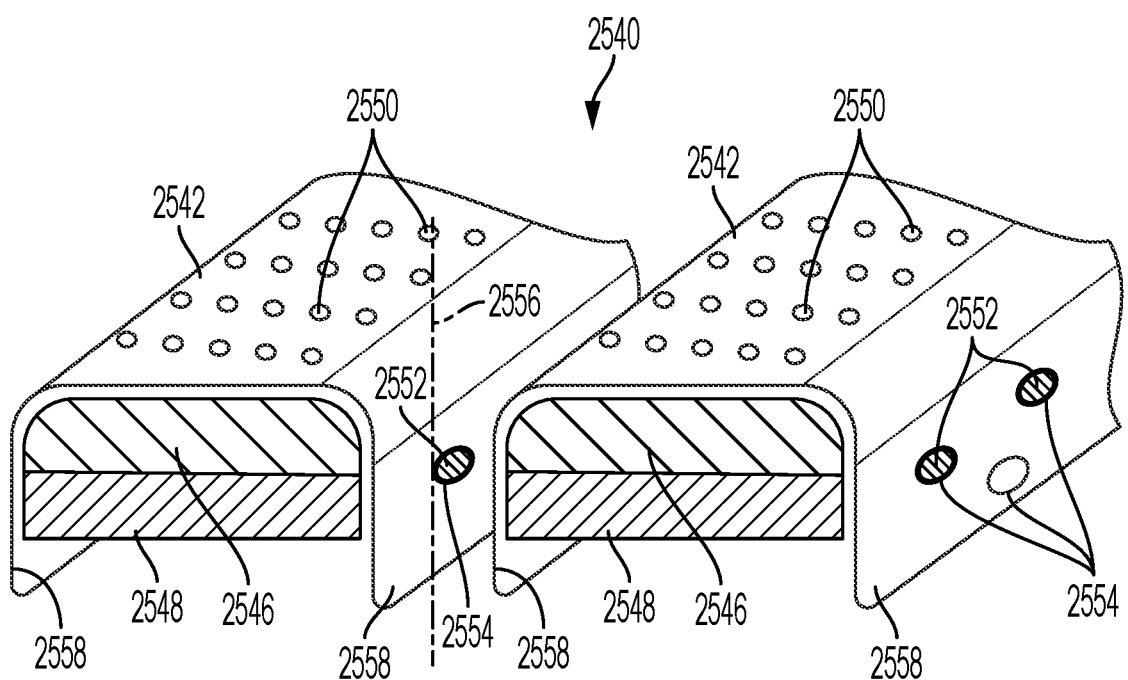

FIG. 32 illustrates insert molded electrodes, according to at least one aspect of the present disclosure.

Figure 33:
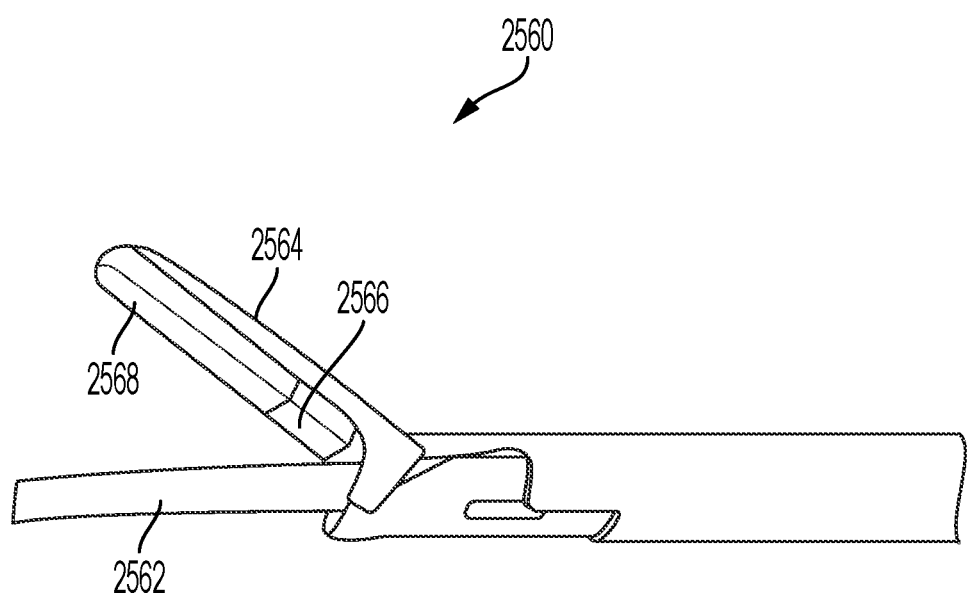

FIG. 33 illustrates an end-effector comprising an ultrasonic blade, a clamp arm, and a clamp arm pad comprising an electrically conductive film, according to at least one aspect of the present disclosure.

Figure 34:
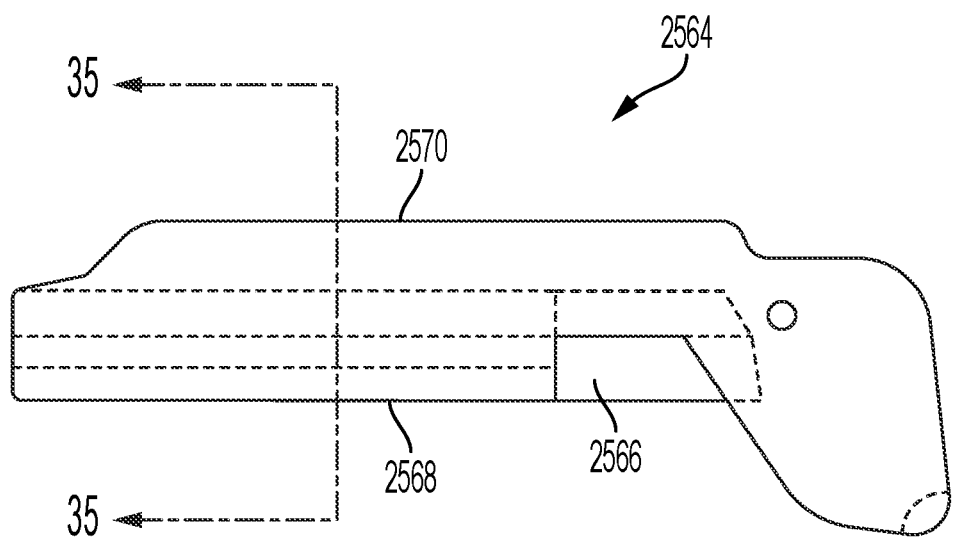

FIG. 34 illustrates the clamp arm shown in FIG. 33.

Figure 35:
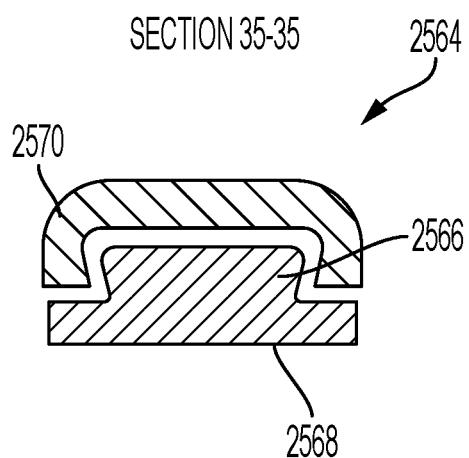

FIG. 35 is a section view of the clamp arm taken along section 35-35 in FIG. 34.

Figure 36:
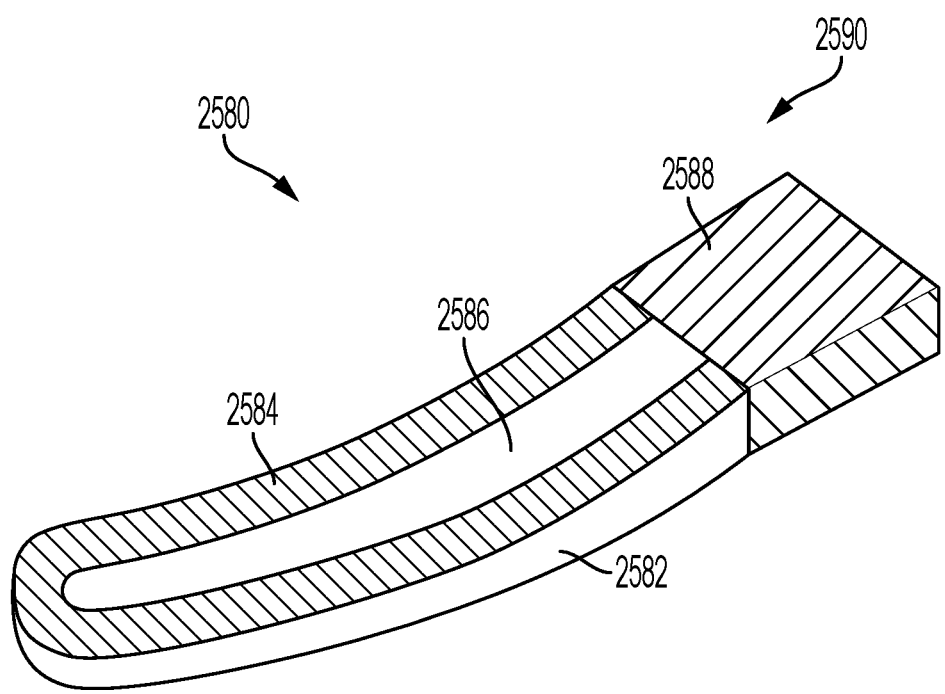

FIG. 36 illustrates a clamp arm comprising a partially electrically conductive clamp arm pad, according to at least one aspect of the resent disclosure.

Figure 37:
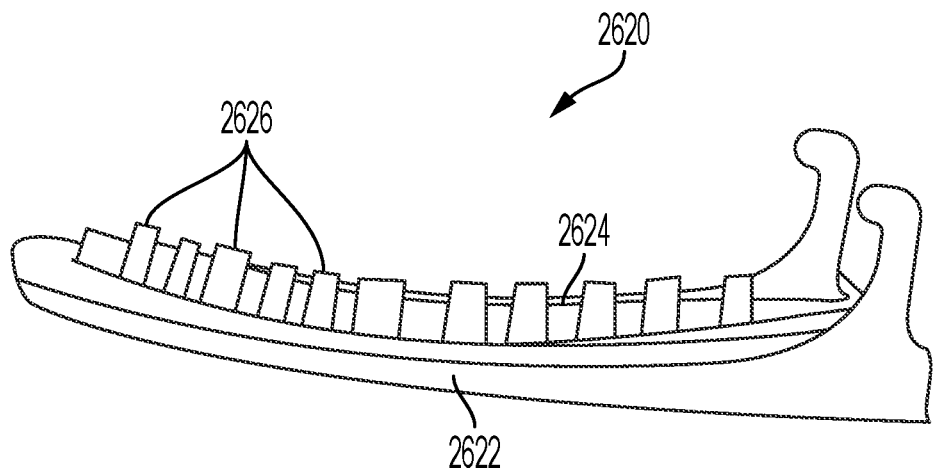

FIG. 37 illustrates a clamp arm comprising a clamp jaw, a clamp arm pad comprising exposed teeth, according to at least one aspect of the present disclosure.

Figure 38:
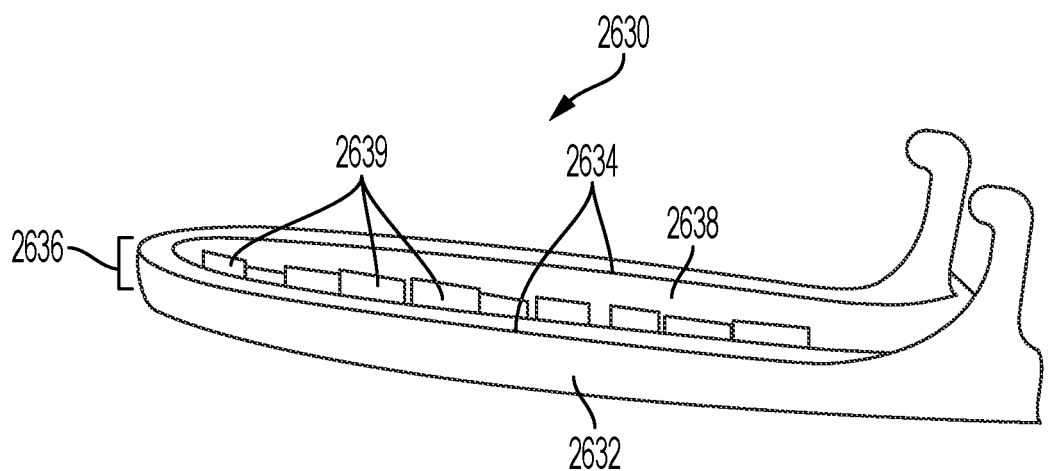

FIG. 38 illustrates a clamp arm comprising a clamp jaw comprising raised sidewalls and a raised lip, and a clamp arm pad comprising a plurality of teeth, according to at least one aspect of the present disclosure.

Figure 39:
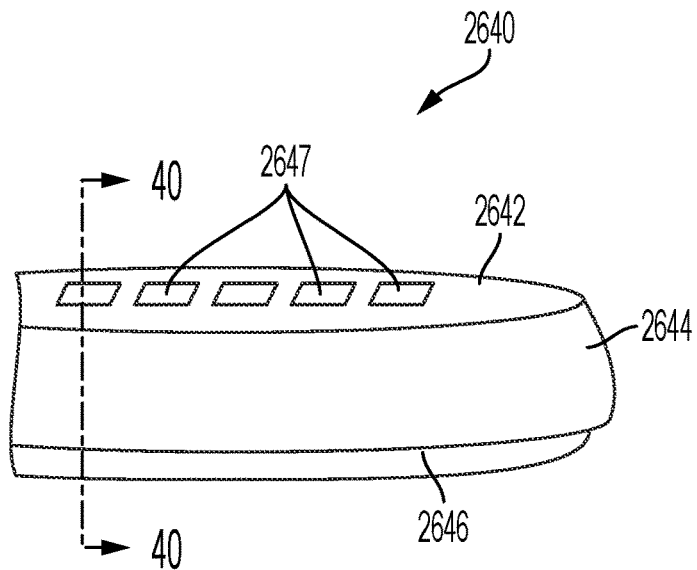
Figure 40:
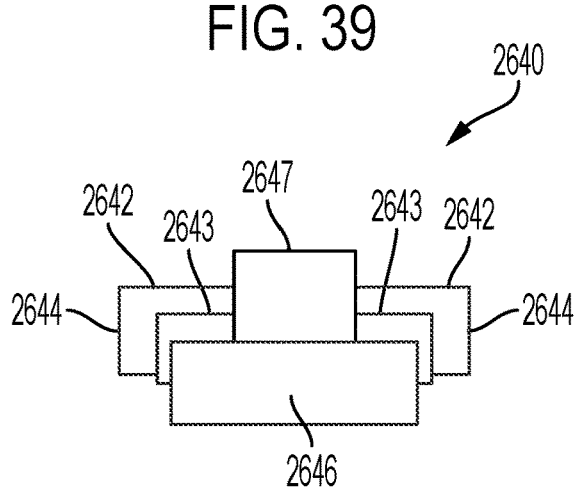
Figure 41:
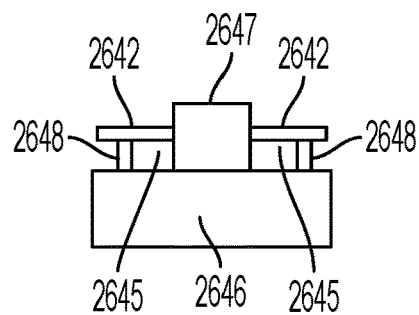

FIGS. 39-42 illustrates an electrode with a perimeter wall, according to at least one aspect of the present disclosure, where:

FIG. 39 illustrates a clamp arm comprising an electrode with a perimeter wall supported by a clamp jaw and a clamp arm pad, according to tat least one aspect of the present disclosure;

FIG. 40 is a section view of the clamp jaw taken along section 40-40 in FIG. 39; and FIG. 41 is an alternative or additional feature where a sealant such as silicone or other fluid polymer may be provided in the space beneath the electrode and the above the clamp jaw to prevent tissue from going and accumulating under the electrode, according to at least one aspect of the present disclosure.

Figure 42:
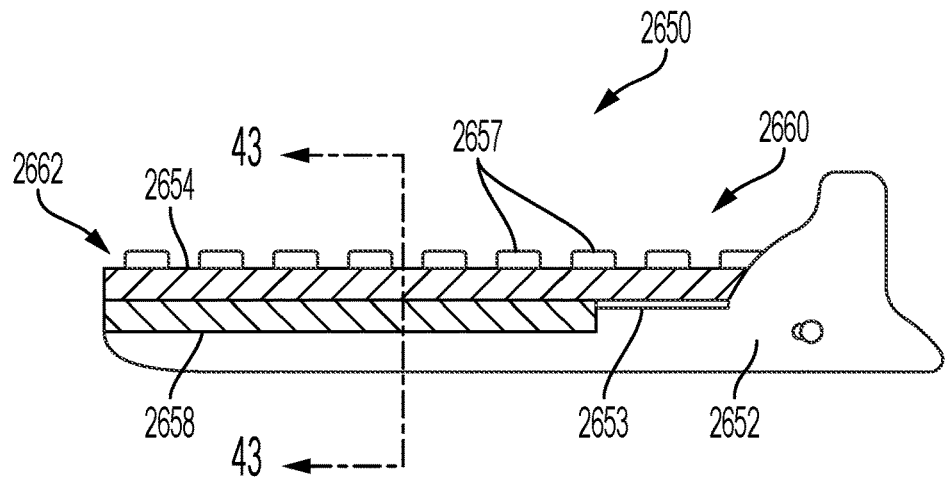

FIG. 42 illustrates a clamp arm comprising a clamp jaw, an electrode, a clamp arm pad (FIG. 43) comprising a plurality of teeth, and a deflectable ledge along the lateral sides of the electrode, according to at least one aspect of the present disclosure.

Figure 43:
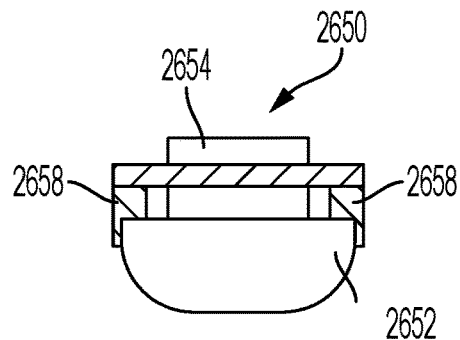
Figure 44:
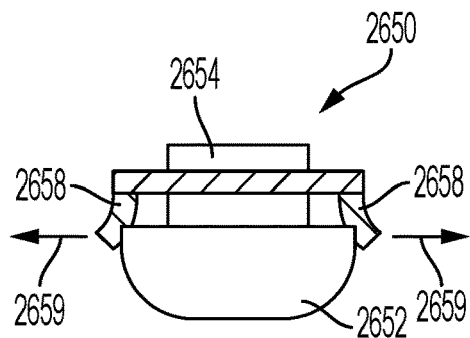

FIGS. 43 and 44 are section views of the clamp arm shown in FIG. 42 taken at section 43-43, where:

FIG. 43 shows the electrode and the skirt in an undeflected state; and

FIG. 44 shows the electrode and the skirt in a deflected state where the skirt shifts laterally in the direction indicated by the arrows.

Figure 45:
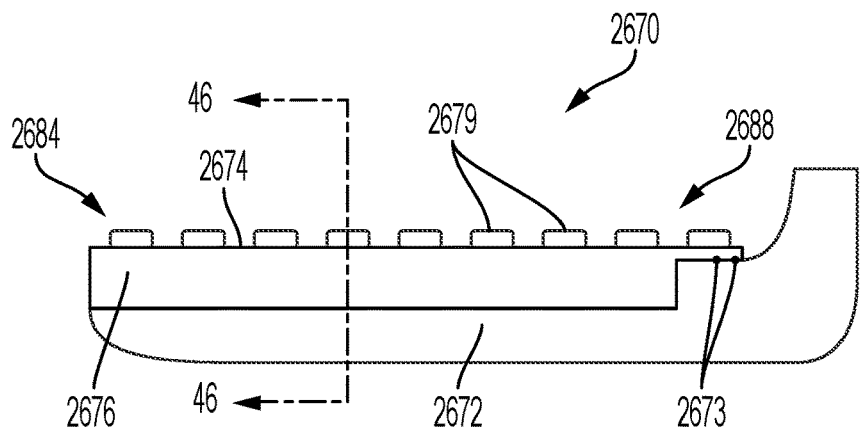

FIG. 45 illustrates a clamp arm comprising a clamp jaw, an electrode, and sidewalls extending downwardly from the electrode past the sidewalls of the clamp jaw, and clamp arm pad (FIG. 46) comprising a plurality of teeth, according to at least one aspect of the present disclosure.

Figure 46:
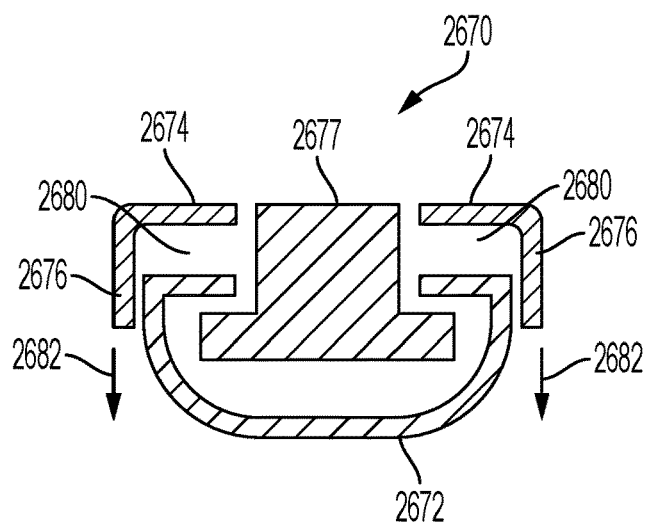

FIG. 46 is a section view of the clamp arm shown in FIG. 45 along section line 46-46.

Figure 47:
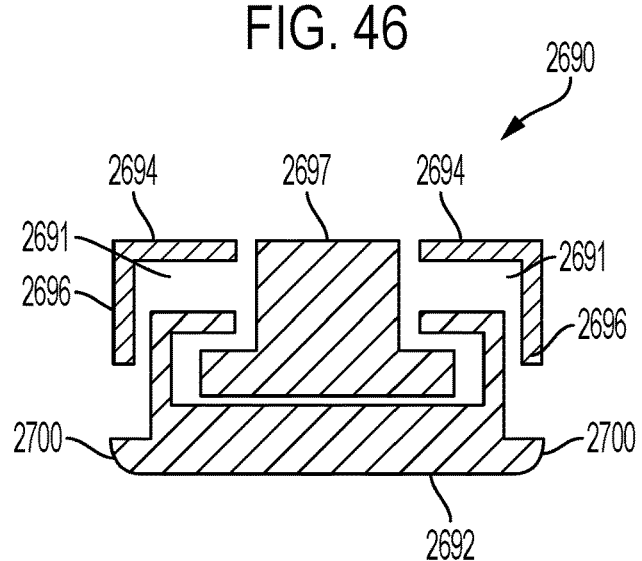

FIG. 47 illustrates an alternative clamp arm to the clamp arm shown in FIGS. 45-46, according to at least one aspect of the present disclosure.

Figure 48:
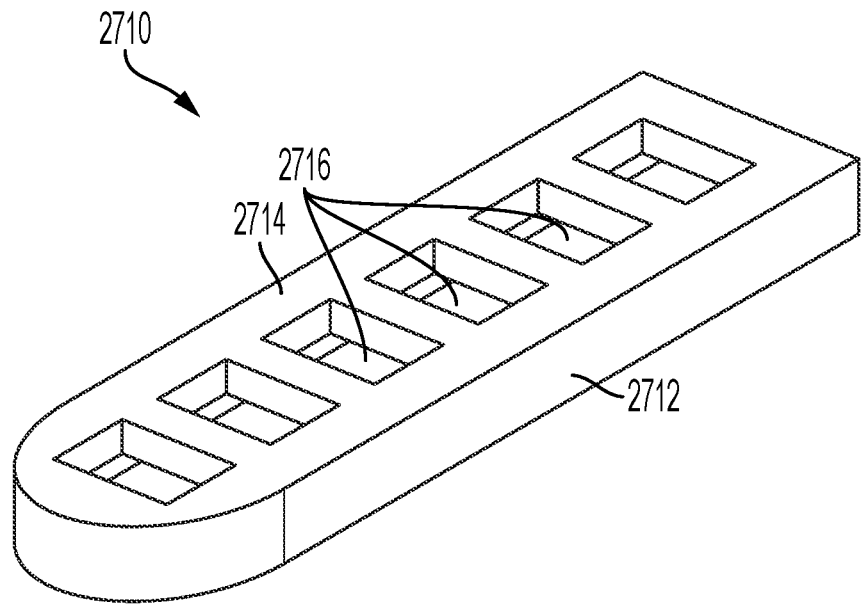

FIG. 48 is a top perspective view of an electrode comprising a lip extending downwardly from a top surface of the electrode, according to at least one aspect of the present disclosure.

Figure 49:
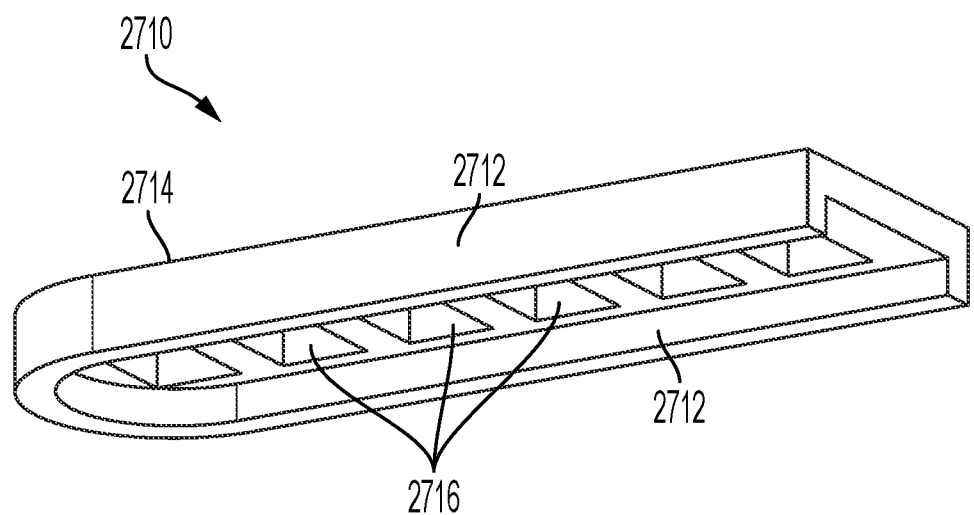

FIG. 49 is a bottom perspective view of the electrode shown in FIG. 48 showing the downwardly extending lip.

Figure 50:
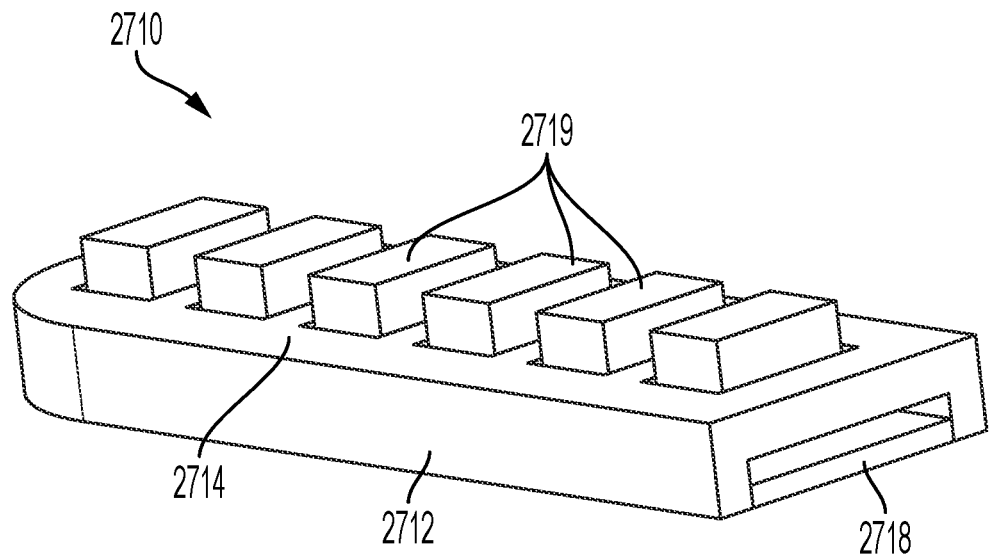

FIG. 50 is a top perspective view of the electrode shown in FIGS. 48-49 with a clamp arm pad with teeth extending through the apertures.

Figure 51:
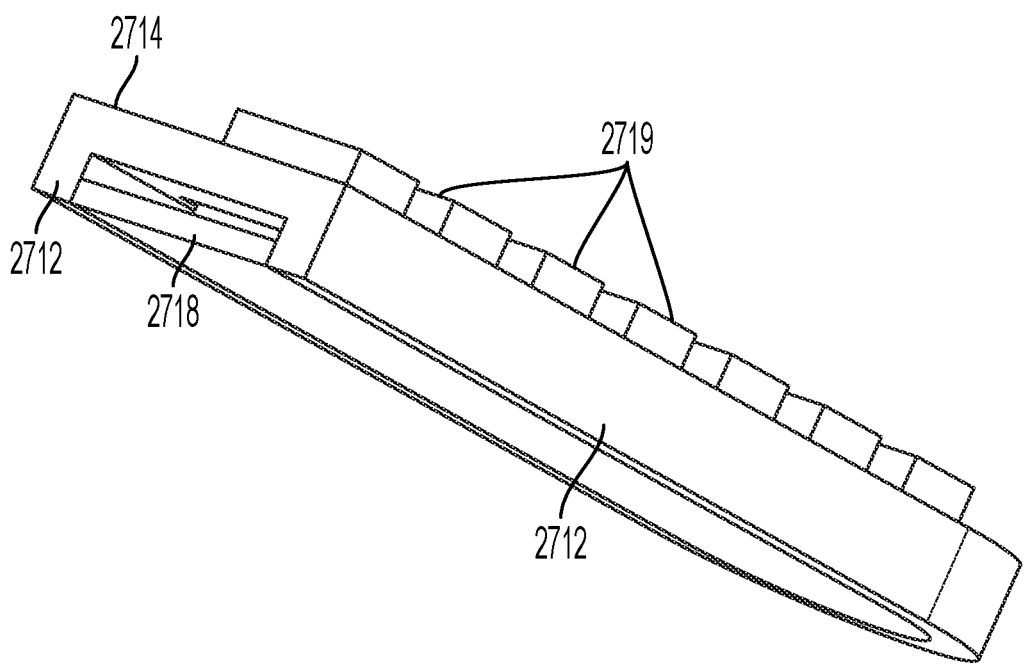

FIG. 51 is a top perspective view of the electrode shown in FIGS. 48-49 with a clamp arm pad with teeth extending through the apertures.

FIG. 52 illustrates an end effector comprising a clamp arm and an ultrasonic blade, according to at least one aspect of the present disclosure.

Figure 53:
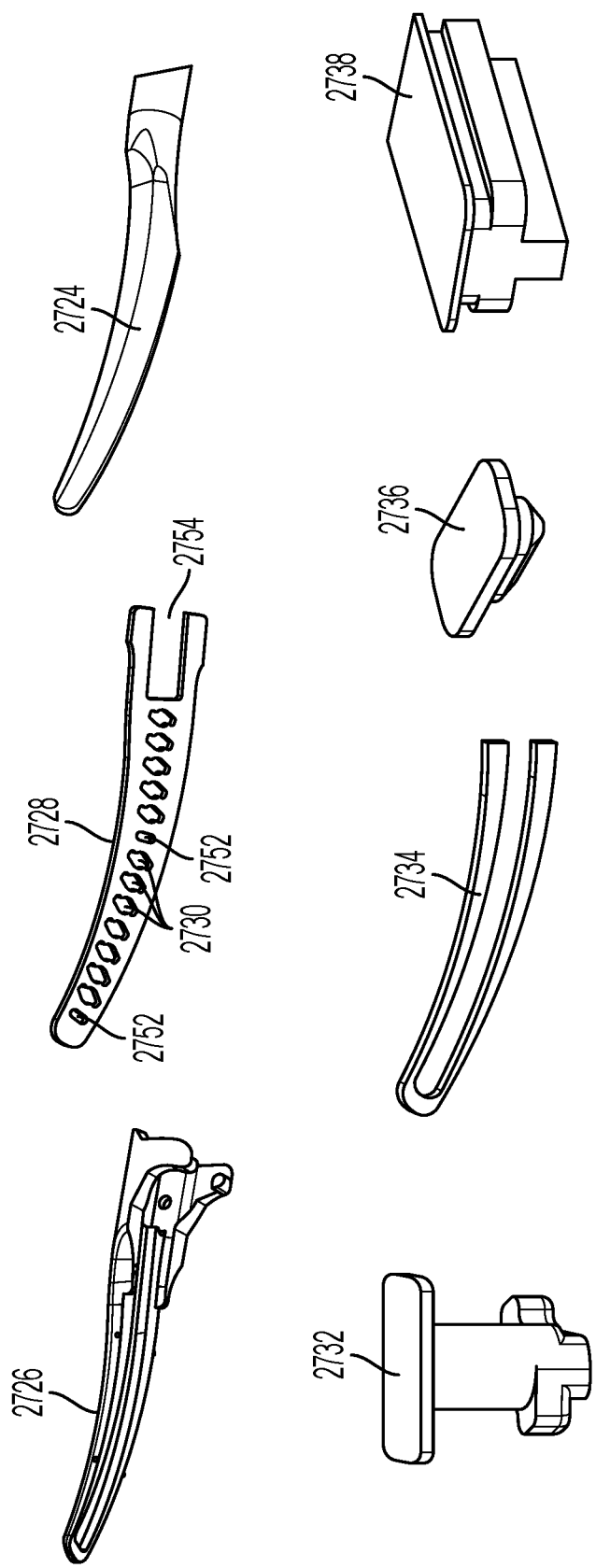

FIG. 53 illustrates components of an end-effector comprising a clamp arm comprising a clamp jaw, an electrode comprising a plurality of apertures sized and configured to receive a plurality of individual tissue pad units, a single piece elastic/hyper elastic block, small wear resistant gap pads, and a large wear resistant gap pads, according to at least one aspect of the present disclosure.

Figure 54:
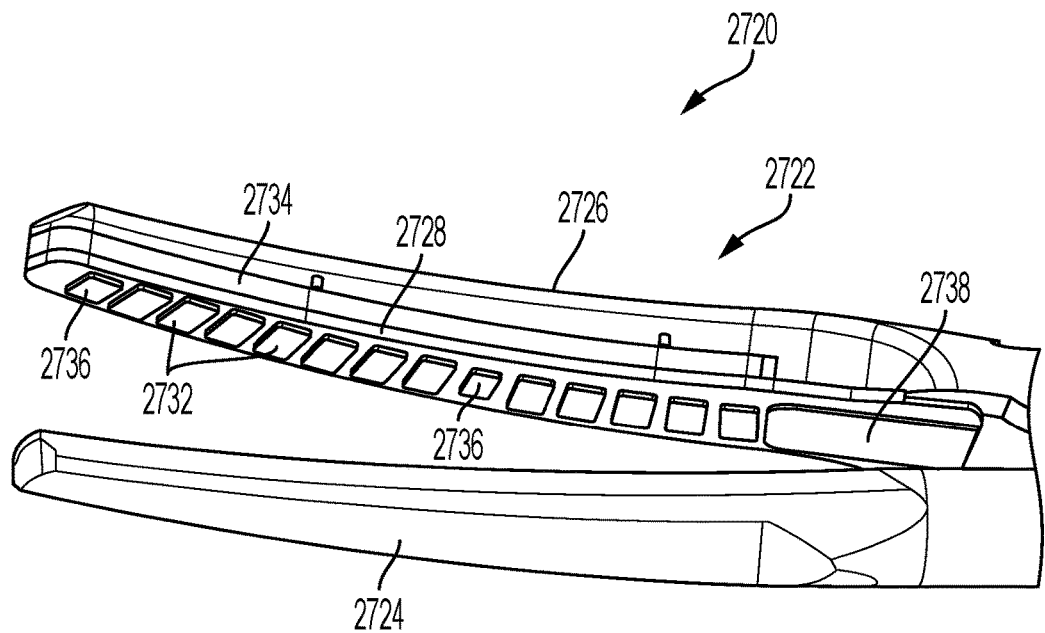

FIG. 54 illustrates an assembled version of the end-effector comprising the components illustrated in FIG. 53.

Figure 55:
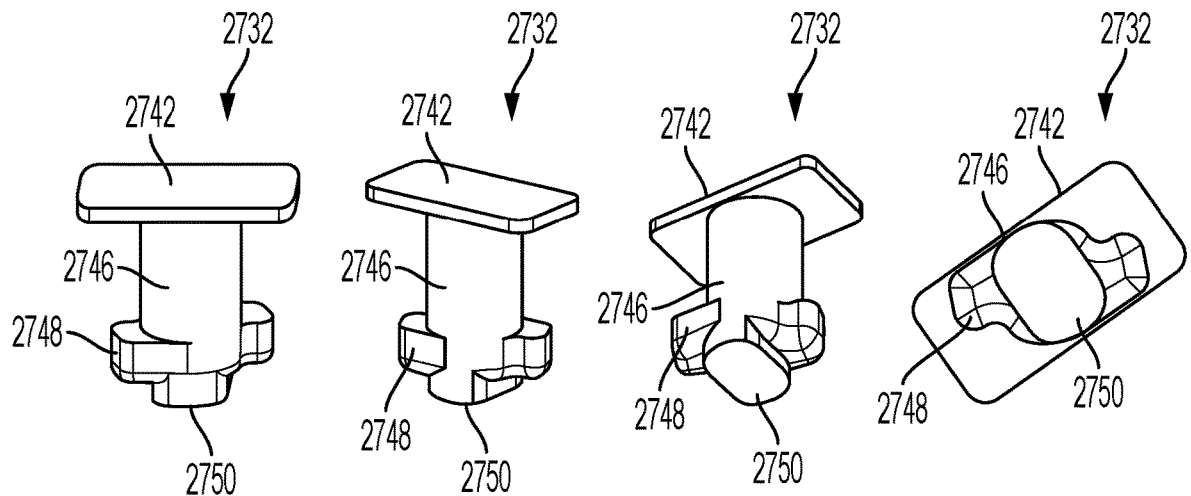

FIG. 55 illustrates various views of the individual tissue pad unit, according to at least one aspect of the present disclosure.

Figure 56:
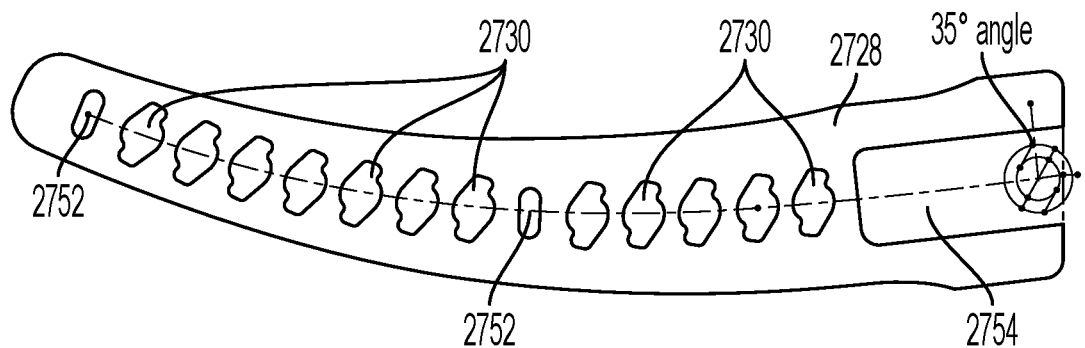

FIG. 56 illustrates the electrode, according to at least one aspect of the present disclosure.

Figure 57:
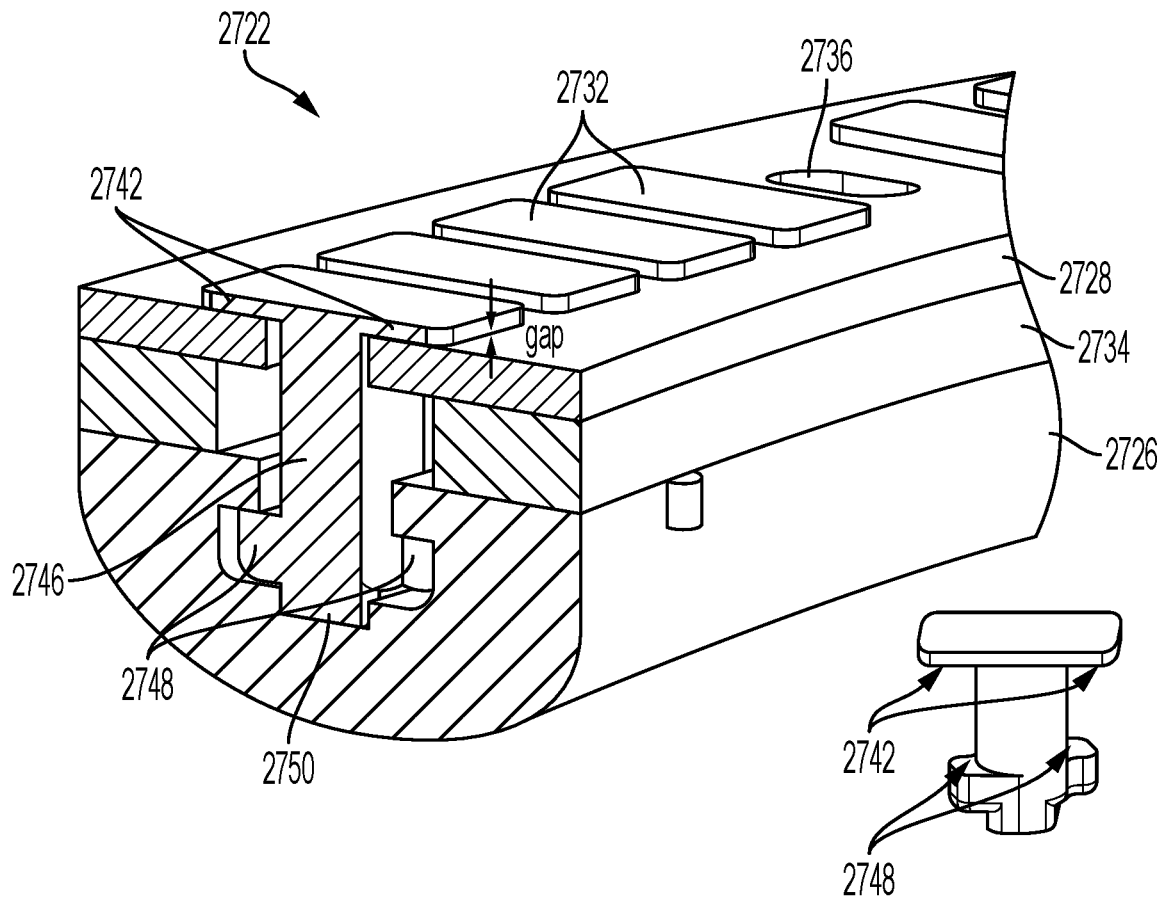

FIG. 57 illustrates a section view of the clamp arm showing the elastic/hyper elastic block, according to at least one aspect of the present disclosure.

Figure 58:
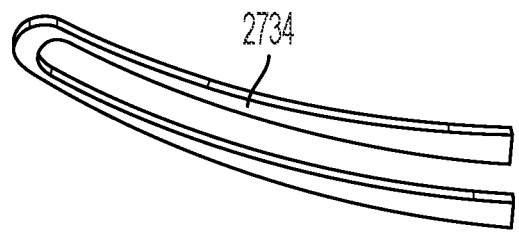

FIG. 58 is a perspective view of the elastic/hyper elastic block.

Figure 59:
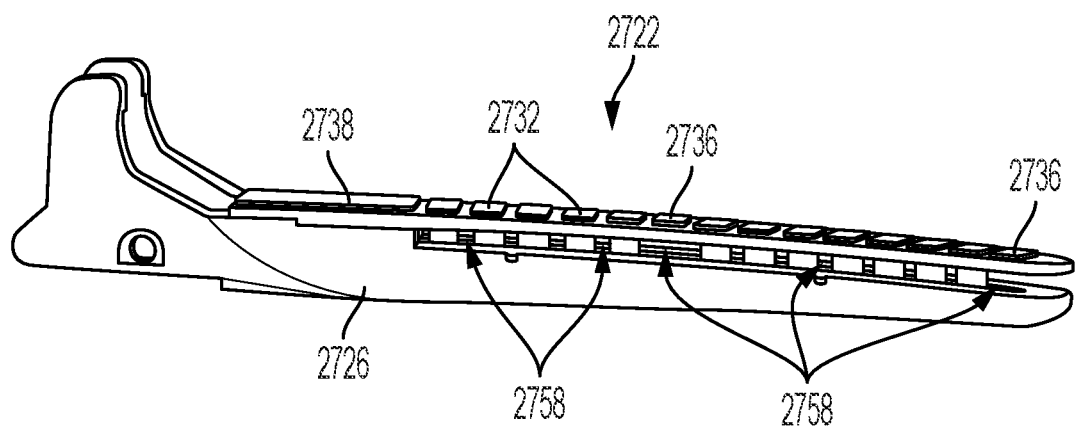

FIG. 59 is perspective views of a sub-assembly comprising the clamp jaw, electrode, and the individual tissue pad units, according to at least one aspect to the present disclosure.

Figure 60:
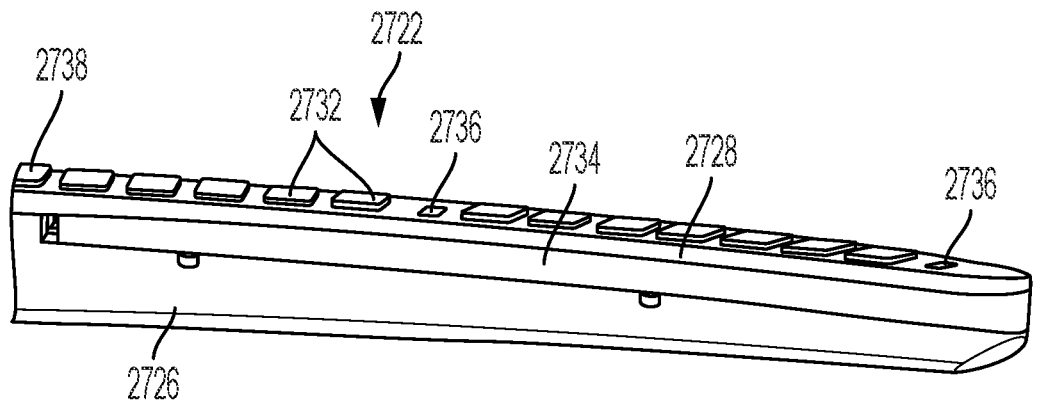

FIG. 60 is a perspective view of the clamp arm assembly comprising the elastic/hyper elastic block of FIG. 58 assembled to the sub-assembly, according to at least one aspect of the present disclosure.

Figure 61:
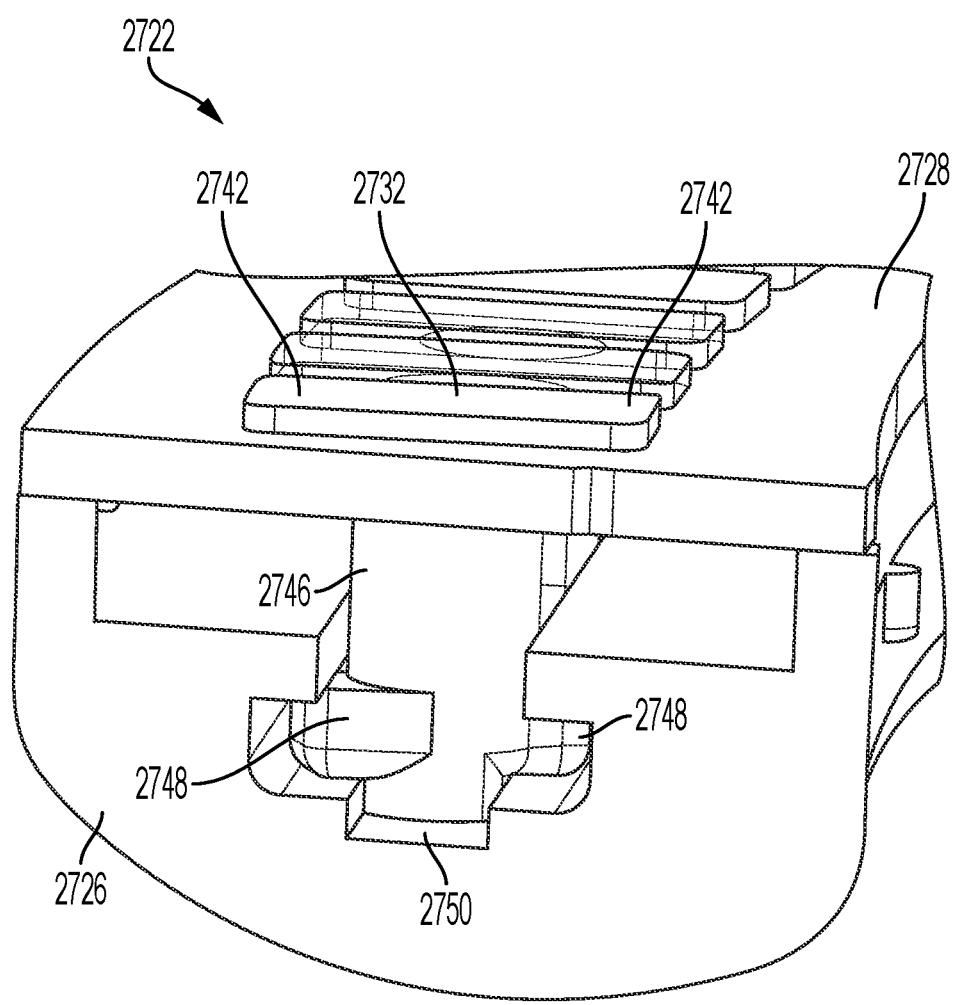

FIG. 61 is perspective views of a sub-assembly comprising the clamp jaw, electrode, and the individual tissue pad units, according to at least one aspect to the present disclosure.

Figure 62:
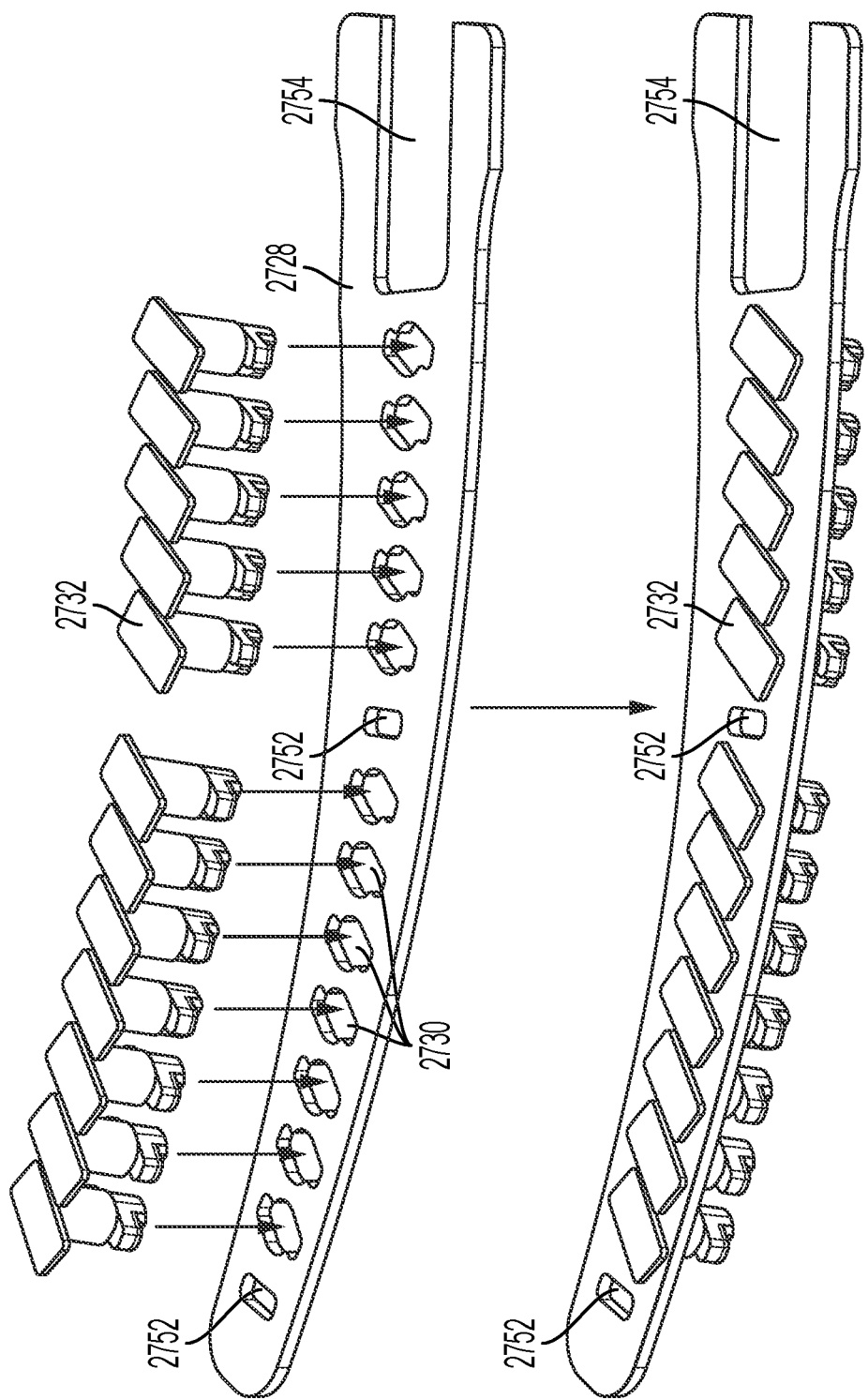

FIG. 62 illustrates a first assembly step, according to at least one aspect of the present disclosure, where the individual tissue pad units are inserted into the electrode.

Figure 63:
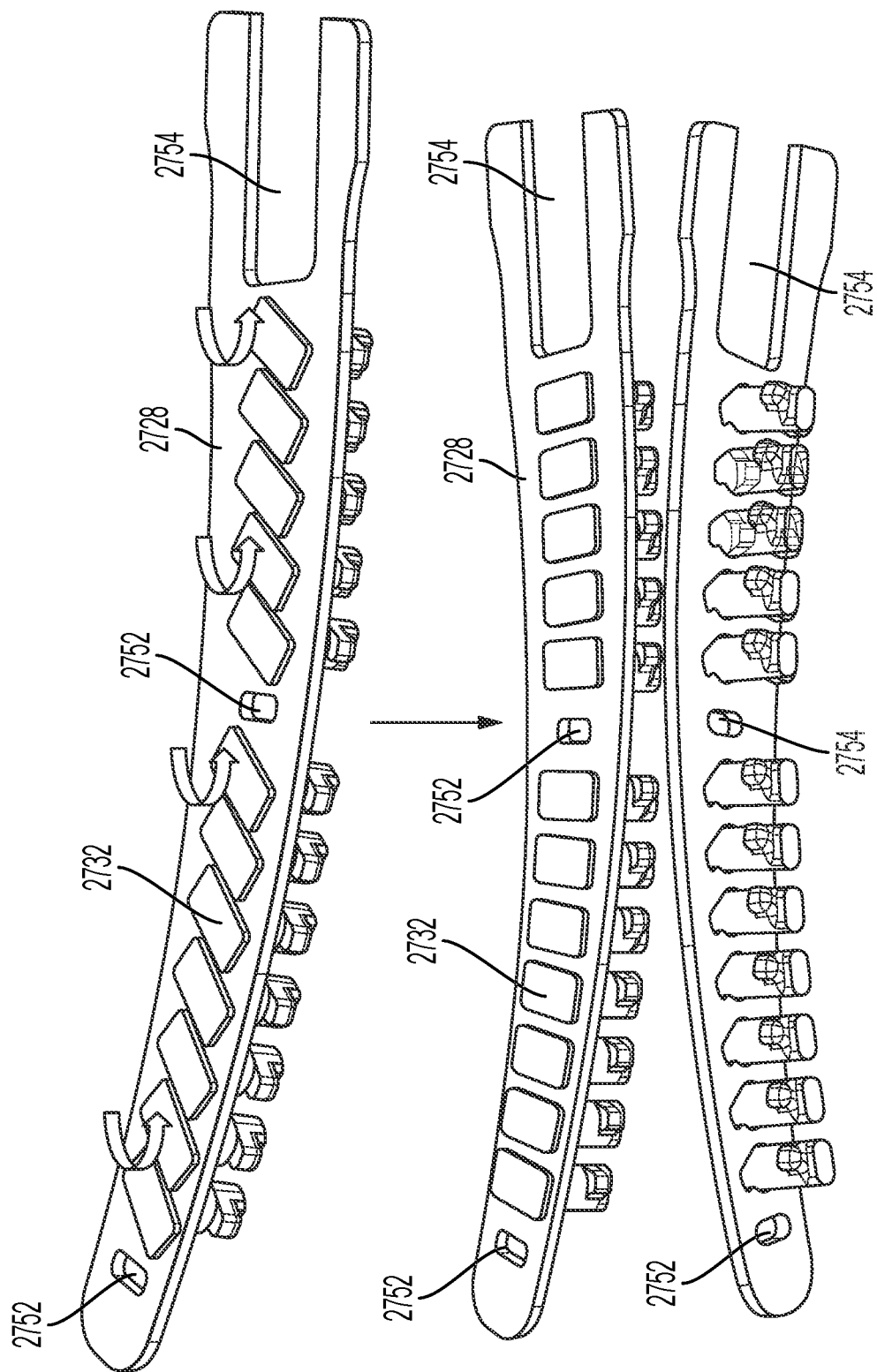
Figure 64:
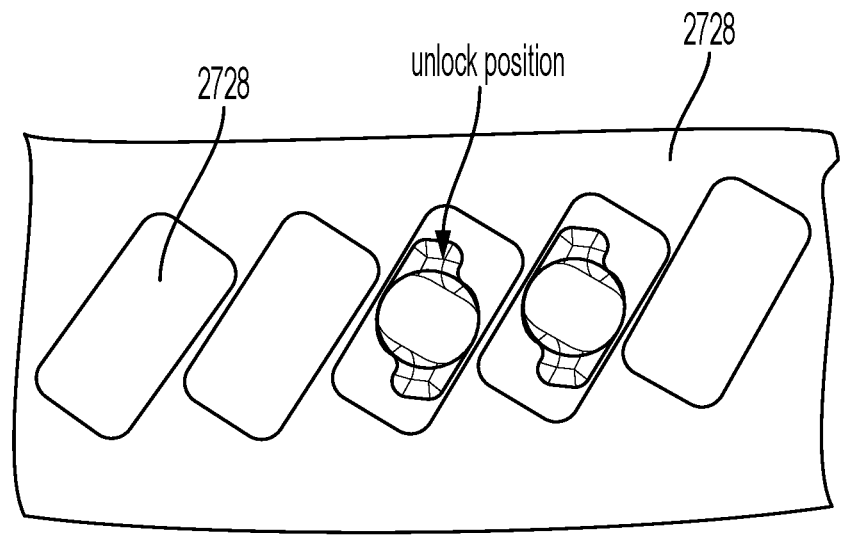
Figure 65:
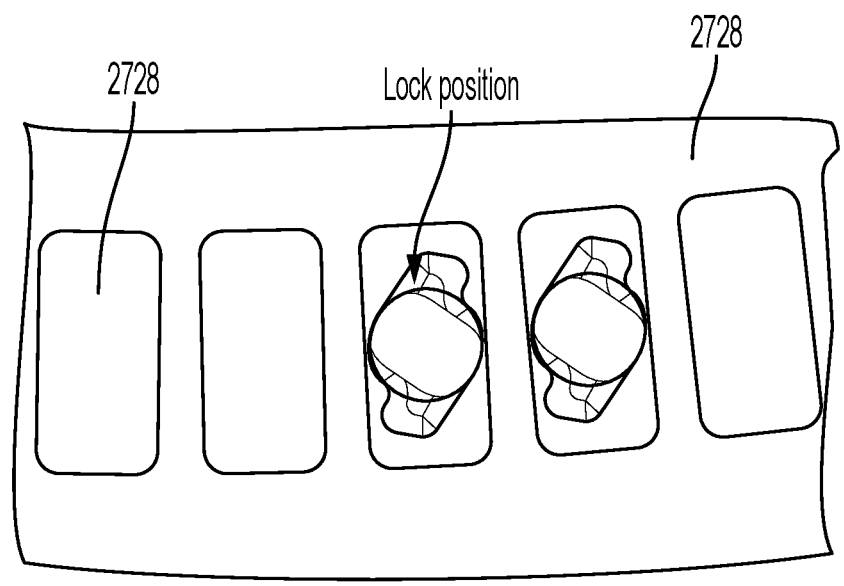

FIGS. 63-65 illustrate a second assembly step, according to at least one aspect of the present disclosure, where:

FIG. 63 illustrates the individual tissue pad units locked into the electrode;

FIG. 64 illustrates the tissue pad unit in the unlocked position; and

FIG. 65 illustrates the tissue pad unit in the locked position.

Figure 66:
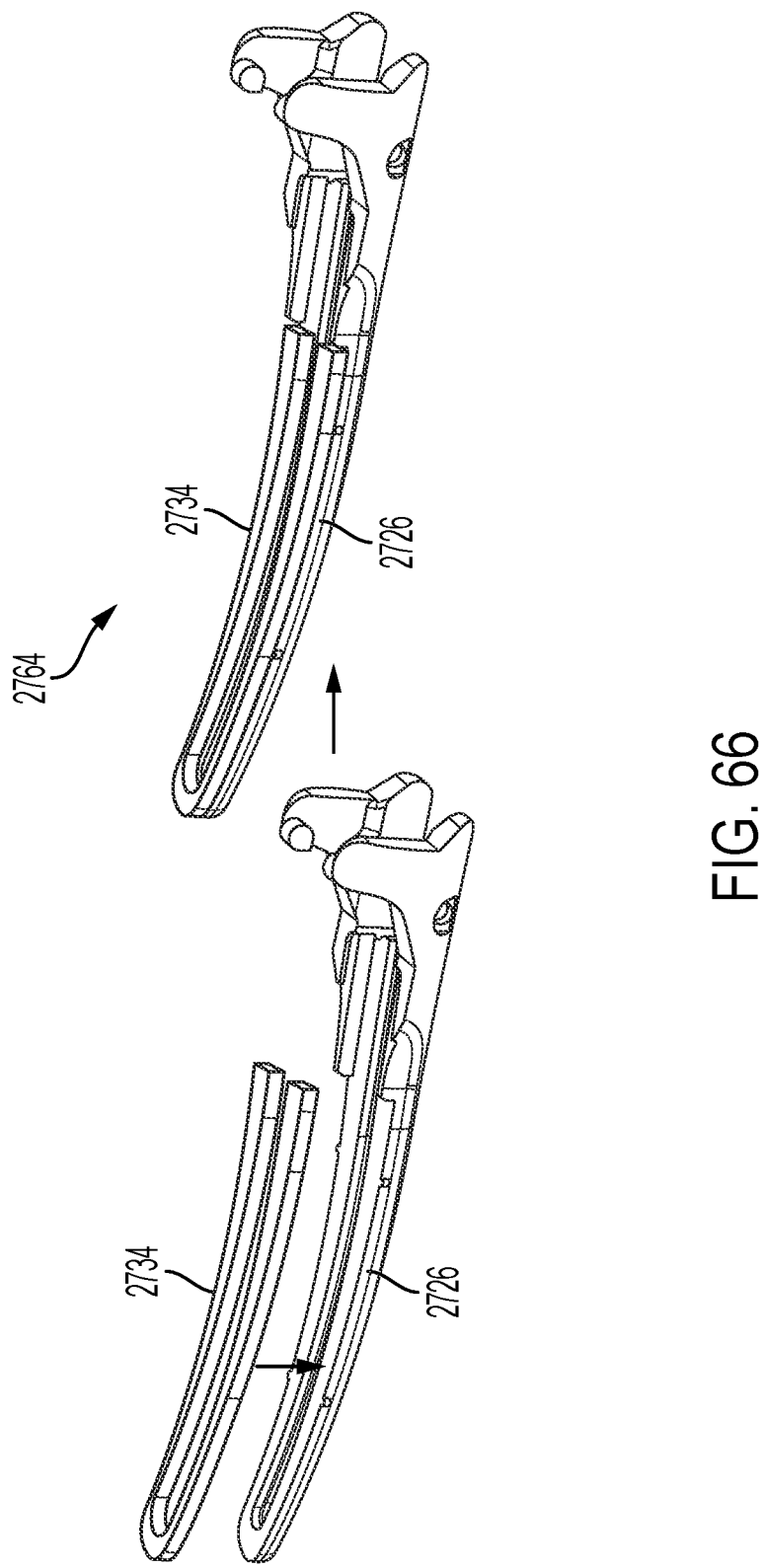

FIG. 66 illustrates a third assembly step, according to at least one aspect of the present disclosure, where the single piece elastic/hyper elastic block is bound to the clamp jaw.

Figure 67:
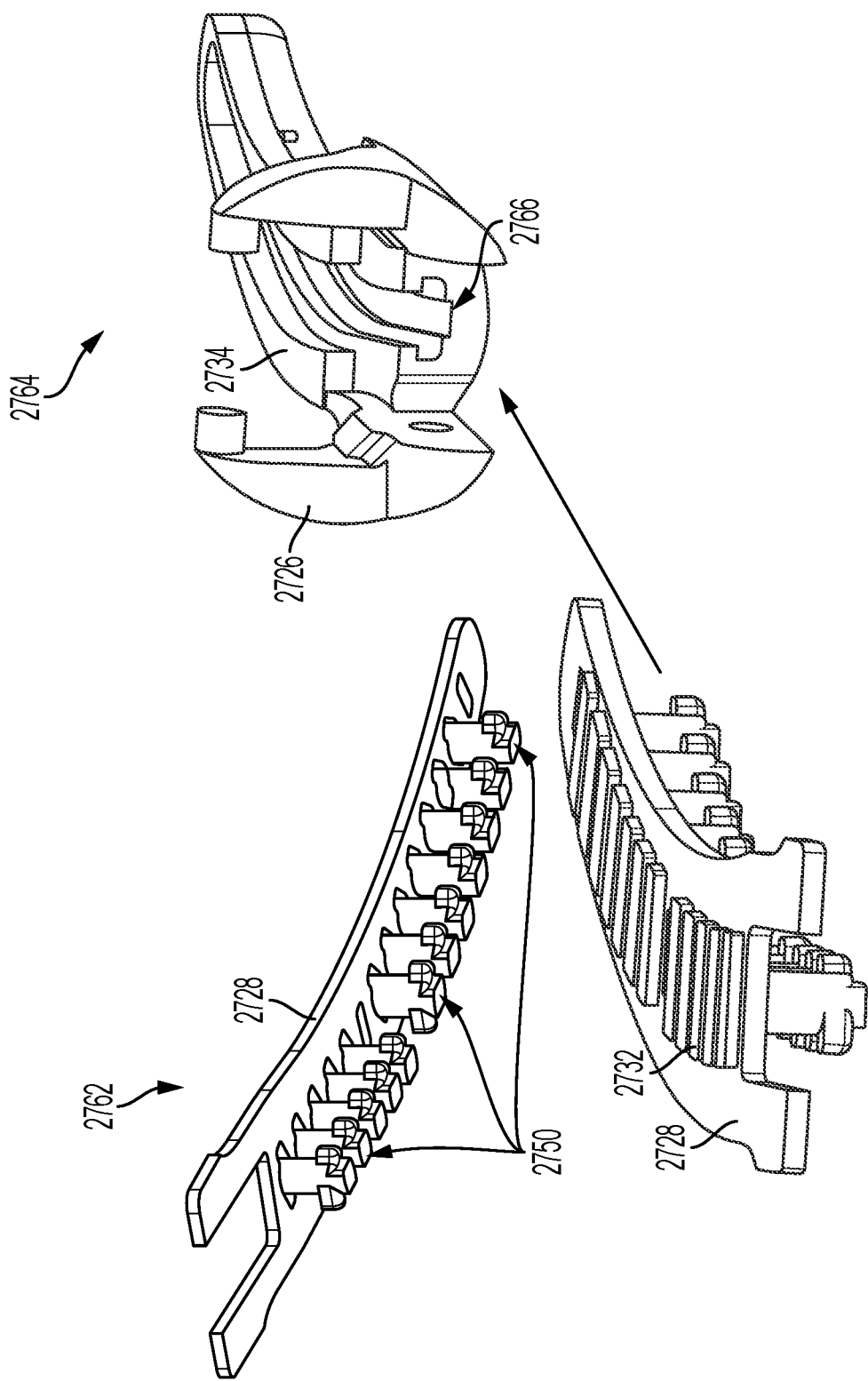
Figure 68:
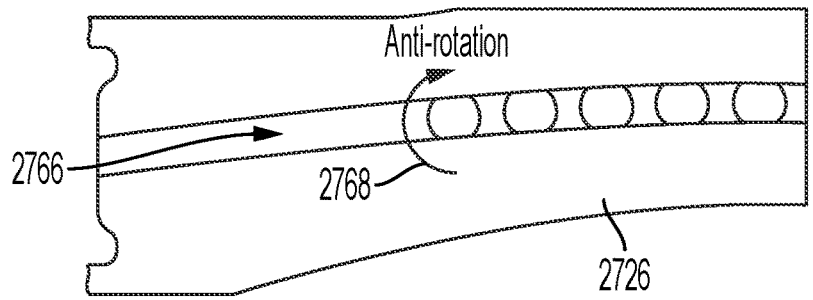
Figure 69:
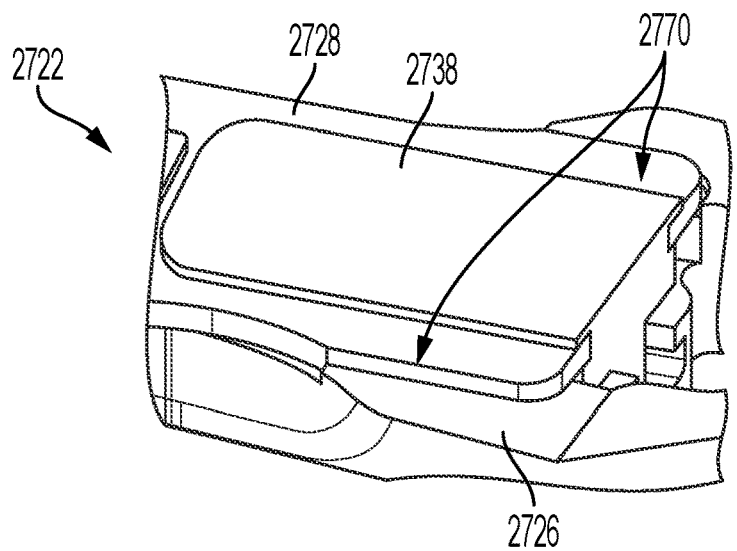
Figure 70:
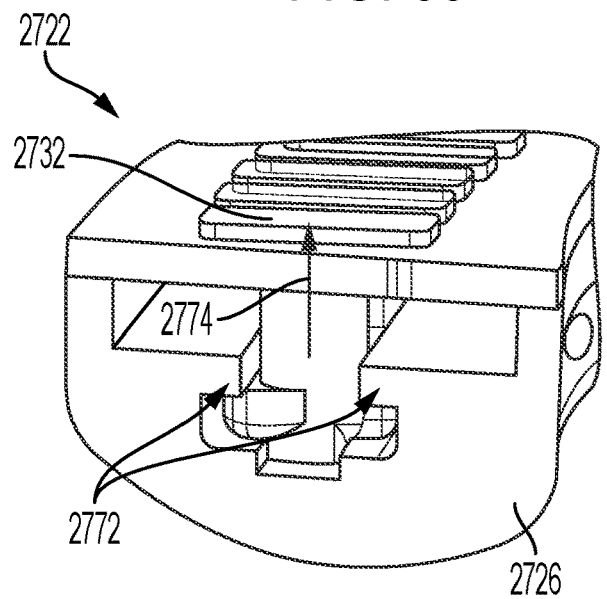
Figure 71:
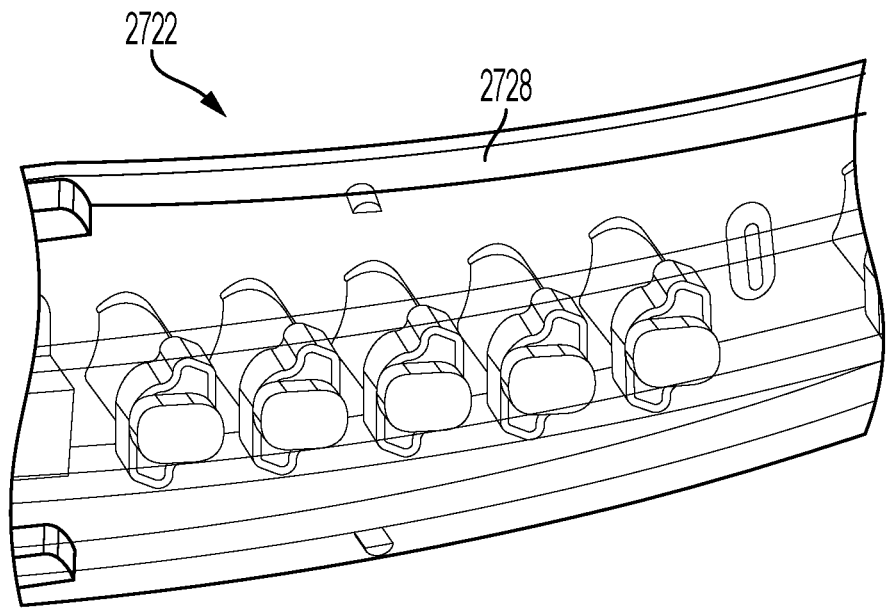
Figure 72:
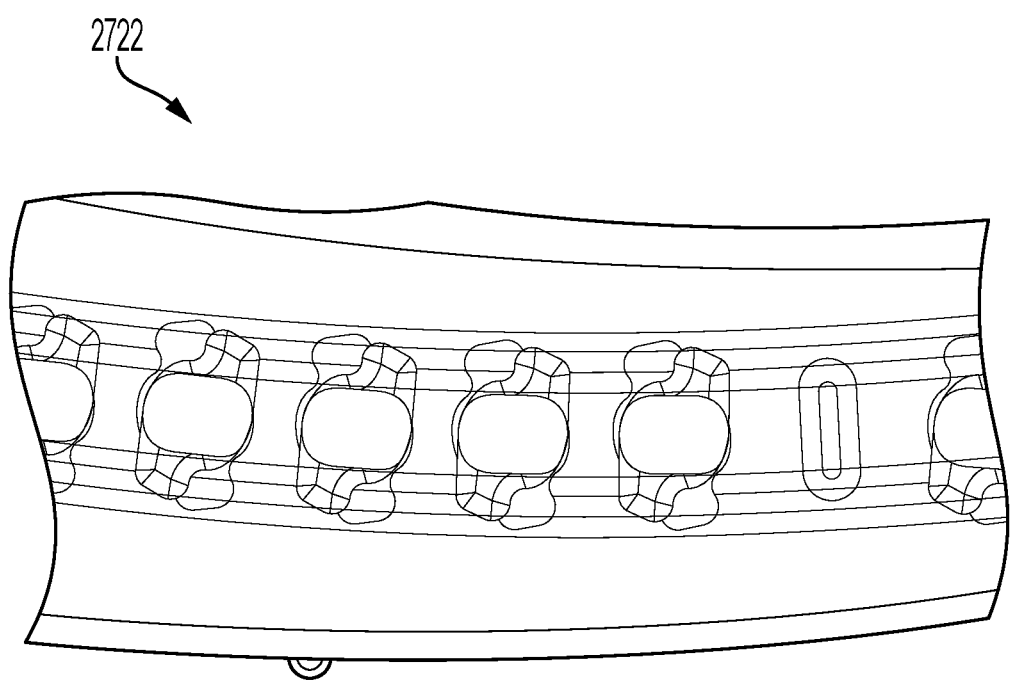

FIGS. 67-72 illustrate a fourth assembly step, according to at least one aspect of the present disclosure, where:

FIG. 67 illustrates the first sub-assembly produced in the second assembly step described in FIGS. 63-65 is assembled with the second sub-assembly produced in the third assembly as described in step of FIG. 66 to produce the clamp arm;

FIG. 68 illustrate the pad tips roughly aligned with the clamp arm slot;

FIG. 69 illustrates the electrode bound to the clamp arm at bound points;

FIG. 70 illustrates the clamp arm feature that prevents the tissue pad units from coming out in the direction shown by the arrow;

FIG. 71 is a detail view of the electrode bound to the clamp arm at bound points;

FIG. 72 is a detail view of the electrode bound to the clamp arm at bound points.

Figure 73:
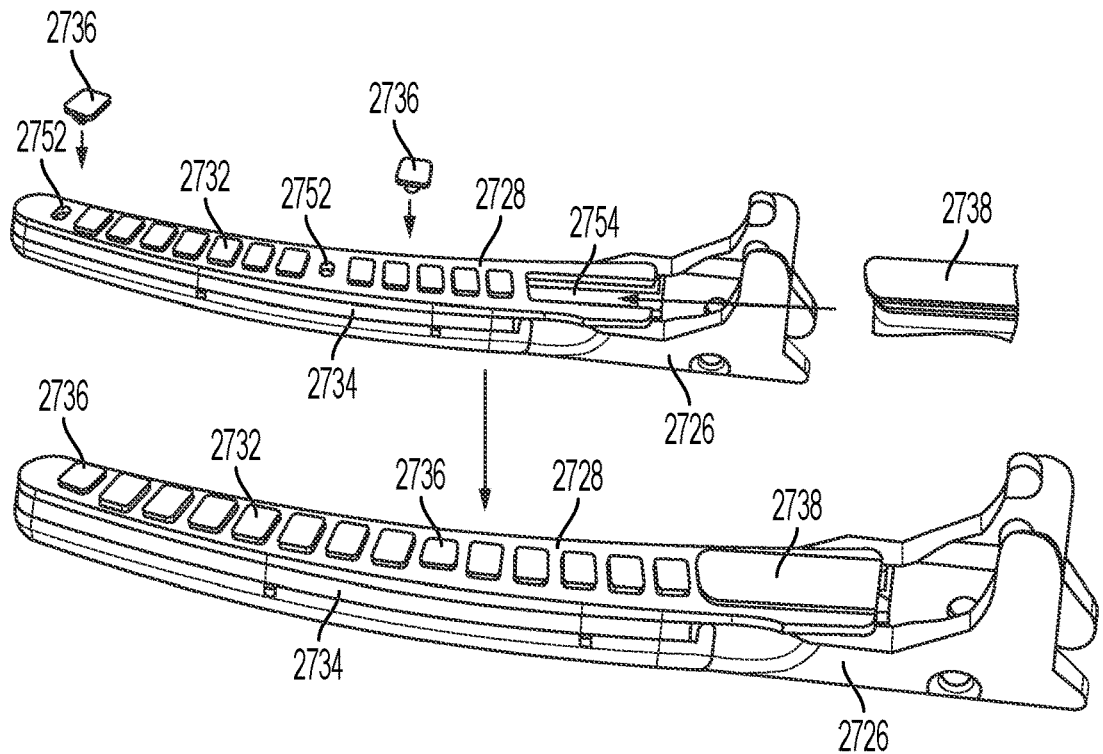
Figure 74:
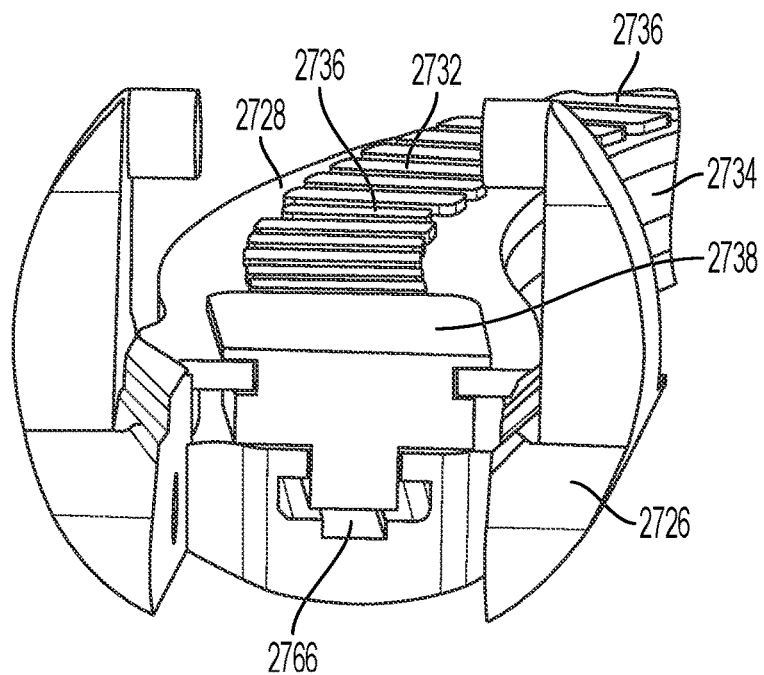

FIGS. 73-74 illustrate a fifth assembly step, according to at least one aspect of the present disclosure, where:

FIG. 73 illustrates the assembly of two small wear resistant gap pads are press fit into the slots defined by the electrode and the large wear resistant gap pad is slid into the slot defined by the electrode; and FIG. 74 is an end view of the clamp arm.

Figure 75:
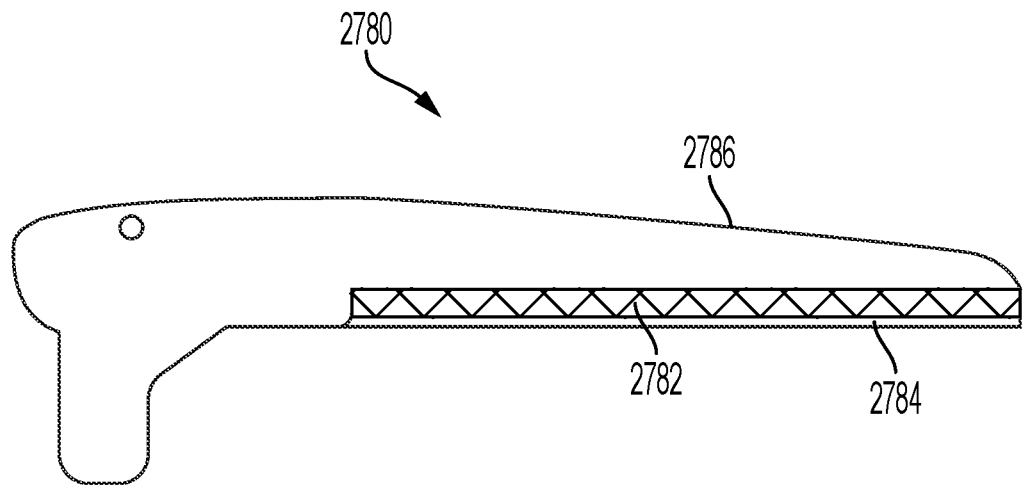

FIG. 75 illustrates a clamp arm comprising fill material between the electrode and the clamp jaw, according to at least one aspect of the present disclosure.

Figure 76:
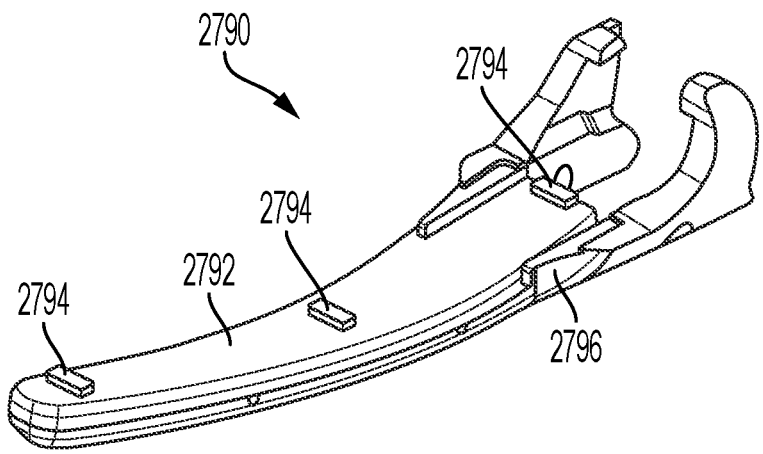
Figure 77:
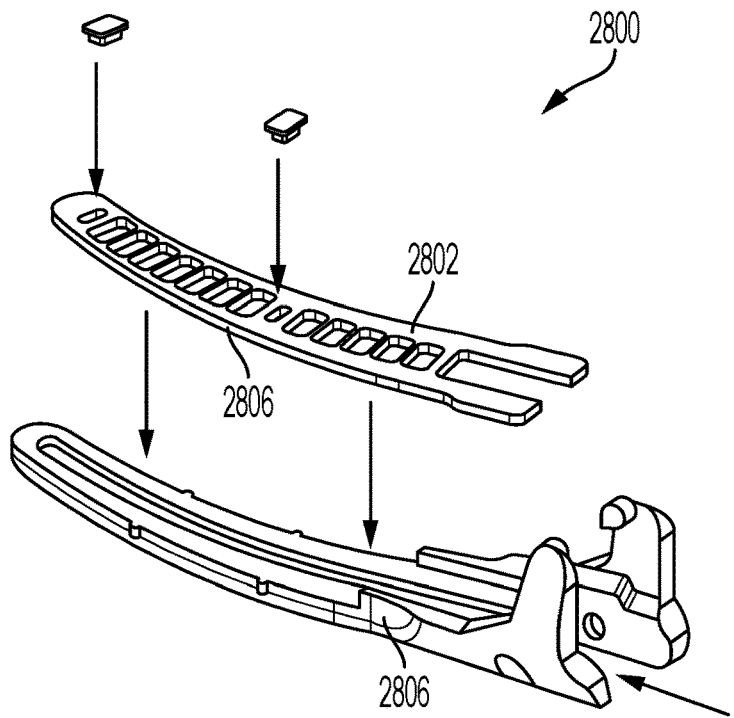
Figure 78:
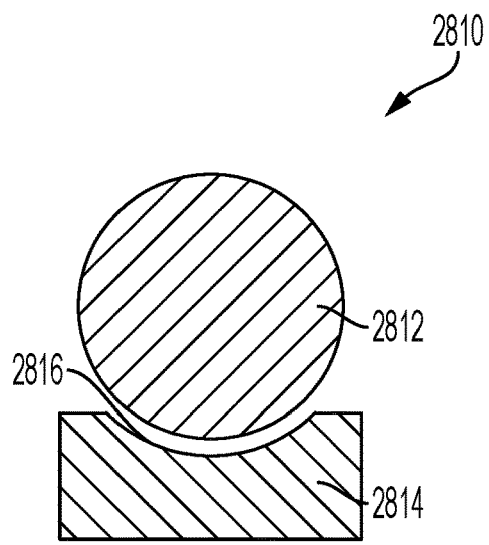

FIGS. 76-78 illustrate various apparatuses to address these desired improvements, according to at least one aspect of the present disclosure, where:

FIG. 76 that shows a clamp arm that is easier to manufacture by eliminating a separate clamp arm electrode and building up a surface of the clamp arm and eliminating the separate electrode blade;

FIG. 77 shows a clamp arm to deter tissue accumulation between the electrode and the clamp jaw by adding a skirt to the perimeter of the electrode or alternatively to the perimeter of the clamp jaw; and FIG. 78 that shows a section view of an end-effector comprising an ultrasonic blade and a clamp arm configured to improve distal tissue grasping.

Figure 79:
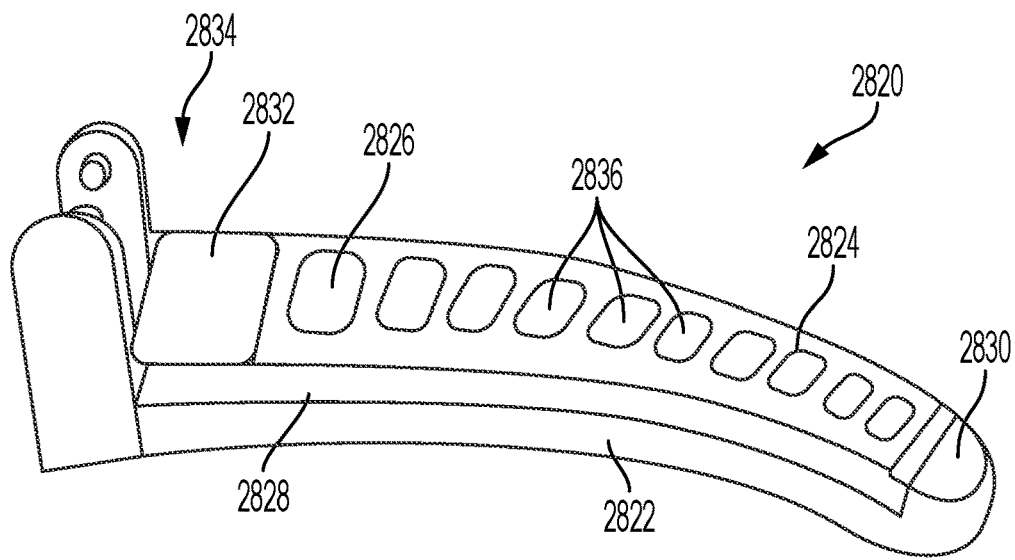

FIG. 79 illustrates a clamp arm comprising a clamp jaw, an electrode, a clamp arm pad comprising a plurality of teeth, and a curtain located on either side of the electrode to minimize pinch point of tissue, and a bull nose/clamp arm bumper to minimize delamination of the electrode by making contact with tissue first during blunt dissection, according to at least one aspect of the present disclosure.

Figure 80:
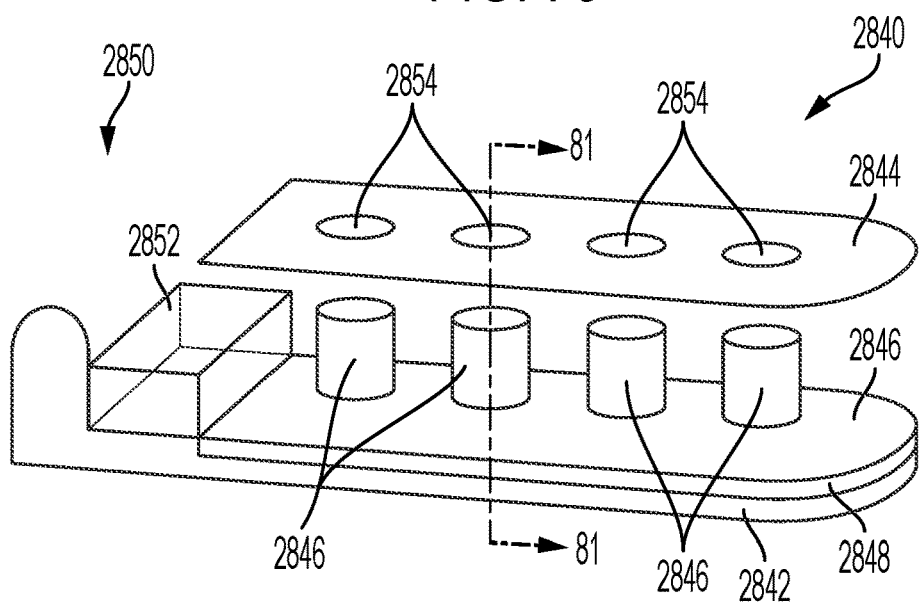
Figure 81:
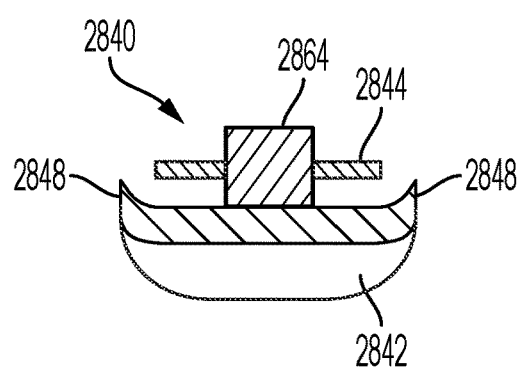

FIGS. 80-81 illustrate an alternative clamp arm comprising a clamp jaw, an electrode, a clamp arm pad comprising a plurality of teeth, and a curtain located on either side of the clamp arm pad, according to at least one aspect of the present disclosure, where:

FIG. 80 is an exploded view of the clamp arm; and

FIG. 81 is a section view of the clamp arm.

Figure 82:
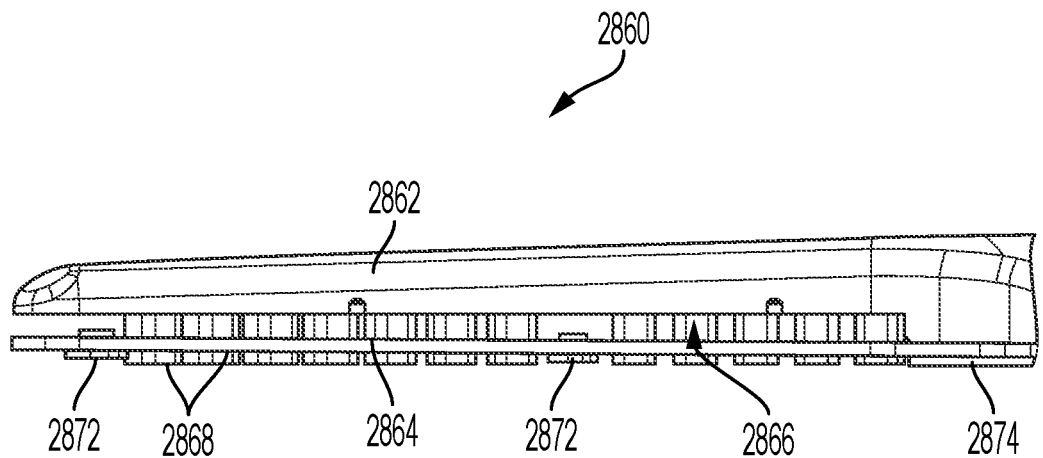

FIG. 82 is a side view of a clamp arm, according to at least one aspect of the present disclosure.

Figure 83:
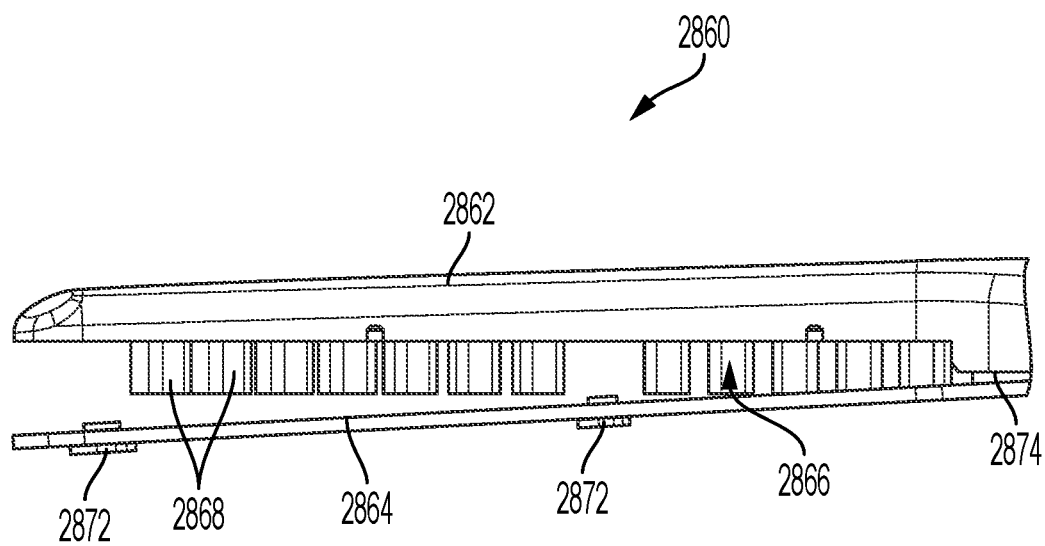
Figure 84:
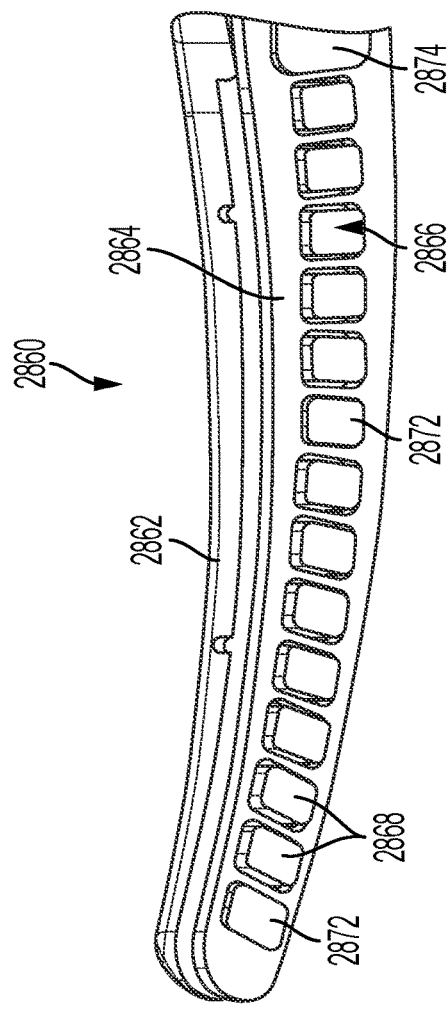

FIG. 83 is a side view of a clamp arm with the cantilevered electrode in a deflected state to pull tissue off the teeth of the clamp arm pad, according to at least one aspect of the present disclosure FIG. 84 is a bottom perspective view of the clamp arm, according to at least one aspect of the present disclosure.

Figure 85:
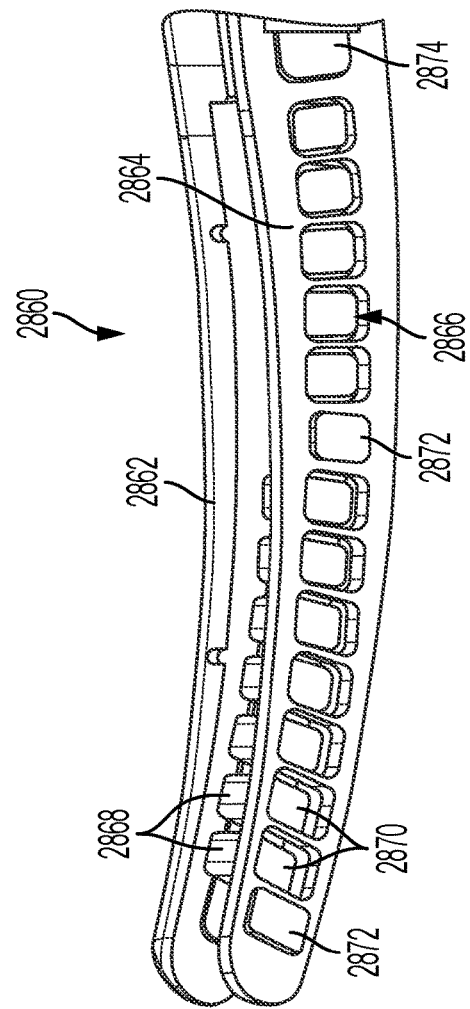

FIG. 85 is a bottom perspective view of the clamp arm with the cantilevered electrode in a deflected state to pull tissue off the teeth of the clamp arm pad, according to at least one aspect of the present disclosure.

Figure 86:
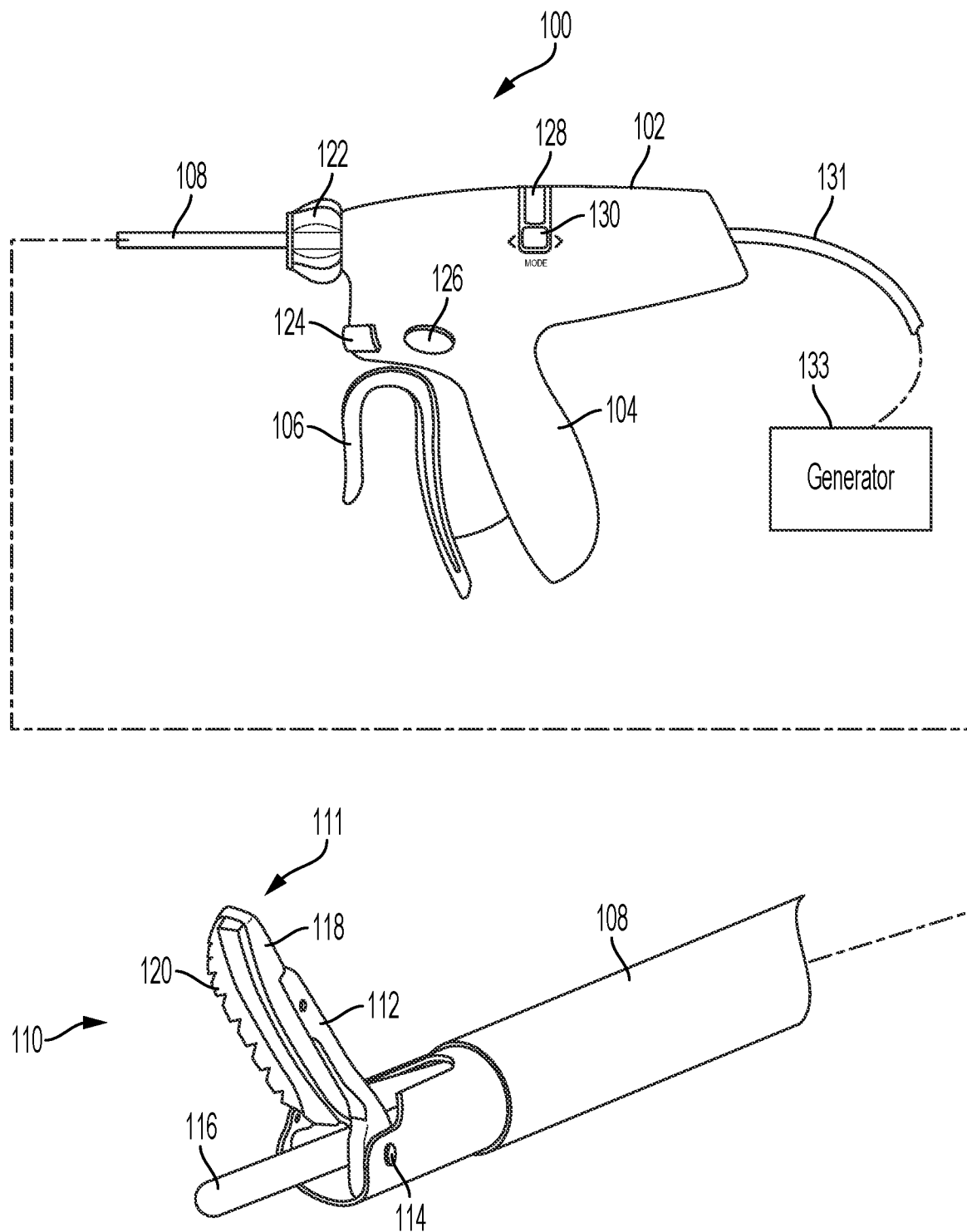

FIG. 86 illustrates a surgical device comprising a mode selection button switch on the device, according to at least one aspect of the present disclosure.

Figure 87A:
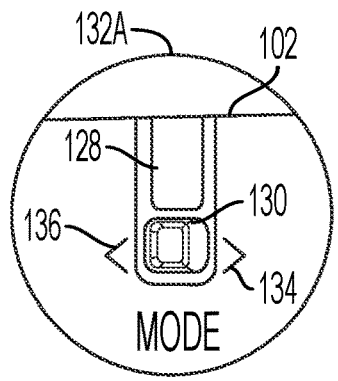
Figure 87B:
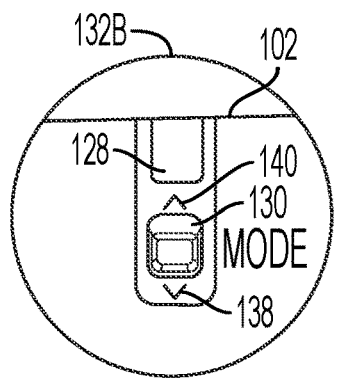
Figure 87C:
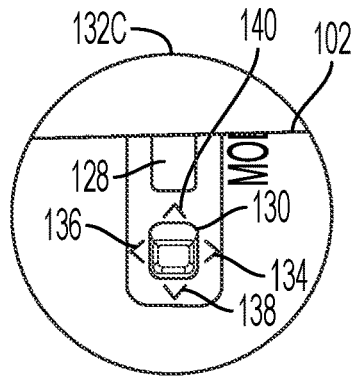

FIGS. 87A-87C illustrate three options for selecting the various operating modes of the surgical device, according to at least one aspect of the present disclosure, where:

FIG. 87A shows a first mode selection option where the button switch can be pressed forward or backward to cycle the surgical instrument through the various modes;

FIG. 87B shows a second mode selection option where the button switch is pressed up or down to cycle the surgical instrument through the various modes; and FIG. 87C shows a third mode selection option where the button switch is pressed forward, backward, up, or down to cycle the surgical instrument through the various modes.

Figure 88:
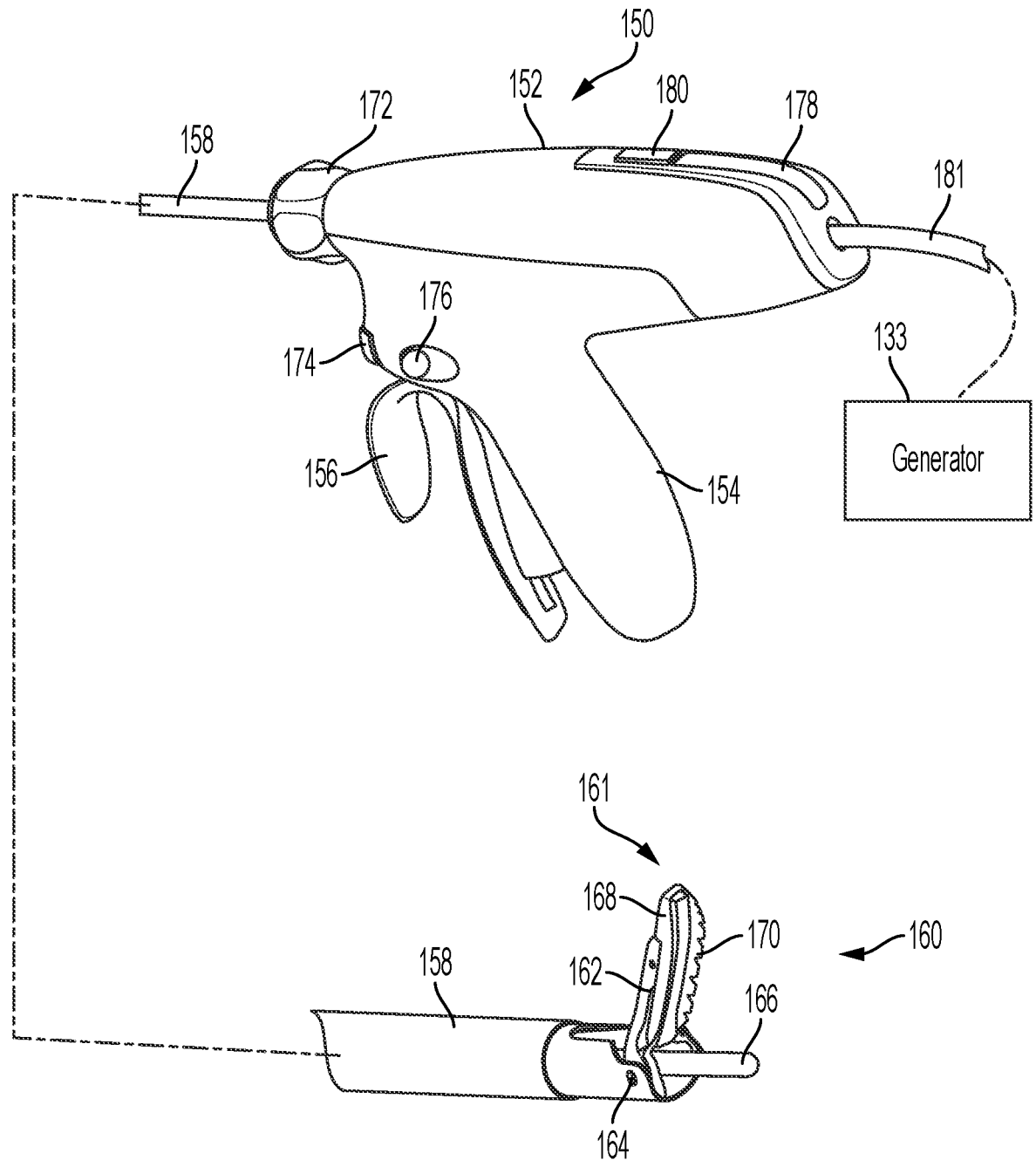

FIG. 88 illustrates a surgical device comprising a mode selection button switch on the back of the device, according to at least one aspect of the present disclosure.

Figure 89A:
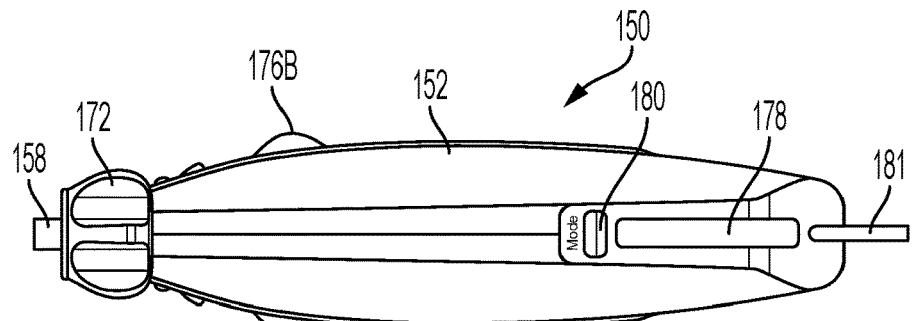

FIG. 89A shows a first mode selection option where as the mode button switch is pressed to toggled through various modes, colored light indicates the selected mode on the user interface.

Figure 89B:
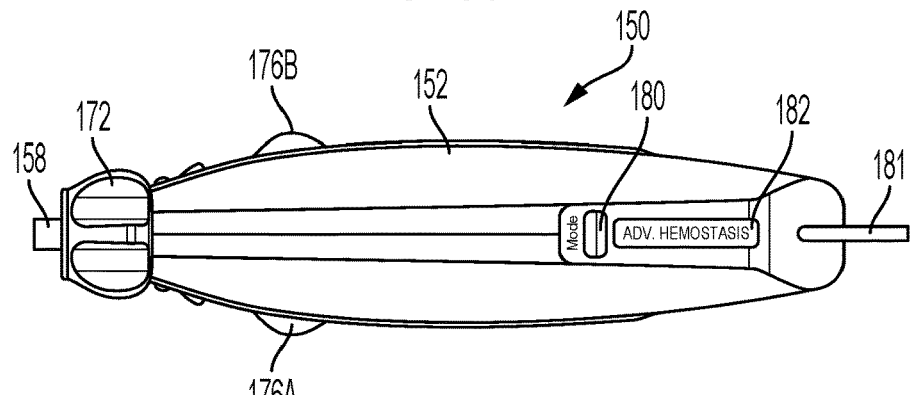

FIG. 89B shows a second mode selection option where as the mode button switch is pressed to toggle through various modes a screen indicates the selected mode (e.g., LCD, e-ink).

Figure 89C:
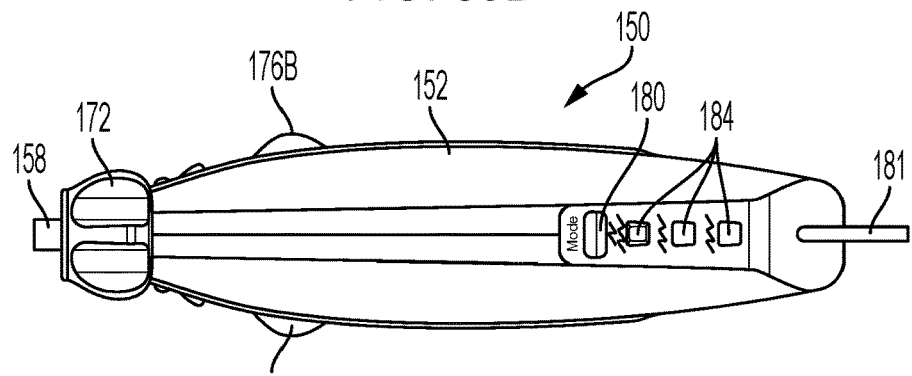

FIG. 89C shows a third mode selection option where as the mode button switch is pressed to toggle through various modes, labelled lights indicate the selected mode.

Figure 89D:
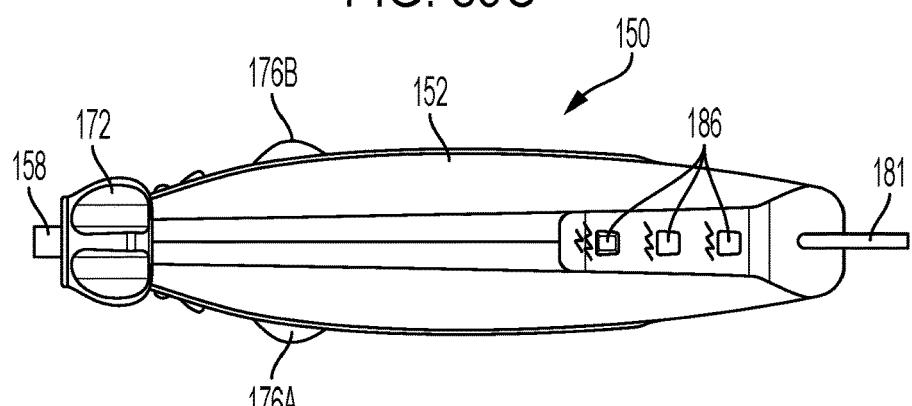

FIG. 89D shows a fourth mode selection option where as a labeled button switch is pressed to select a mode, when a labeled button switch is selected, it is illuminated to indicate mode selected.

Figure 90:
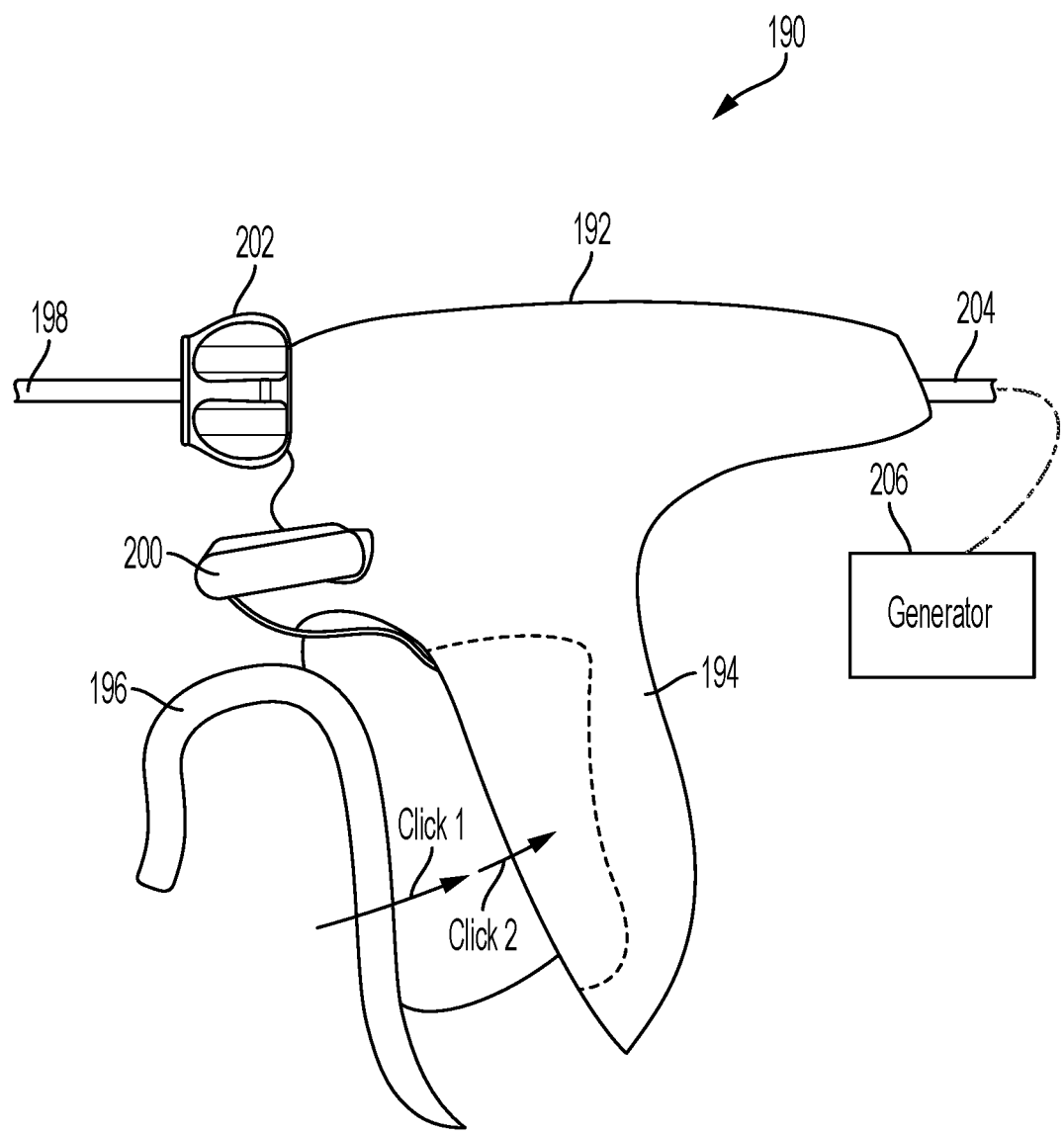

FIG. 90 illustrates a surgical device comprising a trigger activation mechanism, according to at least one aspect of the present disclosure.

Figure 91:
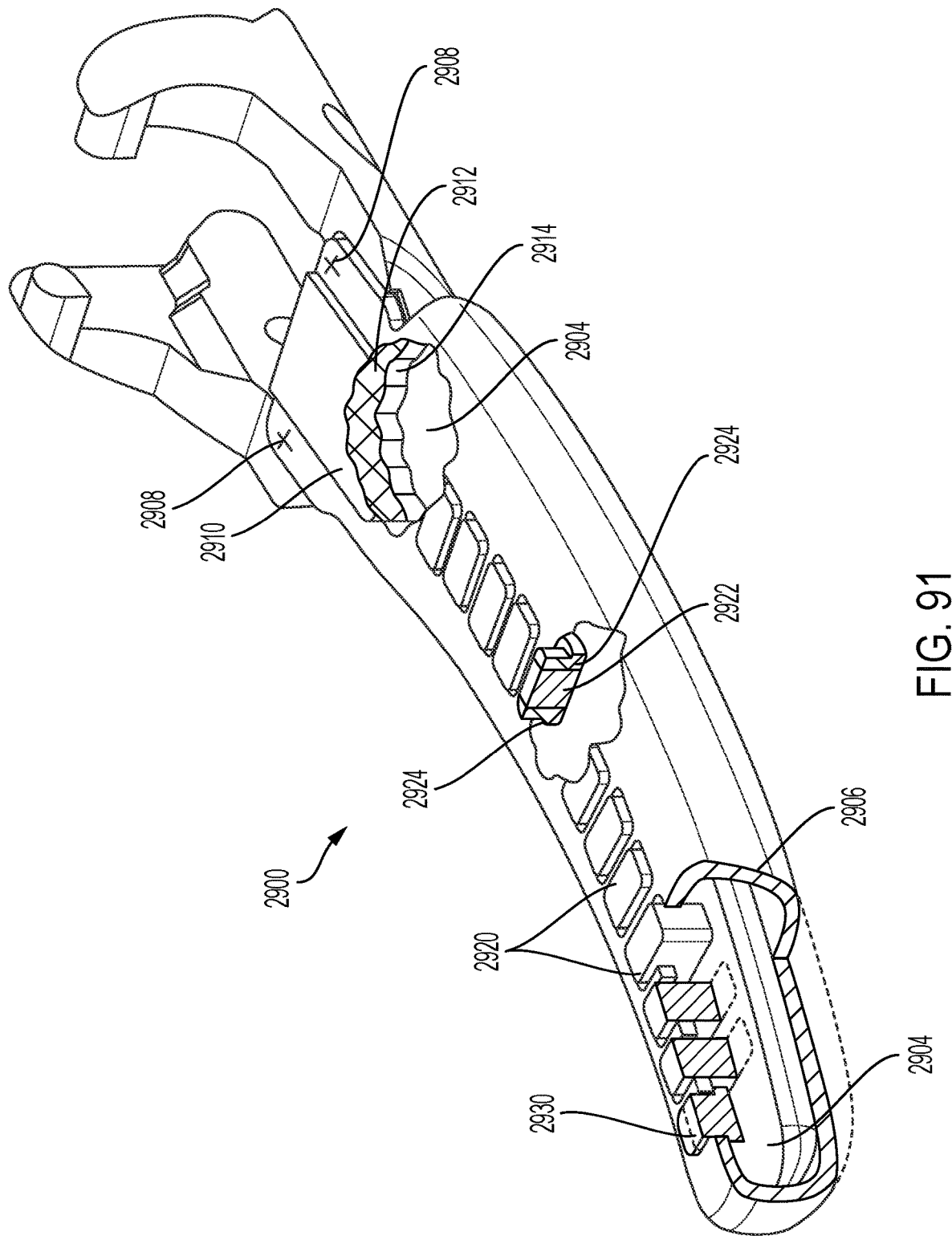

FIG. 91 illustrates an alternative clamp arm comprising a metal clamp jaw, an electrode, a plurality of clamp arm pads, and gap pads, according to at least one aspect of the present disclosure.

Figure 92:
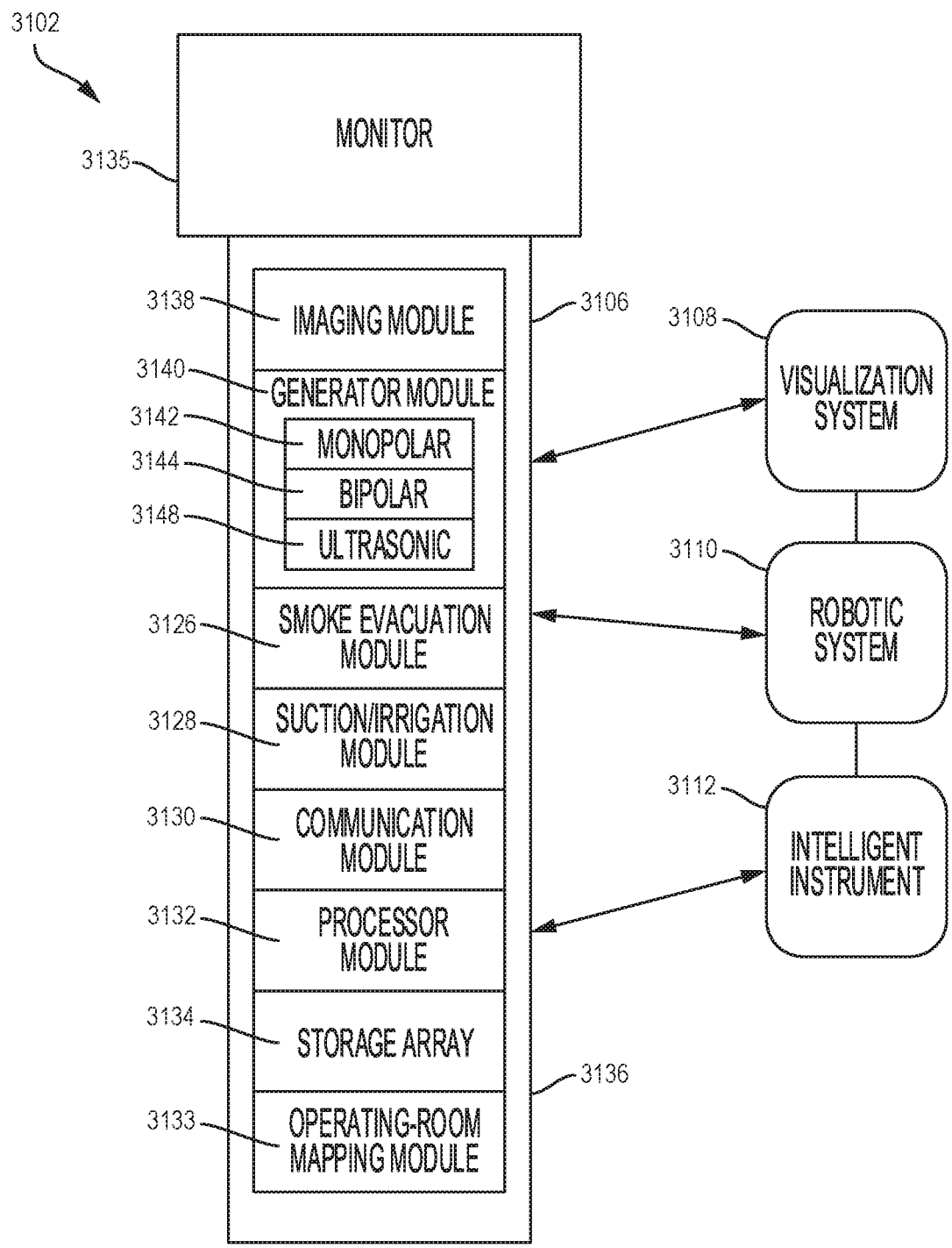

FIG. 92 is a surgical system comprising a surgical hub paired with a visualization system, a robotic system, and an intelligent instrument, in accordance with at least one aspect of the present disclosure.

Figure 93:
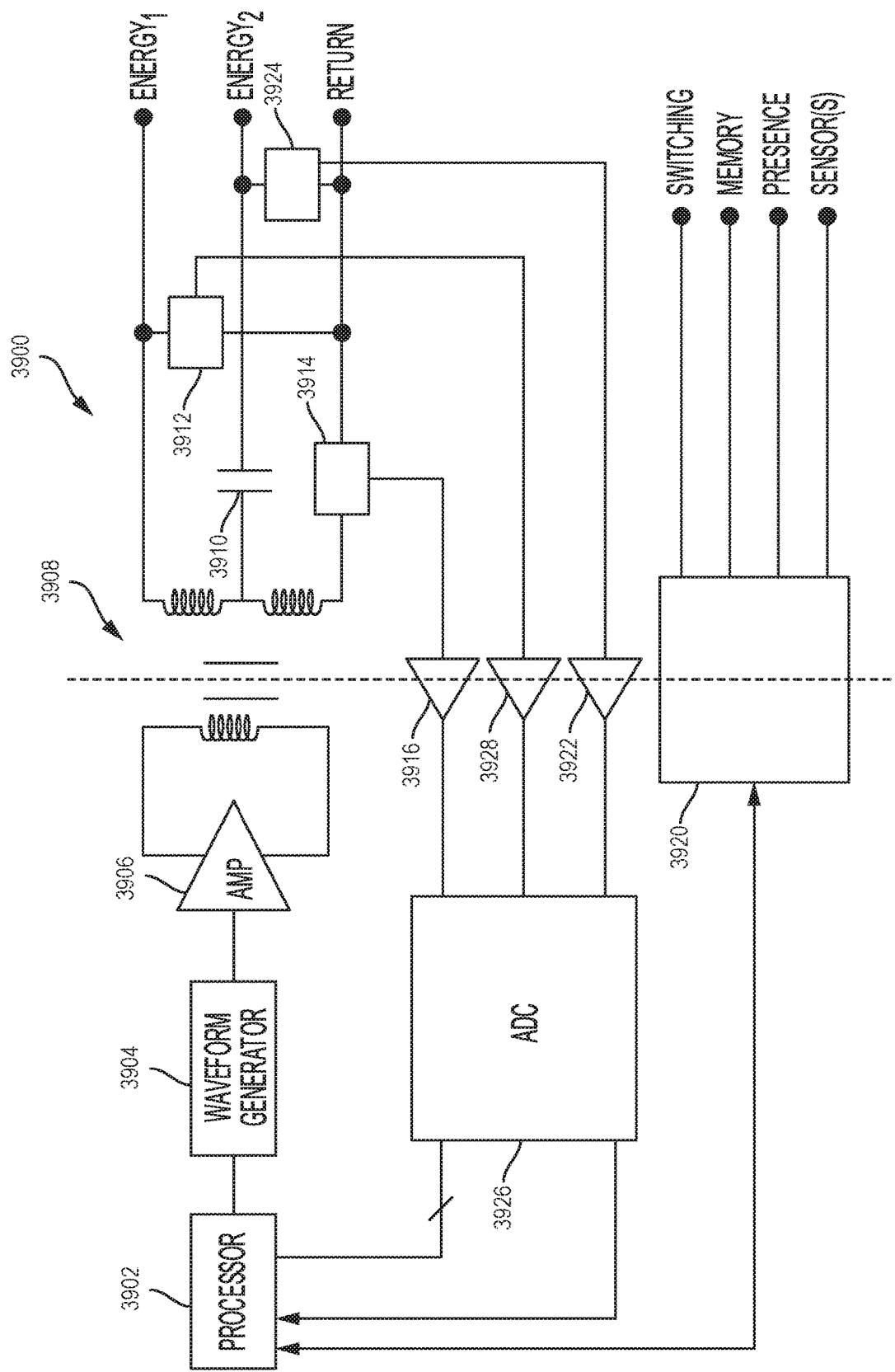

FIG. 93 illustrates an example of a generator, in accordance with at least one aspect of the present disclosure.

Figure 94:
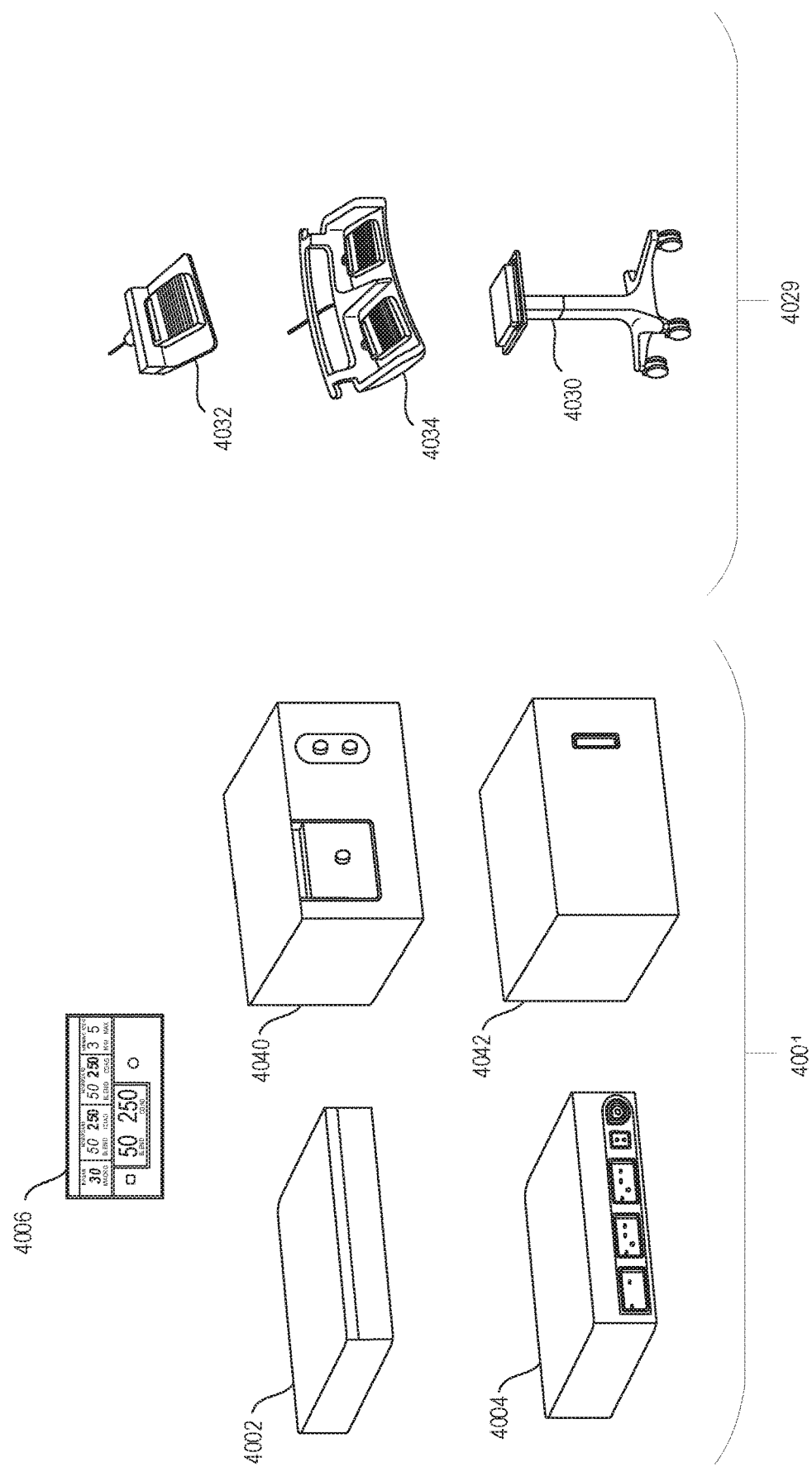

FIG. 94 is a diagram of various modules and other components that are combinable to customize modular energy systems, in accordance with at least one aspect of the present disclosure.

Figure 95A:
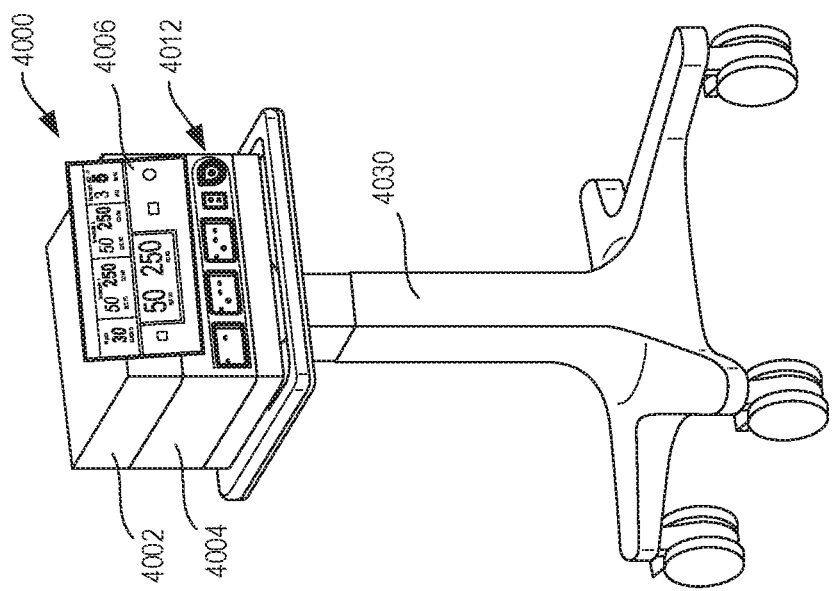

FIG. 95A is a first illustrative modular energy system configuration including a header module and a display screen that renders a graphical user interface (GUI) for relaying information regarding modules connected to the header module, in accordance with at least one aspect of the present disclosure.

Figure 95B:
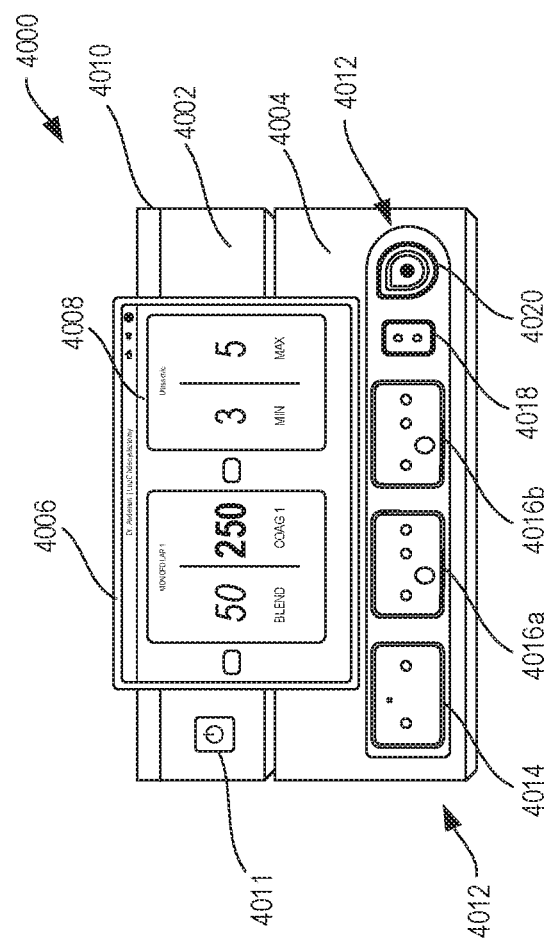

FIG. 95B is the modular energy system shown in FIG. 95A mounted to a cart, in accordance with at least one aspect of the present disclosure.

Figure 96:
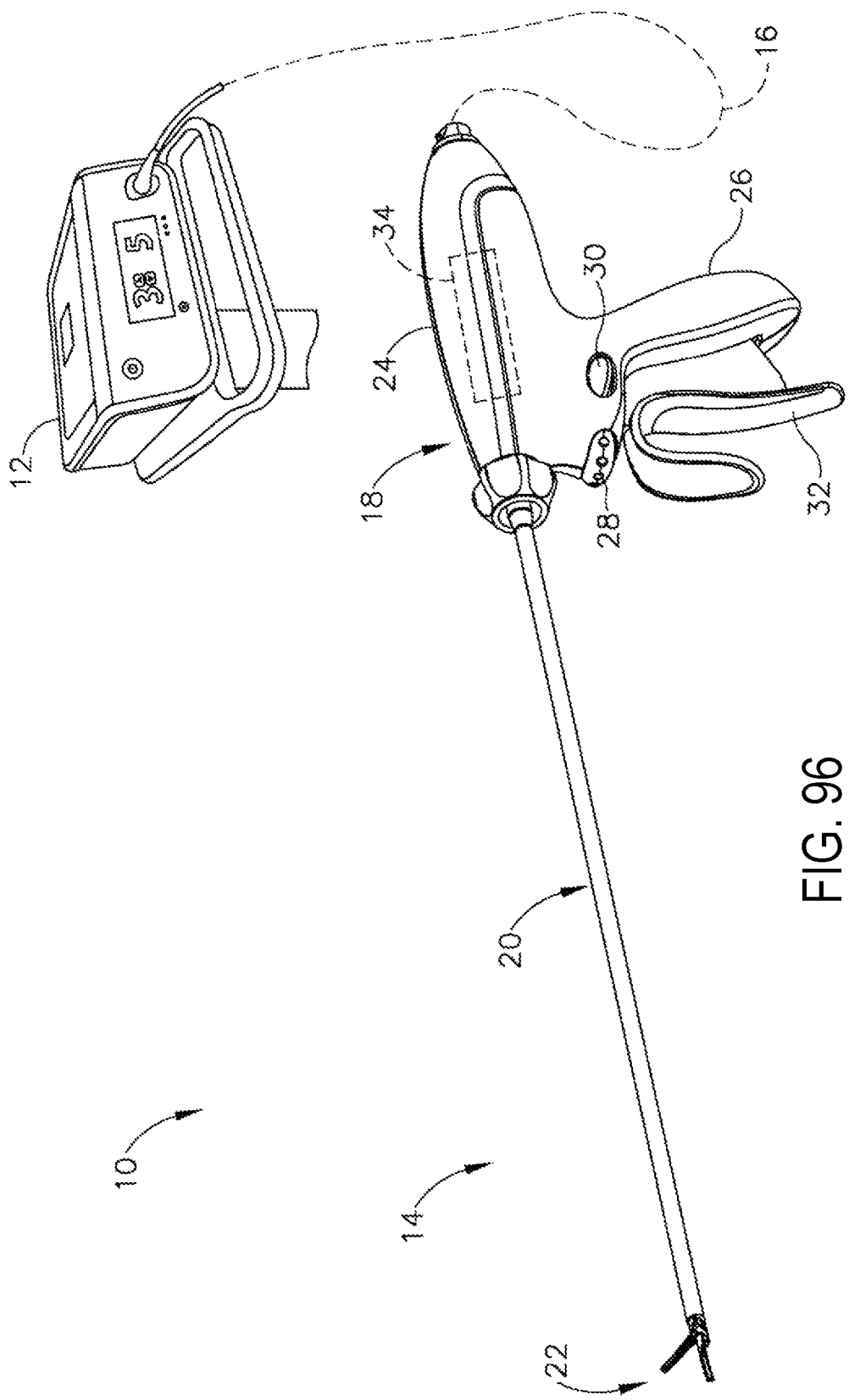

FIG. 96 depicts a perspective view of an exemplary surgical system having a generator and a surgical instrument operable to treat tissue with ultrasonic energy and bipolar RF energy, in accordance with at least one aspect of the present disclosure.

Figure 97:
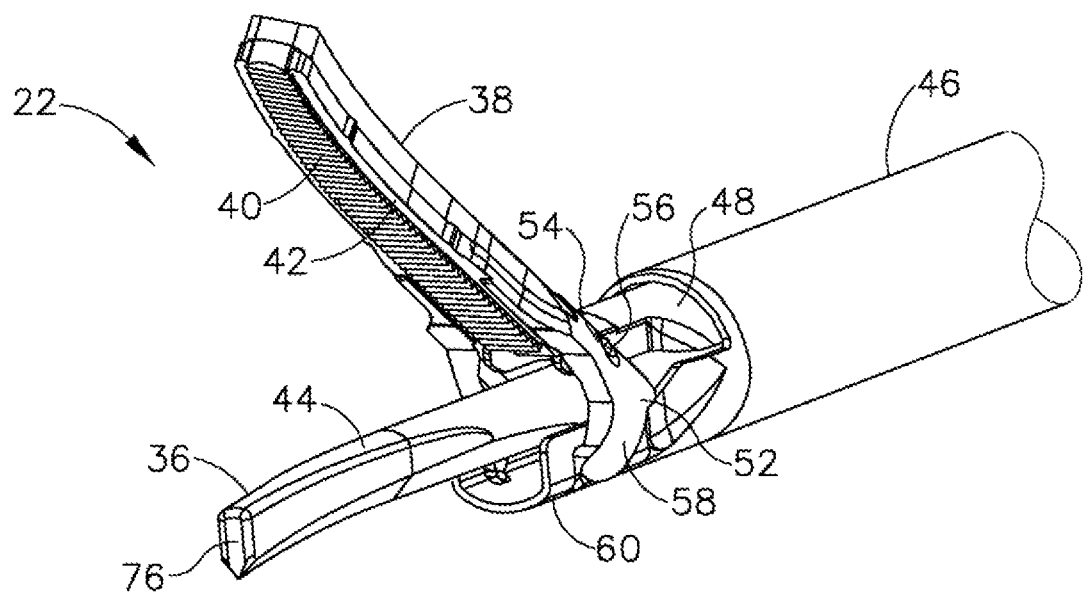

FIG. 97 depicts a top perspective view of an end effector of the surgical instrument of FIG. 96, having a clamp arm that provides a first electrode and an ultrasonic blade that provides a second electrode, in accordance with at least one aspect of the present disclosure.

Figure 98:
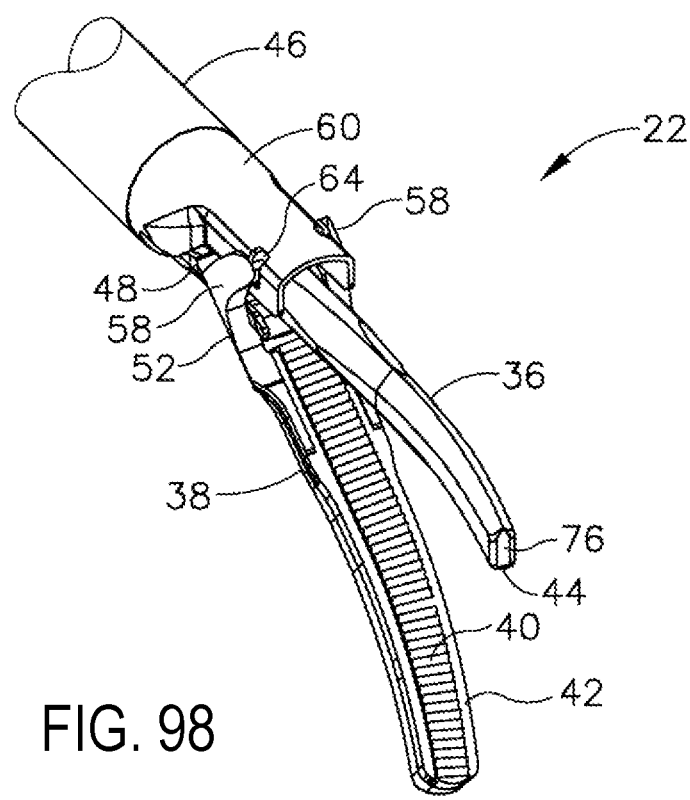

FIG. 98 depicts a bottom perspective view of the end effector of FIG. 97, in accordance with at least one aspect of the present disclosure.

Figure 99:
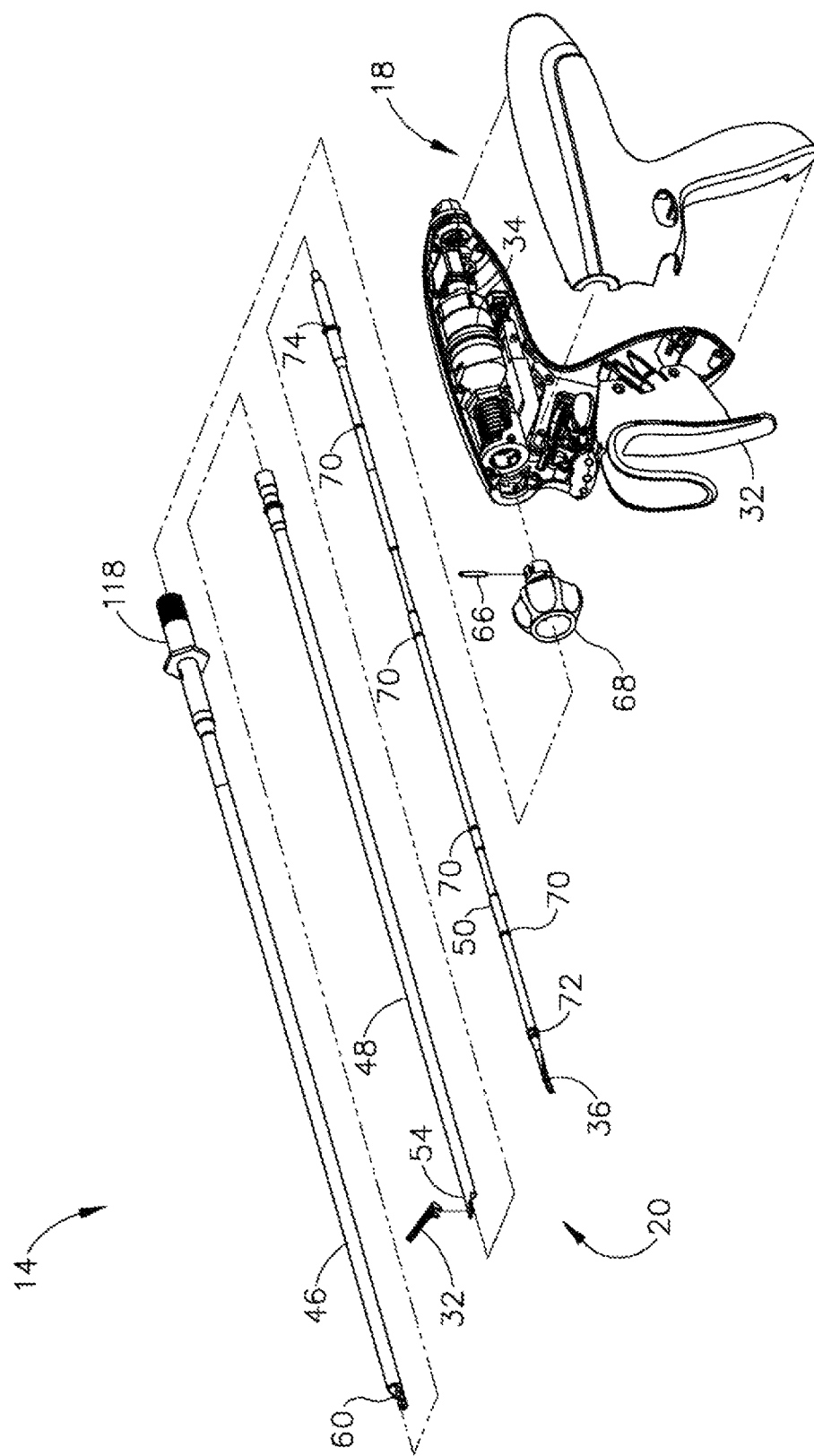

FIG. 99 depicts a partially exploded perspective view of the surgical instrument of FIG. 96, in accordance with at least one aspect of the present disclosure.

Figure 100:
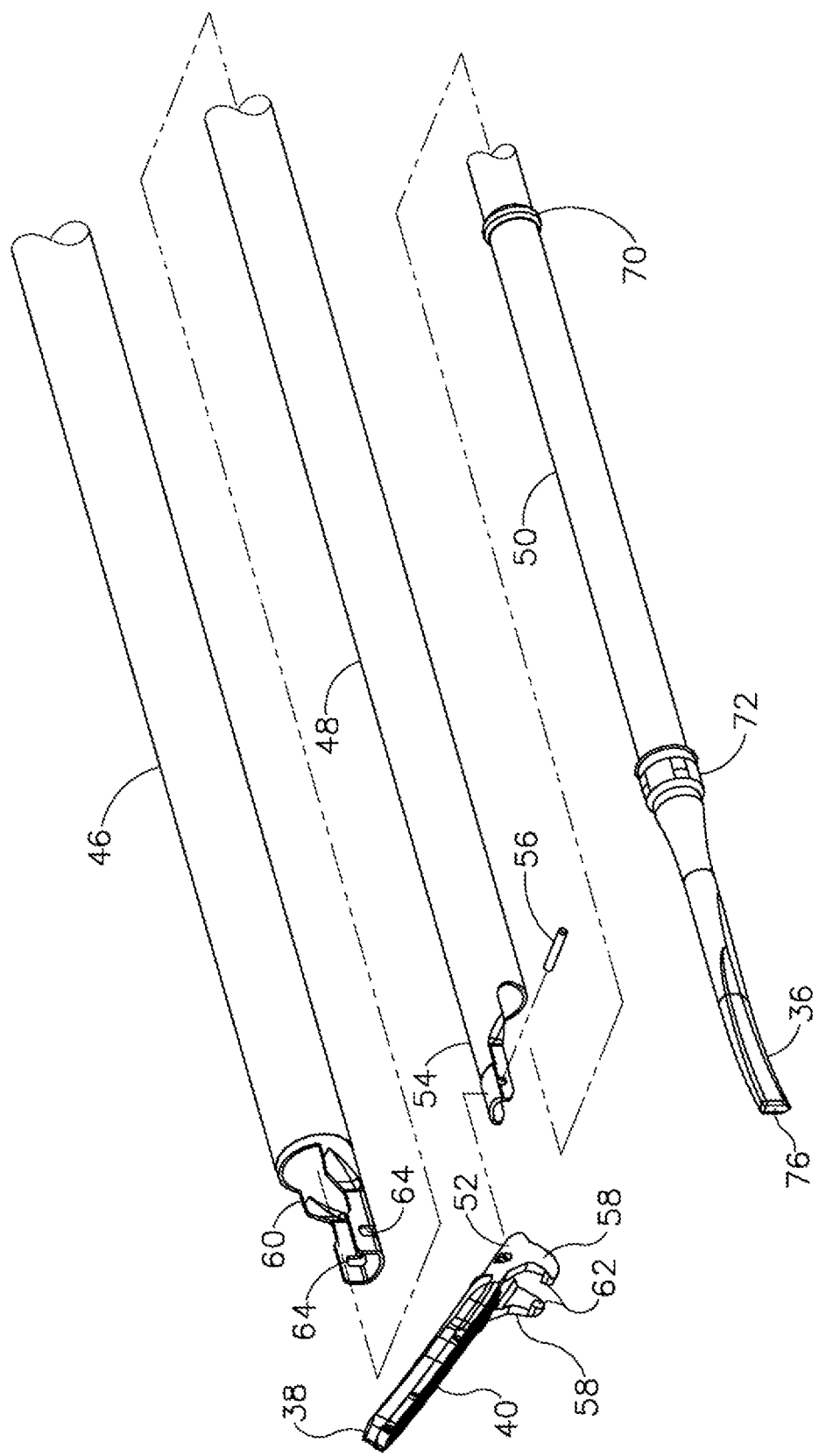

FIG. 100 depicts an enlarged exploded perspective view of a distal portion of the shaft assembly and the end effector of the surgical instrument of FIG. 96, in accordance with at least one aspect of the present disclosure.

Figure 101:
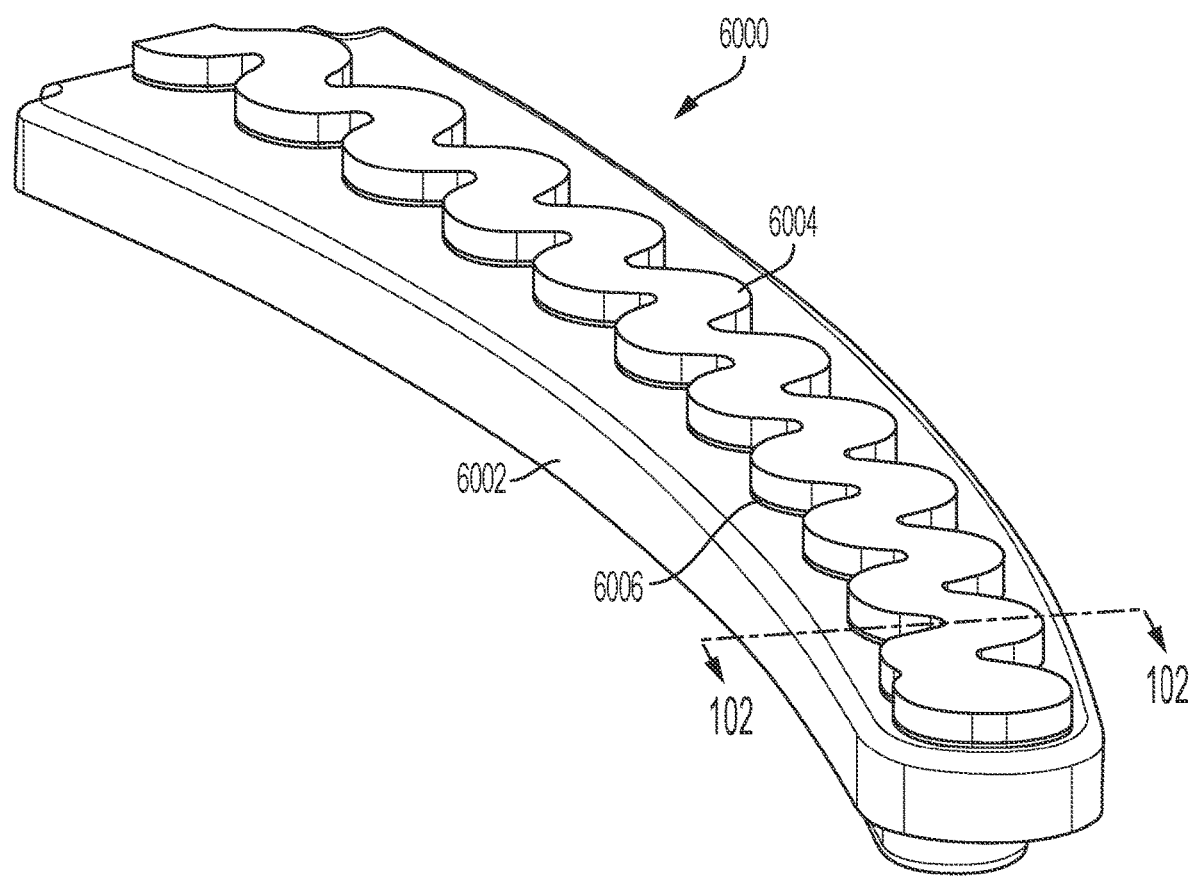

FIG. 101 illustrates a perspective view of a clamp arm pad, in accordance with at least one non-limiting aspect of the present disclosure.

Figure 102:
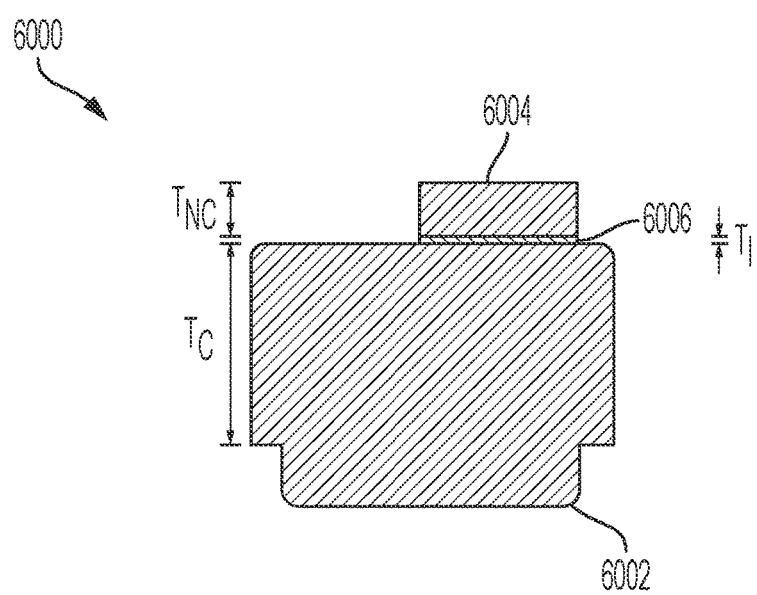

FIG. 102 illustrates a sectioned front view of the clamp arm pad of FIG. 101.

Figure 103A:
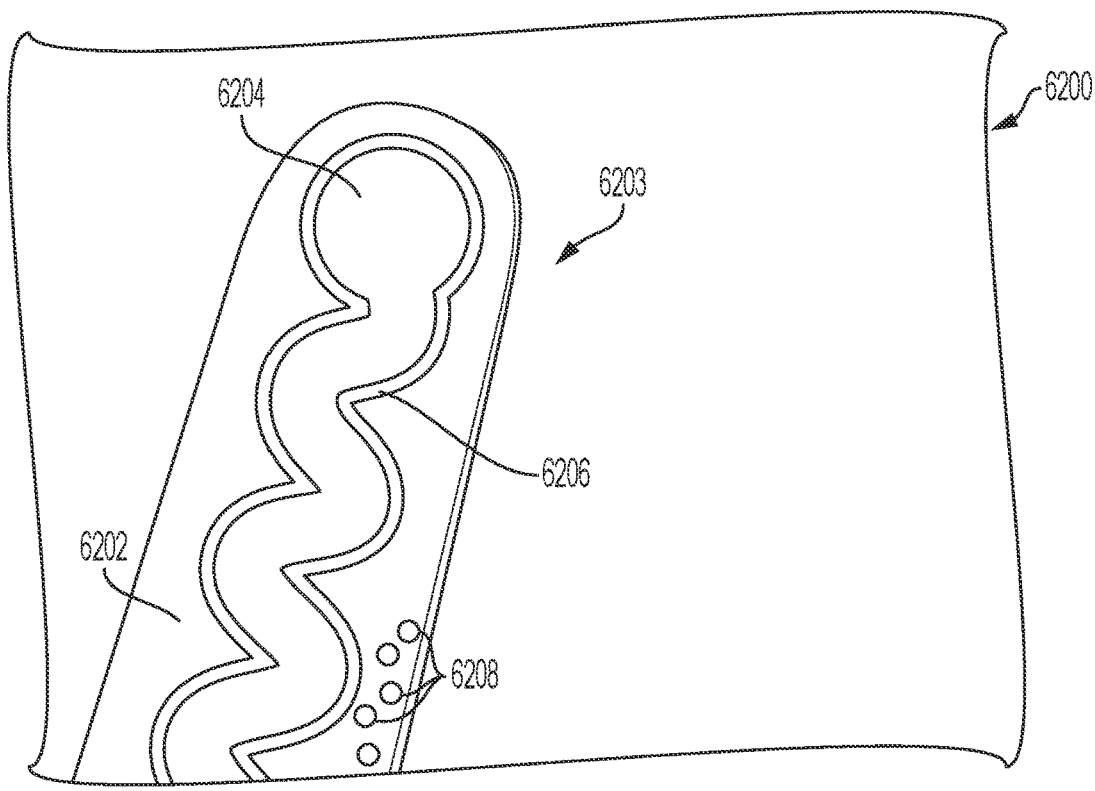
Figure 103B:
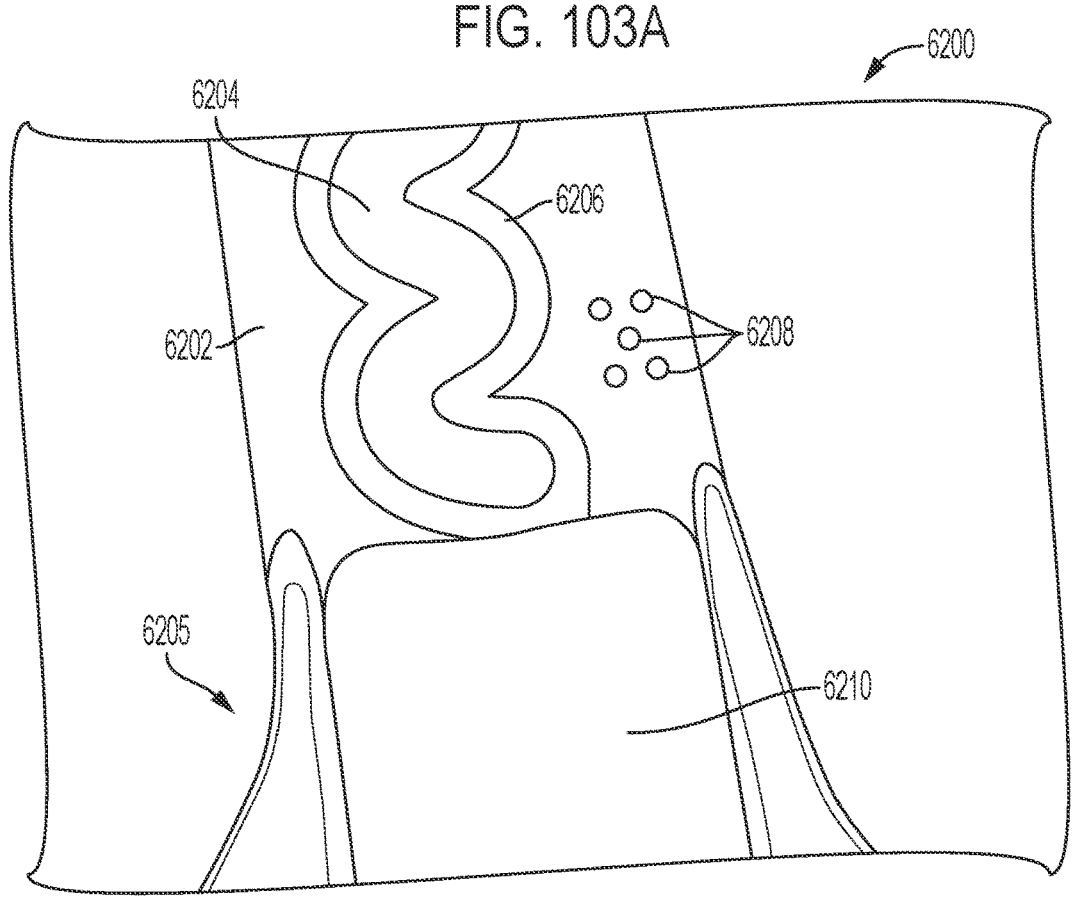

FIGS. 103A and 103B illustrate top views of a distal portion and a proximal portion of another clamp arm pad, in accordance with at least one non-limiting aspect of the present disclosure.

Figure 104:
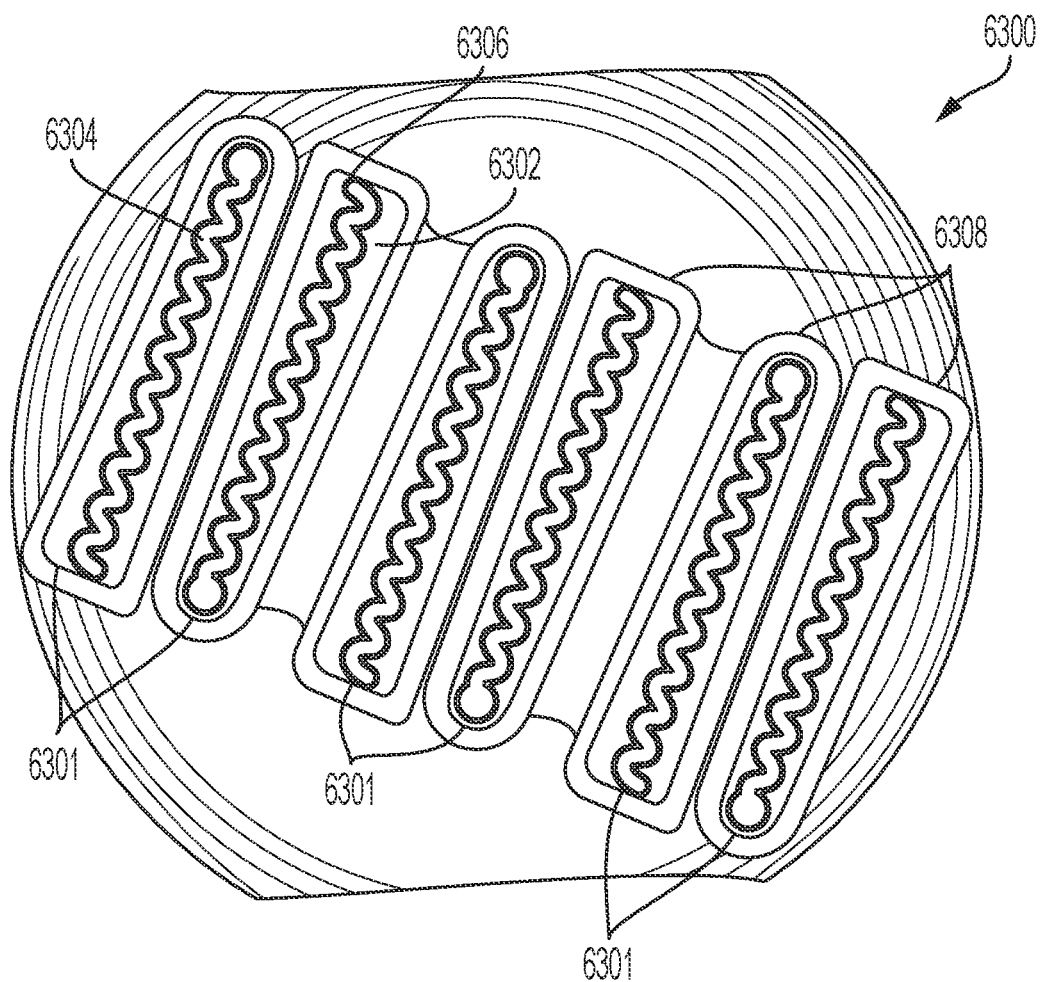

FIG. 104 illustrates a top view of a piece of manufacturing support equipment configured to produce clamp arm pads, in accordance with at least one non-limiting aspect of the present disclosure.

Figure 105:
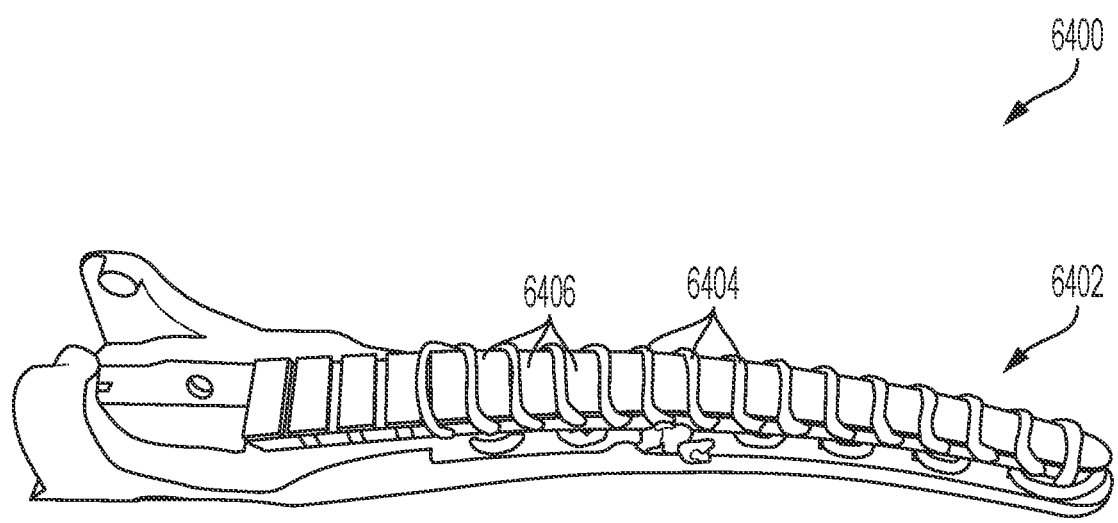
Figure 106A:
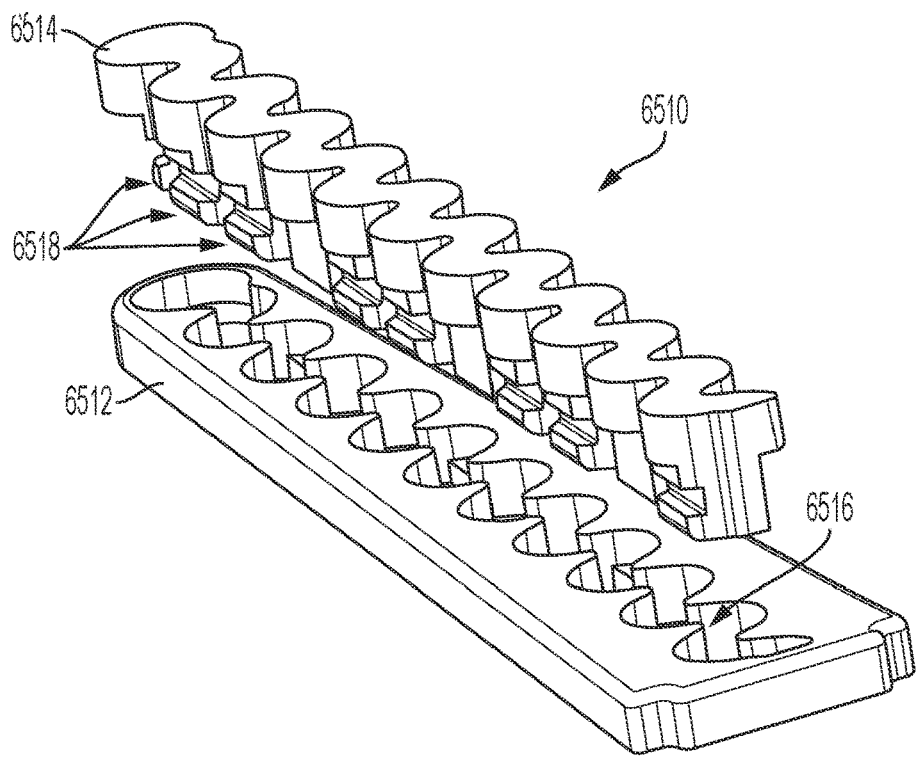
Figure 106B:
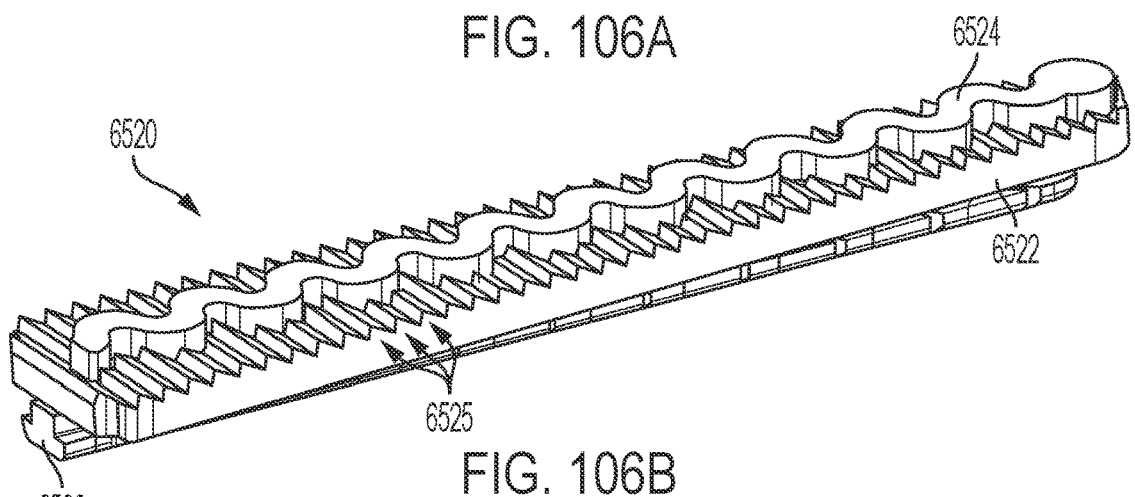
Figure 106C:
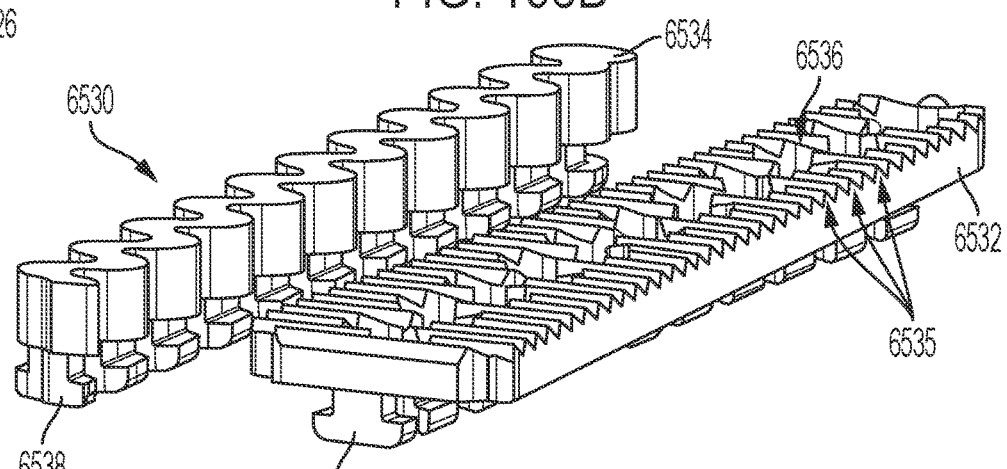

FIG. 105 illustrates a clamp arm featuring another clamp arm pad in accordance with at least one non-limiting aspect of the present disclosure FIGS. 106A through 106C illustrate perspective views of other clamp arm pads, in accordance with at least one non-limiting aspect of the present disclosure.

Figure 107A:
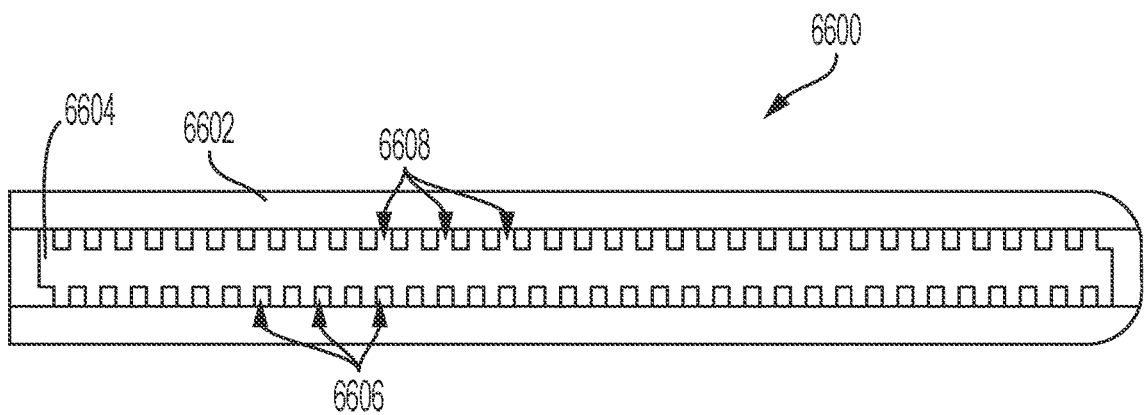
Figure 107B:
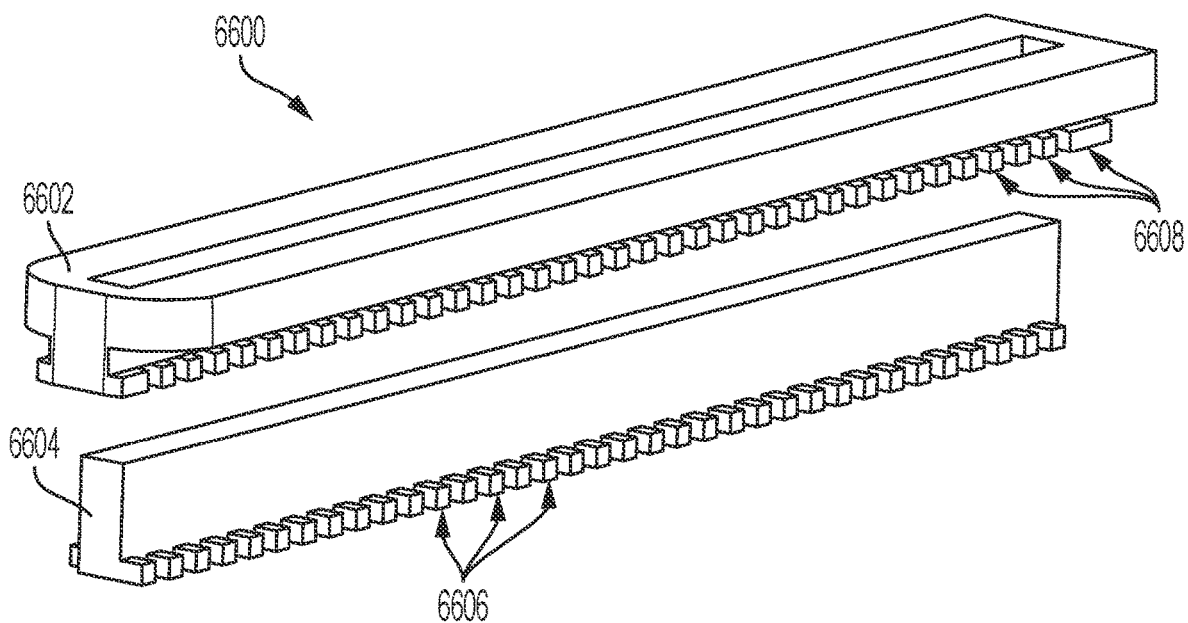
Figure 108A:
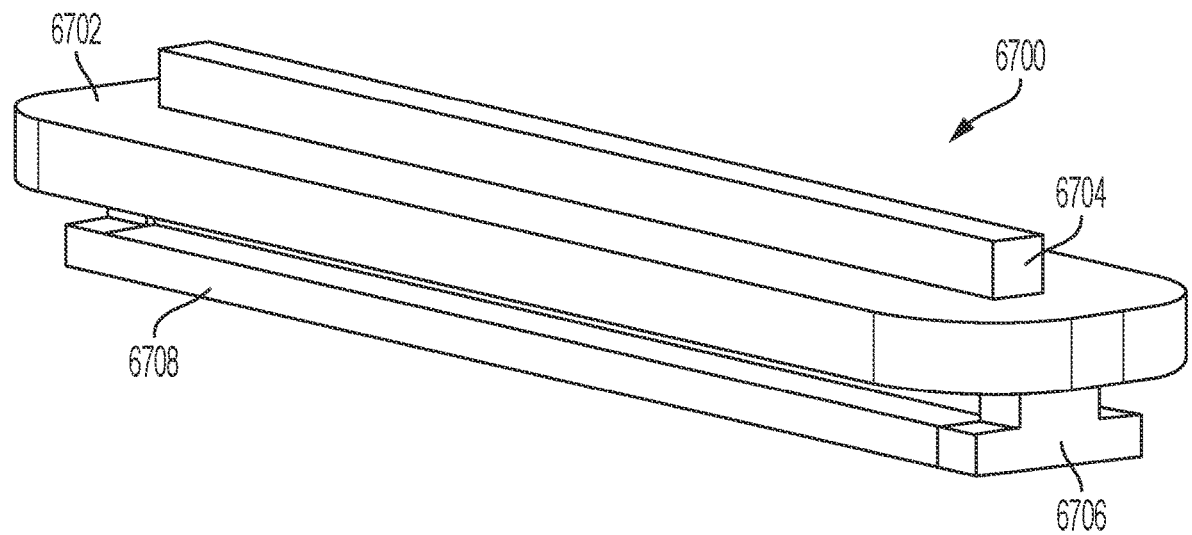
Figure 108B:
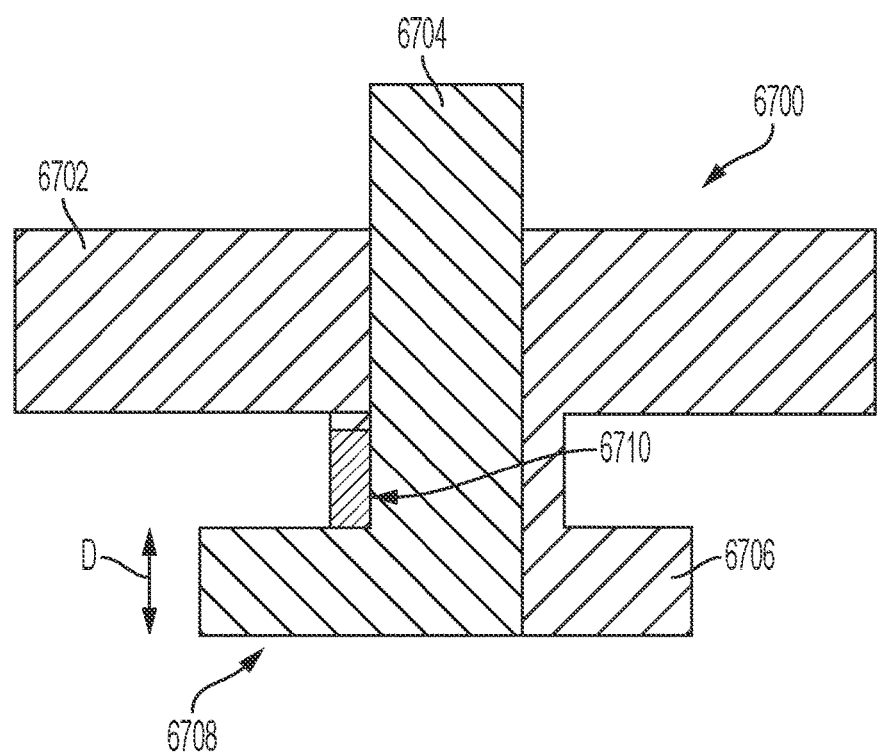

FIGS. 107A and 107B illustrate top and perspective views of another clamp arm pad respectively, in accordance with at least one non-limiting aspect of the present disclosure FIGS. 108A and 108B illustrate perspective and sectioned front views of another clamp arm pad respectively, in accordance with at least one non-limiting aspect of the present disclosure.

Figure 109:
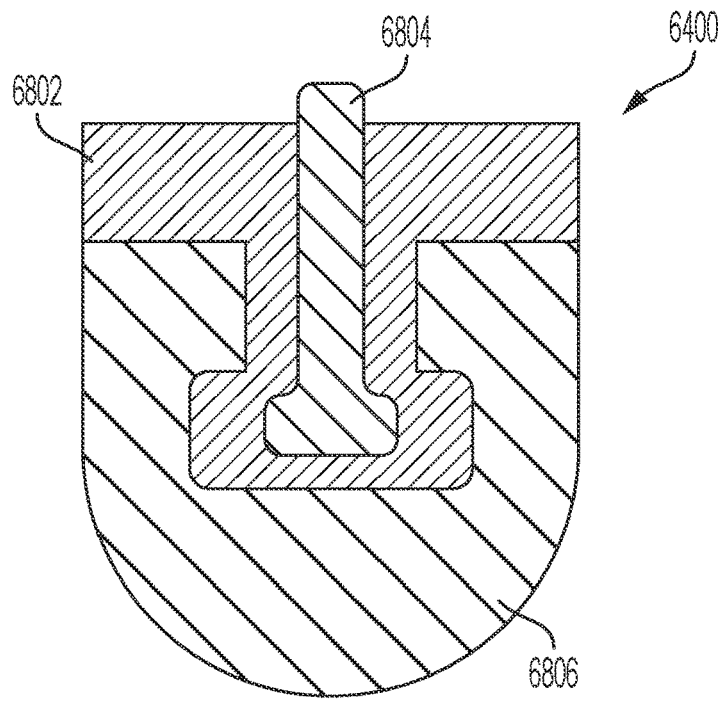

FIG. 109 illustrates a sectioned front view of another clamp arm pad, in accordance with at least one non-limiting aspect of the present disclosure.

Figure 110A:
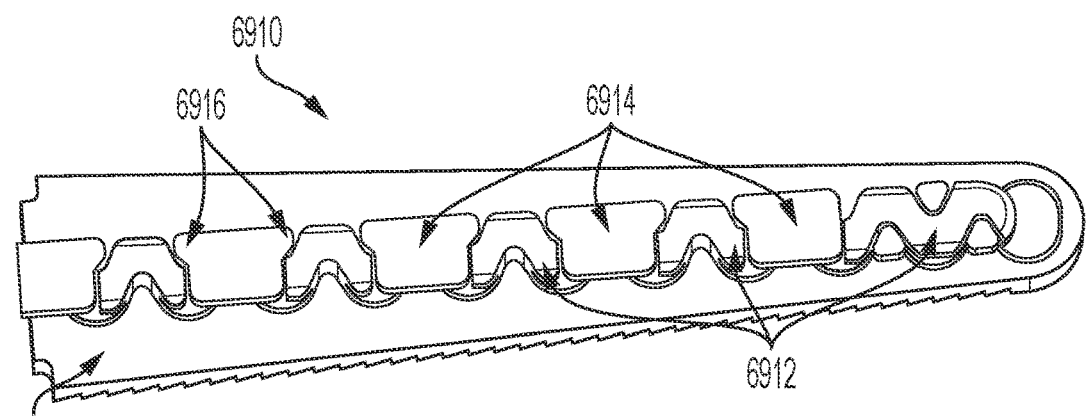
Figure 110B:
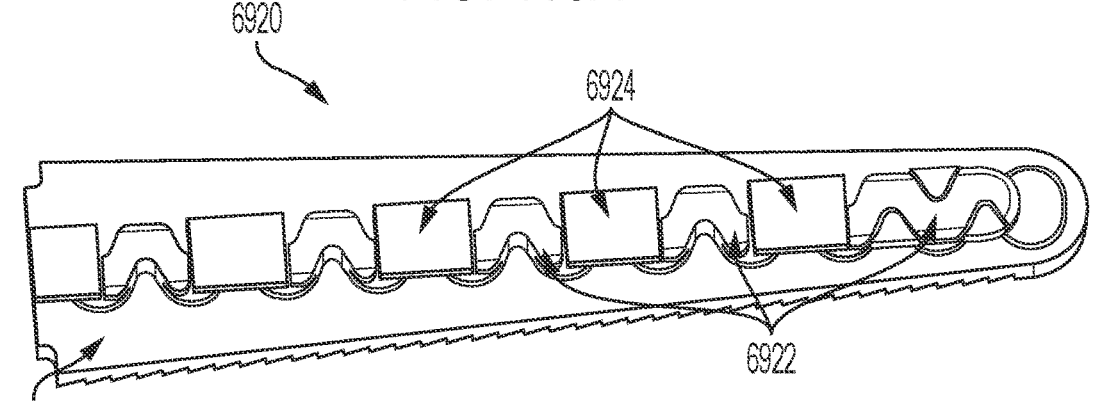

FIGS. 110A and 110B illustrate top perspective views of other clamp arm pads configurations, in accordance with at least one non-limiting aspect of the present disclosure.

Figure 111:
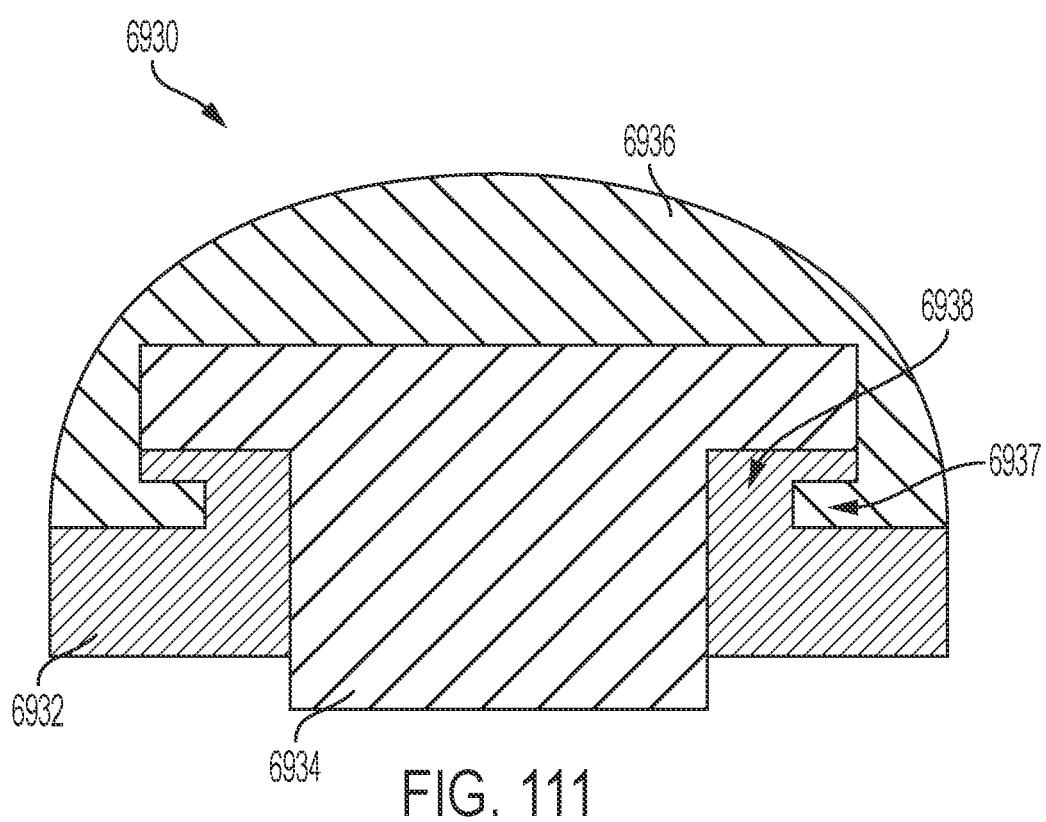

FIG. 111 illustrates a sectioned front view of another clamp arm pad, in accordance with at least one non-limiting aspect of the present disclosure.

Figure 112A:
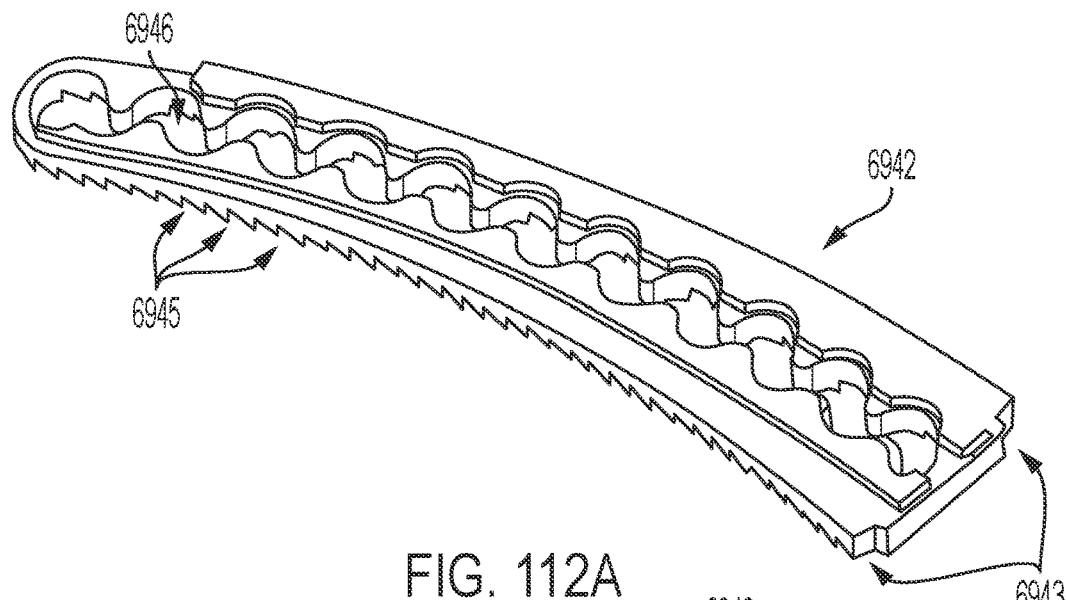
Figure 112B:
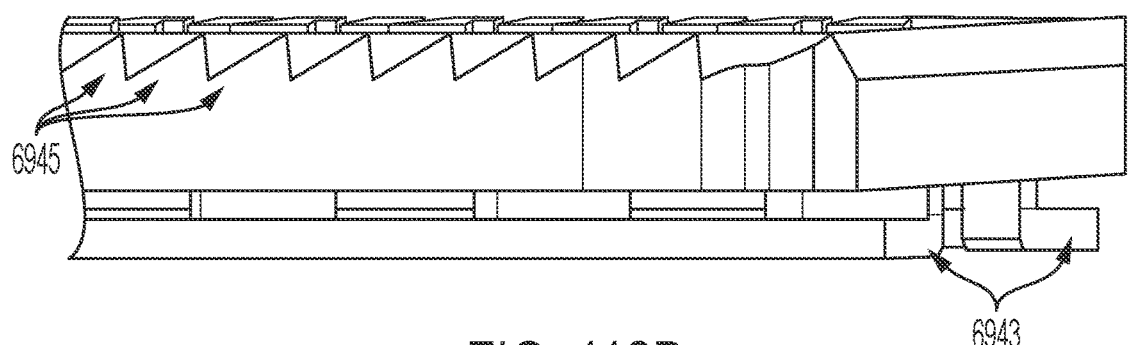

FIGS. 112A and 112B illustrate a perspective view of an electrically conductive pad, in accordance with at least one non-limiting aspect of the present disclosure.

Figure 112C:
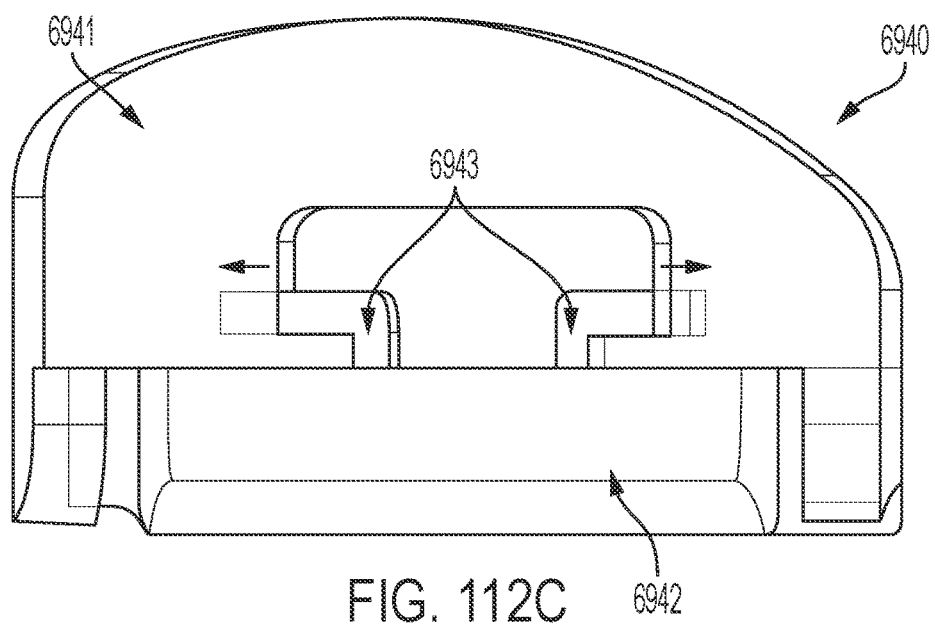

FIG. 112C illustrates a sectioned front view of a clamp arm including the electrically conductive pad of FIG. 112A, in accordance with at least one non-limiting aspect of the present disclosure.

Figure 113A:
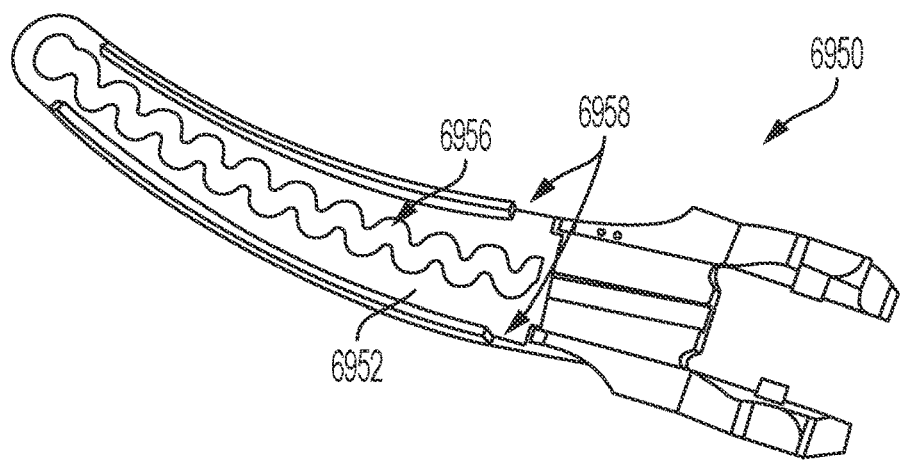

FIG. 113A illustrates a top view of a clamp arm, in accordance with at least one non-limiting aspect of the present disclosure.

Figure 113B:
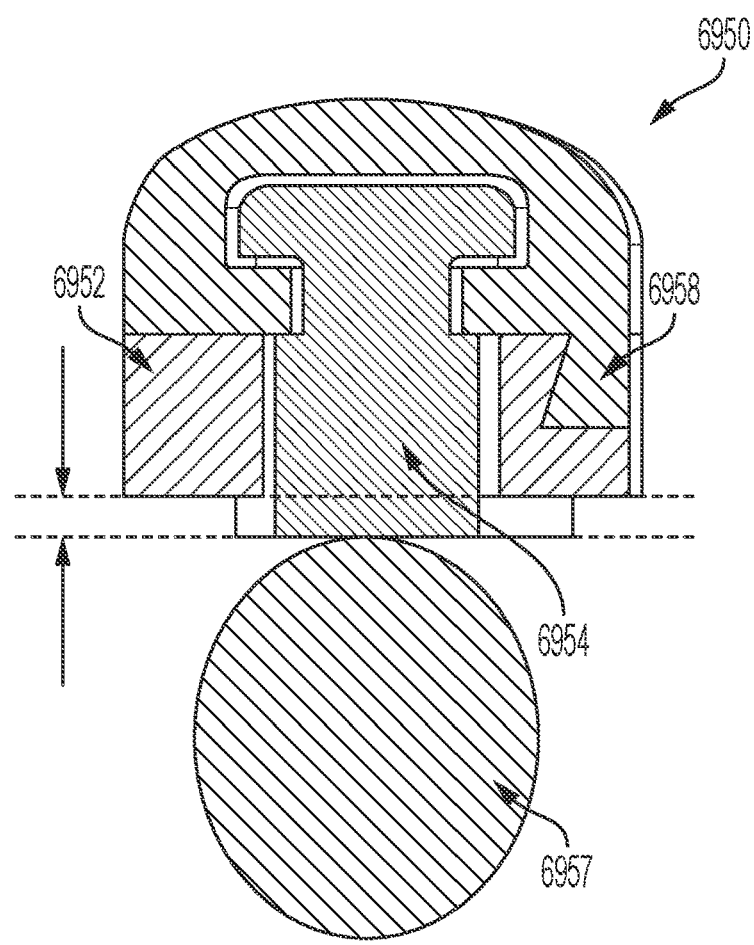

FIG. 113B illustrates a sectioned front view of the clamp arm of FIG. 113A, in accordance with at least one non-limiting aspect of the present disclosure.

Figure 114A:
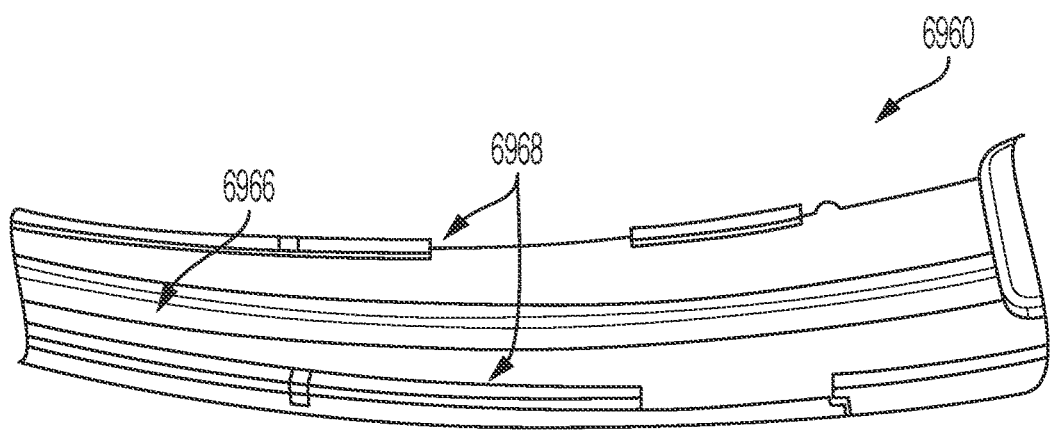

FIG. 114A illustrates a top view of a clamp arm, in accordance with at least one non-limiting aspect of the present disclosure.

Figure 114B:
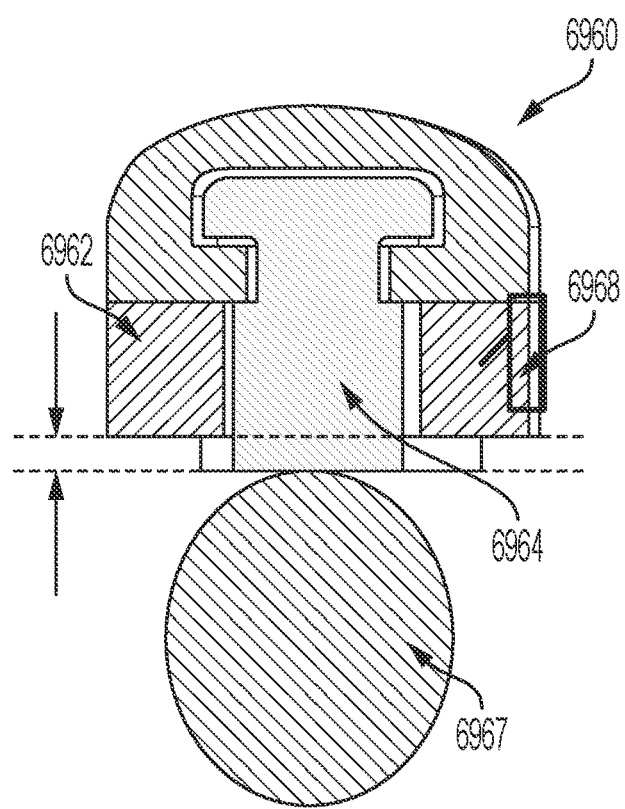

FIG. 114B illustrates a sectioned front view of the clamp arm of FIG. 114A, in accordance with at least one non-limiting aspect of the present disclosure.

Figure 115:
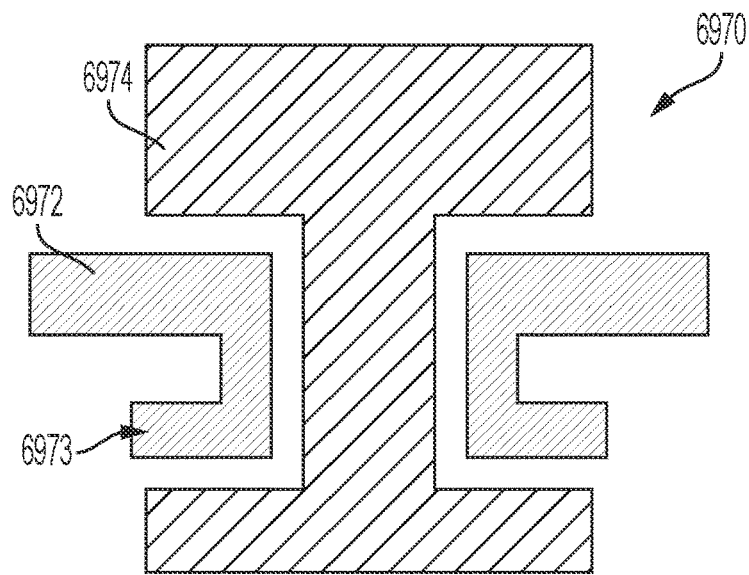

FIG. 115 illustrates a sectioned front view of a clamp arm pad configuration, in accordance with at least one non-limiting aspect of the present disclosure.

Figure 116:
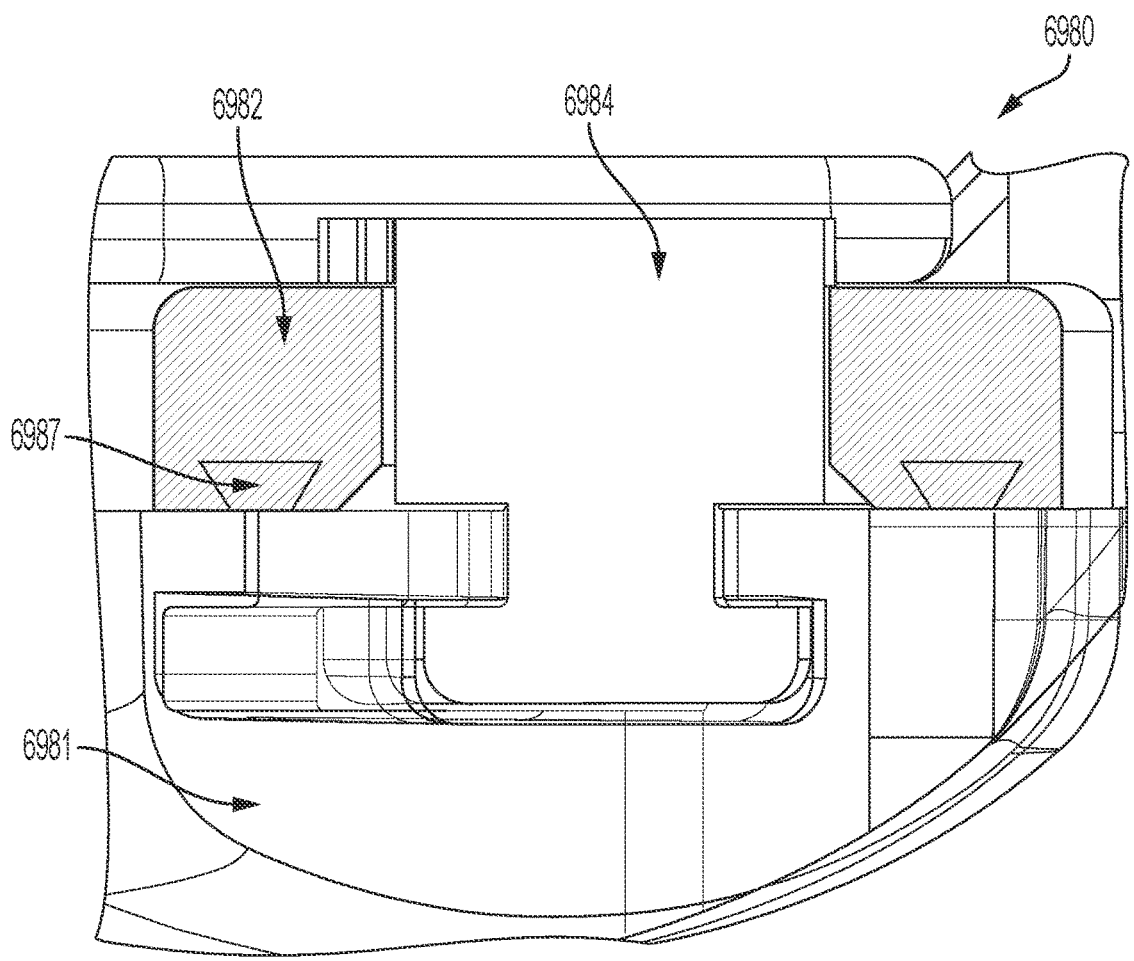

FIG. 116 illustrates a front view of a clamp arm, in accordance with at least one non-limiting aspect of the present disclosure.

Figure 117A:
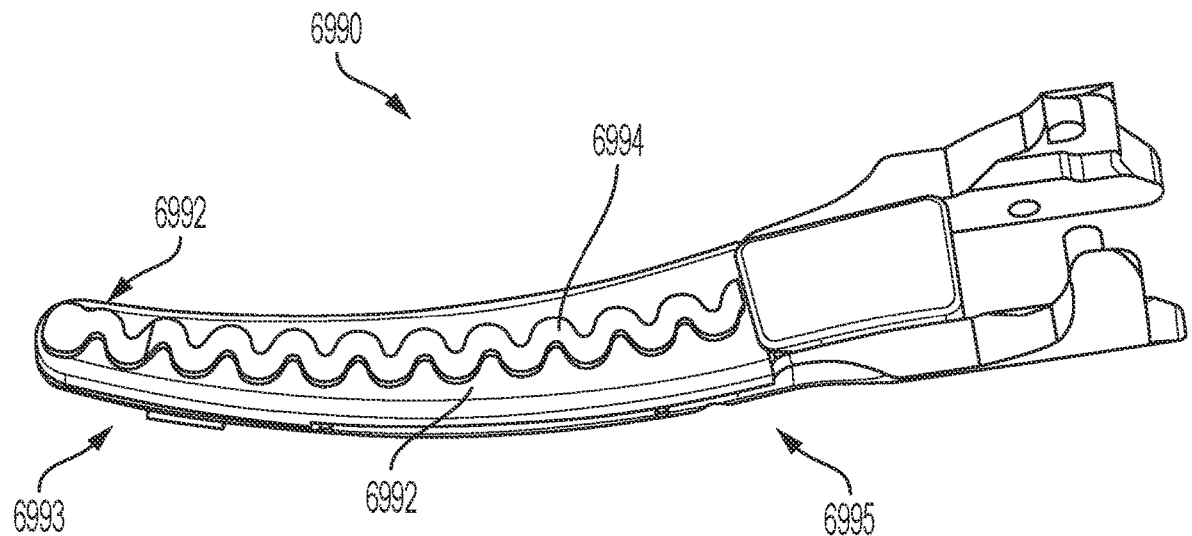

FIG. 117A illustrates a top view of a clamp arm, in accordance with at least one non-limiting aspect of the present disclosure.

Figure 117B:
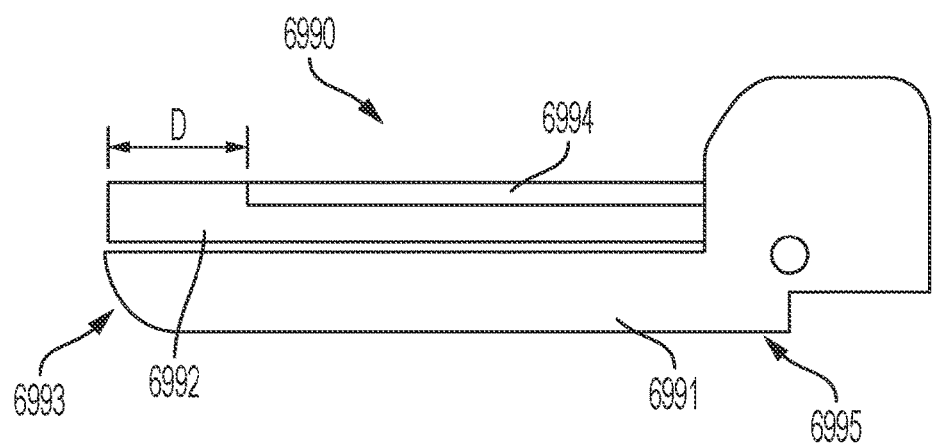

FIG. 117B illustrates a side vie of the clamp arm of FIG. 117A, in accordance with at least one non-limiting aspect of the present disclosure.

Figure 118:
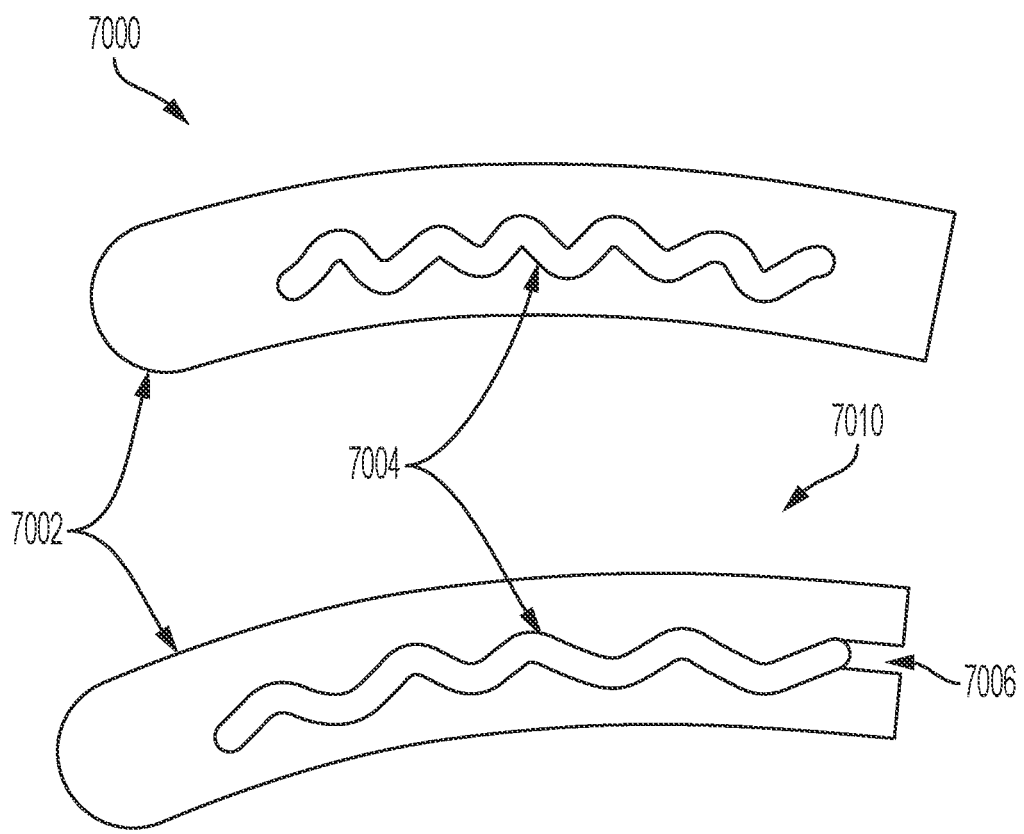

FIG. 118 illustrates a top view of two clamp arms, in accordance with at least one non-limiting aspect of the present disclosure.

Figure 119:
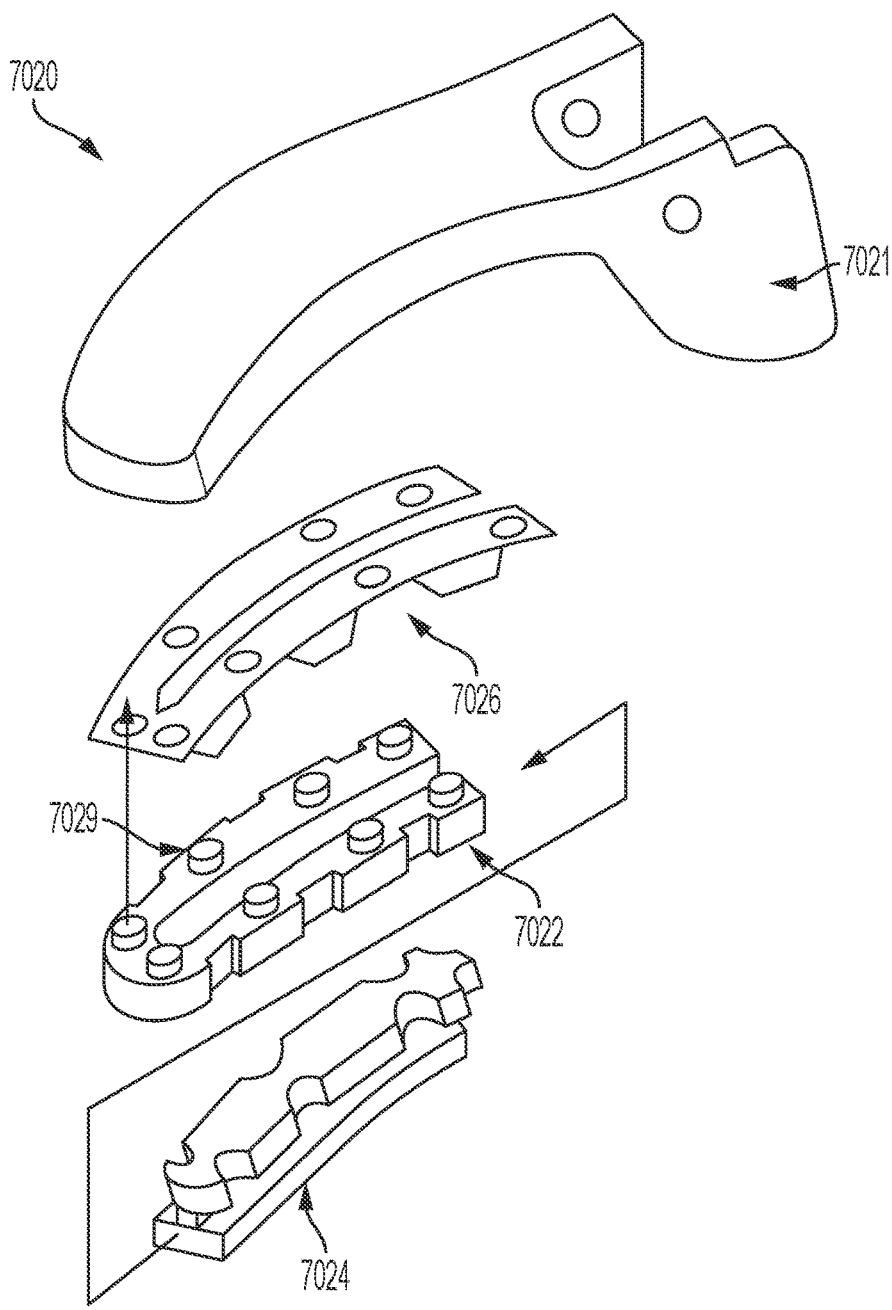

FIG. 119 illustrates an assembly drawing of a clamp arm, in accordance with at least one non-limiting aspect of the present disclosure.

Figure 120A:
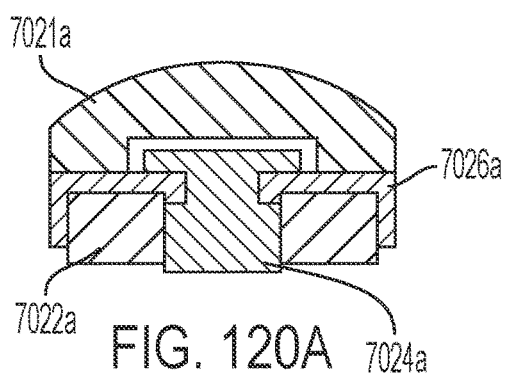
Figure 120B:
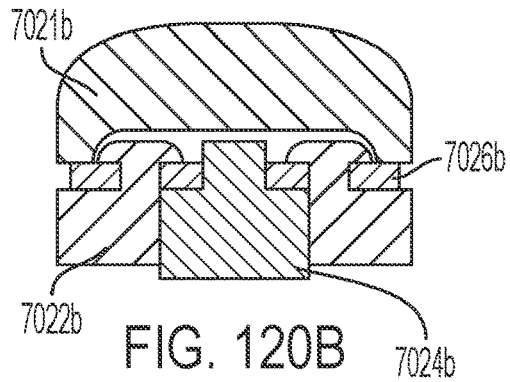

FIGS. 120A and 120B illustrate sectioned front views of the clamp arm of FIG. 119, in accordance with at least one non-limiting aspect of the present disclosure.

FIGS. 121A through 121D illustrate various views of an assembly of a clamp arm, in accordance with at least one non-limiting aspect of the present disclosure.

FIGS. 122A through 122D illustrate various views of an assembly of a clamp arm, in accordance with at least one non-limiting aspect of the present disclosure.

Figure 123A:
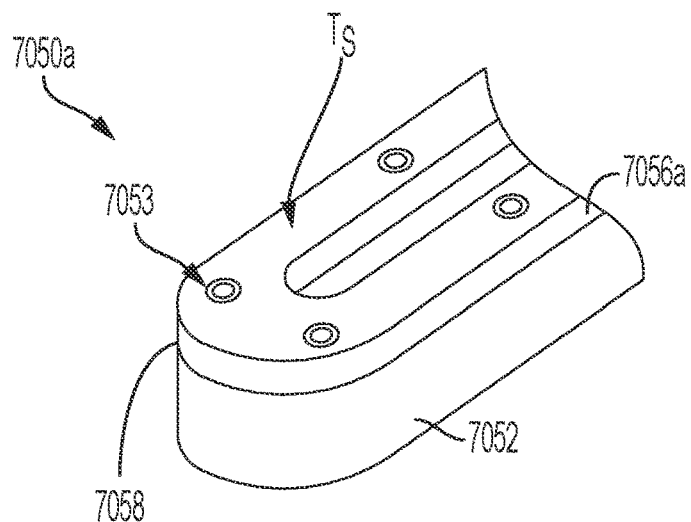
Figure 123B:
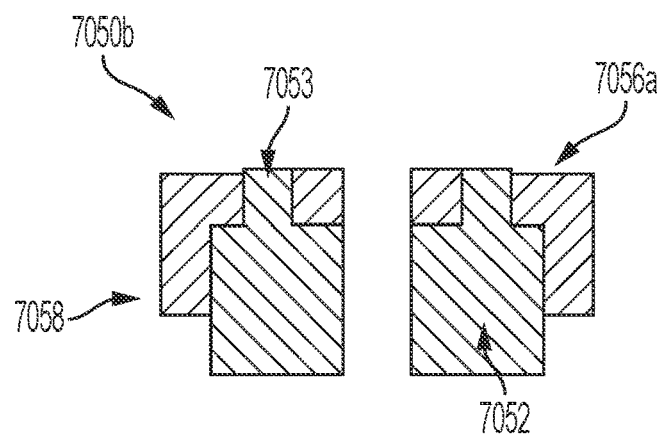
Figure 123C:
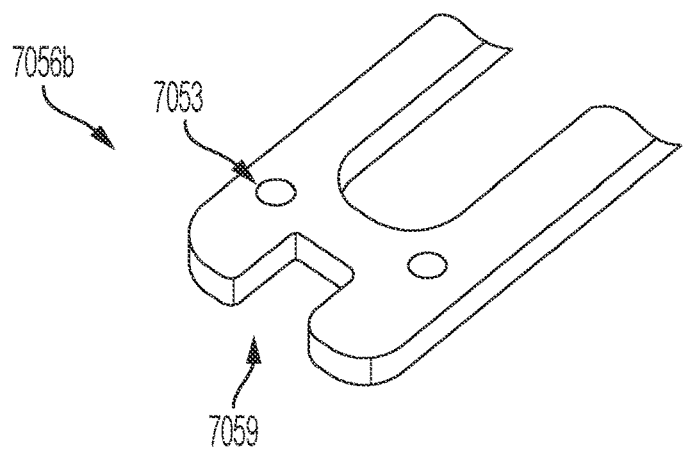
Figure 124A:
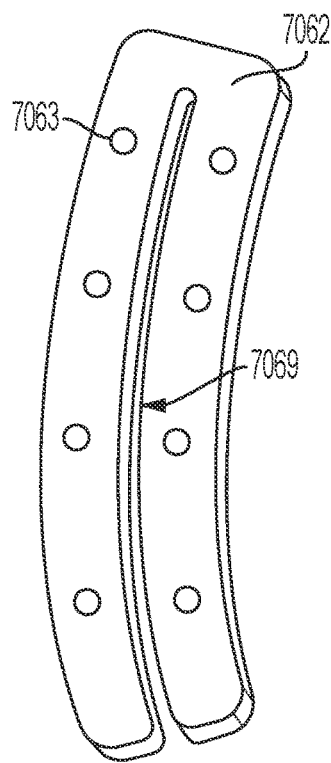
Figure 124B:
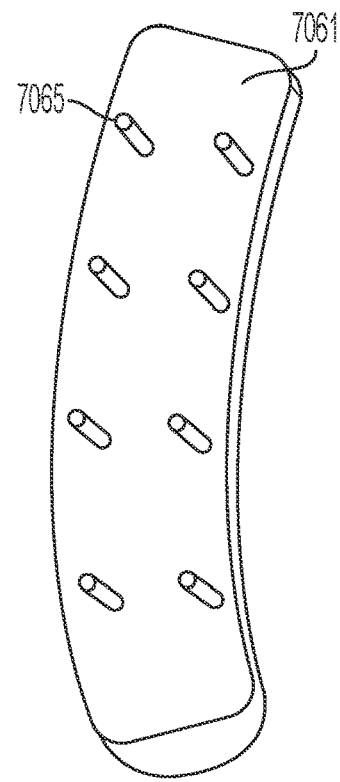
Figure 214C:
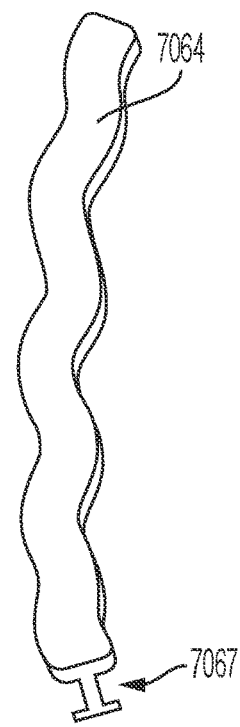
Figure 124D:
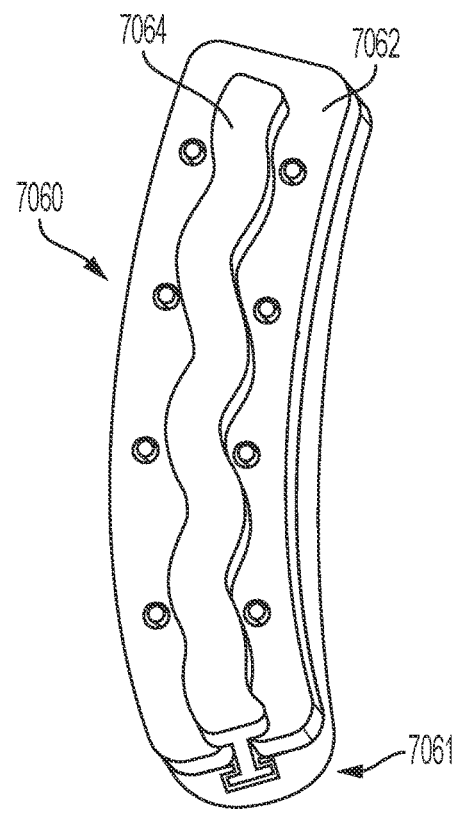

FIGS. 123A through 123C illustrate several clamp pad configurations, in accordance with at least one non-limiting aspect of the present disclosure.

FIGS. 124A through 124D illustrate several top perspective views of various components of a clamp arm assembly, in accordance with at least one non-limiting aspect of the present disclosure.

Figure 125A:
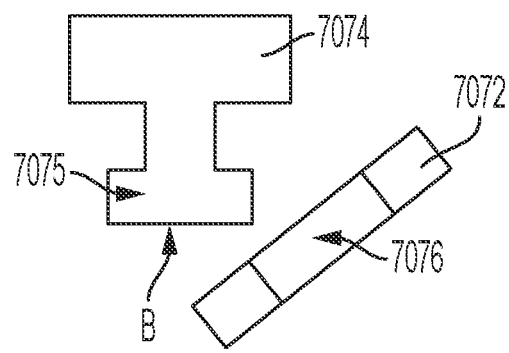
Figure 125B:
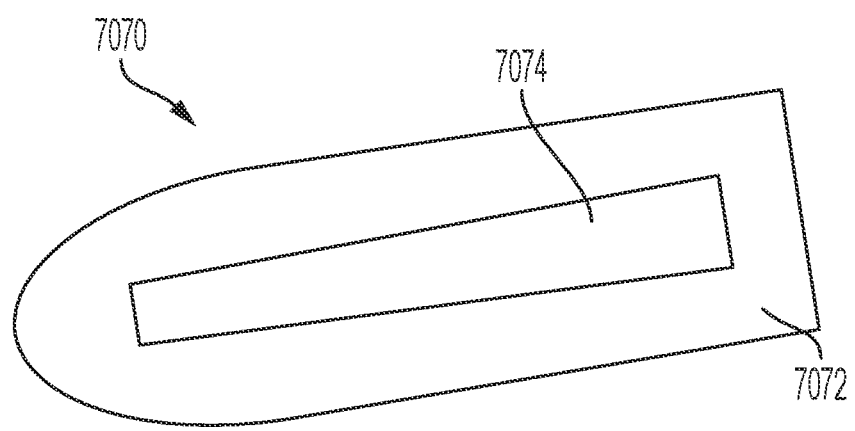

FIGS. 125A and 125B illustrate another clamp pad configuration, in accordance with at least one aspect of the non-limiting disclosure.

Figure 126A:
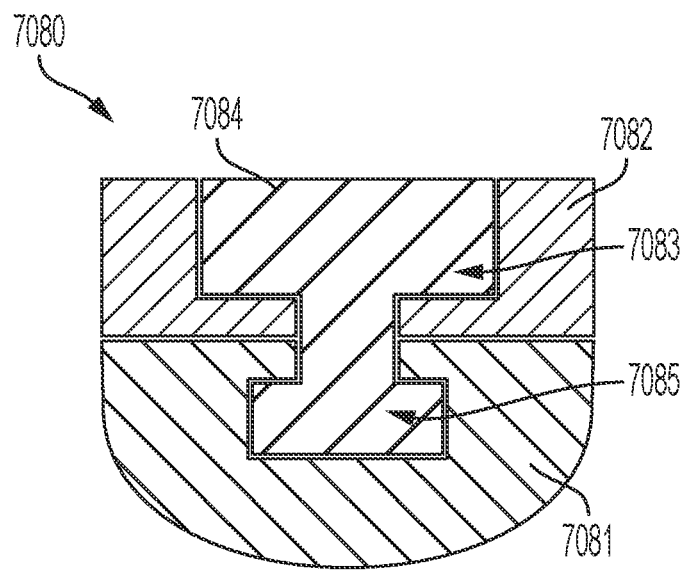
Figure 126B:
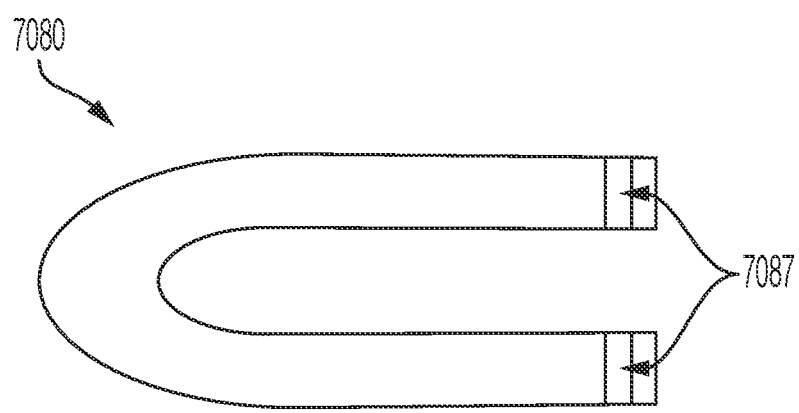

FIGS. 126A and 126B illustrate another clamp pad configuration, in accordance with at least one aspect of the non-limiting disclosure.

Figure 127A:
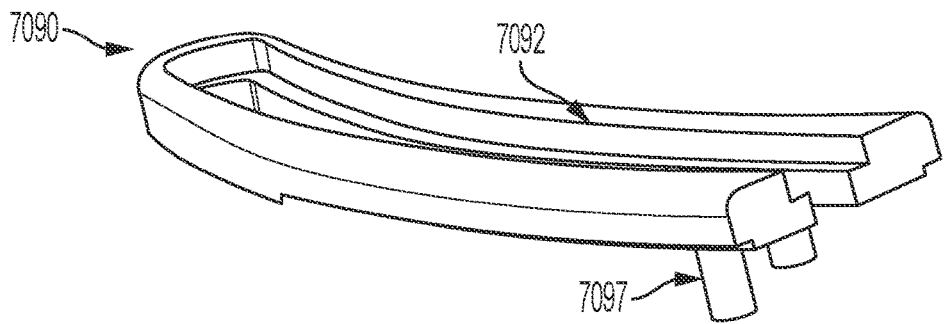
Figure 127B:
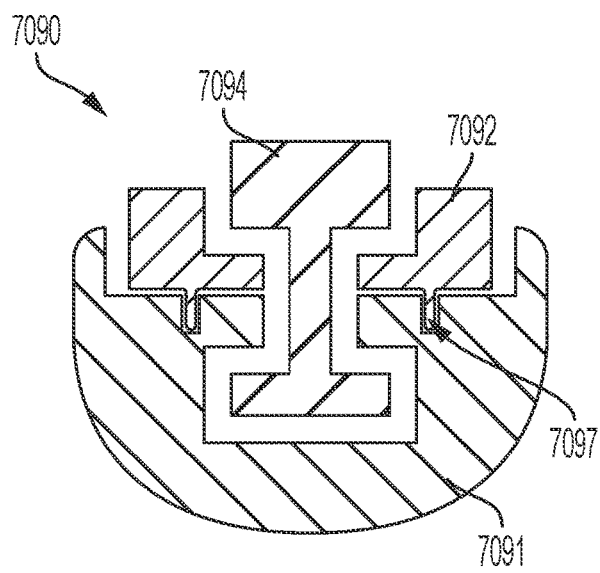
Figure 127C:
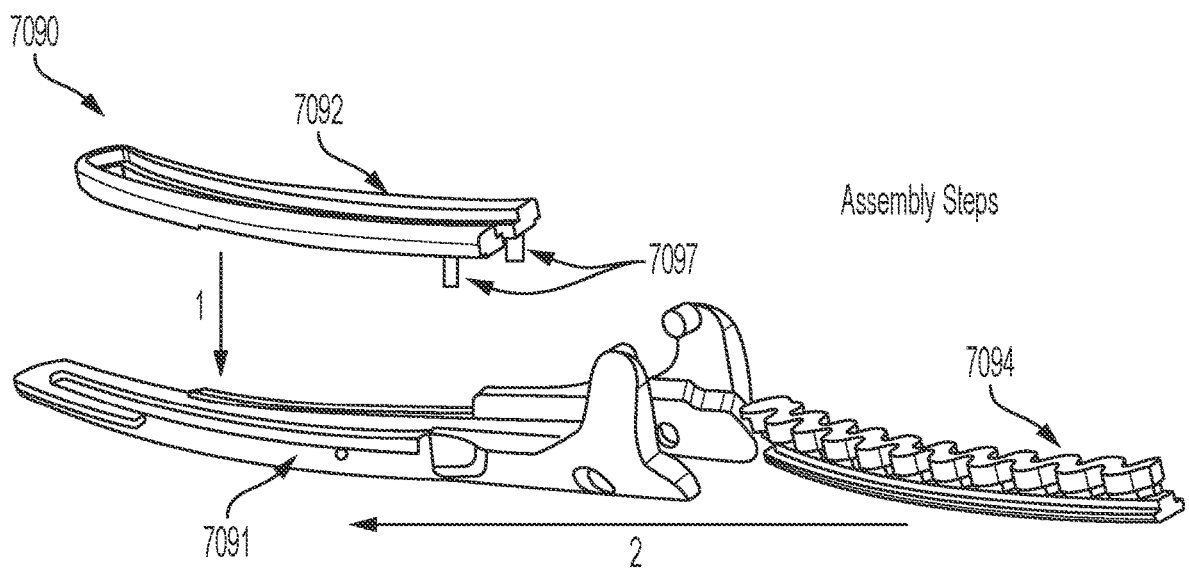

FIGS. 127A through 127C illustrate another clamp pad configuration, in accordance with at least one aspect of the non-limiting disclosure.

Figure 128:
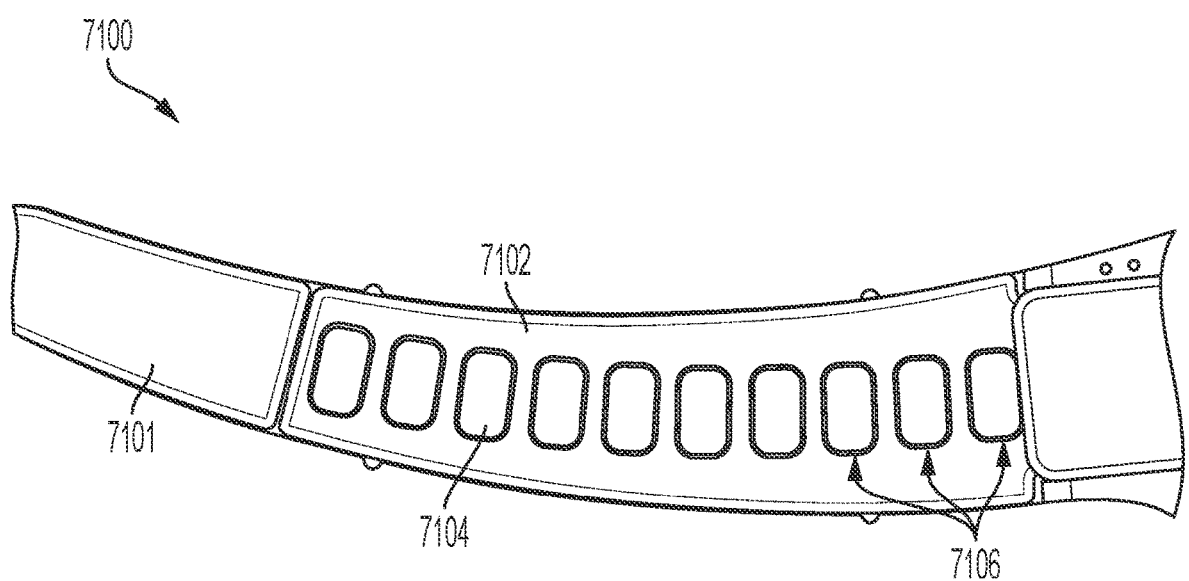

FIG. 128 illustrates a top view of a clamp pad configuration, in accordance with at least one aspect of the non-limiting disclosure.

Figure 129A:
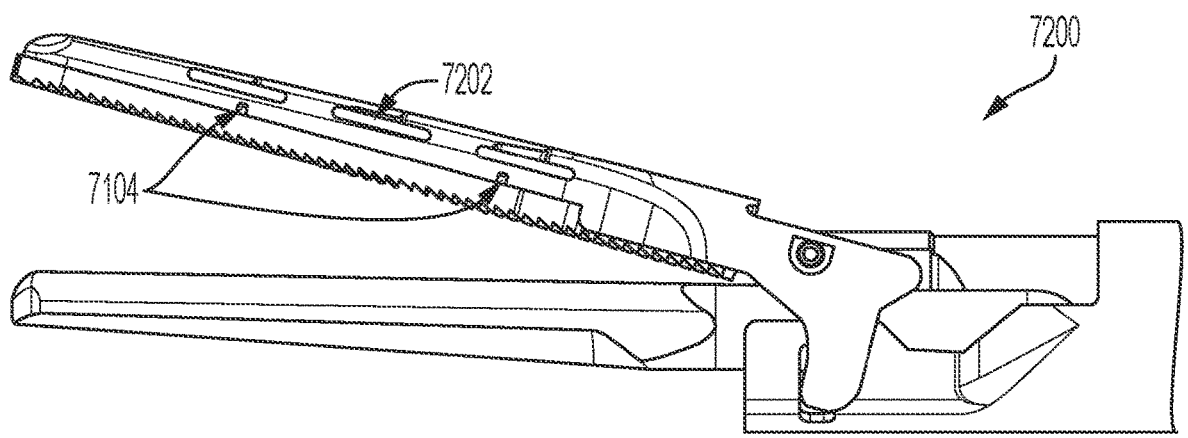
Figure 129B:
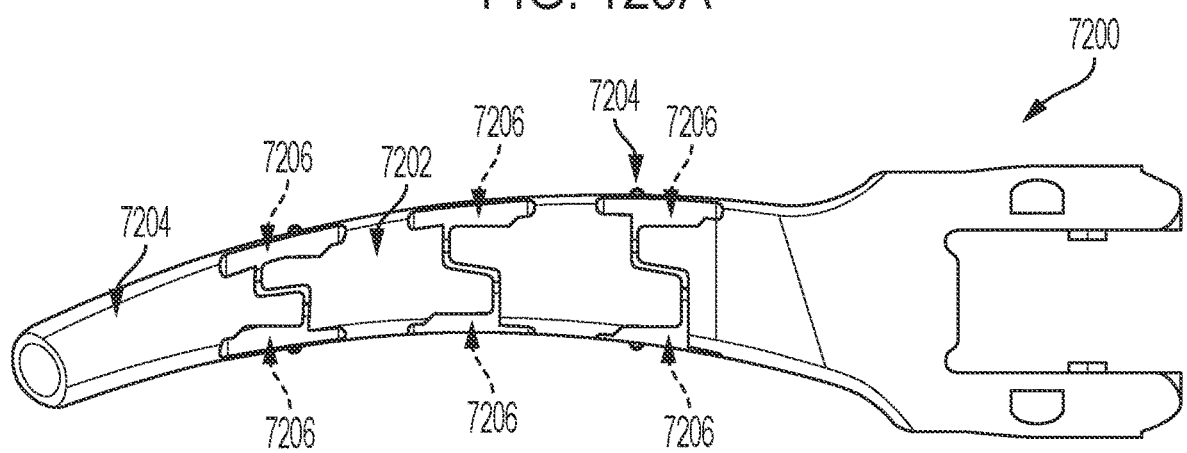
Figure 129C:
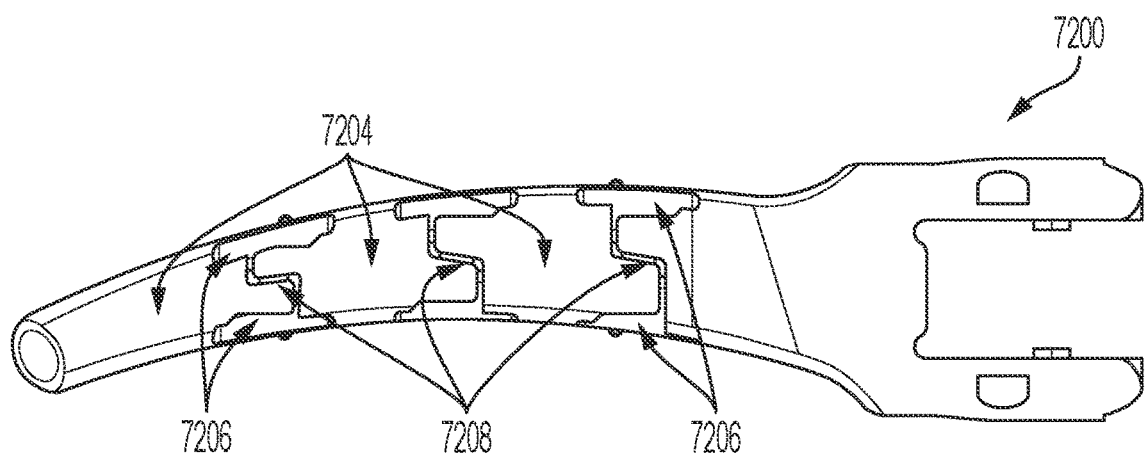

FIGS. 129A through 129C illustrate side and top views of a configurable clamp arm assembly, in accordance with at least one non-limiting aspect of the present disclosure.

Figure 130:
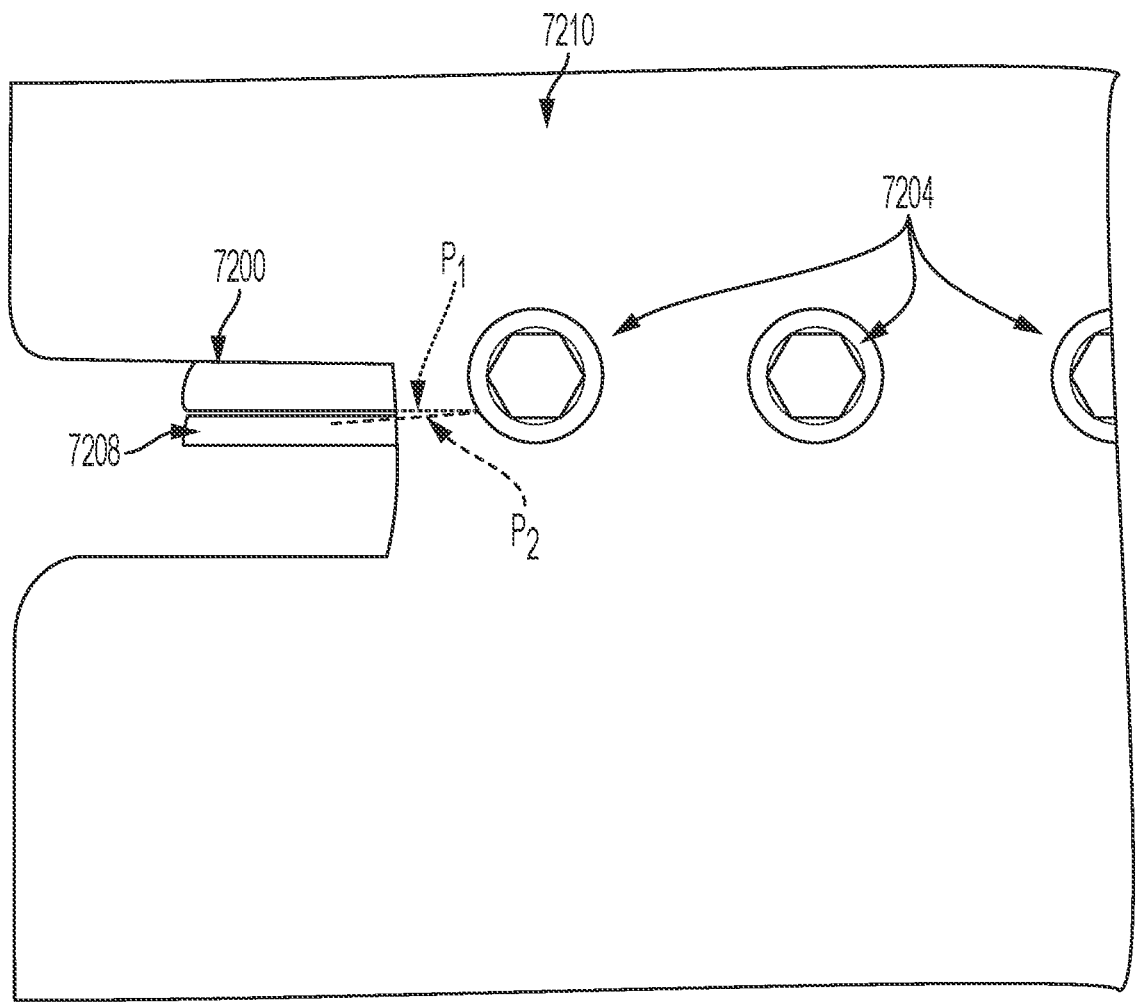
Figure 131:
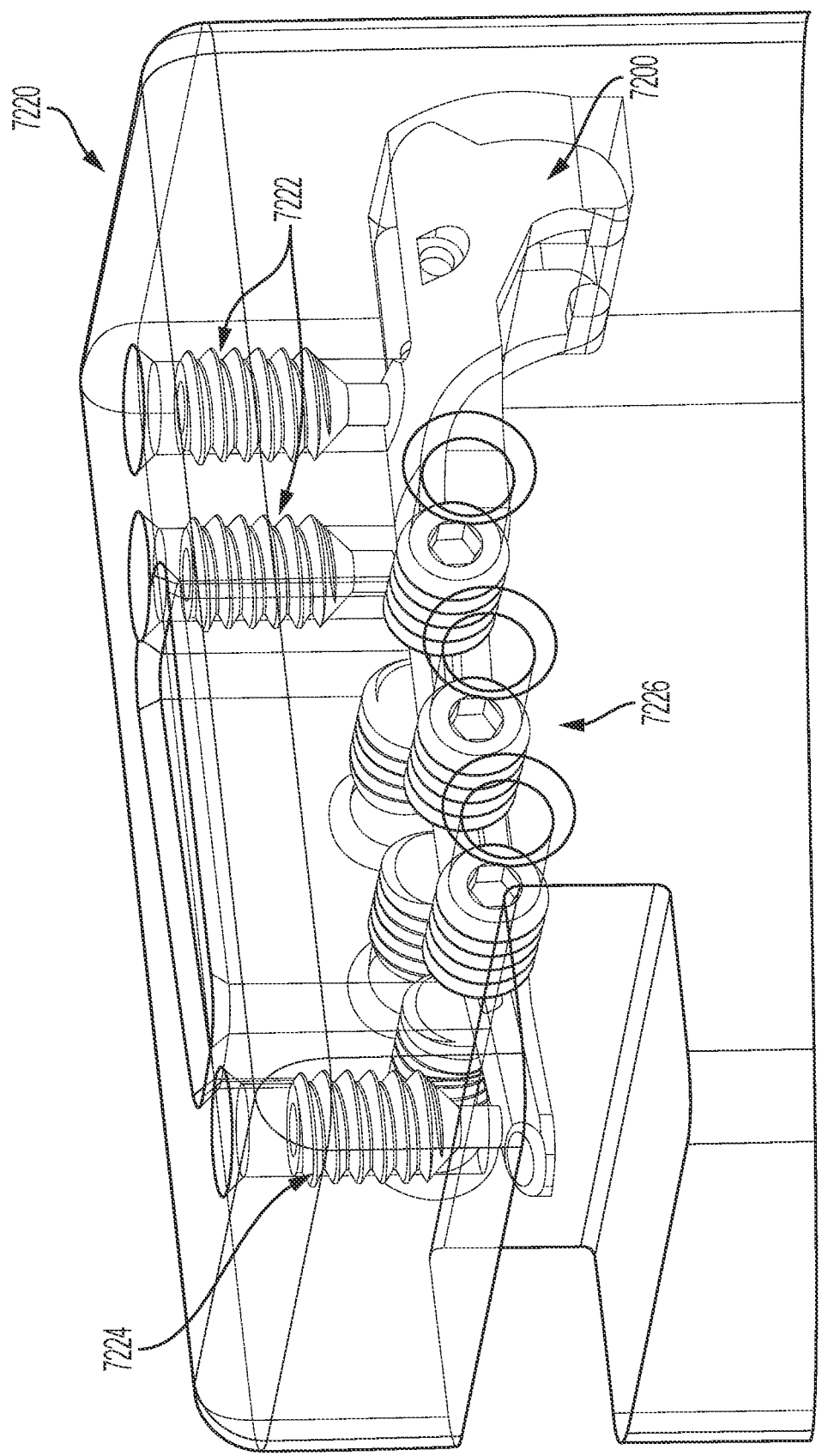
Figure 132:
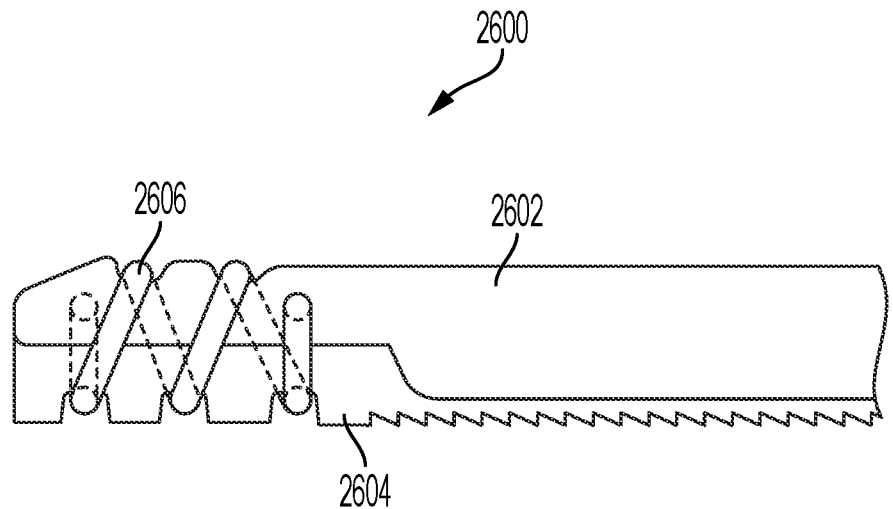

FIG. 130 illustrates a side view of the configurable clamp arm assembly of FIGS. 129A through 129C positioned within a configuration block, in accordance with at least one non-limiting aspect of the present disclosure FIG. 131 illustrates a side view of the configurable clamp arm assembly of FIGS. 129A through 129C positioned within an alternate configuration fixture, in accordance with at least one non-limiting aspect of the present disclosure FIG. 132 illustrates a clamp arm comprising a clamp jaw, a clamp arm pad, and a wrapped wire electrode, according to at least aspect of the present disclosure.

Figure 133:
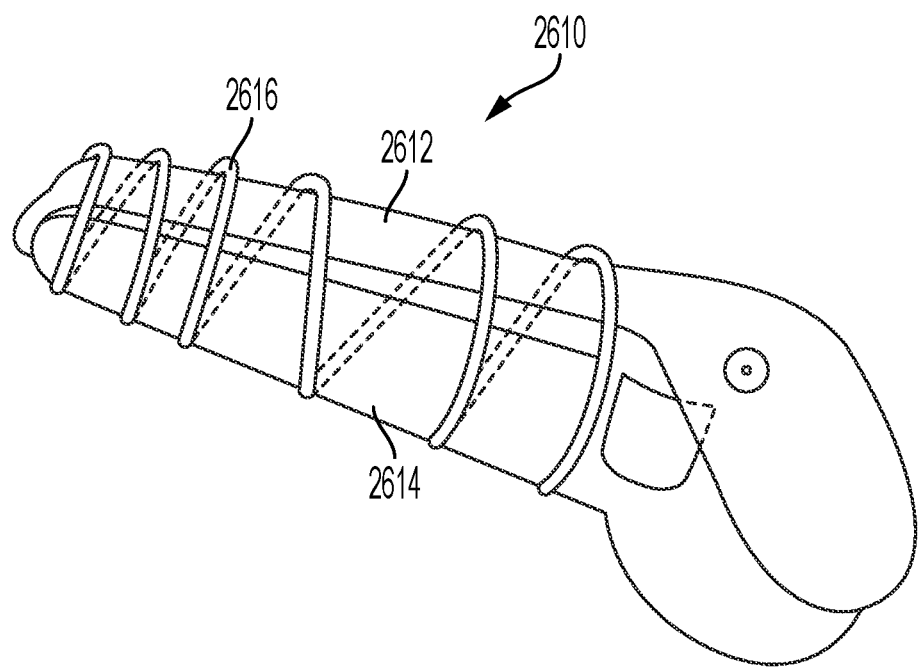

FIG. 133 illustrates a clamp arm comprising a clamp jaw, a clamp arm pad, and a wrapped wire electrode, according to at least aspect of the present disclosure.

DESCRIPTION

Applicant of the present application owns the following U.S. Provisional patent applications, filed on Dec. 30, 2019, the disclosure of each of which is herein incorporated by reference in its respective entirety:

U.S. Provisional Patent Application Ser. No. 62/955,294, entitled USER INTERFACE FOR SURGICAL

INSTRUMENT WITH COMBINATION ENERGY MODALITY END-EFFECTOR;

U.S. Provisional Patent Application Ser. No. 62/955,299, entitled ELECTROSURGICAL INSTRUMENTS FOR COMBINATION ENERGY DELIVERY; and U.S. Provisional Patent Application Ser. No. 62/955,306, entitled SURGICAL INSTRUMENTS.

Applicant of the present application owns the following U.S. Patent Applications, and which are each herein incorporated by reference in their respective entireties:

U.S. patent application Ser. No. 16/887,499, entitled USER INTERFACE FOR SURGICAL INSTRUMENT WITH COMBINATION ENERGY MODALITY END-EFFECTOR;

U.S. patent application Ser. No. 16/887,493, entitled METHOD OF OPERATING A COMBINATION ULTRASONIC/BIPOLAR RF SURGICAL DEVICE WITH A COMBINATION ENERGY MODALITY END-EFFECTOR;

U.S. patent application Ser. No. 16/887,506, entitled DEFLECTABLE SUPPORT OF RF ENERGY ELECTRODE WITH RESPECT TO OPPOSING ULTRASONIC BLADE;

U.S. patent application Ser. No. 16/887,515, entitled NON-BIASED DEFLECTABLE ELECTRODE TO MINIMIZE CONTACT BETWEEN ULTRASONIC BLADE AND ELECTRODE;

U.S. patent application Ser. No. 16/887,519, entitled DEFLECTABLE ELECTRODE WITH HIGHER DISTAL BIAS RELATIVE TO PROXIMAL BIAS;

U.S. patent application Ser. No. 16/887,532, entitled DEFLECTABLE ELECTRODE WITH VARIABLE COMPRESSION BIAS ALONG THE LENGTH OF THE DEFLECTABLE ELECTRODE;

U.S. patent application Ser. No. 16/887,554, entitled ASYMMETRIC SEGMENTED ULTRASONIC SUPPORT PAD FOR COOPERATIVE ENGAGEMENT WITH A MOVABLE RF ELECTRODE;

U.S. patent application Ser. No. 16/887,561, entitled VARIATION IN ELECTRODE PARAMETERS AND DEFLECTABLE ELECTRODE TO MODIFY ENERGY DENSITY AND TISSUE INTERACTION;

U.S. patent application Ser. No. 16/887,568, entitled TECHNIQUES FOR DETECTING ULTRASONIC BLADE TO ELECTRODE CONTACT AND REDUCING POWER TO ULTRASONIC BLADE;

U.S. patent application Ser. No. 16/887,576, entitled CLAMP ARM JAW TO MINIMIZE TISSUE STICKING AND IMPROVE TISSUE CONTROL;

U.S. patent application Ser. No. 16/887,579, entitled PARTIALLY CONDUCTIVE CLAMP ARM PAD TO ENABLE ELECTRODE WEAR THROUGH AND MINIMIZE SHORT CIRCUITING;

U.S. patent application Ser. No. 10/289,787, entitled ULTRASONIC CLAMP COAGULATOR APPARATUS HAVING AN IMPROVED CLAMPING END-EFFECTOR; and U.S. patent application Ser. No. 11/243,585, entitled ULTRASONIC CLAMP COAGULATOR APPARATUS HAVING AN IMPROVED CLAMPING END-EFFECTOR.

Applicant of the present application owns the following U.S. patent applications that were filed on May 28, 2020, and which are each herein incorporated by reference in their respective entireties:

U.S. patent application Ser. No. 16/885,813, entitled METHOD FOR AN ELECTROSURGICAL PROCEDURE;

U.S. patent application Ser. No. 16/885,820, entitled ARTICULATABLE SURGICAL INSTRUMENT;

U.S. patent application Ser. No. 16/885,823, entitled SURGICAL INSTRUMENT WITH JAW ALIGNMENT FEATURES;

U.S. patent application Ser. No. 16/885,826, entitled SURGICAL INSTRUMENT WITH ROTATABLE AND ARTICULATABLE SURGICAL END EFFECTOR;

U.S. patent application Ser. No. 16/885,838, entitled ELECTROSURGICAL INSTRUMENT WITH ASYNCHRONOUS ENERGIZING ELECTRODES;

U.S. patent application Ser. No. 16/885,851, entitled ELECTROSURGICAL INSTRUMENT WITH ELECTRODES BIASING SUPPORT;

U.S. patent application Ser. No. 16/885,860, entitled ELECTROSURGICAL INSTRUMENT WITH FLEXIBLE WIRING ASSEMBLIES;

U.S. patent application Ser. No. 16/885,866, entitled ELECTROSURGICAL INSTRUMENT WITH VARIABLE CONTROL MECHANISMS;

U.S. patent application Ser. No. 16/885,870, entitled ELECTROSURGICAL SYSTEMS WITH INTEGRATED AND EXTERNAL POWER SOURCES;

U.S. patent application Ser. No. 16/885,873, entitled ELECTROSURGICAL INSTRUMENTS WITH ELECTRODES HAVING ENERGY FOCUSING FEATURES;

U.S. patent application Ser. No. 16/885,879, entitled ELECTROSURGICAL INSTRUMENTS WITH ELECTRODES HAVING VARIABLE ENERGY DENSITIES;

U.S. patent application Ser. No. 16/885,881, entitled ELECTROSURGICAL INSTRUMENT WITH MONOPOLAR AND BIPOLAR ENERGY CAPABILITIES;

U.S. patent application Ser. No. 16/885,888, entitled ELECTROSURGICAL END EFFECTORS WITH THERMALLY INSULATIVE AND THERMALLY CONDUCTIVE PORTIONS;

U.S. patent application Ser. No. 16/885,893, entitled ELECTROSURGICAL INSTRUMENT WITH ELECTRODES OPERABLE IN BIPOLAR AND MONOPOLAR MODES;

U.S. patent application Ser. No. 16/885,900, entitled ELECTROSURGICAL INSTRUMENT FOR DELIVERING BLENDED ENERGY MODALITIES TO TISSUE;

U.S. patent application Ser. No. 16/885,917, entitled CONTROL PROGRAM ADAPTATION BASED ON DEVICE STATUS AND USER INPUT;

U.S. patent application Ser. No. 16/885,923, entitled CONTROL PROGRAM FOR MODULAR COMBINATION ENERGY DEVICE; and U.S. patent application Ser. No. 16/885,931, entitled SURGICAL SYSTEM COMMUNICATION PATHWAYS.

Before explaining various forms of surgical instruments in detail, it should be noted that the illustrative forms are not limited in application or use to the details of construction and arrangement of parts illustrated in the accompanying drawings and description. The illustrative forms may be implemented or incorporated in other forms, variations and modifications, and may be practiced or carried out in various ways. Further, unless otherwise indicated, the terms and expressions utilized herein have been chosen for the purpose of describing the illustrative forms for the convenience of the reader and are not for the purpose of limitation thereof.

Further, it is understood that any one or more of the following-described forms, expressions of forms, examples, can be combined with any one or more of the other following-described forms, expressions of forms, and examples.

Various forms are directed to improved ultrasonic and/or electrosurgical (RF) instruments configured for effecting tissue treating, dissecting, cutting, and/or coagulation during surgical procedures. In one form, a combined ultrasonic and electrosurgical instrument may be configured for use in open surgical procedures, but has applications in other types of surgery, such as minimally invasive laparoscopic, orthoscopic, or thoracoscopic procedures, for example, non-invasive endoscopic procedures, either in hand held or and robotic-assisted procedures. Versatility is achieved by selective application of multiple energy modalities simultaneously, independently, sequentially, or combinations thereof. For example, versatility may be achieved by selective use of ultrasonic and electrosurgical energy (e.g., monopolar or bipolar RF energy) either simultaneously, independently, sequentially, or combinations thereof.

In one aspect, the present disclosure provides an ultrasonic surgical clamp apparatus comprising an ultrasonic blade and a deflectable RF electrode such that the ultrasonic blade and deflectable RF electrode cooperate to effect sealing, cutting, and clamping of tissue by cooperation of a clamping mechanism of the apparatus comprising the RF electrode with an associated ultrasonic blade. The clamping mechanism includes a pivotal clamp arm which cooperates with the ultrasonic blade for gripping tissue therebetween. The clamp arm is preferably provided with a clamp tissue pad (also known as "clamp arm pad") having a plurality of axially spaced gripping teeth, segments, elements, or individual units which cooperate with the ultrasonic blade of the end-effector to achieve the desired sealing and cutting effects on tissue, while facilitating grasping and gripping of tissue during surgical procedures.

In one aspect, the end-effectors described herein comprise an electrode. In other aspects, the end-effectors described herein comprise alternatives to the electrode to provide a compliant coupling of RF energy to tissue, accommodate pad wear/thinning, minimize generation of excess heat (low coefficient of friction, pressure), minimize generation of sparks, minimize interruptions due to electrical shorting, or combinations thereof. The electrode is fixed to the clamp jaw at the proximal end and is free to deflect at the distal end. Accordingly, throughout this disclosure the electrode may be referred to as a cantilever beam electrode or as a deflectable electrode.

In other aspects, the end-effectors described herein comprise a clamp arm mechanism configured to apply high pressure between a pad and an ultrasonic blade to grasp and seal tissue, maximize probability that the clamp arm electrode contacts tissue in limiting or difficult scenarios, such as, for example, thin tissue, tissue under lateral tension, tissue tenting/vertical tension especially tenting tissue away from clamp arm.

In other aspects, the end-effectors described herein are configured to balance match of surface area/current densities between electrodes, balance and minimize thermal conduction from tissue interface, such as, for example, impacts lesion formation and symmetry, cycle time, residual thermal energy.

In other aspects, the end-effectors described herein are configured to minimize sticking, tissue adherence (minimize anchor points) and may comprise small polyimide pads.

In various aspects, the present disclosure provides a combination ultrasonic/bipolar RF energy surgical device. The combination ultrasonic/bipolar RF energy surgical device comprises an end-effector. The end-effector comprises a clamp arm and an ultrasonic blade. The clamp arm comprises a movable clamp jaw, a compliant polymeric pad, and at least one bipolar RF electrode. The at least one electrode is coupled to a positive pole of an RF generator and the ultrasonic blade is coupled to the negative pole of the RF generator. The ultrasonic blade is acoustically coupled to an ultrasonic transducer stack that is driven by an ultrasonic generator. In various aspects, the end-effector comprises electrode biasing mechanisms.

In one general aspect, the present disclosure is directed to a method for using a surgical device comprising a combination of ultrasonic and advanced bipolar RF energy with a movable RF electrode on at least one jaw of an end-effector. The movable RF electrode having a variable biasing force from a proximal end to a distal end of the movable RF electrode. The movable RF electrode being segmented into discrete portions than can be put in electrical communication or isolated from each other. The movable RF electrode being made of a conductive or partially conductive material. It will be appreciated that any of the end effectors described in this disclosure may be configured with an electrode biasing mechanism.

In one aspect, the present disclosure provides a limiting electrode biasing mechanism to prevent ultrasonic blade to electrode damage. Generally, in various aspects, the present disclosure provides an end-effector for use with a ultrasonic/RF combination device, where the end-effector comprises an electrode. In one aspect, the combination ultrasonic/bipolar RF energy surgical device comprises an electrode biasing mechanism. In one aspect, the limiting electrode biasing mechanism is configured to prevent or minimize ultrasonic blade to electrode damage. The electrode is fixed to the clamp jaw at the proximal end and is free to deflect at the distal end. Accordingly, throughout this disclosure the electrode may be referred to as a cantilever beam electrode or as a deflectable electrode.

In various aspects, the present disclosure provides an electrode cantilever beam fixated at only one end comprising a biasing threshold mechanism. In one aspect, the deflectable cantilever electrode is configured for combination ultrasonic/bipolar RF energy surgical devices.

In one aspect, the combination ultrasonic/RF energy surgical device comprises an ultrasonic blade, a clamp arm, and at least one electrode which crosses over the ultrasonic blade. In one aspect, the electrode is configured to be deflectable with respect to the clamp arm and includes features to change the mechanical properties of the tissue under compression between the electrode and the ultrasonic blade. In another aspect, the electrode includes a feature to prevent inadvertent contact between the electrode and the ultrasonic blade to prevent or minimize ultrasonic blade to electrode damage.

In various aspects, the electrode comprises a metallic spring element attached at a proximal end of the clamp jaw of the end-effector. The metallic spring element defines openings for receives therethrough one or more clamp arm pads (also known as "tissue pads" or "clamp tissue pads") and comprises integrated minimum gap elements. This configuration of the electrode provides a method of preventing tissue from accumulating around the biasing mechanism that can impact the performance of the electrode. This configuration also minimizes the binding between the wear pads and the biasing spring, increases the strength of the electrode to clamp arm connection, minimizes inadvertent release of the clamp arm pads by attaching the polyimide pads to the electrode, and balance matches the surface area/current densities between electrodes. The electrode is fixed to the clamp jaw at the proximal end and is free to deflect at the distal end. Accordingly, throughout this disclosure the electrode is deflectable and may be referred to as a cantilever beam electrode or deflectable electrode.

Figure 1:
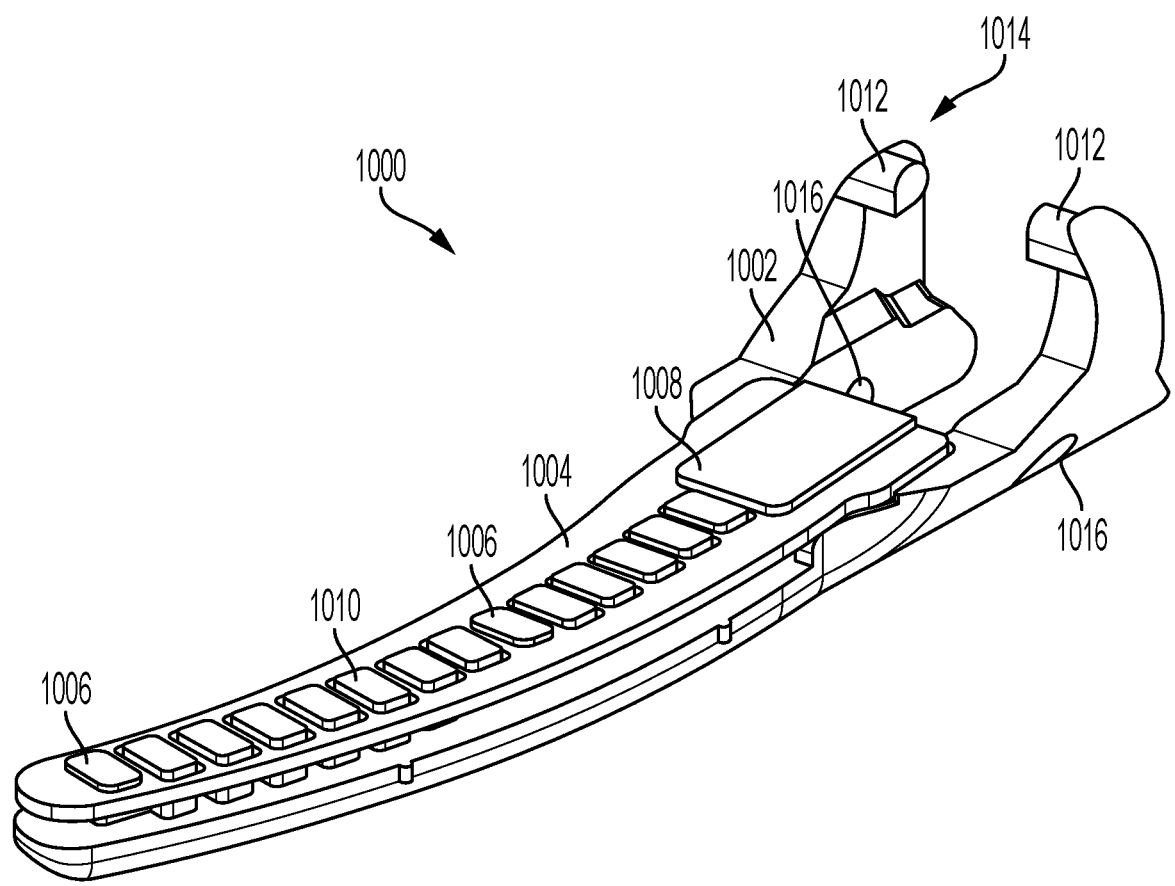
FIG. 1 is a perspective view of a clamp arm portion of an end-effector for use with a combined ultrasonic/RF device, according to at least one aspect of the present disclosure.

FIGS. 1-9 illustrate one aspect of an end-effector comprising a deflectable/cantilever electrode configured for use with a combination ultrasonic/bipolar RF energy device, according to at least one aspect of the present disclosure. FIG. 1 is a perspective view of a clamp arm 1000 portion of an end-effector for use with a combined ultrasonic/RF device, according to at least one aspect of the present disclosure. For conciseness and clarity of disclosure, the ultrasonic blade, which functions as the other clamp arm of the end-effector is not shown. The end-effector is configured such that the ultrasonic blade is one pole of the bipolar RF circuit and the clamp arm 1000 is the opposite pole. A consistent RF electrode gap is maintained between the clamp arm 1000 and the ultrasonic blade to prevent the ultrasonic blade from contacting the electrode resulting in blade breakage or a short circuit. Tissue under treatment is clamped and compressed between the clamp arm 1000 and the ultrasonic blade.

The clamp arm 1000 includes a frame 1002, an electrode 1004, at least one small electrically nonconductive gap pad 1006, at least one large electrically nonconductive gap pad 1008, at least one electrically nonconductive clamp arm pad 1010. In one aspect, the small and large gap pads 1006, 1008 are configured to set a gap between the electrode 1004 and the ultrasonic blade. The clamp arm pad 1010 is configured to grasp tissue between the clamp arm 1000 and the ultrasonic blade to assist with sealing and cutting of the tissue. In other aspects, the small and large nonconductive gap pads may be swapped. In other aspects, the nonconductive gap pads are simply sized differently regardless of the relative size difference between the nonconductive gap pads.

Pivotal movement of the clamp arm 1000 with respect to the end-effector is effected by the provision of at least one, and preferably a pair of, lever portions 1012 of the clamp arm 1000 frame 1002 at a proximal end 1014 thereof. The lever portions 1012 are positioned on respective opposite sides of an ultrasonic waveguide and end-effector, and are in operative engagement with a drive portion of a reciprocable actuating member. Reciprocable movement of the actuating member, relative to an outer tubular sheath and the ultrasonic waveguide, thereby effects pivotal movement of the clamp arm 1000 relative to the end-effector about pivot points 1016. The lever portions 1012 can be respectively positioned in a pair of openings defined by the drive portion, or otherwise suitably mechanically coupled therewith, whereby reciprocable movement of the actuating member acts through the drive portion and lever portions 1012 to pivot the clamp arm 1000.

Figure 2:
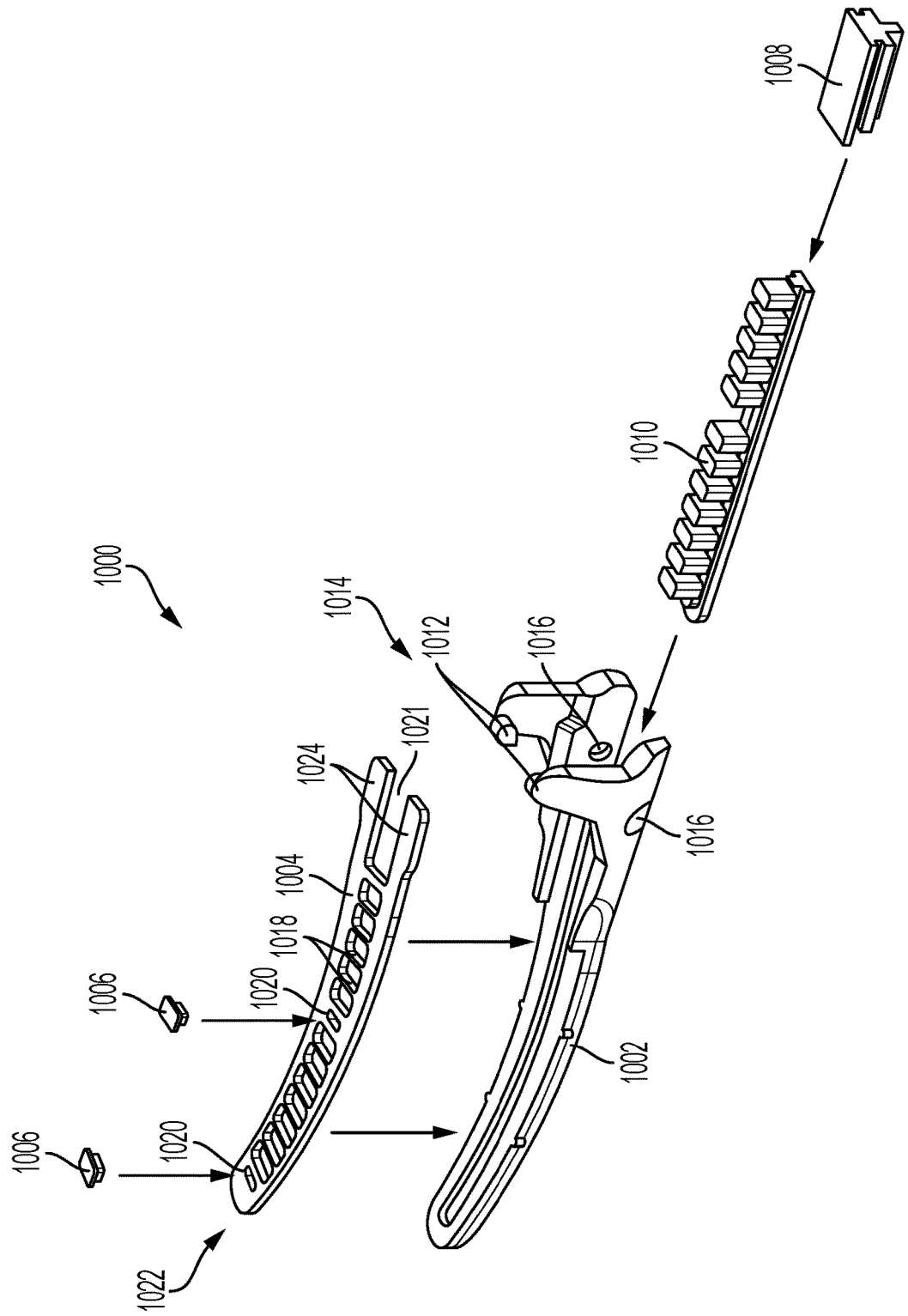
FIG. 2 is an exploded view of the clamp arm shown in FIG. 1, according to at least one aspect of the present disclosure.

FIG. 2 is an exploded view of the clamp arm 1000 shown in FIG. 1, according to at least one aspect of the present disclosure. In various aspects, the electrode 1004 is made of a metallic spring material attached at a proximal end 1014 of the frame 1002 of the clamp arm 1000 such that the electrode 1004 can deflect. The metallic spring electrode 1004 defines openings 1018 for receiving therethrough elements of the clamp arm pad 1010 and defines additional openings 1020, 1021 for receiving the gap pads 1006, 1008 to set a minimum gap between the electrode 1004 and the ultrasonic blade. At least one of the gap pads 1006 is disposed on a distal end 1022 of the electrode 1004. The gap pads 1006, 1008 are thus integrated with the electrode 1004. In this configuration, the electrode 1004 prevents tissue from accumulating around the biasing mechanism, e.g., cantilevered spring, that can impact the performance of the electrode 1004. This configuration also minimizes the binding between the wearable clamp arm pads 1010 and the biasing spring electrode 1004, increases the strength of the electrode 1004 to the clamp arm connection, minimizes inadvertent release of the clamp arm pads 1018 by attaching the gap pads 1006, 1008 to the electrode 1004, and balance matches the surface area/current densities between electrodes. The electrode 1004 is attached to the frame 1002 by two protrusions 1024. The electrode protrusions 1024 are attached to the proximal end 1014 of the frame 1002 as shown in FIGS. 3 and 4.

Figure 3:
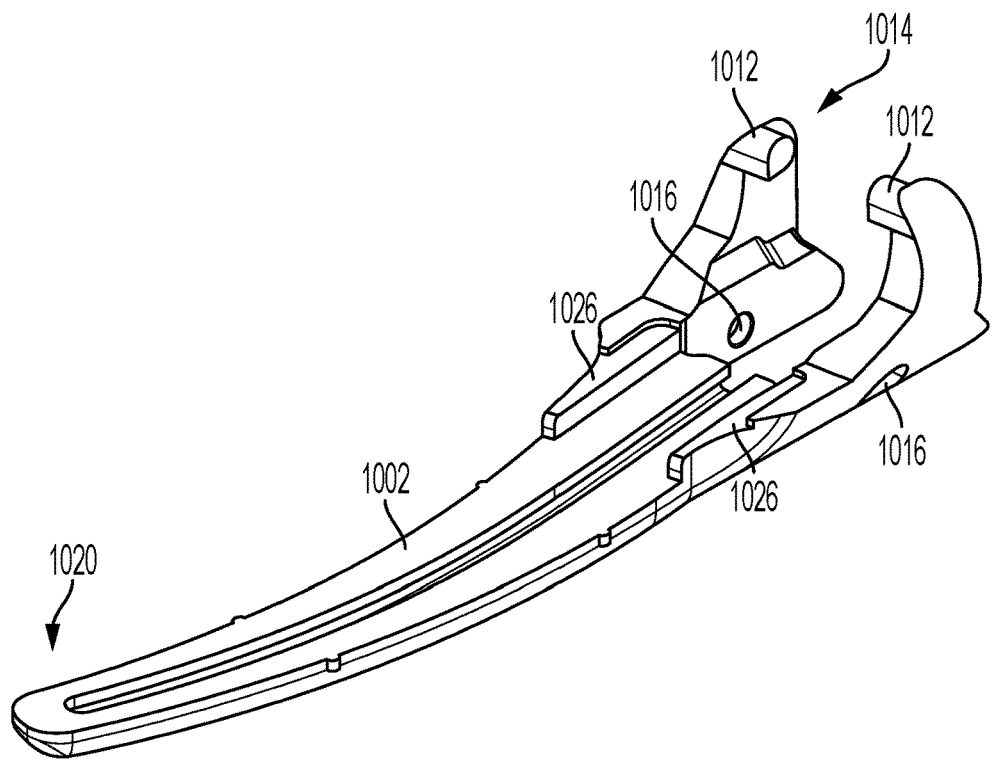
FIGS. 3 and 4 are perspective views of the frame, according to at least one aspect of the present disclosure.
Figure 4:
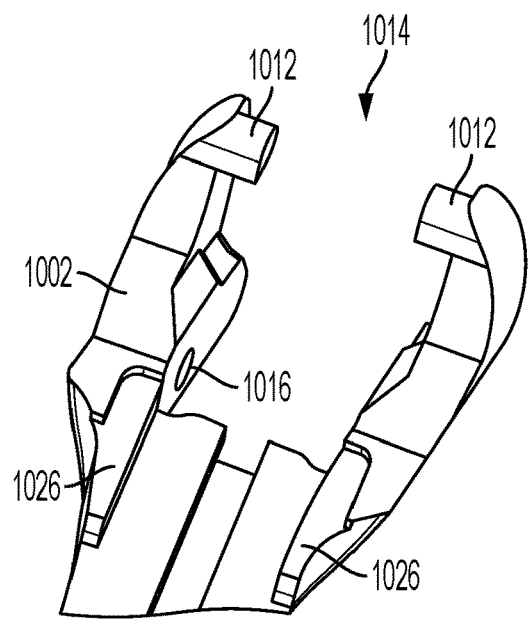

FIGS. 3 and 4 are perspective views of the frame 1002, according to at least one aspect of the present disclosure. These views illustrate the connection surfaces 1026 on the proximal end 1014 of the fame 1002 for attaching the proximal end of the electrode 1004 to the frame 1002. In one aspect, the electrode protrusions 1024 are welded to the connection surfaces 1026 of the frame 1002 such that the electrode 1004 behaves in a deflectable manner.

Figure 5:
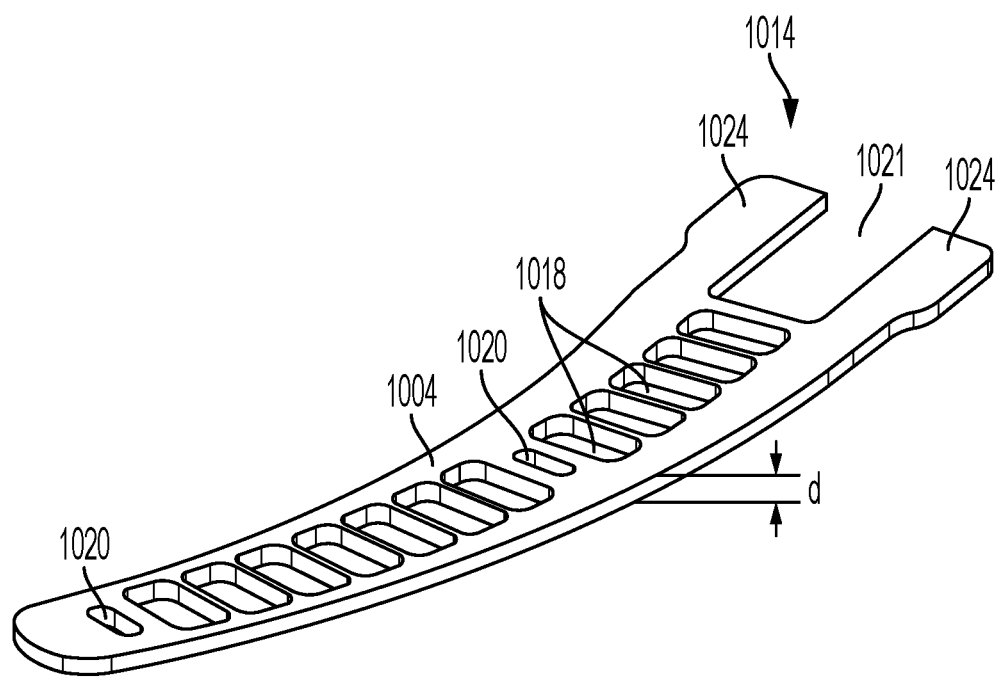
FIG. 5 is a perspective view of the electrode, according to at least one aspect of the present disclosure.
Figure 8:
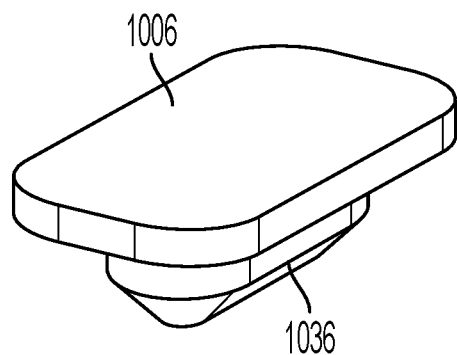
FIG. 8 is a perspective top view of the small gap pad, according to at least one aspect of the present disclosure.
Figure 9:
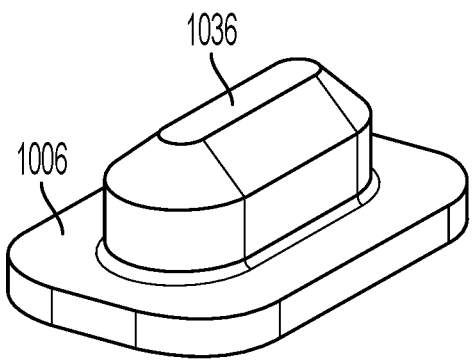
FIG. 9 is a perspective bottom view of the small gap pad shown in FIG. 8.

FIG. 5 is a perspective view of the electrode 1004, according to at least one aspect of the present disclosure. This view illustrates the bias in the electrode 1004 made of spring material as indicated by the curvature of the electrode 1004 along a longitudinal length. The openings 1018, 1020, 1021 for receiving the gap pads 1006, 1008 and the clamp arm pads 1010. In one aspect, the electrode 1004 has a thickness "d" of 0.010" and may be selected within a range of thicknesses of 0.005" to 0.015", for example. With reference also to FIGS. 8 and 9, the openings 1020 are sized and configured to receive a protrusion 1036 defined on a bottom portion of the gap pads 1006.

Figure 6:
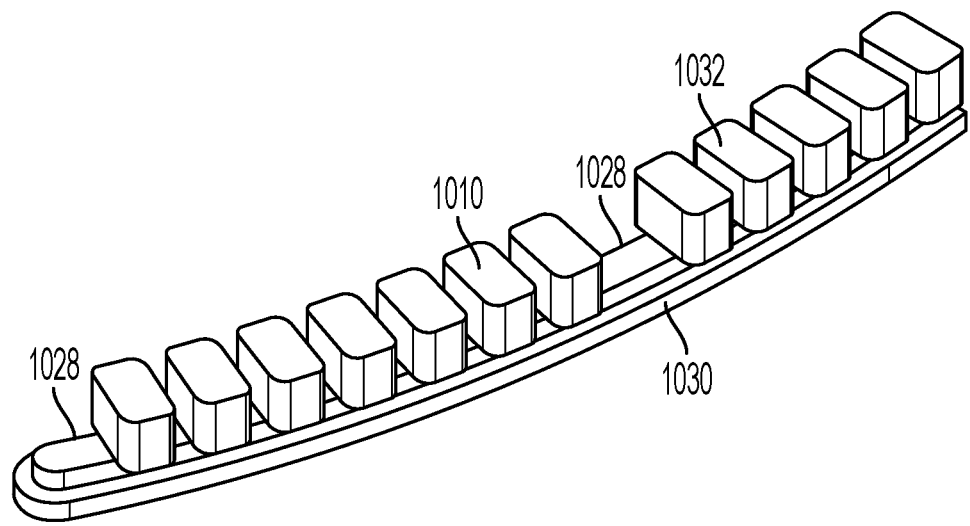
FIG. 6 is a perspective view of the clamp arm pad, according to at least one aspect of the present disclosure.

FIG. 6 is a perspective view of the clamp arm pad 1010, according to at least one aspect of the present disclosure. The clamp arm pad 1010 comprises a plurality of clamp arm elements 1032 protruding from a backbone 1030. Throughout this disclosure, the clamp arm elements 1032 also are referred to as "teeth." In one aspect, the clamp arm pad 1010 defines apertures 1028 in a position where the gap pads 1006 are located on the electrode 1004. With reference also to FIGS. 8 and 9, the apertures 1028 defined by the clamp arm pad 1010 are sized and configured to receive the protrusion 1036 defined on a bottom portion of the gap pads 1006. In one aspect, the clamp arm pad 1010 material is softer than the gap pad 1006, 1008 material. In one aspect, the clamp arm pad 1010 is made of a non-stick lubricious material such as polytetrafluoroethylene (PTFE) or similar synthetic fluoropolymers of tetrafluoroethylene. PTFE is a hydrophobic, non-wetting, high density and resistant to high temperatures, and versatile material and non-stick properties. In contrast, the gap pads 1006, 1008 are made of a polyimide material, and in one aspect, is made of a durable high-performance polyimide-based plastic known under the tradename VESPEL and manufactured by DuPont or other suitable polyimide, polyimide polymer alloy, or PET (Polyethylene Terephthalate), PEEK (Polyether Ether Ketone), PEKK (Poly Ether Ketone Ketone) polymer alloy, for example. Unless otherwise noted herein below, the clamp arm pads and gap pads described herein below are made of the materials described in this paragraph.

Figure 7:
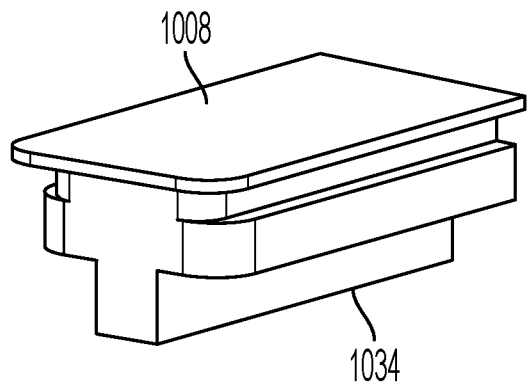
FIG. 7 is a perspective top view of the large gap pad, according to at least one aspect of the present disclosure.

FIG. 7 is a perspective top view of the large gap pad 1008, according to at least one aspect of the present disclosure. The large gap pad 1008 comprises a protrusion 1034 sized and configured to fit within the opening 1021 at the proximal end 1014 of the electrode 1004. FIG. 8 is a perspective top view of the small gap pad 1006, according to at least one aspect of the present disclosure. FIG. 9 is a perspective bottom view of the small gap pad 1006 shown in FIG. 8. As shown in FIGS. 8 and 9, the small gap pads 1006 include a protrusion 1036 at the bottom portion sized and configured to be received within the openings 1020 defined by the electrode 1004 and the apertures 1028 defined by the clamp arm pad 1010. The small and large gap pads 1006, 1008 are made of a polyimide material, and in one aspect, is made of a durable high-performance polyimide-based plastic known under the tradename VESPEL and manufactured by DuPont. The durability of the polyimide material ensures that the electrode gap remains relatively constant under normal wear and tear.

In one aspect, the present disclosure also provides additional end-effector configurations for combination ultrasonic and bipolar RF energy devices. This portion of the disclosure provides end-effector configurations for use in combination ultrasonic and bipolar RF energy devices. In these configurations, the end-effector maintains a consistent gap between the RF electrode gap and the ultrasonic blade, which functions as one pole of the bipolar RF circuit, and the clamp arm, which functions as the opposite pole of the bipolar RF circuit. In conventional end-effector configurations, the electrode gap is set by a soft PTFE clamp arm pad which may be subject to wear during surgery. When the clamp arm pad wears through, the ultrasonic blade can contact the electrode resulting in blade breakage or an electrical short circuit, both of which are undesirable.

To overcome these and other limitations, various aspects of the present disclosure incorporate a deflectable RF electrode in combination with a clamp arm pad comprising a non-stick lubricious compliant (e.g., PTFE) pad fixed to the clamp arm. The RF electrode contains wear-resistant, electrically nonconductive pads which contact the blade to set the blade-to-electrode gap. The compliant clamp arm pad extends through openings defined by the electrode and reacts to the clamping force from the ultrasonic blade. As the compliant clamp arm pad wears, the electrode deflects to maintain a constant gap between the blade and the electrode. Such configuration provides a consistent gap between the electrode and the ultrasonic blade throughout the life of the device, prevents shorting and ultrasonic blade breakage, which can occur when the ultrasonic blade touches the electrode, and enables the electrode material to be positioned directly on the side that is opposite the ultrasonic blade to improve sealing performance. The electrode is fixed to the clamp jaw at the proximal end and is free to deflect at the distal end. Accordingly, throughout this disclosure the electrode may be referred to as a cantilever beam electrode or deflectable electrode.

Figure 10:
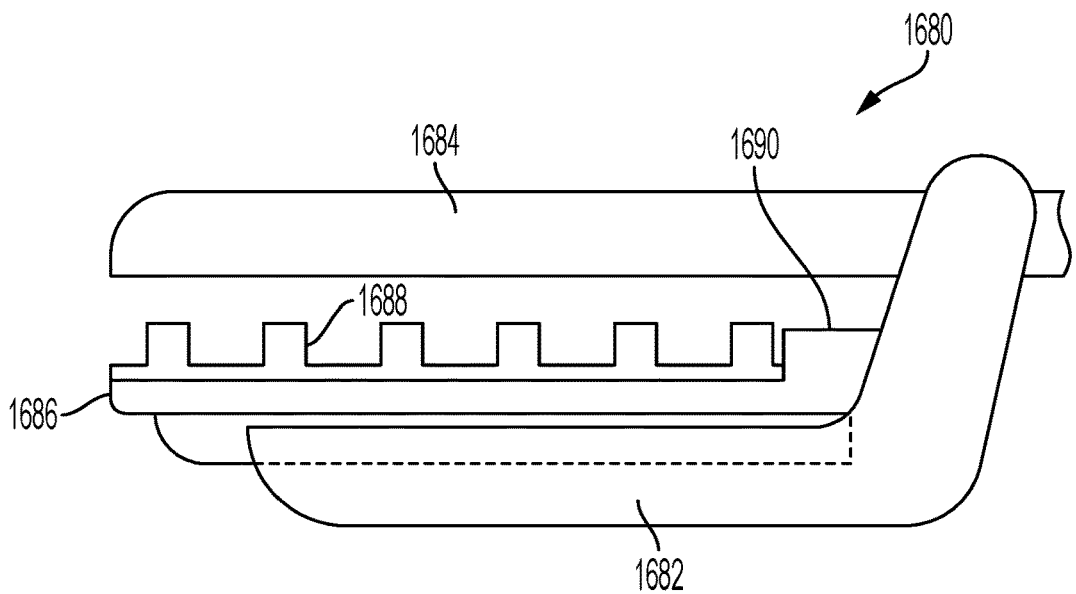
FIGS. 10-12 illustrate an effector comprising a shortened clamp arm for deflectable/cantilever electrode applications, according to various aspects of the present disclosure, where.
Figure 11:
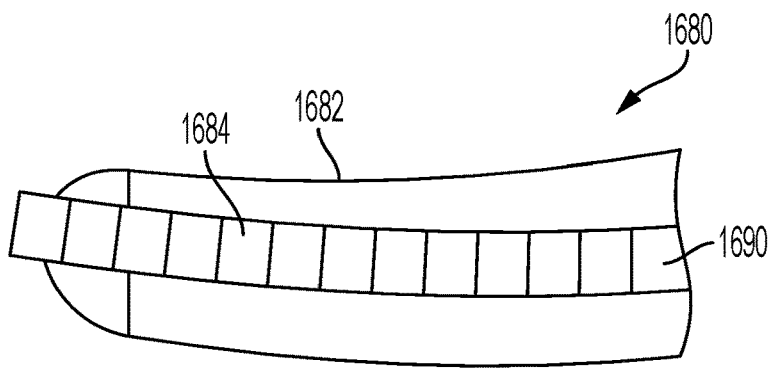
Figure 12:
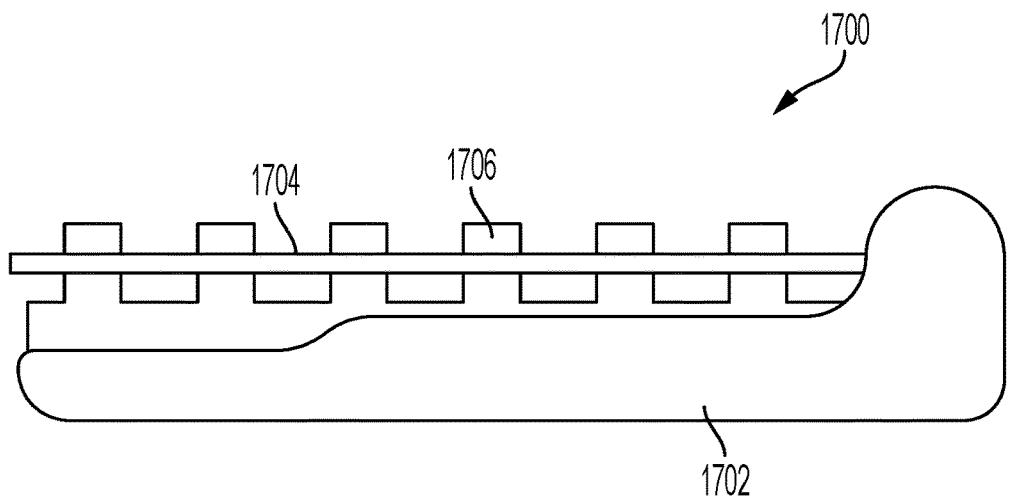

In one aspect, the present disclosure provides asymmetric cooperation of the clamp arm/electrode/pad to effect the ultrasonic blade-RF electrode interaction. In one aspect, the present disclosure provides a shortened clamp arm. FIGS. 10-12 illustrate an effector comprising a shortened clamp arm for deflectable/cantilever electrode applications, according to various aspects of the present disclosure. In one aspect, the end-effector is configured for asymmetric cooperation of the clamp arm, electrode, and clamp arm pad to effect the ultrasonic blade/RF electrode interaction. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

In one aspect, a distal end of the clamp arm is shortened and a length of the clamp arm pad is kept the same length such that a distal end of the clamp arm pad extends beyond the distal end of the clamp arm. This would allow the electrode to hyper-extend to minimize potential for electrically shorting the distal end of the clamp arm. It also may have the benefit of extending the life of the clamp arm pad because of the additional exposed clamp arm pad material to be worn through. This configuration also can eliminate the use of the distal and middle gap setting clamp arm pads, previously referred to herein, for example, as wear resistant clamp arm pads for setting and maintaining a gap between the electrode and the ultrasonic blade.

FIG. 10 is a side view of an end-effector 1680 comprising a shortened clamp arm 1682, an ultrasonic blade 1684, an electrode 1686, and a clamp arm pad 1688, according to at least one aspect of the present disclosure. FIG. 11 is a top view of the end-effector 1680. As shown in FIGS. 10-11, the ultrasonic blade 1684 and the electrode 1686 are substantially the same length. The clamp arm 1682 is shortened to allow the electrode 1686 to overextend to prevent an electrical short circuit. In one aspect, a gap setting pad 1690 is provided at a proximal end 1692 of the end-effector 1680.

FIG. 12 illustrates a clamp arm 1700 comprising a clamp jaw 1702, an electrode 1704, and a clamp arm pad 1706, according to at least one aspect of the present disclosure. Free up space distally on clamp arm. The clamp arm 1700 is configured for use with an end-effector comprising an ultrasonic blade as disclosed in other sections herein. This configuration frees up space distally 1708 on the clamp jaw 1702. The clamp arm pad 1706 (e.g., PTFE) is fully supported underneath, but space is freed in the t-slot region and on the side walls to allow for more clamp arm pad 1706 burn through and further deflection of the electrode 1704 away from the ultrasonic blade (not shown).

In one aspect, the present disclosure provides an end-effector that employs the thermal behavior of the pad to deflect the electrode. In one aspect, the length of the clamp arm pad may be the same length as the ultrasonic blade and as the clamp arm pad expands or changes shape due to pressure or heat, the thermal expansion properties of the clamp arm pad material (e.g., PTFE) can be used to deflect the electrode out of the path of the ultrasonic blade.

In one aspect, a non-biased electrode and pad are provided. The non-biased but deflectable pad varies in position with respect to the clamp arm as the pad wears. The non-biased electrode is configured to minimize contact between the ultrasonic blade and the RF electrode. The clamp arm pad comprises a feature for securing the electrode to the clamp arm pad. In one aspect, as the height of the clamp arm pad wears or is cut through, the height of the electrode with respect to the clamp arm is progressively adjusted. In another aspect, once the clamp arm is moved away from the ultrasonic blade the electrode remains in its new position. The electrode is fixed to the clamp arm at the proximal end and is free to deflect at the distal end. Accordingly, throughout this disclosure the electrode may be referred to as a cantilever beam electrode or as a deflectable electrode.

Configurations of end-effectors comprising a deflectable/cantilever electrode described hereinabove with respect to FIGS. 1-12 may be combined with a biased electrode as described herein below with respect to FIGS. 13-18.

In one aspect, the present disclosure provides an end-effector for a combination ultrasonic/bipolar RF energy surgical device that employs pressure or clamp jaw compression to adjust the height of the electrode as the clamp arm pad wears. In one aspect, the clamp arm pad follows the clamp arm biased electrode with wearable stops. In one aspect, the clamp arm pad contains a feature for securing the electrode to the pad. As the pad height wears or is cut through, the electrode height with respect to the clamp arm is progressively adjusted. Once the clamp arm is moved away from the ultrasonic blade, the electrode stays in its new position.

Achieving sufficient clamp arm pad life on a combination ultrasonic/bipolar RF energy surgical device requires maintaining a sufficiently small yet non-zero clamp arm pad-to-electrode gap throughout the life of the instrument to provide desirable ultrasonic and bipolar RF tissue effects. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

The existing (seed) electrode is a flat electrode, which is practically horizontal or parallel to the clamp arm in the free state (no load). The electrode is fixed to the clamp arm at the proximal end and is free to deflect at the distal end. Accordingly, throughout this disclosure the electrode may be referred to as a cantilever beam electrode or as a deflectable/cantilever electrode. When clamped on tissue, the tissue loads the electrode, causing it to deflect toward the clamp arm.

In one aspect, the electrode "follows" the pad as it wears. In this aspect, the electrode is biased toward the clamp arm in the free state (whether by being a formed/curved electrode, or by attaching/welding the electrode non-parallel to the clamp arm) using any suitable fastening technique such as welding, laser welding, brazing, soldering, pressing, among other fastening techniques. Wearable stop features (on the pad or elsewhere) keep the electrode away from the clamp arm, until said stop features are worn away during use. Once worn away, the electrode is able to approach the clamp arm. These features could be tooth or ratchet shaped, a vertical taper, or other.

In one aspect, the present disclosure provides a deflectable/cantilever electrode, wherein in a free state, the electrode is biased toward clamp arm and may attached at an angle and made of a preformed curve using any suitable fastening technique such as welding, laser welding, brazing, soldering, pressing, among other fastening techniques.

In one aspect, the present disclosure provides an end-effector with a deflectable/cantilever electrode comprising wearable stop features to prevent the electrode from reaching or contacting the clamp arm. As the stop features wear, the electrode moves toward the clamp arm until it reaches the next stop. In one aspect, the stop features wear simultaneously with the clamp arm pad to maintain the appropriate gap between the clamp arm pad and the electrode. The features may be entirely separate from the clamp arm pad. The features can be configured to withstand clamping loads, but wear away due to heat (melting/flowing) or abrasion. Possible examples include teeth on one or more clamp arm pads (PTFE, polyimide, or other) and tapered profile on one or more clamp arm pads (PTFE, polyimide, or other).

Figure 13:
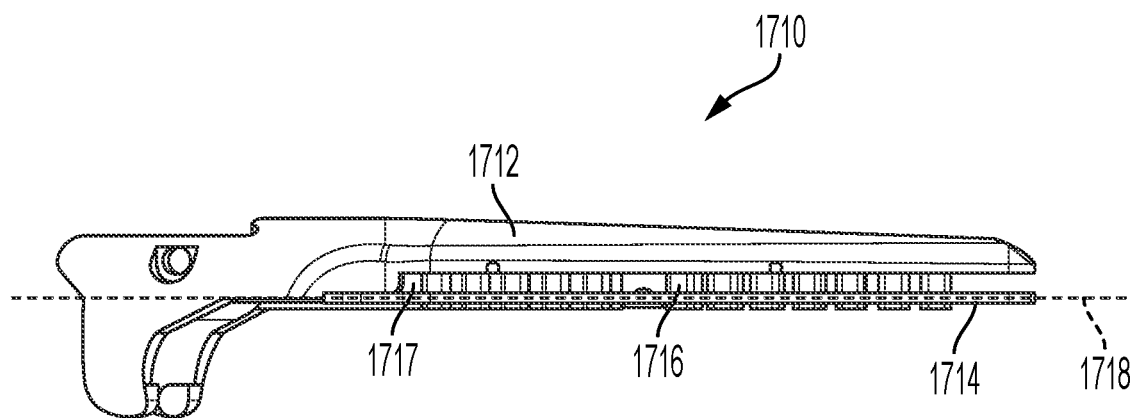
FIG. 13 illustrates an end-effector clamp arm comprising a clamp jaw, an electrode, and a clamp arm pad, according to at least one aspect of the present disclosure.

FIG. 13 illustrates an end-effector clamp arm 1710 comprising a clamp jaw 1712, an electrode 1714, and a clamp arm pad 1716, according to at least one aspect of the present disclosure. The clamp arm 1710 is configured for use with an end-effector comprising an ultrasonic blade (not shown) as described throughout this disclosure. The clamp arm 1710 also comprises a wear resistant gap pad 1717 to set a gap between the electrode 1714 and the ultrasonic blade. As shown, in the free state, the electrode 1714 is biased in a level or horizontal 1718 orientation. The electrode 1714 is fixed to the clamp jaw 1712 at the proximal end and is free to deflect at the distal end. Accordingly, throughout this disclosure the electrode 1714 may be referred to as a cantilever beam electrode or as a deflectable electrode.

Figure 14:
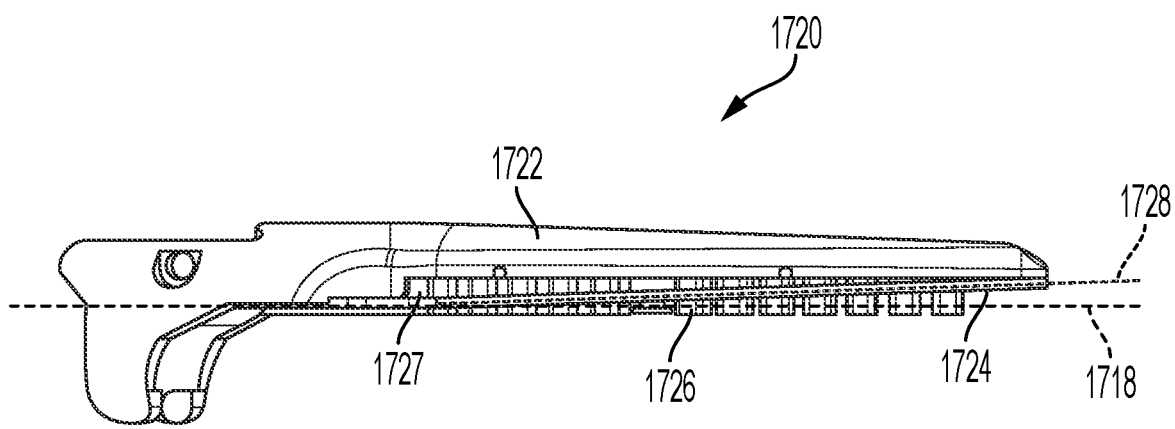
FIG. 14 illustrates an end-effector clamp arm comprising a clamp jaw, an electrode, and a clamp arm pad, according to at least one aspect of the present disclosure.

FIG. 14 illustrates an end-effector clamp arm 1720 comprising a clamp jaw 1722, an electrode 1724, and a clamp arm pad 1726, according to at least one aspect of the present disclosure. The clamp arm 1720 is configured for use with an end-effector comprising an ultrasonic blade (not shown) as described throughout this disclosure. The clamp arm 1720 also comprises a wear resistant gap pad 1727 to set a gap between the electrode 1724 and the ultrasonic blade. As shown, in the free state, the electrode 1724 is configured pre-formed, bent, or is otherwise biased toward the clamp jaw 1722 along line 1728 away from the horizontal 1718 orientation. The electrode 1724 is fixed to the clamp arm 1720 at the proximal end and is free to deflect at the distal end. Accordingly, throughout this disclosure the electrode 1724 may be referred to as a cantilever beam electrode or as a deflectable electrode. To prevent the biased electrode 1724 from bending toward the clamp jaw 1722 under the biasing force, the clamp arm 1720 further comprises a retainer to prevent the biased electrode 1724 from bending toward the clamp jaw 1722 and maintaining the biased electrode 1724 in a substantially flat configuration (e.g., parallel, level, or horizontal) relative to the ultrasonic blade. Examples of retainers such as a retainer tooth 1738 and a retainer wall 1760 with a tapered profile are described below in FIGS. 15-18.

Figure 15:
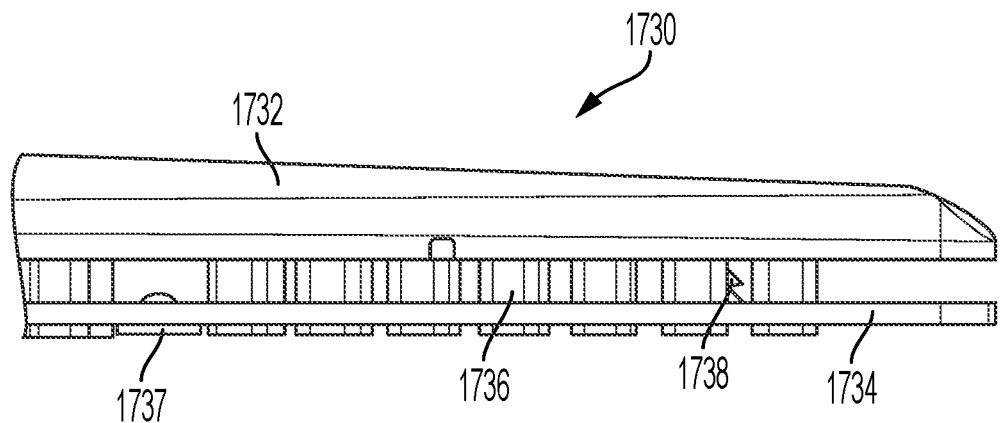
FIG. 15 illustrates an end-effector clamp arm comprising a clamp jaw, an electrode, and a clamp arm pad, according to at least one aspect of the present disclosure.
Figure 16:
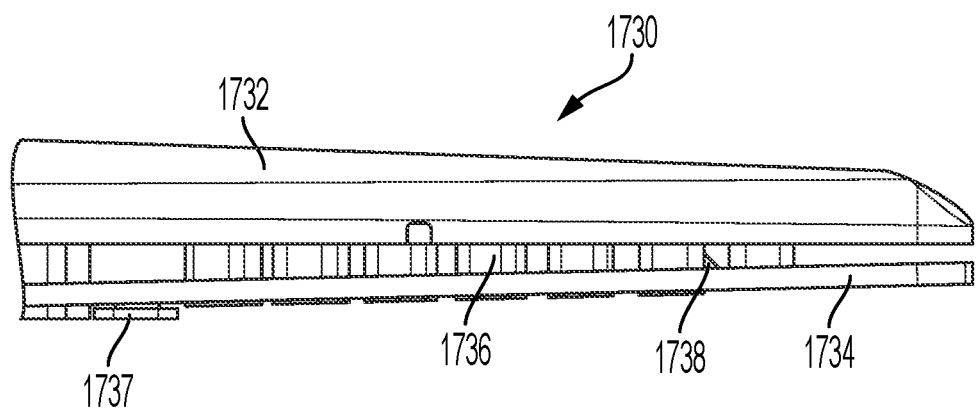
FIG. 16 illustrates bottom retainer tooth that is worn away such that the electrode can move toward the clamp jaw due to the pre-formed curve, according to at least one aspect of the present disclosure.

FIG. 15 illustrates an end-effector clamp arm 1730 comprising a clamp jaw 1732, an electrode 1734, and a clamp arm pad 1736, according to at least one aspect of the present disclosure. The clamp arm 1730 is configured for use with an end-effector comprising an ultrasonic blade (not shown) as described throughout this disclosure. The clamp arm 1730 also comprises a wear resistant gap pad 1737 to set a gap between the electrode 1744 and the ultrasonic blade. In the free state, the electrode 1734 is configured pre-formed curved, bent, or otherwise biased toward the clamp jaw 1732. However, a retainer tooth 1738, or similar feature, is provided on the clamp arm pad 1736 to prevent the electrode 1734 from springing in toward the clamp jaw 1732. In FIG. 16, when the bottom retainer tooth 1738 is worn away, the electrode 1734 can move toward the clamp jaw 1732 due to the pre-formed curve, according to at least one aspect of the present disclosure. The electrode 1734 is fixed to the clamp arm 1730 at the proximal end and is free to deflect at the distal end. Accordingly, throughout this disclosure the electrode 1734 may be referred to as a cantilever beam electrode or as a deflectable electrode.

Figure 17:
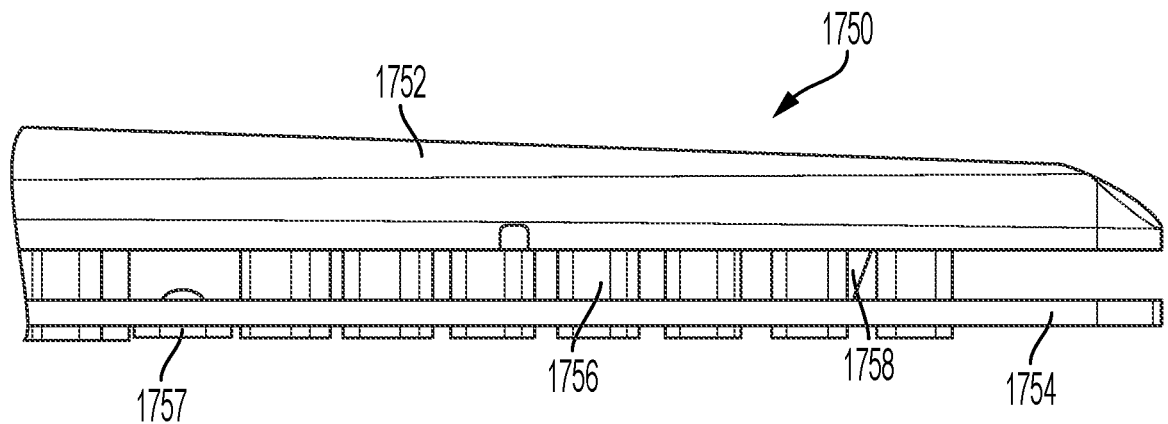
FIG. 17 illustrates an end-effector clamp arm comprising a clamp jaw, an electrode, and a clamp arm pad, according to at least one aspect of the present disclosure.
Figure 18:
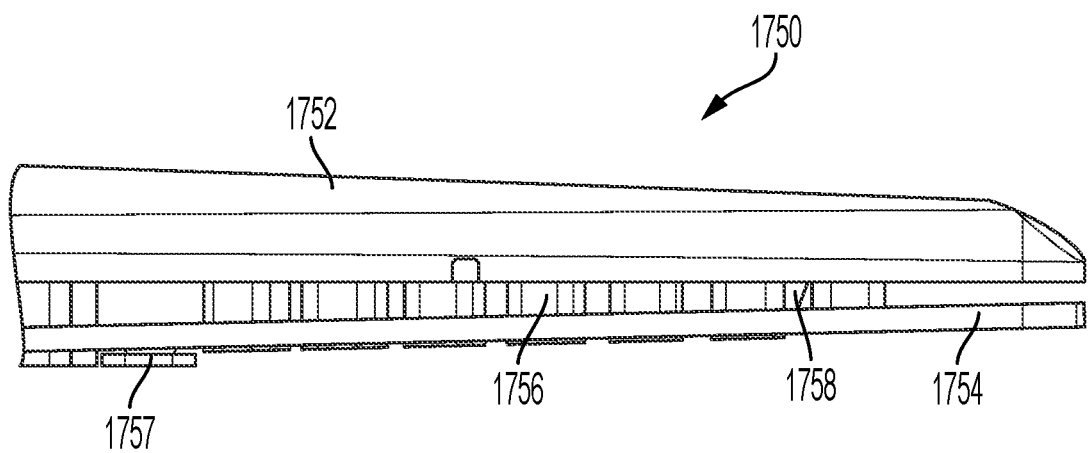
FIG. 18 illustrates a retainer wall with a tapered profile worn away such that there is sufficient melting/flowing away from the retainer wall with the tapered profile region to allow the electrode to move toward the clamp jaw due to the pre-formed curve, according to at least one aspect of the present disclosure.

FIG. 17 illustrates an end-effector clamp arm 1750 comprising a clamp jaw 1752, an electrode 1754, and a clamp arm pad 1756, according to at least one aspect of the present disclosure. The clamp arm 1750 is configured for use with an end-effector comprising an ultrasonic blade (not shown) as described throughout this disclosure. The clamp arm 1750 also comprises a wear resistant gap pad 1757 to set a gap between the electrode 1754 and the ultrasonic blade. In the free state, the electrode 1754 is configured pre-formed with a curve, bent, or otherwise biased toward 1758 the clamp jaw 1752. However, a retainer wall 1760 having a tapered profile, or similar feature, is provided on the clamp arm pad 1756 to prevent the electrode 1754 from springing in toward the clamp jaw 1752.

In FIG. 17, when the tapered profile retainer wall 1760 is worn away, there is sufficient melting/flowing away from the tapered profile retainer wall 1760 region to allow the electrode 1754 to move toward the clamp jaw 1752 due to the pre-formed curve, according to at least one aspect of the present disclosure. The electrode 1754 is fixed to the clamp jaw 1752 at the proximal end and is free to deflect at the distal end. Accordingly, throughout this disclosure the electrode 1754 may be referred to as a cantilever beam electrode or as a deflectable electrode.

In one aspect, the present disclosure provides an end-effector for a combination ultrasonic/bipolar RF energy surgical device that employs a constant pressure distribution biasing mechanism. In one aspect, the end-effector includes an elastic compressible support for mounting and insulating a deflectable electrode. In one aspect, a hollow honeycomb or chambered elastomer support attachment cushion can be employed to allow all or part of the electrode attached to it to deflect but be biased towards the ultrasonic blade. This configuration could provide the added benefit of thermally insulating the electrode from the rest of the metallic clamp jaw. This would also provide an elastomer "curtain" around the electrode to minimize tissue accumulation behind the electrode. In one aspect, a non-strut deflectable geometry for the elastomer cells will enable the deflection force to be held constant over a predefined range of deflections. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

The above configuration prevents lateral skew of the electrode under compression to prevent shorting. Further, the deflectable electrode is affixed to the elastomer and the elastomer is affixed to the metallic clamp arm. The solid height of the spring is limited from driving allowable compression while maintaining as much metallic clamp arm as possible. Thermal conduction from tissue interface is balanced and minimizes—impacts lesion formation and symmetry, cycle time, and residual thermal energy.

Configurations of end-effectors comprising a deflectable/cantilever electrode described hereinabove with respect to FIGS. 1-12 may be combined with a flexible electrode disposed above a lattice cushion and a plurality of hard spacers to set a gap between the flexible electrode and the ultrasonic blade as described herein below with respect to FIGS. 19-21.

Configurations of a biased electrode as described hereinabove with respect to FIGS. 13-18 may be combined with a flexible electrode disposed above a lattice cushion and a plurality of hard spacers to set a gap between the flexible electrode and the ultrasonic blade as described herein below with respect to FIGS. 19-21.

Configurations of end-effectors comprising a deflectable/cantilever electrode described hereinabove with respect to FIGS. 1-12 in combination with a biased electrode as described hereinabove with respect to FIGS. 13-18 may be combined with a flexible electrode disposed above a lattice cushion and a plurality of hard spacers to set a gap between the flexible electrode and the ultrasonic blade as described herein below with respect to FIGS. 19-21.

FIGS. 19-20 illustrate an end-effector 1810 comprising a clamp arm 1812, an ultrasonic blade 1814, a lattice cushion 1816, a flexible electrode 1818 disposed above the lattice cushion 1816, and a plurality of hard spacers 1820 to set a gap between the flexible electrode 1818 and the ultrasonic blade 1814, according to at least one aspect of the present disclosure. FIG. 21 is an exploded view of the end-effector 1810 shown in FIGS. 19-20. A clamp arm pad 1822 is disposed inside a slot 1825 formed within the lattice cushion 1816. The lattice cushion 1816 acts as a spring-like element. The hard spacers 1820 are used to set a gap between the flexible electrode 1818 and the ultrasonic blade 1814.

In FIG. 19 the clamp arm 1812 is open and tissue 1824 of non-uniform thickness ($T_{1a}$, $T_{2a}$, $T_{3a}$) is disposed over the flexible electrode 1818. In FIG. 20 the clamp arm 1812 is closed to compress the tissue 1824. The lattice cushion 1816 on the clamp arm 1812 results in consistent tissue 1824 ($T_{1b}$, $T_{2b}$, $T_{3b}$) compression across variable thickness tissue 1824 ($T_{1a}$, $T_{2a}$, $T_{3a}$), such that:

$$\frac{T_{1a}}{T_{1b}} = \frac{T_{2a}}{T_{2b}} = \frac{T_{3a}}{T_{3b}}$$

Additional background disclosure may be found in EP3378427, WO2019/006068, which are herein incorporated by reference in their entirety.

In one aspect, the present disclosure provides an end-effector for a combination ultrasonic/bipolar RF energy surgical device with means for insuring distal tip contact with bias using a zero gap bipolar RF energy system. In various aspects, the present disclosure provides a deflectable electrode for a combination ultrasonic/bipolar RF energy surgical device with a higher distal bias than proximal bias. In one aspect, the present disclosure provides a combination energy device comprising a bipolar electrode that is deflectable with respect to the clamp arm. The combination energy device comprises features to change the mechanical properties of the tissue compression proximal to distal to create a more uniform or differing pattern of pressure than due to the clamping forces alone. In one aspect, the present disclosure provides a non-linear distal distributing mechanism and in another aspect the present disclosure provides electrical non-linear distribution of energy density. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

Configurations of end-effectors comprising a deflectable/cantilever electrode described hereinabove with respect to FIGS. 1-12 may be combined with a conductive polymer clamp arm pad as described herein below with respect to FIGS. 22-36.

Configurations of a biased electrode as described hereinabove with respect to FIGS. 13-18 may be combined with a conductive polymer clamp arm pad as described herein below with respect to FIGS. 22-36.

Configurations of a flexible electrode disposed above a lattice cushion and a plurality of hard spacers to set a gap between the flexible electrode and the ultrasonic blade as described hereinabove with respect to FIGS. 19-21 may be combined with a conductive polymer clamp arm pad as described herein below with respect to FIGS. 22-36.

Configurations of a biased electrode as described hereinabove with respect to FIGS. 13-18 may be combined with a flexible electrode disposed above a lattice cushion and a plurality of hard spacers to set a gap between the flexible electrode and the ultrasonic blade as described hereinabove with respect to FIGS. 19-21 may be combined with a conductive polymer clamp arm pad as described herein below with respect to FIGS. 22-36.

Configurations of a biased electrode as described hereinabove with respect to FIGS. 13-18 may be combined with a flexible electrode disposed above a lattice cushion and a plurality of hard spacers to set a gap between the flexible electrode and the ultrasonic blade as described hereinabove with respect to FIGS. 19-21 may be combined with a conductive polymer clamp arm pad as described herein below with respect to FIGS. 22-36.

Configurations of end-effectors comprising a deflectable/cantilever electrode described hereinabove with respect to FIGS. 1-12 in combination with a biased electrode as described hereinabove with respect to FIGS. 13-18 may be combined with a conductive polymer clamp arm pad as described herein below with respect to FIGS. 22-36.

Configurations of end-effectors comprising a deflectable/cantilever electrode described hereinabove with respect to FIGS. 1-12 in combination with a biased electrode as described hereinabove with respect to FIGS. 13-18 may be combined with a flexible electrode disposed above a lattice cushion and a plurality of hard spacers to set a gap between the flexible electrode and the ultrasonic blade as described hereinabove with respect to FIGS. 19-21 may be combined with a conductive polymer clamp arm pad as described herein below with respect to FIGS. 22-36.

In various aspects, the present disclosure provides a combination ultrasonic/bipolar RF energy surgical device comprising an ultrasonic pad with partially or fully electrically conductive portions such that the pad behaves as both the blade support/wear pad and the bipolar RF electrode. In one aspect, the present disclosure provides a partially conductive clamp arm pad to enable electrode wear and minimize short circuiting in a combination bipolar RF and ultrasonic energy device where the clamp arm pad has conductive and non-conductive portions allowing it to act as one of the RF electrodes while also acting as a wearable support structure for the ultrasonic blade. In another aspect, the present disclosure provides conductive portions around the perimeter of the clamp arm pad and not positioned directly on the side that is opposite the ultrasonic blade contact area. In another aspect, a portion of the conductive clamp arm pad is degradable or wearable preventing contact from the ultrasonic blade from interrupting the conductivity of the remaining portions of the conductive clamp arm pad.

In one aspect, the present disclosure provides an end-effector for a combination ultrasonic/bipolar RF energy surgical device comprising a conductive polymer ultrasonic clamp arm pad. In one aspect, the end-effector comprises a clamp arm pad doped with tin oxide. FIG. 22 is a section view of a conductive polymer clamp arm pad 2440, according to at least one aspect of the present disclosure. The conductive polymer clamp arm pad 2440 comprises tin oxide 2442 ($SnO_2$) embedded in a polymer material 2444, such as Teflon (PTFE), to make the clamp arm pad 2440 electrically conductive. The doping may be achieved using a cold spray process. Once doped, the conductive polymer clamp arm pad 2440 can achieve traditional ultrasonic tissue clamp arm pad functions such as, for example, contacting the ultrasonic blade, absorbing heat from the ultrasonic blade, and assisting in tissue grasping and clamping. The tin oxide doped clamp arm pad 2440 functions as one of the two electrodes or poles of the bipolar RF circuit to deliver RF energy to tissue grasped between the ultrasonic blade and the clamp arm pad 2440. The tin oxide doped clamp arm pad 2440 is biocompatible, electrically conductive, thermally conductive, enables a large portion of the clamp arm pad 2440 to be used to improve wear resistance of the clamp arm pad 2440, and is white in color. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

In one aspect, the present disclosure provides a conductive polymer ultrasonic clamp arm pad as an electrode replacement. To improve the life of the ultrasonic clamp arm pad and improve the RF tissue effects, the present disclosure provides an electrode that is improved, easier to make, and less costly to make. In one aspect, the present disclosure provides a clamp arm pad comprising hard polyimide polymer layers and electrically conductive layers to allow the clamp arm pad to achieve traditional functions as well as carry bipolar electricity to eliminate the need for a separate electrode in the clamp arm of a combined energy end-effector. In this manner, the clamp jaw can be me manufactured in a manner similar to the ultrasonic-only clamp jaw with the new clamp arm pad material swapped for the traditional ultrasonic-only clamp arm pad. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

Benefits include improved ultrasonic performance, including clamp arm pad wear, similar to current ultrasonic-only instruments because there are no electrode gaps between elements "squares" of polymer. The cost of the improved clamp jaw will be similar to current ultrasonic-only clamp jaws because of the need for a separate electrode component is eliminated and provides multiple small polymer square elements. In addition, the manufacturing steps needed to make the clamp jaw are the same as the manufacturing steps required for making current ultrasonic-only clamp jaws. Manufacturing the improved clamp jaw requires only the substitution of the clamp arm pad and does require the production of an additional electrode component to add to the clamp jaw and eliminates assembly steps.

FIG. 23 is a perspective view of a clamp arm pad 2450 configured to replace a conventional electrode, according to at least one aspect of the present disclosure. The clamp arm pad 2450 comprises electrically non-conductive layers 2452 and electrically conductive layers 2454 in a sandwich-like configuration. This configuration eliminates the need for a spring loaded electrode plate. The electrically non-conductive layers 2452 can be made of polymer, polyimide, Teflon (PTFE) and similar electrically non-conductive materials. The conductive layers 2454 may be made of thin electrically conductive polymer, metal foil, or carbon loaded material. The clamp arm pad 2450 may be manufactured such that the majority of the material contacting the ultrasonic blade are the electrically non-conductive layers 2452. In one aspect, 75% of the material contacting the ultrasonic blade is electrically non-conductive material such as PTFE. In another aspect, 85% of the material contacting the ultrasonic blade is electrically non-conductive material such as PTFE. In another aspect, 95% of the material contacting the ultrasonic blade is electrically non-conductive material such as PTFE. Additionally, as the clamp arm pad 2450 wears, the electrically conductive layers 2452 will still have available surface area to conduct RF electricity through the tissue and return electrode (e.g., ultrasonic blade).

FIG. 24 illustrates a clamp arm 2460 comprising the clamp arm pad 2450 described in FIG. 23, according to at least one aspect of the present disclosure. In the illustrated clamp arm 2460, the non-conductive layers 2452 have a large surface area compared to the conductive layers 2454, which appear as thin layers or foils.

FIG. 25 illustrates clamp arm pads configured as described in FIGS. 23-24, according to at least one aspect of the present disclosure. The first clamp arm pad 2470 is new and comprises teeth 2472 formed integrally therewith. The second clamp arm pad 2476 is new and without teeth. The third clamp arm pad 2478 worn and may be representative of either the first clamp arm pad 2470 or the second clamp arm pad 2476.

In one aspect, the present disclosure provides a composite clamp arm pad for a combination ultrasonic/bipolar RF energy surgical device. FIG. 26 is a section view of a clamp arm 2480 comprising a composite clamp arm pad 2482 in contact with tissue 2484, according to at least one aspect of the present disclosure. The end-effector 2480 comprises an upper clamp jaw 2486 and an adhesive 2488 to fixedly attach the composite clamp arm pad 2482 to the upper clamp jaw 2486. The composite clamp arm pad 2482 comprises thin electrically non-conductive layers 2490 (e.g., PTFE) and thin electrically conductive layers 2492 (e.g., thin stainless steel foils). The electrically conductive layers 2492 form the electrode portion of the composite clamp arm pad 2482. The electrically conductive layers 2492 (e.g., thin stainless steel foils) deform as the electrically non-conductive layers 2490 (e.g., PTFE) wear-away. The thickness of the electrically conductive layers 2492 enables the electrode portion of the composite clamp arm pad 2482 to deform as the electrically non-conductive layers 2490 wear-away. Advantageously, the electrically conductive layers 2492 conduct some of the heat away from the electrically non-conductive layers 2490 to keep the composite clamp arm pad 2482 cooler. As described above, the composite clamp arm pad 2482 is fixed to the upper clamp jaw 2486 by an adhesive 2488. The adhesive 2488 may be filled with carbon to make it electrically conductive and connect the electrode portions of the composite clamp arm pad 2482 to the upper clamp jaw 2486. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

In one aspect, the clamp arm pad comprises cooperative conductive and insulative portions. In one aspect, the present disclosure provides a combination ultrasonic/bipolar RF energy surgical device where the clamp arm pad has conductive and non-conductive portions allowing it to act as one of the RF electrodes while also acting as the wearable support structure for the ultrasonic blade. In another aspect, the conductive portions of the clamp arm pad are disposed around the perimeter of the pad and are not positioned directly on the side that is opposite the ultrasonic blade contact area. In another aspect, the conductive portion of the clamp arm pad is degradable or wearable to prevent contact with the ultrasonic blade from interrupting the conductivity of the remaining conductive portions of the clamp arm pad.

In one aspect, the present disclosure provides a clamp arm pad for use with combination ultrasonic/bipolar RF energy devices where portions of the clamp arm pad include electrically conductive material and other portions include electrically non-conductive material. The electrode is adapted and configured for use with a combination ultrasonic/RF energy device and is deflectable under load, where the electrode is one pole of the bipolar RF circuit and the ultrasonic blade is the opposite pole of the bipolar RF circuit.

In various aspects, the clamp arm pad may be manufactured using a variety of techniques. One technique comprises a two shot process of molding conductive and non-conductive materials in the same compression mold. This process effectively creates a single clamp arm pad with portions that can act as a bipolar RF electrode and others that will act as electrical insulators. Another technique comprises a super sonic cold spray embedding of metallic elements into a polymeric (e.g., Teflon, PTFE) pad or matrix. Another technique comprises 3D printing of multiple materials (e.g., Teflon, PTFE, and doped conductive polymer), printing/ transfer printing conductive or functional inks onto clamp arm pad. Another technique comprises metals and conductive materials (e.g., graphite/carbon) may be applied to the clamp arm pad using chemical vapor deposition, physical vapor deposition, sputter deposition, vacuum deposition, vacuum metalizing, or thermal spray. Another technique comprises conductive/loaded clamp arm pad electrodes provide continuity through the pad with micro randomly oriented and positioned particles or macro oriented structures (e.g., fabric, woven, long constrained fibers. Another technique comprises making the surface of the clamp arm pad conductive, providing wear-through electrodes, 3D printing, thermal spraying, cold spraying, coatings/paints/epoxies, sheet/foil/wire/film wrapping or laminating, vacuum metalizing, printing/transferring, among other techniques. In another technique, polymer electrodes filled with conductive material.

In one aspect, the end-effector clamp arm comprises a fixed polymer electrode. FIG. 27 illustrates a clamp arm 2500 comprising a clamp jaw 2502 to support a carrier 2504 or stamping attached to the clamp jaw 2502 and a clamp arm pad 2506, according to at least one aspect of the present disclosure. The clamp arm pad 2506 comprises an electrically conductive pad 2508 and an electrically non-conductive pad 2510. The electrically conductive pad 2508 is made of an electrically conductive polymer and acts as one of the electrodes of the bipolar RF circuit. The clamp jaw 2502 and the carrier 2504 may be made of stainless steel and attached using any suitable fastening technique such as welding, laser welding, brazing, soldering, pressing, among other fastening techniques, for example. The electrically conductive pad 2508 may comprise a polymer such as, for example, silicone, fluorosilicone, PTFE, and similar materials. The electrically conductive pad 2508 is overmolded onto the carrier 2504 using PTFE, silicone, fluorosilicone filled with silver particles, silver over aluminum, silver over copper, copper, nickel, graphite, carbon (amorphous, chopped fiber), gold, platinum, stainless steel, iron, or zinc, or combinations thereof.

FIG. 28 is a section view taken at section 28-28 in FIG. 27 and FIG. 29 is a section view taken at section 29-29 in FIG. 27. The sections views 28-28 and 29-29 show the clamp arm 2500 comprising the clamp jaw 2502, the support carrier 2504, the electrically conductive pad 2508, and the electrically non-conductive pad 2510.

FIG. 30 is a section view of an alternative implementation of a clamp arm 2520 comprising a clamp jaw 2522, an electrically conductive pad 2524, and an electrically non-conductive pad 2526, according to at least one aspect of the present disclosure. The electrically conductive pad 2524 is made of an electrically conductive polymer and acts as one of the electrodes in the bipolar RF circuit.

FIG. 31 is a section view of an alternative implementation of a clamp arm 2530 comprising a clamp jaw 2532, a carrier 2534 or stamping welded to the clamp jaw 2532, an electrically conductive pad 2536, and an electrically non-conductive pad 2538, according to at least one aspect of the present disclosure. The electrically conductive pad 2536 is made of an electrically conductive polymer and acts as one of the electrodes in the bipolar RF circuit. The electrically conductive pad 2536 is overmolded over the carrier 2534 or stamping.

In one aspect, the end-effector clamp arm comprises a film over metal insert molded electrode assembly. In one aspect, a film may be provided over a metal (e.g., stainless steel) insert molded electrode assembly. A film over metal such as stainless steel can be insert molded to form an electrode assembly. The film on the insert molded electrode may be etched to form micro-holes, slots, honeycomb, among other patterns, to enable conduction of RF energy as well as to cut the periphery of the component. The film may be formed onto or bond onto a stainless steel electrode using IML/FIM (In-Mold Labeling/Film Insert Molding) processes described herein below. The charged film electrode may be placed into a polymer injection mold tool to mold a polymer to the back of the electrode and film. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

FIG. 32 illustrates insert molded electrodes 2540, according to at least one aspect of the present disclosure. The insert molded electrode 2540 comprises an electrically conductive element 2546, a molded polymer pad 2548, and a film 2542 coating. Features 2550 such as micro-holes, slots, honeycomb, or similar features, are formed in the film 2542 to allow the passage of RF energy. Retention features 2552 also are formed on the film 2542. The side walls 2558 of the film 2542 extend below the bottom of the polymer pad 2548 may be folded around the bottom of the polymer pad 2548 and over molded with retention posts. The retention features 2552 are molded into the holes 2554 defined by the film 2542. Although the two insert molded electrodes 2540 are shown with a gap between them, in actuality, the two insert molded electrodes 2540 are fit line-to-line 2556 via mold pressure.

The conductive element 2546 may be made of an electrically conductive metal such as stainless steel or similar conductive material. The conductive element 2546 can be about 0.010" thick and may be selected within a range of thicknesses of 0.005" to 0.015" and can be formed by tamping or machining. The film 2544 can be about 0.001" to 0.002" thick and may be made of polyimide, polyester, or similar materials. Alternatively to mechanical retention, such as posts, the film 2544 can be directly bonded to the conductive element 2546. One example includes DuPont Pyralux HXC Kapton film with epoxy adhesive backing having a thickness of 0.002".

Advantageously, the non-stick surface prevents tissue from sticking to the insert molded electrode 2540. The non-stick surface eliminates short circuiting of opposing electrodes by setting a gap within the range of 0.002" to 0.004" along the entire length of the insert molded electrode 2540. The non-stick surface minimizes lateral spread of RF energy due to coverage of side walls 2558 of the insert molded electrode 2540. Also, the insert molded electrode 2540 exhibits structural soundness and provides an easier more robust electrical connection than a multi-layer flexible circuit.

In one aspect, the end-effector comprises a conductive clamp arm and pad constructs for combination ultrasonic/bipolar RF energy surgical devices. In one aspect, the present disclosure provides a clamp arm assembly comprising a conductive or selectively conductive thin film, foil, or laminate that is applied to, around or on the clamp arm assembly to serve as a durable "pole" in a combination ultrasonic/bipolar RF energy surgical device. Further, an algorithm, software, or logic is provided to manage conditions of electrical short circuiting. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

FIG. 33 illustrates an end-effector 2560 comprising an ultrasonic blade 2562, a clamp arm 2564, and a clamp arm pad 2566 comprising an electrically conductive film 2568, according to at least one aspect of the present disclosure.

FIG. 34 illustrates the clamp arm 2564 shown in FIG. 33. The clamp arm 2564 comprising a clamp jaw 2570 to support the clamp arm pad 2566. A thin electrically conductive film 2568 is disposed over the clamp arm pad 2566 to form an electrode of one of the poles of the bipolar RF circuit.

FIG. 35 is a section view of the clamp arm 2564 taken along section 35-35 in FIG. 34. The clamp jaw 2570 can be made of metal such as stainless steel. The clamp arm pad 2566 can be made of an electrically non-conductive complaint material such as PTFE, silicone, high temperature polymer, or similar materials. The electrically conductive film 2568 or foil can be made of an electrically conductive material such as titanium, silver, gold, aluminum, zinc, and any alloys thereof including stainless steel.

FIG. 36 illustrates a clamp arm 2580 comprising a partially electrically conductive clamp arm pad 2582, according to at least one aspect of the resent disclosure. An electrically conductive foil 2584 covers a portion of an electrically non-conductive pad 2586. The electrically non-conductive pad 2588 at the proximal end 2590 sets a gap between the clamp arm pad 2582 and the ultrasonic blade.

Elements of the electrically conductive film 2568, foil, or laminate may include, for example, a single layer of thin conductive material such as metals (titanium, silver, gold, zinc, aluminum, magnesium, iron, etc. and their alloys or stainless steels), plated metals (nickel and then gold over copper, for example) or polymers filled heavily with conductive materials such as metal powder, or filings. Preferably, it is a biocompatible metal foil such as titanium, silver, gold, zinc, or stainless steel selected from a thickness within the range of 0.001" to 0.008" (0.025 mm-0.20 mm).

The film 2568, foil, or laminate may include a thin polymer coating, film or layer covering the thin conductive material described above. This coating, film or layer is highly resistive, that is, it is not an effective conductor of bipolar RF energy to adjacent tissue. The coating may be perforated to allow for energy delivery from the electrode to tissue.

The conductive material may be perforated or contain holes or windows through the full thickness of the conductive material to minimize the thermal capacitance of this layer (testing has shown that long and/or thick foils result in longer transection times due to thermal energy being removed from the treatment sight. These perforations, holes or windows also may allow for retention of the foil to other parts or layers. These perforations, holes or windows may be patterned across the entire foil sheet or may be localized at the treatment site or away from the treatment site such as, for example, on the sides of the clamp arm only.

If present, the thin polymer coating, film or layer may be perforated or contain full thickness holes or windows such that the conductive film, foil or laminate is in direct communication with tissue for delivery of bipolar radiofrequency energy to the tissue. For coatings, these holes or windows may be formed by selective coating or coating removal.

Ideally, the conductive film 2568, foil, or laminate is in direct contact with the clamp arm structure that is typically fabricated from stainless steel. The resulting conductive path then allows for simplicity of construction in that the path is formed by necessary structural component, namely a support tube or actuator that connects directly to the clamp arm and then the conductive film, foil or laminate.

In one aspect, the conductive film 2568, foil, or laminate is backed by a relatively soft, high temperature, low wear polymer or elastomer pad made from materials such as PTFE, silicone, polyimide, high temperature thermoplastics, among other materials. The compliance of this relatively soft pad allows for a wide range of component tolerances to obtain a zero or near zero gap between the jaw and the ultrasonic blade along its full tissue effecting length when the jaw is fully closed, thus allowing tissue to be sealed and cut along this length. The compliance also eliminates or greatly dampens any audible vibration of the conductive layer that may occur when the ultrasonic blade is closed against the conductive layer.

The conductive film 2568, foil, or laminate may include a rigid to semi-rigid polymer on its backside/back surface (that is the surface away from the tissue and toward the clamp arm). This part is made from injection moldable polymers or polymer alloys and adhered to the film, foil or laminate by way of Film Insert Molding (FIM) or In-Mold Labeling (IML).

In testing, thin stainless steel, copper, or aluminum foils are quiet in operation (no "screeching" or emitting of obtuse squeals). The thin stainless steel, copper, or aluminum foils provide a robust surface against which the ultrasonic blade can act. Robust enough that materials such as silicone rubber that would otherwise tear and serve as a poor pad material are usable and do not easily tear or split.

The proximal portion of the jaw clamping surface may not include the conductive film, foil or laminate because this area of the jaw contacts the blade first and will be more likely result in shunting of power/shorting in this area.

In one aspect, the present disclosure provides a short circuit mitigation algorithm for activating an output including bipolar RF energy.

A short alert is not given to the user if it occurs after the energy delivered for the activation exceeds a threshold amount (thereby indicating that the tissue thinned but has likely received an adequate dose of bipolar RF energy for the sealing, coagulation of tissue), or an activation time threshold has been exceeded (again, thereby indicating that the tissue has thinned but has likely received and adequate dose), or both energy and activation time thresholds have been exceeded.

A process of making a film over stainless steel insert molded electrode assembly comprises etching the film and forming apertures (micro-holes, slots, or honeycomb) for passing RF energy; cutting periphery of the electrode component; forming a film onto/bond onto stainless steel electrode if needed; placing the charged film and electrode into a polymer injection mold tool; molding the polymer to the back of the electrode and film.

FIG. 132 illustrates a clamp arm 2600 comprising a clamp jaw 2602, a clamp arm pad 2604, and a wrapped wire electrode 2606, according to at least aspect of the present disclosure. The clamp jaw 2602 is made of stainless steel and the clamp arm pad 2604 is made of a polymer (e.g., PTFE). The wrapped wire electrode 2606 is made an electrical conductor.

FIG. 133 illustrates a clamp arm 2610 comprising a clamp jaw 2612, a clamp arm pad 2614, and a wrapped wire electrode 2616, according to at least aspect of the present disclosure. The clamp jaw 2612 is made of stainless steel and the clamp arm pad 2614 is made of a polymer (e.g., PTFE). The wrapped wire electrode 2616 is made an electrical conductor.

Additional disclosure material may be found in U.S. Pat. No. 9,764,164; U.S. Patent Application Publication No. 2017/0164997; U.S. Patent Application Publication No. 2017/0056059; and U.S. Pat. No. 7,442,193, each of which is herein incorporated by reference in their entirety.

In one aspect, the clamp arm pad can be comprised of a typically non-conductive material, such as PTFE, for example, which can be impregnated with electrically conductive particles, such as medical grade stainless steel, for example, such that the pad is sufficiently conductive to permit current to flow between the ultrasonic blade and the clamp arm.

In some variations, the clamp arm pad itself is conductive. By way of example only, the clamp arm pad may be formed of a molded, carbon filled PTFE.

In various aspects, the present disclosure provides a combination ultrasonic/bipolar RF energy surgical device configured to control tissue effects, charring, and/or tissue sticking to the clamp arm, ultrasonic blade, or electrode. In one aspect, a clamp arm jaw is configured with features or aspects to minimize tissue sticking to end-effector components and improve tissue control. In one aspect, the tissue path or clamp area control features are provided to adjust the tissue path relative to the clamp arm/ultrasonic blade to create a predefined location of contact reducing sticking of tissue to the clamp arm or ultrasonic blade and charring of tissue due to excess heat or prolonged application of heat.

In one aspect, the end-effector comprises a side guard to prevent tissue accumulation on end-effector components. In one aspect, the end-effector comprises tissue path or clamp arm area control features to adjust the tissue path relative to the clamp arm/blade to create a predefined location of contact. The control features are configured to reduce sticking and charring of tissue to the end-effector elements such as the clamp arm. Clamp jaw, clamp arm pad, or ultrasonic blade.

In one aspect, the present disclosure provides a clamp arm with raised sidewalls or guards to surround the electrode to prevent exposure and prevent tissue from entering the area inside the sidewalls. In one implementation, the sidewalls of the clamp arm may be extruded out and around the clamp arm pad to an extent, but not enough to cause the tissue to begin to fold. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

FIG. 37 illustrates a clamp arm 2620 comprising a clamp jaw 2622, a clamp arm pad 2624 comprising exposed teeth 2626, according to at least one aspect of the present disclosure. The exposed teeth 2626 prevent tissue from entering the area inside the exposed teeth 2626.

FIG. 38 illustrates a clamp arm 2630 comprising a clamp jaw 2632 comprising raised sidewalls 2634 and a raised lip 2636, and a clamp arm pad 2638 comprising a plurality of teeth 2639, according to at least one aspect of the present disclosure. The raised sidewalls 2634 and raised lip 2636 prevent tissue from accumulating inside 2637 the sidewalls 2634 and the raised lip 2636.

In one aspect, the present disclosure provides an end-effector comprising an electrode with a perimeter wall and silicone seal located on the clamp arm. FIGS. 39-41 illustrates an electrode comprising a perimeter wall. FIG. 39 illustrates a clamp arm 2640 comprising an electrode 2642 having a perimeter wall 2644 supported by a clamp jaw 2646 and a clamp arm pad 2647, according to tat least one aspect of the present disclosure. FIG. 40 is a section view of the clamp jaw 2640 taken along section 173-173 in FIG. 39. Since it would be desirable to prevent or minimize tissue penetration and accumulation/sticking between the electrode 2642 and the clamp jaw 2644, in one aspect, the perimeter wall 2644 around the electrode 2642 is sized and configured to prevent tissue from going and accumulating under the electrode 2642 in the space 2643 defined between the electrode 2642, the clamp jaw 2646, and the clamp arm pad 2647. The electrode 2642 is adapted and configured for use with a combination ultrasonic/bipolar RF energy surgical device and is deflectable under load, where the electrode 2642 is one pole of the bipolar RF circuit and the ultrasonic blade is the opposite pole of the bipolar RF circuit.

FIG. 41 is an alternative or additional feature of the electrode comprising a perimeter wall shown in FIGS. 39-40. In the aspect illustrated in FIG. 141, a sealant 2648 such as silicone or other fluid polymer may be provided in the space 2645 beneath the electrode 2642 and above the clamp jaw 2646 to prevent tissue from going and accumulating under the electrode 2642, according to at least one aspect of the present disclosure.

In one aspect, the present disclosure provides an end-effector comprising a skirt for deflectable/cantilevered electrode. It is common for tissue to stick to RF electrodes and fluid to accumulate between the electrode and the clamp jaw after heating in RF based energy surgical devices. Thus, it would be desirable to mitigate tissue/fluid accumulation between an electrode and a clamp arm or prevent tissue pinching. In one aspect, FIGS. 42-44 of the present disclosure illustrate an electrode to prevent or minimize tissue and fluid accumulation between the electrode and the clamp arm thereby limiting the deflecting function of the electrode or inhibiting the return of the electrode to the neutral position when unclamped. The electrode is fixed to the clamp jaw at the proximal end and is free to deflect at the distal end. Accordingly, throughout this disclosure the electrode may be referred to as a cantilever beam electrode or as a deflectable electrode. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

Overlapping configuration of skirt for adding incremental stiffness to the deflectable electrode. When deflected, the skirt displaces outwardly to clean/expel tissue around the clamp arm.

FIG. 42 illustrates a clamp arm 2650 comprising a clamp jaw 2652, an electrode 2654, a clamp arm pad 2656 (FIG. 43) comprising a plurality of teeth 2657, and a deflectable ledge 2658 along the lateral sides of the electrode 2654, according to at least one aspect of the present disclosure. FIGS. 43-44 are section views of the clamp arm 2650 shown in FIG. 42 taken at section 176-176. FIG. 43 shows the electrode 2654 and the skirt 2658 in an undeflected state and FIG. 44 shows the electrode 2654 and the skirt 2658 in a deflected state where the skirt 2658 shifts laterally in the direction indicated by the arrows 2659.

With reference now to FIGS. 42-43, the clamp arm 2650 is configured for use with an end-effector comprising an ultrasonic blade for use in a combined ultrasonic/bipolar RF energy device. A proximal end 2660 of the electrode 2654 is attached to the clamp jaw 2652 by any suitable fastener 2653 or fastening technique such as welding, laser welding, brazing, soldering, pressing, among other fastening techniques, for example. A distal end 2662 of the electrode 2654 is free to move as in a cantilever. As previously described, the clamp arm pad 2656 is made of a compliant material such as Teflon (PTFE) although similar polymers could be substituted therefor. The electrode 2654 is fixed to the clamp jaw 2652 at the proximal end and is free to deflect at the distal end. Accordingly, throughout this disclosure the electrode 2654 may be referred to as a cantilever beam electrode or as a deflectable electrode.

The deflectable ledge comprises an overmolded elastomeric skirt 2658 on the lower perimeter of the electrode 2654 disposed between the electrode 2654 and the clamp jaw 2652 and overlapping the electrode 2654. The overmolded skirt 2658 prevents tissue and fluid from accumulating or getting pinched between the electrode 2654 and the clamp jaw 2652 when they are in the deflected state. Additionally, the overlapping configuration of the overmolded skirt 2658 to the clamp jaw 2652 may stiffen the electrode 2654 if required for a particular implementation. When the electrode 2654 is deflected toward the clamp jaw 2652, the overmolded skirt 2658 displaces outwardly to clean and expel tissue from the periphery of the clamp arm 2658 electrode 2654 or the clamp jaw 2652.

In one aspect, the present disclosure provides an end-effector comprising an electrode curtain. It is common for tissue to stick between the clamp jaw and the RF electrodes after heating in RF based energy surgical devices. Thus, as previously discussed, it would be desirable to reduce tissue build up between the electrode and the clamp arm in a combination ultrasonic/bipolar RF energy surgical device. Accordingly, as shown in FIGS. 45-47 of the present disclosure, various clamp arms are configured to reduce tissue build up and sticking points. In one aspect, the clamp arms comprise an electrode, which extends downwardly along the sides of the clamp arm akin to a curtain to reduce gaps where tissue can enter and build up during RF sealing. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

FIG. 45 illustrates a clamp arm 2670 comprising a clamp jaw 2672, an electrode 2674, and sidewalls 2676 extending downwardly from the electrode 2674 past the sidewalls 2678 of the clamp jaw 2672, and clamp arm pad 2677 (FIG. 46) comprising a plurality of teeth 2679, according to at least one aspect of the present disclosure. FIG. 46 is a section view of the clamp arm 2670 shown in FIG. 45 along section line 46-46. With reference to FIGS. 45-46, the clamp arm 2670 is configured for use with an end-effector comprising an ultrasonic blade for use in a combination ultrasonic/bipolar RF energy surgical device. The sidewalls 2676 of the electrode 2674 cover the lateral sides of the clamp jaw 2672 and extend around the distal end 2684 of the clamp jaw 2672 to close off the gap and prevent tissue build up in the space 2680 defined between the electrode 2674 and the clamp jaw 2672. The arrows 2682 indicate the deflection path of the electrode 2674. As previously described, the clamp arm pad 2686 is made of a compliant material such as PTFE or similar polymer material. The electrode 2674 is attached to the proximal end 2688 of the clamp jaw 2672 by any suitable fastener 2673 or fastening technique such as welding, laser welding, brazing, soldering, pressing, among other fastening techniques, for example. The electrode 2674 is fixed to the clamp jaw 2672 at the proximal end and is free to deflect at the distal end. Accordingly, throughout this disclosure the electrode 2674 may be referred to as a cantilever beam electrode or as a deflectable electrode.

FIG. 47 illustrates an alternative clamp arm 2690 to the clamp arm 2670 shown in FIGS. 45-46, according to at least one aspect of the present disclosure. The clamp arm 2690 comprises a clamp jaw 2692, an electrode 2694 with sidewalls 2696 extending downwardly from the electrode 2694 past the sidewalls 2698 of the clamp jaw 2692, and a clamp arm pad 2697. The sidewalls 2698 prevent tissue build up in the space 2691 defined between the electrode 2694 and the clamp jaw 2692. The clamp arm 2690 further comprises a deflection stop surface 2700 away from a tissue interface. The electrode 2694 is fixed to the clamp jaw 2692 at the proximal end and is free to deflect at the distal end. Accordingly, throughout this disclosure the electrode 2694 may be referred to as a cantilever beam electrode or as a deflectable electrode.

In one aspect, the present disclosure provides an end-effector comprising a deflectable/cantilevered electrode comprising a shield lip to prevent tissue accumulation in the end-effector or components thereof. It is common for tissue to stick between the clamp jaw and the RF electrodes after heating in RF based energy surgical devices. Thus, as previously discussed, it would be desirable to prevent or minimize tissue accumulation between an electrode and a clamp jaw. FIG. 48 is a top perspective view of an electrode 2710 comprising a lip 2712 extending downwardly from a top surface 2714 of the electrode 2710, according to at least one aspect of the present disclosure. FIG. 49 is a bottom perspective view of the electrode 2710 shown in FIG. 48 showing the downwardly extending lip 2712. FIGS. 50-51 is a top perspective view of the electrode 2710 shown in FIGS. 48-49 with a clamp arm pad 2718 with teeth 2719 extending through the apertures 2716.

With reference now to FIGS. 48-51, the electrode 2710 defines apertures 2716 to receive elements of a clamp arm pad therethrough. The electrode 2710 is configured for use with an end-effector comprising an ultrasonic blade for use in an ultrasonic/bipolar RF combination energy device. The electrode 2710 is fixed to the clamp jaw at the proximal end and is free to deflect at the distal end. Accordingly, throughout this disclosure the electrode 2710 may be referred to as a cantilever beam electrode or as a deflectable electrode.

Accordingly, FIGS. 48-51 shield lip 2712 for the electrode 2710 to prevent tissue accumulation in the space defined between the electrode 2710 and the clamp jaw. The lip 2712 surrounds the clamp arm and the electrode 2710 to prevent tissue from entering the space between the electrode 2710 and the clamp jaw. An insulating coating could be added to the lip 2712 to prevent any electrode activity from coming from the lip 2712. The electrode 2710 is fixed to the clamp jaw at the proximal end and is free to deflect at the distal end. Accordingly, throughout this disclosure the electrode may be referred to as a cantilever beam electrode or as a deflectable electrode. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

In one aspect, the present disclosure provides an end-effector comprising a deflectable/cantilevered electrode with compressed block and individual clamp arm pad units. In one aspect, the deflectable/cantilevered electrode with compressed block and individual clamp arm pad units is configured to reduce trade off decisions between ultrasonic devices and bipolar RF devices with precise dissection and multiple reliable sealing functionalities. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

In one aspect, the end-effector utilizes individual clamp arm pads with collar features to prevent the electrode delaminating when the jaw is open, and utilizes a pre-compressed block to prevent tissue fragments from going into side crevices between the electrode and the clamp jaw to lower the risk of getting stuck.

In one aspect, the end-effector architecture includes an end-effector clamp arm side that has multiple individual clamp arm pad units. Each of the individual clamp arm pad units has a collar feature to constrain the electrode from delaminating when the jaw is open, increase the pad volume against to ultrasonic blade tip, and a foot/tip features to get aligned and constrained with a slot feature on the clamp arm.

In another aspect, the end-effector comprises an electrode having a pad slot feature in specific direction to allow assembly of the electrode and help hold the clamp arm pad in position.

In yet another aspect, the end-effector comprises a compressed block between the electrode and the clamp jaw to prevent tissue fragments going into side crevices and lower the risk of getting stuck, assist holding parts together, and ensure no gap between the pad collar and the electrode before clamping tissue.

FIG. 52 illustrates an end effector 2720 comprising a clamp arm 2722 and an ultrasonic blade 2724, according to at least one aspect of the present disclosure. With reference also to FIGS. 53-54, the clamp arm 2722 comprises a clamp jaw 2726, an electrode 2728 defining a plurality of apertures 2730 sized and configured to receive a plurality of individual tissue pad units 2732, a single piece elastic/hyper elastic block 2734, small wear resistant gap pads 2736, and a large wear resistant gap pads 2738. The single piece elastic/hyper elastic block 2734 is made of elastic or hyper elastic material to provide spring-like characteristics such as, for example, porosint, rubber or sponge, among others. The electrode 2728 functions as one pole of the bipolar RF circuit and the ultrasonic blade 2724 functions as the opposite pole of the bipolar RF circuit. The electrode 2728 is fixed to the clamp jaw 2726 at the proximal end and is free to deflect at the distal end. Accordingly, throughout this disclosure the electrode 2728 may be referred to as a cantilever beam electrode or as a deflectable electrode.

FIG. 55 illustrates various views of the individual tissue pad unit 2732, according to at least one aspect of the present disclosure. The tissue pad unit 2732 comprises a pad collar 2742, a pad neck 2746, a pad foot 2748, and a pad tip 2750. When tissue is clamped, tissue will push the electrode 2728 to a deflected state, at the same time the electrode 2728 will push the slightly compressed elastic block 2734 to a more compressed state. When the tissue is fully cut, the more compressed block 2734 will push on the electrode 2728 back against the tissue pad collar 2740, the block 2734 will remain in a slightly compressed state to maintain zero gap between the tissue pad units 2732 and the electrode 2728. When the clamp jaw 2726 is open, the tissue pad collar 2740 will prevent the electrode 2728 from delaminating.

FIG. 56 illustrates the electrode 2728, according to at least one aspect of the present disclosure. The electrode 2728 defines a plurality of apertures 2730. The plurality of apertures 2730 function as pad slots on the electrode 2728 having a similar shape as the pad foot 2748 shown in FIG. 55. The electrode 2728 also defines two slots 2752 to receive the small wear resistant gap pads 2736 and another slot 2754 to receive the large wear resistant gap pads 2738.

FIG. 57 illustrates a section view of the clamp arm 2722 showing the elastic/hyper elastic block 2734, according to at least one aspect of the present disclosure. In one aspect, the elastic/hyper elastic block 2734 functions as a pre-compressed block 2734 to push the electrode 2728 against the tissue pad collar 2740 and to push the clamp arm 2722 against the pad foot 2748 at contact area (shown at arrows 2756) to hold the parts together and ensure there is no gap between the pad collar 2742 and the electrode 2728 before clamping tissue.

FIG. 58 is a perspective view of the elastic/hyper elastic block 2734. FIGS. 59 and 61 are perspective views of a sub-assembly 2760 comprising the clamp jaw 2726, electrode 2728, and the individual tissue pad units 2732, according to at least one aspect to the present disclosure. This view illustrates side crevices 2758 formed between the electrode 2728 and the clamp jaw 2726. FIG. 60 is a perspective view of the clamp arm 2722 assembly comprising the elastic/hyper elastic block 2734 of FIG. 58 assembled to the sub-assembly 2760, according to at least one aspect of the present disclosure. With reference now to FIGS. 58-61, the pre-compressed block 2734 prevents tissue fragments from going into the side crevices 2758 between the electrode 2728 and the clamp jaw 2726 to lower risk of getting stuck.

FIG. 62 illustrates a first assembly step, according to at least one aspect of the present disclosure. In this step the individual tissue pad units 2732 are inserted into the electrode 2728. The tissue pad foot 2748 is aligned with the electrode pad slot 2730 and insert the tissue pad unit 2732 into the electrode pad slot 2730 until the tissue pad collar 2742 sits against the electrode 2728.

FIGS. 63-65 illustrate a second assembly step, according to at least one aspect of the present disclosure. In this step, the individual tissue pad units 2732 are locked into the electrode 2728. The tissue pad unit 2732 is rotated counter-clockwise for 35° (see also FIG. 56), at this 'lock' position the pad foot 2748 and the pad collar 2742 feature pair prevent the tissue pad unit 2732 from falling off from electrode 2728. Also at this position, the pad tips 2750 are roughly aligned to assemble into the clamp arm 2722. This creates a first sub-assembly 2762.

FIG. 66 illustrates a third assembly step, according to at least one aspect of the present disclosure. In this step the single piece elastic/hyper elastic block 2734 is bound to the clamp jaw 2726. This creates a second sub-assembly 2764.

FIGS. 67-72 illustrate a fourth assembly step, according to at least one aspect of the present disclosure. In this step the first sub-assembly 2762 produced in the second assembly step described in FIGS. 63-65 is assembled with the second sub-assembly 2764 produced in the third assembly as described in step of FIG. 66 to produce the clamp arm 2722. The pad tips 2750 are roughly aligned with the clamp arm slot 2766. The first sub-assembly 2762 is then inserted into the second sub-assembly 2764. The clamp arm slot 2766 feature will function to assist aligning the pad tips 2750 and constrain the tissue pad unit 2732 rotation D.O.F. along the pad shaft direction shown by the arrow 2768. Then 3 displacement D.O.F. and 3 rotation D.O.F. of the tissue pad units 2732 are fully constrained by the electrode 2728 and the clamp arm 2722. The electrode 2728 is bound to the clamp arm 2722 at bound points 2770. After assembly, the single piece elastic/hyper elastic block 2734 will be pre-compressed. The clamp arm feature 2772 prevents the tissue pad units 2732 from coming out in the direction shown by the arrow 2774.

FIGS. 73-74 illustrate a fifth assembly step, according to at least one aspect of the present disclosure. In this step the two small wear resistant gap pads 2736 are press fit into the slots 2752 defined by the electrode 2728 and the large wear resistant gap pad 2738 is slid into the slot 2754 defined by the electrode 2728.

In one aspect, the present disclosure provides an end-effector comprising a filled gap between the electrode and the clamp arm. It is common for tissue to stick between the clam jaw and the RF electrodes after heating in RF based energy surgical devices. Thus, as previously discussed, it would be desirable to prevent or minimize tissue sticking in the clamp arm in between the clamp jaw and the electrode. Accordingly, FIG. 75 illustrates a clamp arm 2780 comprising fill material 2782 between the electrode 2784 and the clamp jaw 2786, according to at least one aspect of the present disclosure. The fill material 2782 may be woven nylon or a 3D printed structure. The fill material 2782 prevents tissue from getting into the space 2788 between the electrode 2784 and the clamp jaw 2786. The 3D printed structure may be printed to be a specific shape in order to maximize compression. The electrode 2784 is fixed to the clamp jaw 2786 at the proximal end and is free to deflect at the distal end. Accordingly, throughout this disclosure the electrode 2784 may be referred to as a cantilever beam electrode or as a deflectable electrode. The electrode 2784 is adapted and configured for use with a combination ultrasonic/bipolar RF energy surgical device and is deflectable under load, where the electrode 2784 is one pole of the bipolar RF circuit and the ultrasonic blade is the opposite pole of the bipolar RF circuit.

In one aspect, the present disclosure provides an end-effector comprising a deflectable/cantilever electrode. It would be desirable to improve the ease of manufacturing of the electrode, reduce tissue accumulation between the electrode and the clamp jaw. It is further desirable to prevent or minimize tissue from sticking to the electrode. FIGS. 76-78 illustrate various apparatuses to address these desired improvements, according to at least one aspect of the present disclosure. The electrode is fixed to the clamp jaw at the proximal end and is free to deflect at the distal end. Accordingly, throughout this disclosure the electrode may be referred to as a cantilever beam electrode or as a deflectable electrode. The electrode is adapted and configured for use with a combination ultrasonic/bipolar RF energy surgical device and is deflectable under load, where the electrode is one pole of the bipolar RF circuit and the ultrasonic blade is the opposite pole of the bipolar RF circuit.

In the aspect shown in FIG. 76, a clamp arm 2790 that is easier to manufacture by eliminating a separate clamp arm electrode and building up a surface 2792 of the clamp arm and eliminating the separate electrode blade. The clamp arm now becomes the electrode. Also overmolding the polyimide (Vespel) clamp arm pads 2794 onto the clamp jaw 2796.

In the aspect shown in FIG. 77, a clamp arm 2800 to deter tissue accumulation between the electrode 2802 and the clamp jaw 2804 by adding a skirt 2806 to the perimeter of the electrode 2802 or alternatively to the perimeter of the clamp jaw 2804. This still allows the electrode 2802 to deflect but still deter tissue accumulation. The electrode 2802 is fixed to the clamp jaw 2804 at the proximal end and is free to deflect at the distal end. Accordingly, throughout this disclosure the electrode 2802 may be referred to as a cantilever beam electrode or as a deflectable electrode.

In the aspect shown in FIG. 78, a section view of an end-effector 2810 comprising an ultrasonic blade 2812 and a clamp arm 2814 configured to improve distal tissue grasping. The clamp arm 2814 defines a curvature 2816 at the distal end of the polyimide gap arm pad and/or the distal end of the teeth of the clamp arm pad (PTFE).

In one aspect, the present disclosure provides an end-effector configured to minimize tissue sticking via electrode geometry and a clamp arm bumper/bull element. It is common for tissue to stick to RF electrodes after heating in RF based energy surgical devices. Thus, as previously discussed, it would be desirable to minimize or prevent tissue sticking to the RF electrode. This may be achieved by a new electrode geometry and adding a clamp arm bumper/bull nose to a clamp jaw to minimize electrode delamination. FIG. 79 illustrates a clamp arm 2820 comprising a clamp jaw 2822, an electrode 2824, a clamp arm pad 2826 comprising a plurality of teeth 2836, and a curtain 2828 located on either side of the electrode 2824 to minimize pinch point of tissue, and a bull nose/clamp arm bumper 2830 to minimize delamination of the electrode 2824 by making contact with tissue first during blunt dissection, according to at least one aspect of the present disclosure. The clamp arm 2820 further comprises a hard gap setting pad 2832 at a proximal end 2834 of the clamp arm 2820. The clamp arm pad 2826 is made of a complaint polymer such as Teflon (PTFE) and the hard gap setting pad 2832 is made of hard polyimide material. The electrode 2824 is fixed to the clamp jaw 2822 at the proximal end and is free to deflect at the distal end. Accordingly, throughout this disclosure the electrode 2824 may be referred to as a cantilever beam electrode or as a deflectable electrode. The electrode 2824 is adapted and configured for use with a combination ultrasonic/bipolar RF energy surgical device and is deflectable under load, where the electrode 2824 is one pole of the bipolar RF circuit and the ultrasonic blade is the opposite pole of the bipolar RF circuit.

FIGS. 80-81 illustrate an alternative clamp arm 2840 comprising a clamp jaw 2842, an electrode 2844, a clamp arm pad 2846 comprising a plurality of teeth 2854, and a curtain 2848 located on either side of the clamp arm pad 2846, according to at least one aspect of the present disclosure. FIG. 80 illustrates an assembled view of the clamp arm 2840, FIG. 80 is an exploded view of the clamp arm 2840, and FIG. 81 is a section view of the clamp arm 2840 taken along section 81-81. The curtain 2848 prevent tissue pinching and improves manufacturability of the clamp arm 2840. The proximal end 2850 of the clamp arm 2840 comprises a hard gap setting pad 2852. The electrode 2844 comprises a plurality of apertures 2854 to receive the plurality of the clamp arm pad 2846 teeth. The clamp arm pad 2846 is made of a complaint polymer such as Teflon (PTFE) and the hard gap setting pad 2852 is made of hard polyimide material. The electrode 2844 is fixed to the clamp jaw 2842 at the proximal end and is free to deflect at the distal end. Accordingly, throughout this disclosure the electrode 2844 may be referred to as a cantilever beam electrode or as a deflectable electrode.

In one aspect, the present disclosure provides an end-effector comprising a deflectable electrode comprising anti-tissue sticking features. It is common for tissue to stick to RF electrodes after heating in RF based energy surgical devices. The tissue typically separates and flows into spaces around the electrode and then re-solidifies to form anchor points to the larger tissue body. The anchored tissue needs to be either prevented or detached to ensure no tissue sticking. FIGS. 82-85 illustrate a clamp arm 2860 comprising a clamp jaw 2862, a cantilevered electrode 2864, a clamp arm pad 2866 comprising teeth 2868 received through apertures 2870 defined by the cantilevered electrode 2864, and hard gap setting pads 2872, 2874 according to at least one aspect of the present disclosure. The electrode 2864 is adapted and configured for use with a combination ultrasonic/bipolar RF energy surgical device and is deflectable under load, where the electrode 2864 is one pole of the bipolar RF circuit and the ultrasonic blade is the opposite pole of the bipolar RF circuit.

FIG. 82 is a side view and FIG. 84 is a bottom perspective view of the clamp arm 2860, according to at least one aspect of the present disclosure. Both views show the cantilevered electrode 2864 in an undeflected state. FIG. 83 is a side view and FIG. 85 is a bottom perspective view of the clamp arm 2860 with the cantilevered electrode 2864 in a deflected state to pull tissue off the teeth 2868 of the clamp arm pad 2866, according to at least one aspect of the present disclosure.

With reference now to FIGS. 82-84, in one method, the cantilevered electrode 2864 moves past the end of the pad teeth 2868 to pull the tissue out of the anchor spots before the tissue cools. The cantilevered electrode 2864 can move independently from the clamp jaw 2862 and the clamp arm pad 2866 with a spring force. The apertures 2870 in the cantilevered electrode 2864 for the clamp arm pad 2866 can move off the clamp arm pad 2866 to ensure no anchor are present spots after sealing.

In various aspects, the present disclosure provides combination ultrasonic/bipolar RF energy surgical devices and systems. Various forms are directed to user interfaces for surgical instruments with ultrasonic and/or electrosurgical (RF) end-effectors configured for effecting tissue treating, dissecting, cutting, and/or coagulation during surgical procedures. In one form, a user interface is provided for a combined ultrasonic and electrosurgical instrument that may be configured for use in open surgical procedures, but has applications in other types of surgery, such as minimally invasive laparoscopic procedures, for example, non-invasive endoscopic procedures, either in hand held or and robotic-assisted procedures. Versatility is achieved by selective application of multiple energy modalities simultaneously, independently, sequentially, or combinations thereof. For example, versatility may be achieved by selective use of ultrasonic and electrosurgical energy (e.g., monopolar or bipolar RF energy) either simultaneously, independently, sequentially, or combinations thereof.

In one aspect, the present disclosure provides a user interface for an apparatus comprising an ultrasonic blade and clamp arm with a deflectable RF electrode such that the ultrasonic blade and deflectable RF electrode cooperate to effect sealing, cutting, and clamping of tissue by cooperation of a clamping mechanism of the apparatus comprising the RF electrode with an associated ultrasonic blade. The clamping mechanism includes a pivotal clamp arm which cooperates with the ultrasonic blade for gripping tissue therebetween. The clamp arm is preferably provided with a clamp tissue pad (also known as "clamp arm pad") having a plurality of axially spaced gripping teeth, segments, elements, or individual units which cooperate with the ultrasonic blade of the end-effector to achieve the desired sealing and cutting effects on tissue, while facilitating grasping and gripping of tissue during surgical procedures.

In one aspect, the end-effectors described herein comprise an electrode. In other aspects, the end-effectors described herein comprise alternatives to the electrode to provide a compliant coupling of RF energy to tissue, accommodate pad wear/thinning, minimize generation of excess heat (low coefficient of friction, pressure), minimize generation of sparks, minimize interruptions due to electrical shorting, or combinations thereof. The electrode is fixed to the clamp jaw at the proximal end and is free to deflect at the distal end. Accordingly, throughout this disclosure the electrode may be referred to as a cantilever beam electrode or as a deflectable electrode.

In other aspects, the end-effectors described herein comprise a clamp arm mechanism configured to high pressure between a pad and an ultrasonic blade to grasp and seal tissue, maximize probability that the clamp arm electrode contacts tissue in limiting or difficult scenarios, such as, for example, thin tissue, tissue under lateral tension, tissue tenting/vertical tension especially tenting tissue away from clamp arm.

In other aspects, the end-effectors described herein are configured to balance match of surface area/current densities between electrodes, balance and minimize thermal conduction from tissue interface, such as, for example, impacts lesion formation and symmetry, cycle time, residual thermal energy. In other aspects, the end-effectors described herein are configured to minimize sticking, tissue adherence (minimize anchor points) and may comprise small polyimide pads.

In various aspects, the present disclosure provides a surgical device configured to deliver at least two energy types (e.g., ultrasonic, monopolar RF, bipolar RF, microwave, or irreversible electroporation [IRE]) to tissue. The surgical device includes a first activation button switch for activating energy, a second button switch for selecting an energy mode for the activation button switch. The second button switch is connected to a circuit that uses at least one input parameter to define the energy mode. The input parameter can be modified remotely through connection to a generator or through a software update.

In one aspect, at least one of the energy modes is a simultaneous blend of RF and ultrasonic energy, and the input parameter represents a duty cycle of the RF and ultrasonic energy.

In one aspect, the second button switch is configurable to select from a list of predefined modes and the number of modes in the list is defined by a second input parameter defined by a user.

In one aspect, the input parameter is either duty cycle, voltage, frequency, pulse width, or current.

In one aspect, the device also includes a visual indicator of the selected energy mode within the portion of device in the surgical field In one aspect, the second button switch is a separate control from the end effector closure trigger.

In one aspect, the second button switch is configured to be activated second stage of the closure trigger. The first stage of the closure trigger in the closing direction is to actuate the end effector.

In one aspect, at least one of the energy modes is selected from ultrasonic, RF bipolar, RF monopolar, microwave, or IRE.

In one aspect, at least one of the energy modes is selected from ultrasonic, RF bipolar, RF monopolar, microwave, or IRE and is configured to be applied in a predefined duty cycle or pulsed algorithm.

In one aspect, at least one of the energy modes is selected from a sequential application of two or more of the following types of energy: ultrasonic, RF bipolar, RF monopolar, microwave, or IRE.

In one aspect, at least one of the energy modes is a simultaneous blend of two or more of the following types of energy: ultrasonic, RF bipolar, RF monopolar, microwave, and IRE.

In one aspect, at least one of the energy modes is a simultaneous blend of two or more of the following types of energy: ultrasonic, RF bipolar, RF monopolar, microwave, and IRE followed sequentially by one or more of the aforementioned energies.

In one aspect, at least one of the energy modes is one off the following types of energy: Ultrasonic, RF bipolar, RF monopolar, microwave, and IRE followed sequentially by a simultaneous blend of two or more of the aforementioned energies.

In one aspect, at least one of the energy modes is procedure or tissue specific predefined algorithm.

In one aspect, at least one of the energy modes is compiled from learned surgical behaviors or activities.

In one aspect, the input parameter is at least one of: energy type, duty cycle, voltage, frequency, pulse width, current, impedance limit, activation time, or blend of energy.

In one aspect, the second button switch is configurable to select from a list of predefined modes and the number of modes in the list is either predefined or defined by a second input parameter defined by a user.

In one aspect, the aforementioned energy modes are made available to the user through software updates to the generator.

In one aspect, the aforementioned energy modes are made available to the user through software updates to the device.

In one aspect, the preferred selections by the user are made available to multiple generators through either networking, the cloud, or manual transfer.

In one aspect, the device also includes a visual indicator of the selected energy mode within the portion of device in the surgical field.

As used herein a button switch can be a manually, mechanically, or electrically operated electromechanical device with one or more sets of electrical contacts, which are connected to external circuits. Each set of electrical contacts can be in one of two states: either "closed" meaning the contacts are touching and electricity can flow between them, or "open", meaning the contacts are separated and the switch is electrically non-conducting. The mechanism actuating the transition between these two states (open or closed) can be either an "alternate action" (flip the switch for continuous "on" or "off") or "momentary" (push for "on" and release for "off") type.

In one aspect, the present disclosure provides a combination ultrasonic/bipolar RF energy surgical device comprising on device mode selection and visual feedback. As surgical devices evolve and become more capable, the number of specialized modes in which they can be operated increases. Adding extra button switches on a device to accommodate these new additional modes would complicate the user interface and make the device more difficult to use.

Accordingly, the present disclosure provides techniques for assigning different modes to a single physical button switch, which enables a wider selection of modes without adding complexity to the housing design (e.g., adding more and more button switches). In one aspect, the housing is in the form of a handle or pistol grip.

As more specialized modes become available, there is a need to provide multiple modes to a surgeon using the surgical device without creating a complex user interface. Surgeons want to be able to control the mode selection from the sterile field rather than relying on a circulating nurse at the generator. Surgeon want real time feedback so they are confident they know which mode is selected.

FIG. 86 illustrates a surgical device 100 comprising a mode selection button switch 130 on the device 100, according to at least one aspect of the present disclosure. The surgical device 100 comprises a housing 102 defining a handle 104 in the form of a pistol grip. The housing 102 comprises a trigger 106 which when squeezed is received into the internal space defined by the handle 104. The trigger 106 is used to operate a clamp arm 111 portion of an end-effector 110. A clamp jaw 112 is pivotally movable about pivot point 114. The housing 102 is coupled to the end-effector 110 through a shaft 108, which is rotatable by a knob 122.

The end-effector 110 comprises a clamp arm 111 and an ultrasonic blade 116. The clamp arm 111 comprises a clamp jaw 112, an electrode 118, and a clamp arm pad 120. In one aspect, the clamp arm pad 120 is made of a non-stick lubricious material such as PTFE or similar synthetic fluoropolymers of tetrafluoroethylene. PTFE is a hydrophobic, non-wetting, high density and resistant to high temperatures, and versatile material and non-stick properties. The clamp arm pad 120 is electrically non-conductive. In contrast, the electrode 118 is made of an electrically conductive material to deliver electrical energy such as monopolar RF, bipolar RF, microwave, or irreversible electroporation (IRE), for example. The electrode 118 may comprises gap setting pads made of a polyimide material, and in one aspect, is made of a durable high-performance polyimide-based plastic known under the tradename VESPEL and manufactured by DuPont or other suitable polyimide, polyimide polymer alloy, or PET (Polyethylene Terephthalate), PEEK (Polyether Ether Ketone), PEKK (Poly Ether Ketone Ketone) polymer alloy, for example. Unless otherwise noted herein below, the clamp arm pads and gap pads described herein below are made of the materials described in this paragraph.

The electrode 118 and the ultrasonic blade 116 are coupled to the generator 133. The generator 133 is configured to drive RF, microwave, or IRE energy to the electrode 118. The generator 133 also is configured to drive an ultrasonic transducer acoustically coupled to the ultrasonic blade 116. In certain implementations, the electrode 118 is one pole of an electrical circuit and the ultrasonic blade 116 is the opposite pole of the electrical circuit. The housing 102 includes a switch 124 to activate the ultrasonic blade 116. The circuit may be contained in the housing 102 or may reside in the generator 133. The surgical device 100 is coupled to the generator 133 via a cable 131. The cable 131 conducts signals for the electrosurgical functions and the ultrasonic transducer.

In various aspects, the surgical device 100 is configured to deliver at least two energy types (e.g., ultrasonic, monopolar RF, bipolar RF, microwave, or irreversible electroporation [IRE]) to tissue located in the end-effector 110 between the clamp arm 111 and the ultrasonic blade 116. The housing 102 of the surgical device 100 includes a first activation button switch 126 for activating energy and a second "mode" button switch 130 for selecting an energy mode for the activation button switch. The second button switch 130 is connected to a circuit that uses at least one input parameter to define the energy mode. The input parameter can be modified remotely through connection to a generator or through a software update. The energy mode is displayed on a user interface 128.

In one aspect, the surgical instrument 100 provides mode switching through the on device directional selector "mode" button switch 130. The user can press the mode button switch 130 to toggle through different modes and the colored light on the user interface 128 indicates the selected mode.

According to various aspects of the present disclosure, different modes of operation can be assigned to the surgical device by pressing the "mode" button switch 130, where each time the mode button switch 130 is pressed, or pushed and held, the surgical device 100 toggles through the available modes, which are displayed on the user interface 128. Once a mode is selected, the generator 133 will provide the appropriate generator tone and the surgical device 100 will have a lighted indicator on the user interface 128 to indicate which mode was selected.

In the example illustrated in FIG. 86, the "mode" selection button switch 130 is placed symmetrically on both sides of the housing 102. This enables both a right and left handed surgeon to select/toggle through modes without using a second hand. In this aspect, the "mode" selection button switch 130 can toggle in many different directions, which enables the surgeon to select from a list of options and navigate more complex selections remotely from the sterile field without having to ask a circulator to make adjustments at the generator 133. The lighted indicator on the user interface 128 of the surgical device 100, in addition to generator 133 tones, gives the surgeon feedback on which mode is selected.

FIGS. 87A-87C illustrate three options for selecting the various operating modes of the surgical device 100, according to at least one aspect of the present disclosure. In addition to the colored light user interface 128 on the housing 102 of the surgical device 100, feedback for mode selection is audible and/or visible through the generator 133 interface where the generator 133 announces the selected mode verbally and/or shows a description of the selected mode on a screen of the generator 133.

FIG. 87A shows a first mode selection option 132A where the button switch 130 can be pressed forward 136 or backward 134 to cycle the surgical instrument 100 through the various modes.

FIG. 87B shows a second mode selection option 132B where the button switch 130 is pressed up 140 or down 138 to cycle the surgical instrument 100 through the various modes.

FIG. 87C shows a third mode selection option 132C where the button switch 130 is pressed forward 136, backward 134, up 149, or down 138 to cycle the surgical instrument 100 through the various modes.

FIG. 88 illustrates a surgical device 150 comprising a mode selection button switch 180 on the back of the device 150, according to at least one aspect of the present disclosure. The surgical device 150 comprises a housing 152 defining a handle 154 in the form of a pistol grip. The housing 152 comprises a trigger 156 which when squeezed is received into the internal space defined by the handle 154. The trigger 156 is used to operate a clamp arm 161 portion of an end-effector 160. A clamp jaw 162 is pivotally movable about pivot point 164. The housing 152 is coupled to the end-effector 160 through a shaft 158, which is rotatable by a knob 172.

The end-effector 160 comprises a clamp arm 161 and an ultrasonic blade 166. The clamp arm 161 comprises a clamp jaw 162, an electrode 168, and a clamp arm pad 170. In one aspect, the clamp arm pad 170 is made of a non-stick lubricious material such as PTFE or similar synthetic fluoropolymers of tetrafluoroethylene. PTFE is a hydrophobic, non-wetting, high density and resistant to high temperatures, and versatile material and non-stick properties. The clamp arm pad 170 is electrically non-conductive. In contrast, the electrode 168 is made of an electrically conductive material to deliver electrical energy such as monopolar RF, bipolar RF, microwave, or irreversible electroporation (IRE), for example. The electrode 168 may comprises gap setting pads made of a polyimide material, and in one aspect, is made of a durable high-performance polyimide-based plastic known under the tradename VESPEL and manufactured by DuPont or other suitable polyimide, polyimide polymer alloy, or PET (Polyethylene Terephthalate), PEEK (Polyether Ether Ketone), PEKK (Poly Ether Ketone Ketone) polymer alloy, for example. Unless otherwise noted herein below, the clamp arm pads and gap pads described herein below are made of the materials described in this paragraph.

The electrode 168 and the ultrasonic blade 166 are coupled to the generator 133. The generator 133 is configured to drive RF, microwave, or IRE energy to the electrode 168. The generator 133 also is configured to drive an ultrasonic transducer acoustically coupled to the ultrasonic blade 166. In certain implementations, the electrode 168 is one pole of an electrical circuit and the ultrasonic blade 166 is the opposite pole of the electrical circuit. The housing 152 includes a switch 174 to activate the ultrasonic blade 166. The circuit may be contained in the housing 152 or may reside in the generator 133. The surgical device 150 is coupled to the generator 133 via a cable 181. The cable 181 conducts signals for the electrosurgical functions and the ultrasonic transducer.

In various aspects, the surgical device 100 is configured to deliver at least two energy types (e.g., ultrasonic, monopolar RF, bipolar RF, microwave, or irreversible electroporation [IRE]) to tissue located in the end-effector 110 between the clamp arm 111 and the ultrasonic blade 116. The housing 102 of the surgical device 100 includes a first activation button switch 126 for activating energy and a second "mode" button switch 130 for selecting an energy mode for the activation button switch. The second button switch 130 is connected to a circuit that uses at least one input parameter to define the energy mode. The input parameter can be modified remotely through connection to a generator or through a software update. The energy mode is displayed on a user interface 128.

In one aspect, the surgical instrument 150 provides mode switching through the on device directional selector "mode" button switch 180. The user can press the mode button switch 180 to toggle through different modes and the colored light on the user interface 178 indicates the selected mode.

According to various aspects of the present disclosure, different modes of operation can be assigned to the surgical device by pressing the "mode" button switch 180, where each time the mode button switch 180 is pressed, or pushed and held, the surgical device 150 toggles through the available modes, which are displayed on the user interface 178. Once a mode is selected, the generator 133 will provide the appropriate generator tone and the surgical device 150 will have a lighted indicator on the user interface 178 to indicate which mode was selected.

In the example illustrated in FIG. 88, the "mode" selection button switch 180 is placed on the back of the surgical device 150. The location of the "mode" selection button switch 180 is out of the reach of the surgeon's hand holding the surgical device 150 so a second hand is required to change modes. This is intended to prevent inadvertent activation. In order to change modes, a surgeon must use her second hand to intentionally press the mode button switch 180. The lighted indicator on the user interface 178 of the surgical device 150, in addition to generator tones gives the surgeon feedback on which mode is selected.

FIG. 89A shows a first mode selection option where as the mode button switch 180 is pressed to toggled through various modes, colored light indicates the selected mode on the user interface 178.

FIG. 89B shows a second mode selection option where as the mode button switch 180 is pressed to toggle through various modes a screen 182 indicates the selected mode (e.g., LCD, e-ink).

FIG. 89C shows a third mode selection option where as the mode button switch 180 is pressed to toggle through various modes, labelled lights 184 indicate the selected mode.

FIG. 89D shows a fourth mode selection option where as a labeled button switch 186 is pressed to select a mode, when a labeled button switch 180 is selected, it is illuminated to indicate mode selected In one aspect, the present disclosure provides a combination ultrasonic/bipolar RF energy surgical device comprising energy activation with trigger closure. As more functionality is added to advanced energy surgical devices additional button switches or controls are added to the surgical devices. The additional button switches or controls make these advanced energy surgical devices complicated and difficult to use. Additionally, when using an advanced energy surgical device to control bleeding, difficult to use user interfaces or difficult to access capability will cost critical time and attention during a surgical procedure.

According to the present disclosure, monopolar RF energy or advanced bipolar RF energy is activated by closing the trigger by squeezing the trigger past a first closure click to a second activation click and holding closed until energy delivery is ceased by the power source in the generator. Energy also can be immediately reapplied by slightly releasing and re-squeezing the trigger as many times as desired.

FIG. 90 illustrates a surgical device 190 comprising a trigger 196 activation mechanism, according to at least one aspect of the present disclosure. The surgical device 190 comprises a housing 192 defining a handle 194 in the form of a pistol grip. The housing 192 comprises a trigger 196 which when squeezed is received into the internal space defined by the handle 194. The housing 192 is coupled to an end-effector through a shaft 198, which is rotatable by a knob 202. The surgical device 190 is coupled to a generator 206 via a cable 204. The cable 204 conducts signals for the electrosurgical functions and the ultrasonic transducer.

The trigger 196 is configured to operate a clamp arm portion of an end-effector and to trigger electrosurgical energy, thus eliminating the activation button switch 126, 176 shown in FIGS. 86 and 88. The trigger 196 closes to a first audible and tactile click to close the jaws for grasping tissue and further closes to a second audible and tactile click to activate electrosurgical energy such as monopolar or bipolar RF. Microwave, or IRE energy. The full sequence is completed by activating the front button switch which cuts using ultrasonic energy.

Procedure for operating the surgical device 190: squeeze the trigger 196 to a first audible and tactile click; verify targeted tissue in jaws; activate RF energy by further squeezing the trigger 196 to a second audible and tactile click until end tone is heard; cut by pressing ultrasonic front switch 200 until tissue divides.

Modified procedure for operating the surgical instrument 190 for additional capability: activate RF energy with the trigger 196 and hold while simultaneously activation the front button switch 200 to activate the ultrasonic transducer, which will result in simultaneous application of electrosurgical and ultrasonic energy modalities being delivered to the tissue at the same time.

In an alternative implementation, the front button switch 200 for activating ultrasonic energy may be toggled to different speeds via a mode selector on the surgical device 190 or on the power source generator 206.

The surgical instruments 100, 150, 190 and associated algorithms described above in connection with FIGS. 86-90 comprising the end-effectors described in FIGS. 1-85 may be implemented in the following surgical hub system in conjunction with the following generator and modular energy system, for example.

FIG. 91 illustrates an alternative clamp arm comprising a metal clamp jaw, an electrode, a plurality of clamp arm pads, and gap pads, according to at least one aspect of the present disclosure. FIG. 91 illustrates an alternative clamp arm 2900 comprising a metal clamp jaw 2904, an electrode 2906, a plurality of clamp arm pads 2920 extend through holes in the electrode 2906, a gap pad 2930, and a gap pad 2910, according to at least one aspect of the present disclosure. The electrode 2906 is attached to the metal jaw 2906 at weld locations 2908. The electrode 2906 wraps around the metal clamp jaw 2904 and electrode 2906 can deflect. The gap pad 2910 has a top PI layer 2912 and a bottom elastomer layer 2914 for pressure control that is attached directly to the metal clamp jaw 2904. The clamp arm pads 2920 are attached directly to the metal clamp jaw 2904 and are composite pads with a high pressure center zone 2922 made of PTFE for reduced heat and an outer zone 2924 made of PI for electrode 2906 deflection.

In one aspect, the combination ultrasonic/bipolar RF energy surgical device is configured to operate within a surgical hub system. FIG. 92 is a surgical system 3102 comprising a surgical hub 3106 paired with a visualization system 3108, a robotic system 3110, and an intelligent instrument 3112, in accordance with at least one aspect of the present disclosure. Referring now to FIG. 92, the hub 3106 is depicted in communication with a visualization system 3108, a robotic system 3110, and a handheld intelligent surgical instrument 3112 configured in a similar manner to the surgical instruments 100, 150, 190 as described in FIGS. 86-91. The hub 3106 includes a hub display 3135, an imaging module 3138, a generator module 3140, a communication module 3130, a processor module 3132, and a storage array 3134. In certain aspects, as illustrated in FIG. 92, the hub 3106 further includes a smoke evacuation module 3126 and/or a suction/irrigation module 3128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 3136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

In one aspect, the present disclosure provides a generator configured to drive the combination ultrasonic/bipolar RF energy surgical device. FIG. 93 illustrates an example of a generator 3900, in accordance with at least one aspect of the present disclosure. As shown in FIG. 93, the generator 3900 is one form of a generator configured to couple to a surgical instrument 100, 150, 190 as described in FIGS. 86-92, and further configured to execute adaptive ultrasonic and electrosurgical control algorithms in a surgical data network comprising a modular communication hub as shown in FIG. 92. The generator 3900 is configured to deliver multiple energy modalities to a surgical instrument. The generator 3900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 3900 comprises a processor 3902 coupled to a waveform generator 3904. The processor 3902 and waveform generator 3904 are configured to generate a variety of signal waveforms based on information stored in a memory coupled to the processor 3902, not shown for clarity of disclosure. The digital information associated with a waveform is provided to the waveform generator 3904 which includes one or more DAC circuits to convert the digital input into an analog output. The analog output is fed to an amplifier 3906 for signal conditioning and amplification. The conditioned and amplified output of the amplifier 3906 is coupled to a power transformer 3908. The signals are coupled across the power transformer 3908 to the secondary side, which is in the patient isolation side. A first signal of a first energy modality is provided to the surgical instrument between the terminals labeled ENERGY1 and RETURN. A second signal of a second energy modality is coupled across a capacitor 3910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 3912 is coupled across the terminals labeled ENERGY1 and the RETURN path to measure the output voltage therebetween. A second voltage sensing circuit 3924 is coupled across the terminals labeled ENERGY2 and the RETURN path to measure the output voltage therebetween. A current sensing circuit 3914 is disposed in series with the RETURN leg of the secondary side of the power transformer 3908 as shown to measure the output current for either energy modality. If different return paths are provided for each energy modality, then a separate current sensing circuit should be provided in each return leg. The outputs of the first and second voltage sensing circuits 3912, 3924 are provided to respective isolation transformers 3916, 3922 and the output of the current sensing circuit 3914 is provided to another isolation transformer 3918. The outputs of the isolation transformers 3916, 3928, 3922 in the on the primary side of the power transformer 3908 (non-patient isolated side) are provided to a one or more ADC circuit 3926. The digitized output of the ADC circuit 3926 is provided to the processor 3902 for further processing and computation. The output voltages and output current feedback information can be employed to adjust the output voltage and current provided to the surgical instrument and to compute output impedance, among other parameters. Input/output communications between the processor 3902 and patient isolated circuits is provided through an interface circuit 3920. Sensors also may be in electrical communication with the processor 3902 by way of the interface circuit 3920.

In one aspect, the impedance may be determined by the processor 3902 by dividing the output of either the first voltage sensing circuit 3912 coupled across the terminals labeled ENERGY1/RETURN or the second voltage sensing circuit 3924 coupled across the terminals labeled ENERGY2/RETURN by the output of the current sensing circuit 3914 disposed in series with the RETURN leg of the secondary side of the power transformer 3908. The outputs of the first and second voltage sensing circuits 3912, 3924 are provided to separate isolations transformers 3916, 3922 and the output of the current sensing circuit 3914 is provided to another isolation transformer 3916. The digitized voltage and current sensing measurements from the ADC circuit 3926 are provided the processor 3902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 93 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 3912 by the current sensing circuit 3914 and the tissue impedance may be measured by dividing the output of the second voltage sensing circuit 3924 by the current sensing circuit 3914.

As shown in FIG. 93, the generator 3900 comprising at least one output port can include a power transformer 3908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 3900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 3900 can be steered, switched, or filtered to provide the frequency to the end effector of the surgical instrument. The connection of an ultrasonic transducer to the generator 3900 output would be preferably located between the output labeled ENERGY1 and RETURN as shown in FIG. 92. In one example, a connection of RF bipolar electrodes to the generator 3900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

In one aspect, the present disclosure provides a modular energy system configured to drive the combination ultrasonic/bipolar RF energy surgical device. FIG. 94 is a diagram of various modules and other components that are combinable to customize modular energy systems, in accordance with at least one aspect of the present disclosure. FIG. 95A is a first illustrative modular energy system configuration including a header module and a display screen that renders a graphical user interface (GUI) for relaying information regarding modules connected to the header module, in accordance with at least one aspect of the present disclosure. FIG. 95B is the modular energy system shown in FIG. 95A mounted to a cart, in accordance with at least one aspect of the present disclosure.

With reference now to FIGS. 93-95B, ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

A surgical hub can be configured to interchangeably receive a variety of modules, which can in turn interface with surgical devices (e.g., a surgical instrument or a smoke evacuator) or provide various other functions (e.g., communications). In one aspect, a surgical hub can be embodied as a modular energy system 4000, which is illustrated in connection with FIGS. 94-95B. The modular energy system 4000 can include a variety of different modules 4001 that are connectable together in a stacked configuration. In one aspect, the modules 4001 can be both physically and communicably coupled together when stacked or otherwise connected together into a singular assembly. Further, the modules 4001 can be interchangeably connectable together in different combinations or arrangements. In one aspect, each of the modules 4001 can include a consistent or universal array of connectors disposed along their upper and lower surfaces, thereby allowing any module 4001 to be connected to another module 4001 in any arrangement (except that, in some aspects, a particular module type, such as the header module 4002, can be configured to serve as the uppermost module within the stack, for example). In an alternative aspect, the modular energy system 4000 can include a housing that is configured to receive and retain the modules 4001, as is shown in FIG. 92. The modular energy system 4000 can also include a variety of different components or accessories that are also connectable to or otherwise associatable with the modules 4001. In another aspect, the modular energy system 4000 can be embodied as a generator module 3140, 3900 (FIGS. 92-93) of a surgical hub 3106. In yet another aspect, the modular energy system 4000 can be a distinct system from a surgical hub 3106. In such aspects, the modular energy system 4000 can be communicably couplable to a surgical hub 3106 for transmitting and/or receiving data therebetween.

The modular energy system 4000 can be assembled from a variety of different modules 4001, some examples of which are illustrated in FIG. 94. Each of the different types of modules 4001 can provide different functionality, thereby allowing the modular energy system 4000 to be assembled into different configurations to customize the functions and capabilities of the modular energy system 4000 by customizing the modules 4001 that are included in each modular energy system 4000. The modules 4001 of the modular energy system 4000 can include, for example, a header module 4002 (which can include a display screen 4006), an energy module 4004, a technology module 4040, and a visualization module 4042. In the depicted aspect, the header module 4002 is configured to serve as the top or uppermost module within the modular energy system stack and can thus lack connectors along its top surface. In another aspect, the header module 4002 can be configured to be positioned at the bottom or the lowermost module within the modular energy system stack and can thus lack connectors along its bottom surface. In yet another aspect, the header module 4002 can be configured to be positioned at an intermediate position within the modular energy system stack and can thus include connectors along both its bottom and top surfaces. The header module 4002 can be configured to control the system-wide settings of each module 4001 and component connected thereto through physical controls 4011 thereon and/or a graphical user interface (GUI) 4008 rendered on the display screen 4006. Such settings could include the activation of the modular energy system 4000, the volume of alerts, the footswitch settings, the settings icons, the appearance or configuration of the user interface, the surgeon profile logged into the modular energy system 4000, and/or the type of surgical procedure being performed. The header module 4002 can also be configured to provide communications, processing, and/or power for the modules 4001 that are connected to the header module 4002. The energy module 4004, which can also be referred to as a generator module 3140, 3900 (FIGS. 92-93), can be configured to generate one or multiple energy modalities for driving electrosurgical and/or ultrasonic surgical instruments connected thereto, such as is described above in connection with the generator 3900 illustrated in FIG. 93. The technology module 4040 can be configured to provide additional or expanded control algorithms (e.g., electrosurgical or ultrasonic control algorithms for controlling the energy output of the energy module 4004). The visualization module 4042 can be configured to interface with visualization devices (i.e., scopes) and accordingly provide increased visualization capabilities.

The modular energy system 4000 can further include a variety of accessories 4029 that are connectable to the modules 4001 for controlling the functions thereof or that are otherwise configured to work on conjunction with the modular energy system 4000. The accessories 4029 can include, for example, a single-pedal footswitch 4032, a dual-pedal footswitch 4034, and a cart 4030 for supporting the modular energy system 4000 thereon. The footswitches 4032, 4034 can be configured to control the activation or function of particular energy modalities output by the energy module 4004, for example.

By utilizing modular components, the depicted modular energy system 4000 provides a surgical platform that grows with the availability of technology and is customizable to the needs of the facility and/or surgeons. Further, the modular energy system 4000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 4000 can include monopolar energy generators, bipolar energy generators, dual electrosurgical/ultrasonic energy generators, display screens, and various other modules and/or other components, some of which are also described above in connection with FIGS. 1-91.

Referring now to FIG. 95A, the header module 4002 can, in some aspects, include a display screen 4006 that renders a GUI 4008 for relaying information regarding the modules 4001 connected to the header module 4002. In some aspects, the GUI 4008 of the display screen 4006 can provide a consolidated point of control of all of the modules 4001 making up the particular configuration of the modular energy system 4000. In alternative aspects, the header module 4002 can lack the display screen 4006 or the display screen 4006 can be detachably connected to the housing 4010 of the header module 4002. In such aspects, the header module 4002 can be communicably couplable to an external system that is configured to display the information generated by the modules 4001 of the modular energy system 4000. For example, in robotic surgical applications, the modular energy system 4000 can be communicably couplable to a robotic cart or robotic control console, which is configured to display the information generated by the modular energy system 4000 to the operator of the robotic surgical system. As another example, the modular energy system 4000 can be communicably couplable to a mobile display that can be carried or secured to a surgical staff member for viewing thereby. In yet another example, the modular energy system 4000 can be communicably couplable to a surgical hub 4100 or another computer system that can include a display 4104. In aspects utilizing a user interface that is separate from or otherwise distinct from the modular energy system 4000, the user interface can be wirelessly connectable with the modular energy system 4000 as a whole or one or more modules 4001 thereof such that the user interface can display information from the connected modules 4001 thereon.

Referring still to FIG. 95A, the energy module 4004 can include a port assembly 4012 including a number of different ports configured to deliver different energy modalities to corresponding surgical instruments that are connectable thereto. In the particular aspect illustrated in FIGS. 94-95B, the port assembly 4012 includes a bipolar port 4014, a first monopolar port 4016a, a second monopolar port 4018b, a neutral electrode port 4018 (to which a monopolar return pad is connectable), and a combination energy port 4020. However, this particular combination of ports is simply provided for illustrative purposes and alternative combinations of ports and/or energy modalities may be possible for the port assembly 4012.

As noted above, the modular energy system 4000 can be assembled into different configurations. Further, the different configurations of the modular energy system 4000 can also be utilizable for different surgical procedure types and/or different tasks. For example, FIGS. 95A and 95B illustrate a first illustrative configuration of the modular energy system 4000 including a header module 4002 (including a display screen 4006) and an energy module 4004 connected together. Such a configuration can be suitable for laparoscopic and open surgical procedures, for example.

FIGS. 96-100 illustrate an example surgical system 10 with ultrasonic and electrosurgical features including any one of the end-effectors, surgical instruments, and generators described herein. FIG. 96 depicts a surgical system 10 including a generator 12 and a surgical instrument 14. The surgical instrument 14 is operatively coupled with the generator 12 via a power cable 16. The generator 12 is operable to power the surgical instrument 14 to deliver ultrasonic energy for cutting tissue, and electrosurgical bipolar RF energy (i.e., therapeutic levels of RF energy) for sealing tissue. In one aspect, the generator 12 is configured to power the surgical instrument 14 to deliver ultrasonic energy and electrosurgical bipolar RF energy simultaneously or independently.

The surgical instrument 14 of the present example comprises a handle assembly 18, a shaft assembly 20 extending distally from the handle assembly 18, and an end effector 22 arranged at a distal end of the shaft assembly 20. The handle assembly 18 comprises a body 24 including a pistol grip 26 and energy control buttons 28, 30 configured to be manipulated by a surgeon. A trigger 32 is coupled to a lower portion of the body 24 and is pivotable toward and away from the pistol grip 26 to selectively actuate the end effector 22, as described in greater detail below. In other suitable variations of the surgical instrument 14, the handle assembly 18 may comprise a scissor grip configuration, for example. An ultrasonic transducer 34 is housed internally within and supported by the body 24. In other configurations, the ultrasonic transducer 34 may be provided externally of the body 24.

As shown in FIGS. 97 and 98, the end effector 22 includes an ultrasonic blade 36 and a clamp arm 38 configured to selectively pivot toward and away from the ultrasonic blade 36, for clamping tissue therebetween. The ultrasonic blade 36 is acoustically coupled with the ultrasonic transducer 34, which is configured to drive (i.e., vibrate) the ultrasonic blade 36 at ultrasonic frequencies for cutting and/or sealing tissue positioned in contact with the ultrasonic blade 36. The clamp arm 38 is operatively coupled with the trigger 32 such that the clamp arm 38 is configured to pivot toward the ultrasonic blade 36, to a closed position, in response to pivoting of the trigger 32 toward the pistol grip 26. Further, the clamp arm 38 is configured to pivot away from the ultrasonic blade 36, to an open position (see e.g., FIGS. 96-98), in response to pivoting of the trigger 32 away from the pistol grip 26. Various suitable ways in which the clamp arm 38 may be coupled with the trigger 32 will be apparent to those of ordinary skill in the art in view of the teachings provided herein. In some versions, one or more resilient members may be incorporated to bias the clamp arm 38 and/or the trigger 32 toward the open position.

A clamp pad 40 is secured to and extends distally along a clamping side of the clamp arm 38, facing the ultrasonic blade 36. The clamp pad 40 is configured to engage and clamp tissue against a corresponding tissue treatment portion of the ultrasonic blade 36 when the clamp arm 38 is actuated to its closed position. At least a clamping-side of the clamp arm 38 provides a first electrode 42, referred to herein as clamp arm electrode 42. Additionally, at least a clamping-side of the ultrasonic blade 36 provides a second electrode 44, referred to herein as a blade electrode 44. The electrodes 42, 44 are configured to apply electrosurgical bipolar RF energy, provided by the generator 12, to tissue electrically coupled with the electrodes 42, 44. The clamp arm electrode 42 may serve as an active electrode while the blade electrode 44 serves as a return electrode, or vice-versa. The surgical instrument 14 may be configured to apply the electrosurgical bipolar RF energy through the electrodes 42, 44 while vibrating the ultrasonic blade 36 at an ultrasonic frequency, before vibrating the ultrasonic blade 36 at an ultrasonic frequency, and/or after vibrating the ultrasonic blade 36 at an ultrasonic frequency.

As shown in FIGS. 96-100, the shaft assembly 20 extends along a longitudinal axis and includes an outer tube 46, an inner tube 48 received within the outer tube 46, and an ultrasonic waveguide 50 supported within the inner tube 48. As seen best in FIGS. 97-100, the clamp arm 38 is coupled to distal ends of the inner and outer tubes 46, 48. In particular, the clamp arm 38 includes a pair of proximally extending clevis arms 52 that receive therebetween and pivotably couple to a distal end 54 of the inner tube 48 with a pivot pin 56 received through bores formed in the clevis arms 52 and the distal end 54 of the inner tube 48. The first and second clevis fingers 58 depend downwardly from the clevis arms 52 and pivotably couple to a distal end 60 of the outer tube 46. Specifically, each clevis finger 58 includes a protrusion 62 that is rotatably received within a corresponding opening 64 formed in a sidewall of the distal end 60 of the outer tube 46.

In the present example, the inner tube 48 is longitudinally fixed relative to the handle assembly 18, and the outer tube 46 is configured to translate relative to the inner tube 48 and the handle assembly 18, along the longitudinal axis of the shaft assembly 20. As the outer tube 46 translates distally, the clamp arm 38 pivots about the pivot pin 56 toward its open position. As the outer tube 46 translates proximally, the clamp arm 38 pivots in an opposite direction toward its closed position. A proximal end of the outer tube 46 is operatively coupled with the trigger 32, for example via a linkage assembly, such that actuation of the trigger 32 causes translation of the outer tube 46 relative to the inner tube 48, thereby opening or closing the clamp arm 38. In other suitable configurations not shown herein, the outer tube 46 may be longitudinally fixed and the inner tube 48 may be configured to translate for moving the clamp arm 38 between its open and closed positions.

The shaft assembly 20 and the end effector 22 are configured to rotate together about the longitudinal axis, relative to the handle assembly 18. A retaining pin 66, shown in FIG. 99, extends transversely through the proximal portions of the outer tube 46, the inner tube 48, and the waveguide 50 to thereby couple these components rotationally relative to one another. In the present example, a rotation knob 68 is provided at a proximal end portion of the shaft assembly 20 to facilitate rotation of the shaft assembly 20, and the end effector 22, relative to the handle assembly 18. The rotation knob 68 is secured rotationally to the shaft assembly 20 with the retaining pin 66, which extends through a proximal collar of the rotation knob 68. It will be appreciated that in other suitable configurations, the rotation knob 68 may be omitted or substituted with alternative rotational actuation structures.

The ultrasonic waveguide 50 is acoustically coupled at its proximal end with the ultrasonic transducer 34, for example by a threaded connection, and at its distal end with the ultrasonic blade 36, as shown in FIG. 100. The ultrasonic blade 36 is shown formed integrally with the waveguide 50 such that the blade 36 extends distally, directly from the distal end of the waveguide 50. In this manner, the waveguide 50 acoustically couples the ultrasonic transducer 34 with the ultrasonic blade 36, and functions to communicate ultrasonic mechanical vibrations from the transducer 34 to the blade 36. Accordingly, the ultrasonic transducer 34, the waveguide 50, and the ultrasonic blade 36 together define an acoustic assembly. During use, the ultrasonic blade 36 may be positioned in direct contact with tissue, with or without assistive clamping force provided by the clamp arm 38, to impart ultrasonic vibrational energy to the tissue and thereby cut and/or seal the tissue. For example, the blade 36 may cut through tissue clamped between the clamp arm 38 and a first treatment side of the blade 36, or the blade 36 may cut through tissue positioned in contact with an oppositely disposed second treatment side of the blade 36, for example during a "back-cutting" movement. In some variations, the waveguide 50 may amplify the ultrasonic vibrations delivered to the blade 36. Further, the waveguide 50 may include various features operable to control the gain of the vibrations, and/or features suitable to tune the waveguide 50 to a selected resonant frequency. Additional features of the ultrasonic blade 36 and the waveguide 50 are described in greater detail below.

The waveguide 50 is supported within the inner tube 48 by a plurality of nodal support elements 70 positioned along a length of the waveguide 50, as shown in FIGS. 99-100. Specifically, the nodal support elements 70 are positioned longitudinally along the waveguide 50 at locations corresponding to acoustic nodes defined by the resonant ultrasonic vibrations communicated through the waveguide 50. The nodal support elements 70 may provide structural support to the waveguide 50, and acoustic isolation between the waveguide 50 and the inner and outer tubes 46, 48 of the shaft assembly 20. In variations, the nodal support elements 70 may comprise o-rings. The waveguide 50 is supported at its distal-most acoustic node by a nodal support element in the form of an overmold member 72, shown in FIG. 100. The waveguide 50 is secured longitudinally and rotationally within the shaft assembly 20 by the retaining pin 66, which passes through a transverse through-bore 74 formed at a proximally arranged acoustic node of the waveguide 50, such as the proximal-most acoustic node, for example.

In the present example, a distal tip 76 of the ultrasonic blade 36 is located at a position corresponding to an antinode associated with the resonant ultrasonic vibrations communicated through the waveguide 50. Such a configuration enables the acoustic assembly of the instrument 14 to be tuned to a preferred resonant frequency $f_o$ when the ultrasonic blade 36 is not loaded by tissue. When the ultrasonic transducer 34 is energized by the generator 12 to transmit mechanical vibrations through the waveguide 50 to the blade 36, the distal tip 76 of the blade 36 is caused to oscillate longitudinally in the range of approximately 20 to 120 microns peak-to-peak, for example, and in some instances in the range of approximately 20 to 50 microns, at a predetermined vibratory frequency $f_0$ of approximately 50 kHz, for example. When the ultrasonic blade 36 is positioned in contact with tissue, the ultrasonic oscillation of the blade 36 may simultaneously sever the tissue and denature the proteins in adjacent tissue cells, thereby providing a coagulative effect with minimal thermal spread.

As previously discussed, according to some aspects of the present disclosure, clamp arm pads can be configured to replace conventional electrodes using electrically non-conductive layers and electrically conductive layers positioned in various configurations, thereby eliminating the need for spring loaded electrode plates. The aforementioned clamp arm pads can provide numerous benefits, including improved ultrasonic performance, reduced tissue sticking, and ease of manufacture, without significantly increasing the cost of the end effector. It is contemplated that the aforementioned clamp arm pads will wear at a comparable rate to those of exclusively ultrasonic instruments due to the heat and/or abrasion associated with continued use of the surgical instrument.

Unfortunately, the degradation of the aforementioned clamp arm pads due to heat and/or abrasion can increase if clamp arm pad—or the layers of the clamp arm pad—are not properly secured within the clamp arm, degradation can be exacerbated, which can adversely affect the performance of a surgical instrument. For example, the gap between adjacent electrodes (e.g. clamp arm, blade) should be maintained and minimized to reduce degradation, minimize the possibility of an electrical short, and achieve an optimal delivery of RF energy. Additionally, the clamp arm pad height and quantity of clamp arm padding should be maximized to stabilize the tissue sample and support it under a desired amount of clamping force, which can enhance the application of ultrasonic energy. Degradation decreases the amount of clamp arm padding and adversely affects the application of ultrasonic energy. Accordingly, features stabilize and properly position the clamp arm pad—and the layers of the clamp arm pad—and reduce degradation and thus, improve the performance and usable life of the surgical instrument, would be beneficial.

For example, it would be preferable to include intermediate layers that improve the bond between the conductive and non-conductive layers of the clamp arm pad. Alternatively, it would be preferable to alter the composition of the conductive layer such that the electrode can conform to the blade under pressure. The mechanical interface between the electrode and the clamp arm pad can be further modified to improve retention within the clamp jaw. Alternatively and/or additionally, the mechanical arrangement of the clamp arm pads disclosed herein can be attenuated to include a certain degree of flexibility, such that the clamp arm pad is tunable. Conventional clamp arm pads lack such features and are therefore susceptible to detrimental degradation, thereby reducing surgical instrument efficacy in both RF and ultrasonic modalities. Accordingly, there is a further need for the aforementioned multi-layer clamp arm pads to be modified to include additional features—such as those listed above. Such clamp arm pads could further mitigate degradation, thereby improving the delivery of RF and ultrasonic energy and preserving the longevity of a surgical instrument.

The present disclosure will now focus on non-limiting aspects of a multi-layer clamp arm pad capable of providing the aforementioned benefits in response to the aforementioned needs. Such clamp arm pads are exclusively depicted and described to illustrate the benefits of their respective features. Accordingly, none of the specific geometric configurations and/or combinations of features disclosed in the following aspects are intended to limit the scope of the present disclosure. For example, the following features and benefits can be implemented via clamp arm pads in a multitude of configurations, such as the clamp arm pad 2450, 2460, 2470 configurations of FIGS. 23-25 and/or the clamp arm 2520, 2530, 2564 configurations of FIGS. 30, 31, and 35, amongst others. However, it shall be appreciated that any of the features of any of the clamp arm pads of the following aspects can be combined in a variety of geometric configurations based upon a specific user preference and/or intended application.

Referring now to FIG. 101, a perspective view of a clamp arm pad 600 is depicted in accordance with at least one non-limiting aspect of the present disclosure. Similar to the clamp arm pads 2450, 2460, 2470 of FIGS. 23-25 and clamp arms 2520, 2530, 2564 configurations of FIGS. 30, 31, and 35, the non-limiting aspect of FIG. 101, the clamp arm pad 6000 can include a layer of an electrically conductive material 6002 and a layer of an electrically non-conductive material 6004. Once again, the electrically conductive material 6002 and the electrically non-conductive material can include any material (e.g. organic, synthetic) with the desired electrical and structural properties. For example, it might be preferable for the electrically conductive material 6002 and the electrically non-conductive material 6004 can include a "non-stick" material (e.g. polytetrafluoroethylene ("PTFE")) and thus, prevent a tissue sample from sticking to the clamp pad arm 6000 after it has been cut and/or sealed.

As was previously discussed, the geometric configuration of the clamp arm pad 600 of FIG. 101 can be selected to support the forces applied to clamped tissue during the transmission of ultrasonic energy and to reduce the possibility of an inadvertent electrical short during the transmission of radiofrequency energy. For example, the relative thicknesses, widths, lengths, and/or patterns of the electrically conductive material 6002 and the electrically non-conductive material 6004 can be specifically configured to enhance the overall performance of the hybrid surgical instrument. According to the non-limiting aspect of FIG. 101, the electrically non-conductive material 6004 is thicker than the electrically conductive material 6002 and configured to be intermediate to the electrically conductive material 6002 and an ultrasonic blade. Thus, when the electrically conductive material 6002 degrades throughout the useful life of the clamp arm pad 6000, the electrically non-conductive material 6004 can prevent the electrically conductive material 6002—configured as an electrode of the radiofrequency energy circuit—from moving into a high-risk proximity of the ultrasonic blade—configured as a return electrode of the radiofrequency energy circuit. Accordingly, the electrically non-conductive material 6004 can serve as a structural buffer or blockage between the electrically conductive material 6002 and the ultrasonic blade, thereby reducing the probability of undesirable arcing or shorting.

Still referring to FIG. 101, the electrically non-conductive material 6004 can be oriented in a variety of geometric configurations and/or patterns about the electrically conductive material 6002. The configuration and/or pattern can be selected such that a specific surface area of the electrically conductive material 6002 is tissue facing, thereby facilitating a preferred energy path for the radiofrequency energy to flow through the tissue to the return electrode (e.g., the ultrasonic blade). Accordingly, various configurations and/or patterns can deliver varying amounts of energy in accordance with user preference and/or intended application. Alternatively and/or additionally, the pattern can be selected for a preferred mechanical engagement between the multiple layers 6002, 6004, 6006 within the clamp arm 6000. As will be described, sound mechanical engagement can result in less vibration in use and thus, less wear throughout the layers 6002 6004, 6006 of the clamp arm 6000. According to other non-limiting aspects, the pattern can be selected to ensure that the electrically conductive material 6002 will be properly distanced from the ultrasonic blade in an area of interest of the clamp arm 6000.

For example, according to the non-limiting aspect of FIG. 101, the electrically non-conductive material 6004 can be bonded to the electrically conductive material 6002 in a serpentine configuration, which ensures a preferred amount of radiofrequency energy will be transferred through the tissue to the return electrode (e.g., ultrasonic blade), allows for the layers of electrically conductive material 6002 and electrically non-conductive material 6004 to be properly seated within the clamp arm 6000, and ensures that the electrically conductive material 6002 will not contact the ultrasonic blade in areas of interest across the clamp arm 6000, thereby ensuring a low risk of arcing and electrical shorting in those areas. Of course, it shall be appreciated that the serpentine pattern of FIG. 101 is simply presented for illustrative purposes, and that the present disclosure contemplates other non-limiting aspects wherein the electrically non-conductive material 6004 is configured about the electrically conductive material 6002 is any number of patterns in accordance with user preference and/or user preference.

In further reference to FIG. 101, the clamp arm pad 6000 of FIG. 101 can further include a layer of an intermediate material 6006 dispositioned between the layer of electrically conductive material 6002 and the layer of electrically non-conductive material 6004. The layer of intermediate material 6006 also be selected to include preferable properties based, at least in part on, user preference and/or intended application. For example, the intermediate material 6006 can be an adhesive that bonds the electrically conductive material 6002 to the electrically non-conductive material 6004. According to some non-limiting aspects, the intermediate material 6006 can be a free-flowing version of the electrically non-conductive material 6004 (e.g., virgin PTFE, perfluoroalkoxyalkane ("PFA")) that generates bonds the multiple layers of the clamp arm pad 6000 together. According to some non-limiting aspects, it might be desirable for the intermediate material 6006 to include desirable structural properties, such as toughness, flexibility, chemical resistivity, high purity, and/or low stiffness (e.g., fluoropolymer), amongst others. Additionally and/or alternatively, the intermediate material 6006 can be selected based on desirable electrical properties, such as a high dielectric strength, a low dissipation factor, and a low dielectric constant, amongst others. Similar to the electric-ally conductive material 6002 and the electrically non-conductive material 6004, it would be desirable for the intermediate material 6006 to possess resistive properties to mitigate the rate of degradation and wear.

Referring now to FIG. 102, a sectioned front view of the clamp arm pad 6000 of FIG. 101 is depicted in accordance with at least one non-limiting aspect of the present disclosure. According to the non-limiting aspect of FIG. 102, a layer of intermediate material 6006 is clearly depicted between the layer of electrically conductive material 6002 and the layer electrically non-conductive material 6004. Each of the layers of electrically conductive material 6002, electrically non-conductive material 6004, and intermediate material 6004 can include a length, a width, and/or a thickness that can be specifically configured relative to one another to ensure a proper amount of radiofrequency energy transfer and tissue stability, while still mitigating the risk of electrical shorting and/or arcing. For example, each of the layers of electrically conductive material 6002, electrically non-conductive material 6004, and intermediate material 6006 include a thickness $T_C$, $T_I$, $T_{NC}$ respectively. According to the non-limiting aspect of FIG. 102, the layer of intermediate material can include a thickness $T_I$ that is smaller than either thicknesses $T_C$, $T_{NC}$ associated with the layers of electrically conductive material 6002 and the layer of electrically non-conductive material 6004. Of course, the layer of intermediate material 6006 can be geometrically configured to established a desired bond between the layer of electrically conductive material 6002 and layer of electrically non-conductive material 6004.

Referring now to FIGS. 103A and 103B, top views of a distal portion 6203 and a proximal portion 6205 of another clamp arm pad 6200 are respectively depicted in accordance with at least one non-limiting aspect of the present disclosure. According to the non-limiting aspect of FIGS. 103A and 103B, the clamp arm pad 6200 can include a layer of an electrically conductive material 6202 and a layer of an electrically non-conductive material 6204. Once again, both the electrically conductive material 6202 and the electrically non-conductive material 6204 can include a "non-stick" material (e.g. polytetrafluoroethylene ("PTFE")) and thus, prevent a tissue sample from sticking to the clamp pad arm 6200 after it has been cut and/or sealed. According to some non-limiting aspects, the clamp arm pad 6200 can further include a layer of intermediate bonding material 6206 between the electrically conductive material 6202 and the electrically non-conductive material 6204.

Still referring to FIGS. 103A and 103B, the electrically conductive material 6202 of the clamp arm pad 6200 can include electrically conductive materials in any form. The production of the clamp arm pad 6200 of FIGS. 103A and 103B can include the intentional introduction of impurities and/or materials into into the clamp arm pad material for the purpose of modulating its electrical and/or structural properties of the resulting electrode. As such, the electrically conductive material 6202 can be referred to as an extrinsic semiconductor. For example, the electrically conductive material 6202 of FIGS. 103A and 103B can be doped with electrically conductive fibers (e.g., carbon, stainless steel, silver). Of course, it shall be appreciated that the present disclosure contemplates a variety of electrically conductive materials in a variety of forms introduced into the PTFE in a variety of different methods. Additionally and/or alternatively, the layers 6202, 6204 of the clamp arm pad 6200 can be pressure bonded together. In still other non-limiting aspects, the electrically conductive material 6202 and electrically non-conductive material 6204 can be fabricated via resin in a mold. Accordingly, any number of composites can be selected in accordance with user preference and/or intended application.

In further reference to FIG. 104A, the proximal portion 6205 of the clamp arm pad 6200 can include a large wear resistant gap pad 6210 sized and configured to fit within an opening of at the proximal portion 6205 of the electrically conductive material 6202. Of course, the geometric configuration and location of the large wear resistant gap pad 6210 can be specifically configured to alter the RF energy path of the resulting electrode and further reduce the risk of electrical shorting and arcing between the electrically conductive material 6202 and the ultrasonic blade (e.g. return electrode).

Referring now to FIG. 104, a piece of manufacturing support equipment 6300 configured to produce clamp arm pads 6301 is depicted in accordance with at least one non-limiting aspect of the present disclosure. According to the non-limiting aspect of FIG. 104, the clamp arm pads 6310 can include an electrically conductive pad 6302 and an electrically non-conductive pad 6304. Similar to the aspects of FIGS. 101-103, the electrically conductive pad 2536 can be made of an electrically conductive polymer and can be configured as one of the electrodes in the bipolar RF circuit. The manufacturing support equipment 6300 of FIG. 104 can facilitate the overmolding of the electrically conductive pad 6302 and/or electrically non-conductive pad 6304 over the carrier 6308 and/or stamping.

In further reference to FIG. 104, the electrically conductive material 6302 and electrically non-conductive material 6304 can be constructed from resin injected into the manufacturing support equipment 6300, which is configured as a mold. Thus, the gap between the electrically conductive pad 6302 and the electrically non-conductive pad 6304 can be minimized, as the two insert molded electrode pads 6302, 6304 can be fit line-to-line via mold pressure. According to some non-limiting aspects, an intermediate bonding material 6306 between the electrically conductive material 6302 and the electrically non-conductive material 6304. As previously discussed, minimizing the gap can enhance the performance of the surgical instrument and reduce wear by reducing inadvertent vibrations, noise, and improving the transfer of heat. According to other non-limiting aspects, the manufacturing support equipment 6300 can be further configured to facilitate the pressure bonding of the electrically conductive pad 6302 to the electrically non-conductive pad 6304. The manufacturing support equipment 6300 can be further configured for use with various films and coatings, as discussed in prior aspects. Additionally and/or alternatively, the manufacturing support equipment 6300 can be altered to include geometric features (e.g., micro-holes, slots, honeycomb, channels) to mechanically secure the clamp arm pads 6301 into a carrier of the clamp arm. Accordingly, the use of the manufacturing support equipment 6300 can enhance structural soundness and provide an easier, more robust electrical connection than known end effectors.

Referring now to FIG. 105, a perspective view clamp arm 6400 featuring another clamp arm pad 6402 is depicted in accordance with at least one non-limiting aspect of the present disclosure. According to the non-limiting aspect of FIG. 105, the clamp arm 6400 can include a clamp arm pad 6402 that can be sub-divided, with some portions vacant and configured to accommodate an electrically conductive portion 6404. Accordingly, the clamp arm pad 6402 can further include secondary portions 6406 interposed between the electrically conductive portions 6404. In some non-limiting aspects, the secondary portions can include a Teflon-like material (e.g., PTFE) the defines the vacancies. The electrically conductive portions 6404 can include a thread or yarn composed of an electrically conductive material, which provides the clamp arm pad with a certain degree of compliance and/or flexibility. Similar to the aforementioned clamp arm pads, the clamp arm pad 6402 of FIG. 105 can facilitate a seamless transition between precise dissection and sealing tasks via the transfer of RF and ultrasonic energy. The clamp arm pad 6402 minimizes the gap between the electrode formed by the electrically conductive portion 6404 and a return electrode formed by the ultrasonic blade. However, the flexible nature of the electrically conductive portion 6404 enables the clamp arm pad 6402 of FIG. 105 to accommodate pressure or force exerted by the ultrasonic blade without risking structural failure through harmonic activation. Accordingly, the clamp arm pad 6402 is sufficiently thick to provide the tissue with support during ultrasonic activation, but can be compressed during RF activation, thereby reducing the distance between the clamp arm pad 6402 electrode and return electrode of the ultrasonic blade. This allows the clamp arm pad 6402 to enhance surgical instrument performance, by resisting wear and facilitating an optima delivery of RF energy.

In further reference to FIG. 105, the electrically conductive portion 6402 can include a thread or yarn composed of an electrically conductive material, which provides the clamp arm pad with a certain degree of compliance and/or flexibility. The yarn can be electrically non-conductive substrate (e.g., Para-Aramide or Kevlar, Polyester, Polyamide 6.6, Polyamide 6, Ultra-High Molecular Weight Polyehylene, Viscose CV or Rayon, Silk, Meta-Aramide or Nomex, Liquid Crystal Polymers such as Vectran, and/or other continuous filament yarns) that includes a desired flexibility and/or compressibility. However, the electrically non-conductive yarn can be coated with a metal foil (e.g. gold, silver, copper, platinum, titanium, stainless steel, and/or aluminum) to achieve a desired electrical conductivity. For example, the electrically non-conductive yarn can be coated via plasma coating, chemical adhesion, application of a binder, and/or any suitable coating process in accordance with user preference and/or intended application. The resulting electrically conductive yarn 6404 can be threaded through the vacancies of the clamp arm pad 6402, thereby creating an electrode of the radiofrequency circuit. Additionally and/or alternatively, the electrically conductive yarn 6404 can be wound around the clamp arm 6400 thereby creative a woven electrode about a perimeter of the clamp arm pad 6402. As such, the clamp arm pad 6402 can prevent the risk of blade breakage due to harmonic activation in an ultrasonic mode of operation and can provide alternate and/or redundant electrical pathways for the RF circuit through the clamp arm 6400.

Still referring to FIG. 105, it shall be appreciated that the electrically conductive yarn 6404 can be woven about the clamp arm pad 6402 in a variety of patterns, such that the electrically conductive yarn 6404 and electrically non-conductive portions 6406 collectively establish a desired electrode configuration. Accordingly, the clamp arm pad 6402 can include a hybrid configuration of electrically conductive portions 6404 and electrically non-conductive portions 6406 similar to the previously-discussed clamp arm pads. Additionally and/or alternatively, the electrically conductive yarn 6404 composition can be attenuated to achieve any number of desirable electrical properties. In some non-limiting aspects, the electrically conductive yarn 6402 can be woven together with electrically non-conductive yarn including PTFE and/or any other lubricious material to further mitigate the risk of electrical shorting. The pattern can be further attenuated to provide structural enforcement at areas of the clamp arm 6400 expected to bear a bulk of the structural or electrical load. For example, a larger quantity of the electrically conductive yarn 6402 and/or a higher resistive yarn can be configured about a proximal end of the clamp arm 6400 to serve further mitigate clamp arm pad 6402 wear in view of the high stresses applied at that particular location.

FIGS. 106A-C depict multiple perspective views of other clamp arm pads 6510, 6520, 6530, each featuring means of mechanically securing a conductive electrode 6512, 6522, 6530 to a nonconductive pad 6514, 6524, 6534. The conductive electrode 6512, 6522, 6530 can be configured such that the nonconductive pad 6514, 6524, 6534 can be nested within it, thereby constraining the two portions together. Accordingly, the clamp arm pads 6510, 6520, 6530 of FIGS. 106A-C can ensure a consistency of contact and retention of components and reducing inadvertent excitation of the clamp arm pad 6510, 6520, 6530. Accordingly, the non-limiting aspects of FIGS. 106A-C can further mitigate wear and degradation.

For example, according to the non-limiting aspect of FIG. 106A, a perspective view of another clamp arm pad 6510 is depicted in accordance with at least one non-limiting aspect of the present disclosure. The clamp arm pad 6510 of FIG. 106A can include an electrically non-conductive portion 6514 nested within an electrically conductive portion 6512 in a press-fit configuration. According to the non-limiting aspect of FIG. 106A, the electrically conductive portion 6512 can include a channel 6516 constituting a pattern that corresponds to the geometric pattern of the electrically non-conductive portion 6514. According to the non-limiting aspect of FIG. 106A, the pattern can be serpentine, although the present disclosure contemplates a multitude of other geometric patterns that can be selected based on user preference and/or intended application. As such, the electrically conductive portion 6512 can be specifically configured to accommodate the electrically non-conductive portion 6514. The channel 6516 can further include a T-slot configured to receive a corresponding geometric feature 6518 of the electrically non-conductive portion 6514. The channel 6516 can be geometrically configured such that it is slightly smaller than the electrically non-conductive portion 6514, thereby resulting in a press fit between the portions 6512, 6514 of the clamp arm pad 6510 once the feature 6518 is received within the T-slot of the channel 6516.

Referring now to FIGS. 106B and 106C, a perspective view of another clamp arm pad 6520 is depicted in accordance with at least one non-limiting aspect of the present disclosure. According to the non-limiting aspect of FIGS. 106B and 106C, the electrically conductive portion 6522 can include geometric features 6526, 6535 configured to grip a tissue sample. Although the non-limiting aspects of FIG. 106B includes geometric features 6525 that are tooth-like in form, it shall be appreciated that the present disclosure contemplates geometric features of varying shapes and sizes, which can be selected based on user preference and/or intended application. For example, the electrically conductive portion 6532 of the clamp arm pad 6530 of FIG. 106C can include geometric features 6535 configured in a herring bone pattern. FIG. 106C depicts an assembled clamp arm pad 6520, wherein the electrically non-conductive portion 6524 is nested within the electrically conductive portion 6522. Similar to the clamp arm pad 6510 of FIG. 106A, the electrically conductive portion 6522 can include a channel and T-slot configuration. Additionally, the electrically conductive portion 6522 itself can include a geometric feature 6526 configured to be received by a corresponding channel of a clamp arm jaw.

The clamp arm pad 6530 of FIG. 106C is similarly configured to the clamp arm pad 6520 of FIG. 106B, but is depicted as disassembled to illustrate how the features 6538 of the electrically non-conductive portion 6534 can be received by the channel 6536 of the electrically conductive portion 6532. Both clamp arm pads 6520, 6530 of FIGS. 106B and 106C include staggered shelf configuration. That is, both the electrically conductive portions 6522, 6532 and electrically non-conductive portions 6524, 6534 can include shelf type geometric features 6526, 6538, 6539 on both sides. Contrarily, only the electrically non-conductive portion 6514 of the clamp arm pad 6510 includes staggered shelf geometric features 6518, wherein the side of the electrically non-conductive portion 6514 that the shelf-type geometric feature 6518 is on alternates along a longitudinal axis of the clamp arm pad 6510. However, all of the clamp arm pads 6510, 6520, 6530 can be assembled from the top using a press-fit interface.

Referring now to FIGS. 107A and 107B, top and perspective views of another clamp arm pad 6600 are respectively depicted in accordance with at least one non-limiting aspect of the present disclosure. According to the non-limiting aspect of FIGS. 107A and 107B, the clamp arm pad 6600 can include an electrically conductive portion 6602 and an electrically non-conductive portion 6604 that interface via zipper-type T-slot configuration. For example, the electrically conductive portion 6602 includes a plurality of teeth 6606 that are configured to engage a plurality of corresponding teeth 6608 of the electrically non-conductive portion 6604 in an alternating fashion. Accordingly, the plurality of teeth 6606 and the plurality of corresponding teeth 6608 are configured to engage with one another such that the electrically conductive portion 6602 and electrically non-conductive portion 6604 sit flushed with respect to one another at their respective bases. The assembly is best represented in FIG. 107B, which illustrates how the electrically conductive portion 6602 can be press fit from above the electrically non-conductive portion 6604, until the plurality of teeth 6606 properly engage the plurality of corresponding teeth 6606.

Referring now to FIGS. 108A and 108B, perspective and sectioned front views of another clamp arm pad 6700 are respectively depicted in accordance with at least one non-limiting aspect of the present disclosure. According to the non-limiting aspect of FIG. 108A, the clamp arm pad 6700 can include an electrically conductive portion 6702 and an "L" shaped electrically non-conductive portion 6704. The "L" shaped electrically non-conductive portion 6704 can be configured to slide through the electrically conductive portion 6702 from underneath, thereby forming a T-slot to be mechanically coupled to the clamp arm. The electrically conductive portion can include a "T" shaped end piece 6706 configured to abut the "L" shaped electrically non-conductive portion 6704. Additionally, the "L" shaped electrically non-conductive portion 6704 can include a foot 6708 configured to engage a channel of a clamp arm jaw, thereby securing the clamp arm pad 6700 and mitigating inadvertent mechanical excitations.

FIG. 108B illustrates a sectioned front view of the clamp arm pad 6700 in accordance with at least one non-limiting aspect of the present disclosure. As is depicted in FIG. 108B, the "L" shaped electrically non-conductive portion 6704 is constrained in a lateral direction by the electrically conductive portion 6702. However, according to some non-limiting aspects, the electrically non-conductive portion 6704 can be float about a dimension D defined between a top surface of the foot 6708 of the electrically non-conductive portion 6704 and a bottom surface of the electrically conductive portion 6702. As such, according to some aspects of the present disclosure, the clamp arm pad 6700 can include a shoulder 6710 configured to be at least a portion of the dimension D and dispositioned between the top surface of the foot 6708 of the electrically non-conductive portion 6704 and a bottom surface of the electrically conductive portion 6702, thereby limiting and/or eliminating the aforementioned float.

Referring now to FIG. 109, a sectioned front view of another clamp arm pad 6800 is depicted in accordance with at least one non-limiting aspect of the present disclosure. According to the non-limiting aspect of FIG. 109, an electrically non-conductive portion 6804 can be embedded within an electrically conductive portion 6802 of the clamp arm pad 6800, thereby forming an electrode "stack" in a T-slot configuration that can be mechanically integrated within the clamp arm jaw 6806. The electrically non-conductive portion 6804 can be molded within the electrically conductive portion 6802. Alternatively, the electrically non-conductive portion 6804 can be separately formed and bonded within the electrically conductive portion 6802. Of course, it shall be appreciated that any suitable manufacturing technique can be formed to produce the clamp arm pad 6800 of FIG. 109. Likewise, although the non-limiting aspect of FIG. 109 includes a T-slot configuration, it shall be appreciated that the clamp arm pad 6800 can include any suitable geometric configuration, depending on user preference and/or intended application.

Referring now to FIGS. 110A and 110B, top perspective views of other clamp arm pad 6910, 6920 configurations are depicted in accordance with at least one non-limiting aspect of the present disclosure. According to the non-limiting aspect of FIGS. 110A and 110B, the clamp arm pad 6910, 6920 can include whole T-slot sections of electrically conductive portions 6912, 6922 and electrically non-conductive portions 6914, 6924 dispositioned within the clamp arm jaw 6911, 6921 to strengthen the retention of the clamp arm pad 6910, 6920 to mitigate inadvertent mechanical excitations and therefore, reduce wear and degradation. The electrically non-conductive portions 6914, 6924 are positioned over the electrically conductive portions 6912, 6922, thereby establishing a desirable electrode configuration of the clamp arm pad 6910, 6920.

According to the non-limiting aspect of FIG. 110A, the electrically non-conductive portions 6914 can include wings 6916 that extend over and, in some cases, abut or the electrically conductive portions 6912. This further shields the exposed surface area of the electrode, thereby further reducing the risk of electrical shorting and/or arcing. Alternatively and/or additionally, at least a portion of the electrically non-conductive portions 6924 can be squared off, as is depicted in the non-limiting aspect of FIG. 110B. Accordingly, the clamp arm pad 6920 can be configured to increase the exposed surface area of the resulting electrode, thereby optimizing the transmission of RF energy to the return electrode of the ultrasonic blade.

Referring now to FIG. 111, a sectioned front view of another clamp arm pad 6930 is depicted in accordance with at least one non-limiting aspect of the present disclosure. According to the non-limiting aspect of FIG. 111, the clamp arm pad 6930 can include an electrically conductive portion 6932 and an electrically non-conductive portion 6934 mechanically coupled within a clamp arm jaw 6936 via an overhang configuration that secures the electrode stack. For example, a peripheral wings 6938 of the electrically conductive portion 6932 can define a channel configured to accommodate an overhang 6937 of the clamp arm jaw 6936. Since the electrically non-conductive portion 6934 includes a T-slot configuration that is dispositioned between the electrically conductive portion 6932 and the clamp arm jaw 6936, and the electrically conductive portion 6932 is secured in place via the overhang 6937, the electrode stack is stabilized and configured to resist inadvertent mechanical excitations and resist wear and/or degradation.

Referring now to FIG. 112A, a perspective view of an electrically conductive pad 6942 is depicted in accordance with at least one non-limiting aspect of the present disclosure. According to the non-limiting aspect of FIG. 111, the clamp arm pad 6942 can include overhangs 6943 on either side configured to be received by the T-slot of a clamp arm jaw, thereby securing the electrode stack. Similar to previously-discussed aspects, the electrically conductive pad 6942 can further include a channel 6946 configured to accommodate an electrically non-conductive pad configured to reduce the likelihood of electrical shorting and/or arcing with the return electrode (e.g., ultrasonic blade). Additionally and/or alternatively, the electrically conductive pad 6942 can include a plurality of geometric features 6945 configured to grip a tissue sample clamped within the end effector. According to the non-limiting aspect of FIG. 112A, the geometric features can include a tooth-like configuration; however, the present disclosure contemplates other aspects wherein the geometric configuration is varied according the user preference and/or intended application. FIG. 112B provides a more detailed depiction of the overhangs 6943 of the electrically conductive pad 6942 of FIG. 112A.

Referring now to FIG. 112C, a front view of a clamp arm 6940 including the electrically conductive pad 6942 of FIG. 112A is depicted in accordance with at least one non-limiting aspect of the present disclosure. According to the non-limiting aspect of FIG. 112C, the clamp arm 6940 can include a clamp arm jaw 6941 with a T-slot configuration configured to receive a clamp arm pad configuration. The overhangs 6943 of the electrically conductive pad 6942 are depicted as received within the T-slot configuration of the clamp arm jaw 6042. Accordingly, the electrically conductive pad 6042 defines an electrode surface area for the transmission of RF energy. Although the channel 6946 (FIG. 112A) is not depicted, as it is in the center of the electrically conductive pad 6942, an electrically non-conductive pad can be inserted within it, thereby defining a non-conductive pad that can separate the electrode surface from a return electrode (e.g., ultrasonic blade) and reduce the risk of electrical shorting or arcing. According to some non-limiting aspects, the overhang can be tapered to conform with the overall shape of the clamp arm jaw, especially at the distal end.

Referring now to FIG. 113A, a top view of a clamp arm 6950 is depicted in accordance with at least one non-limiting aspect of the present disclosure. According to the non-limiting aspect of FIG. 113A, the clamp arm 6950 can include two lateral tracks 6958 configured to mechanically engage and secure the electrically conductive pad 6952 to the clamp arm 6950. Similar to previously-discussed aspects, the electrically conductive pad 6952 can further include a channel 6956 configured to accommodate an electrically non-conductive pad configured to reduce the likelihood of electrical shorting and/or arcing with the return electrode (e.g., ultrasonic blade).

Referring now to FIG. 113B, a sectioned front view of the clamp arm 6950 of FIG. 113A is depicted in accordance with at least one non-limiting aspect of the present disclosure. According to the non-limiting aspect of FIG. 113B, the lateral tracks 6958 can include a dovetail configuration configured to secure the electrically conductive pad 6952 to the clamp arm 6950. As can be seen from FIG. 113B, the channel 6956 of the electrically conductive pad 6952 can accommodate an electrically non-conductive pad 6954 that can contact a tissue sample 6957. The electrically non-conductive pad 6954 can be secured within the clamp arm 6950 via a T-slot channel, such that the electrode stack is properly secured to the clamp arm 6950, thereby preventing undesirable mechanical excitation and reducing wear and degradation.

Referring now to FIG. 114A, a perspective view of a clamp arm 6960 is depicted in accordance with at least one non-limiting aspect of the present disclosure. According to the non-limiting aspect of FIG. 114A, the clamp arm 6960 can include two lateral tracks 6968 configured to mechanically engage and secure an electrically conductive pad to the clamp arm 6960. Similar to previously-discussed aspects, the clamp arm 6960 can further include a T-slot channel 6966 configured to accommodate a geometric feature of a clamp arm pad including an electrode configured to facilitate the transmission of RF energy while reducing the likelihood of electrical shorting and/or arcing with the return electrode (e.g., ultrasonic blade).

Referring now to FIG. 114B, a sectioned front view of the clamp arm 6960 of FIG. 114A is depicted in accordance with at least one non-limiting aspect of the present disclosure. According to the non-limiting aspect of FIG. 114B, the lateral tracks 6968 can include a barbed configuration configured to secure the electrically conductive pad 6962 to the clamp arm 6960. As can be seen from FIG. 114B, the channel 6966 of the clamp arm 6960 can accommodate an geometric feature of an electrically non-conductive pad 6964 that can contact a tissue sample 6967. The electrically non-conductive pad 6954 can be secured within the clamp arm 6960 via a T-slot channel, such that the electrode stack is properly secured to the clamp arm 6950, thereby preventing undesirable mechanical excitation and reducing wear and degradation.

Referring now to FIG. 115, a sectioned front view of a clamp arm pad 6970 configuration is depicted in accordance with at least one non-limiting aspect of the present disclosure. According to the non-limiting aspect of FIG. 115, the electrically conductive pad 6972 of the clamp arm pad 6970 can include an overhang 6973 configuration similar to that of FIGS. 112A through 112C, wherein the overhang 6973 is configured to engage the "I-beam" electrically non-conductive pad 6974. However, the clamp arm pad 6970 configuration of FIG. 115 includes thicker features, thereby further distancing the electrode from the return electrode (e.g., ultrasonic blade) and fortifying the clamp arm pad 6970 configuration from wear and/or degradation.

Referring now to FIG. 116, a front view of a clamp arm 6980 is depicted in accordance with at least one non-limiting aspect of the present disclosure. According to the non-limiting aspect of FIG. 116, the clamp arm 6980 can include a clamp arm jaw 6981 with a T-slot configuration configured to receive a clamp arm pad 6982, 6984 configuration. Similar to previously discussed aspects, the electrically non-conductive pad 6984 can be secured to the clamp arm jaw 6981 via the T-slot channel. However, according to the non-limiting aspect of FIG. 116, the electrically conductive pad 6982 can include fish-tail style channels 6987 configured to receive geometric features of the clamp arm jam 6981 of a corresponding shape. Accordingly, the electrically conductive pad 6982 can be secured within the clamp arm jaw 6981 and define an electrode surface area for the transmission of RF energy.

Referring now to FIG. 117, a top view of a clamp arm 6990 is depicted in accordance with at least one non-limiting aspect of the present disclosure. The clamp arm 6990 includes a distal portion 6993 and a proximal portion 6995 of the clamp arm jaw 6991. Similar to previously discussed aspects, the clamp arm 6990 further includes an electrically conductive pad 6992 and an electrically non-conductive pad 6994. However, according to the non-limiting aspect of FIG. 117, the electrically nonconductive pad 6992 has been removed in the distal portion 6993 of the clamp arm jaw 6991 to create a larger electrically conductive surface area and thus, facilitate the transfer of more RF energy at the distal end 6993 of the clamp arm 6990. Alternatively and/or additionally, the electrically conductive pad 6992 can be raised to be flush with the electrically non-conductive pad 6994 in the distal portion 6993 of the clamp arm 6990. Accordingly, a clinician can better control the sealing of tissue clamped at the distal end of the clamp arm 6990.

Referring now to FIG. 117B, a side vie of the clamp arm 6990 of FIG. 117A is depicted in accordance with at least one non-limiting aspect of the present disclosure. Accordingly, FIG. 117B clearly depicts the absence of the electrically non-conductive pad 6994 at the distal portion of the clamp arm 6990. It is further evident that the electrically conductive pad 6992 can be raised to be flush with the electrically non-conductive pad 6994 in the distal portion 6993 of the clamp arm 6990. As such, the clamp arm 6990 of FIGS. 117A and 117B can mitigate the risk of electrical shorting and/or arcing in the proximal end 6995 of the clamp arm jaw 6991 while ensuring the flow of RF energy to the return electrode (e.g. ultrasonic blade) in the distal portion 6993 of the clamp arm jaw 6991. Additionally, the surface area of the distal portion 6993 can be defined by a dimension D that can be predetermined based upon a desired percentage of the clamp arm 6990 desired for sealing.

Referring now to FIG. 118, a top view of two clamp arms 7000, 7010 is depicted in accordance with at least one non-limiting aspect of the present disclosure. The clamp arms 7000, 7010 of FIG. 118 are configured similarly to the clamp arm 6990 of FIG. 117A. However, according to the non-limiting aspect of FIG. 118, the electrically non-conductive pad 7004 can stop prior to the distal portion of the clamp arm 7000, 7010. Accordingly, the electrically conductive portion 7002 of the clamp arms 7000, 7010 is not level with the electrically non-conductive pads 7004. As such, the electrically non-conductive pads 7004 are surrounded by the electrically conductive pad 7002, thereby forming the electrode. According to the non-limiting aspect of FIG. 118, the clamp pad configurations are essentially the same, only the electrically non-conductive pad 7004 of clamp arm 7010 is anchored to a wear resistant gap pad 7006 at the proximal end and is configured in a serpentine pattern that has a longer wavelength than the serpentine pattern of clamp arm 7000. This illustrates how the electrically non-conductive pad 7004 and ultimately the electrode can be include any geometric configuration to tailor the flow of RF energy in accordance with any user preference and/or intended application.

Referring now to FIG. 119, an assembly drawing of a clamp arm 7020 is depicted in accordance with at least one non-limiting aspect of the present disclosure. According to the non-limiting aspect of FIG. 119, the clamp arm 7020 can include a carrier component 7026 (e.g., stamping, pan). The carrier component 7026 can be coupled to the bottom of an electrically conductive pad 7022 via preferred manufacturing process (e.g. insert welding, heat staking, overmolding) and then welded to the underside of the clamp arm jaw 7021. For example, the carrier component 7026 of FIG. 119 can be insert welded to the bottom surface of the electrically conductive pad 7022, thereby forming an electrode of the RF energy circuit.

Still referring to FIG. 119, the carrier component 7026 can include a plurality of holes and/or indents configured to accommodate a plurality of corresponding posts 7029 on the electrically conductive pad 7022. Additionally and/or alternatively, the electrically conductive pad 7022 can include a plurality of standing ribs positioned on the bottom, wherein the ribs can be fed through holes and/or embossed areas on the carrier component 7026. Nonetheless, it shall be appreciated that any geometrical features configured to mechanically couple the electrically conductive pad 7022 to the carrier component 7026. Once the electrically conductive pad 7022 is mechanically coupled to the carrier component 7026, the electrically non-conductive pad 7024 can be coupled to the electrically conductive pad 7022, thereby completing the electrode configuration.

Referring now to FIGS. 120A and 120B, sectioned front views of the clamp arm 7020 of FIG. 119 are depicted in accordance with at least one non-limiting aspect of the present disclosure. In the aspects of FIGS. 120A and 120B, the clamp arm jaw 7021a, 7021b, accommodates an electrically non-conductive pad 7024a, 7024b within a channel, and a carrier plate 7026a, 7026b mechanically couples the electrically conductive pad 7022a to the electrically non-conductive pad 7024a, 7024b. However, in the non-limiting aspect of FIG. 120B, the carrier component 7026b further includes sidewalls that constrain the electrically conductive pad 7022b from lateral motion, thereby further securing the electrode to the clamp arm 7020.

Figure 121A:
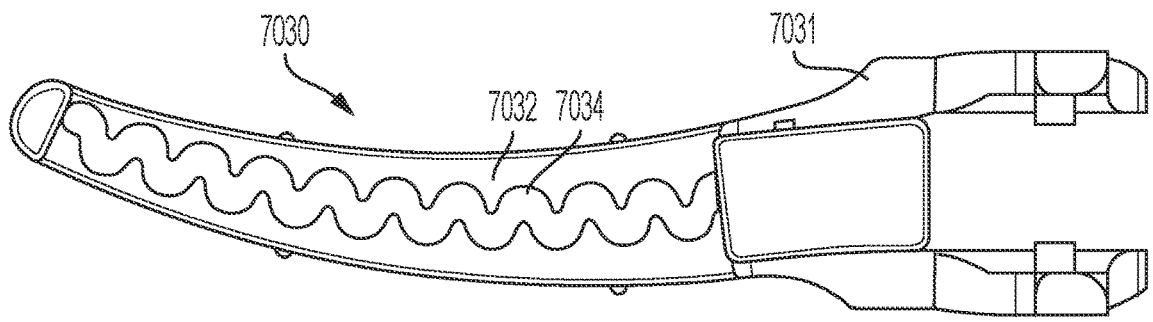
Figure 121B:
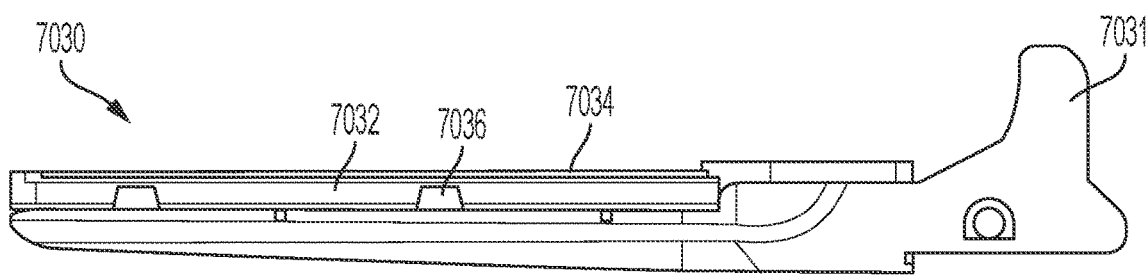
Figure 121C:
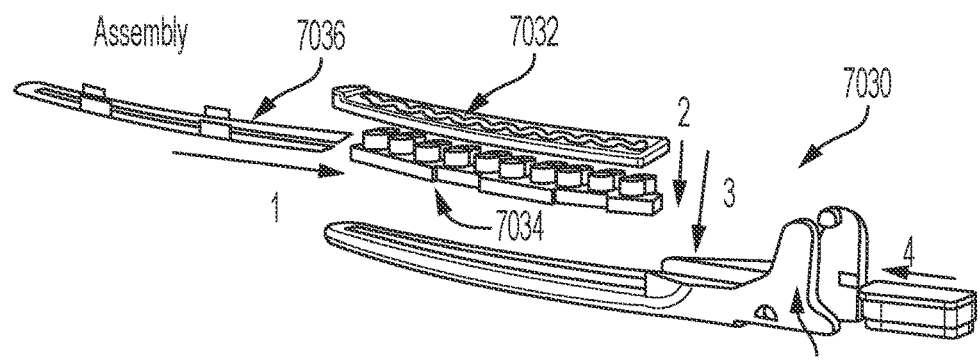
Figure 121D:
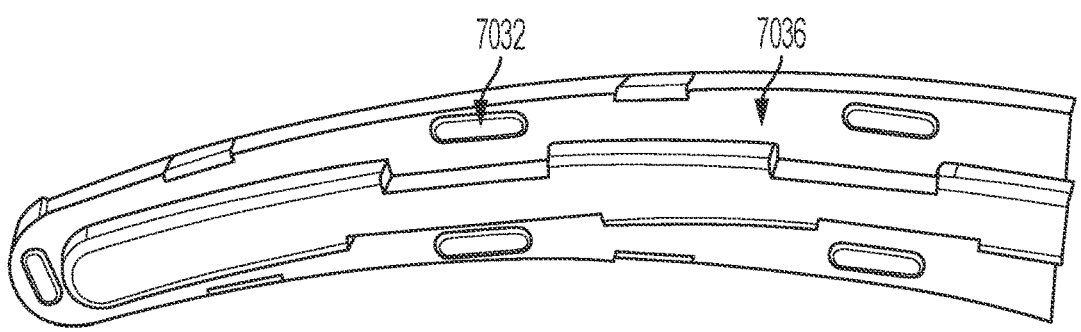
Figure 122A:
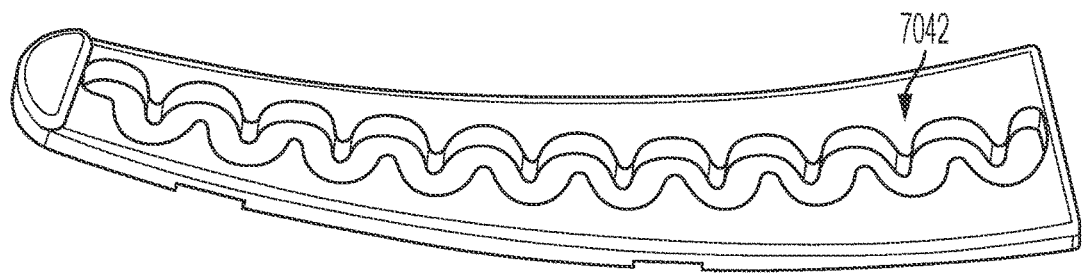
Figure 122B:
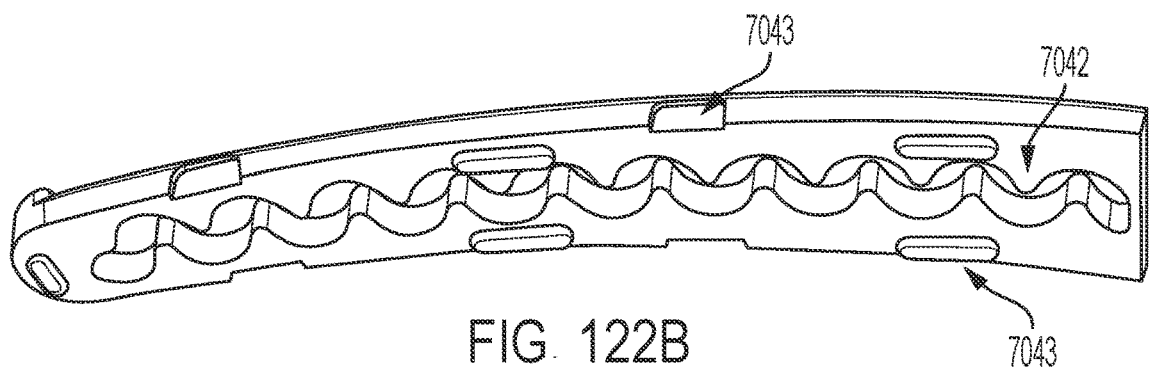
Figure 122C:
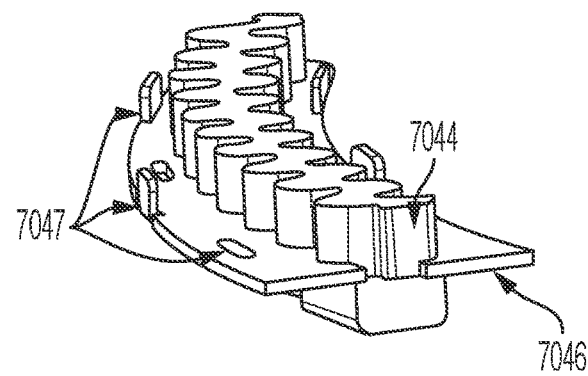
Figure 122D:
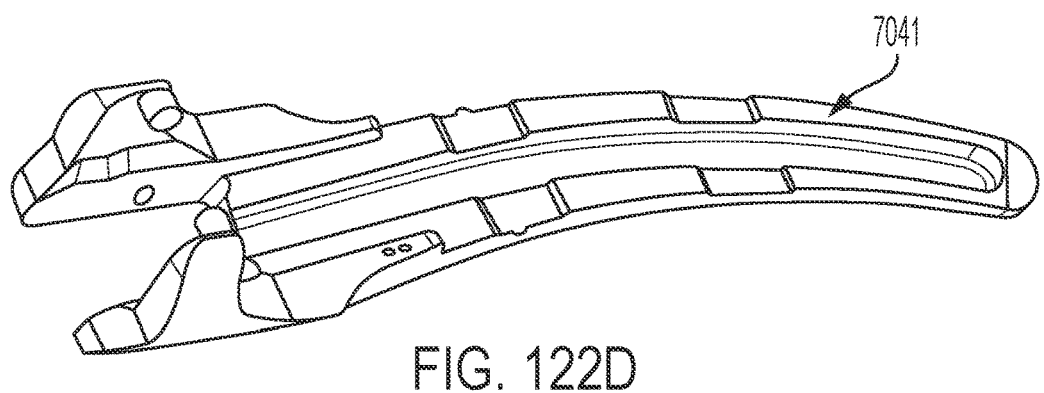

Referring now to FIGS. 121A through 121D, various views illustrating the assembly of a clamp arm 7030 are depicted in accordance with at least one non-limiting aspect of the present disclosure. According to the non-limiting aspect of FIGS. 121A through 121D, the carrier component 7036 can first be installed underneath the electrically non-conductive pad 7034. The electrically conductive pad 7032 can then be installed on top of the electrically non-conductive pad 7034 such that the electrically non-conductive pad is sandwiched between the carrier component 7036 and the electrically conductive pad 7032 and protrudes out of a channel defined within the electrically conductive pad 7032, as is depicted in FIG. 121C. After the carrier component 7036 is properly coupled to the resulting electrode, the entire electrode assembly, including the carrier component is installed within the clamp jaw 7031. According to the non-limiting aspect of FIG. 121C, the carrier component 7036 can include a channel to facilitate the T-slot configuration of the electrically non-conductive pad 7034, as previously discussed. FIG. 121D depicts a bottom view of the assembled electrode properly installed on the carrier component 7036, illustrating how the electrically conductive pad 7032 can include posts that protrude through holes of the carrier component 7036. Accordingly, the electrode can be further secured to and installed within the clamp jaw 7031. Of course, the present disclosure contemplates various other means of mechanically coupling the electrically conductive pad 7032 to the carrier component 7036, including the aforementioned ribs, indents, etc.

Referring now to FIGS. 122A through 122D, various views illustrating the assembly of a clamp arm 7040 are depicted in accordance with at least one non-limiting aspect of the present disclosure. According to the non-limiting aspect of FIGS. 122A through 122D, the carrier component 7046 can first be installed underneath the electrically non-conductive pad 7044. The electrically conductive pad 7042 can then be installed on top of the electrically non-conductive pad 7044 such that the electrically non-conductive pad is sandwiched between the carrier component 7036 and the electrically conductive pad 7042 and protrudes out of a channel defined within the electrically conductive pad 7042. After the carrier component 7046 is properly coupled to the resulting electrode, the entire electrode assembly, including the carrier component is installed within the clamp jaw 7041.

Specifically, the non-limiting aspect of FIGS. 121B and 121C illustrate how the carrier component 7046 can include one or more geometric features 7047 configured to mechanically engage corresponding geometric features of the electrically conductive pad 7042 to ensure a proper fit and to resist inadvertent motions caused by the harmonic activation of the ultrasonic blade. Once the electrically non-conductive pad 7044 is properly seated within the carrier component 7046, the electrically conductive pad 7042 can be installed over the electrically non-conductive pad 7044 and secured to the carrier component 7046 via the plurality of geometric features 7043, 7047. Of course, the present disclosure contemplates various other means of mechanically coupling the electrically conductive pad 7042 to the carrier component 7046, including the aforementioned ribs, holes, posts, etc.

Referring now to FIGS. 123A through 123C, several clamp pad 7050a, 7050b configurations are depicted in accordance with at least one non-limiting aspect of the present disclosure. According to the non-limiting aspects of FIGS. 123A through 123C, the electrically conductive clamp pads 7052 can include a conductive material (e.g. silicone) molded it to a carrier 7056a, 7056b and/or stamping. Accordingly, the clamp pads 7052 can be overmolded onto the carrier 7056a, 7056b, which allows for an enhanced attachment. As such, the clamp pad 7052 can melt through a plurality of holes 7053 in the carrier 7056a, 7056b to enhance electrode resistance to lateral vibration. The carrier can be configured with a predetermined thickness $T_S$. For example, according to some non-limiting aspects, the carrier 7056a, 7056b can be greater than or equal to 0.005 inches and less than or equal to 0.007 inches thick. Accordingly, the electrically conductive pad 7052 can include a thickness greater than or equal to 0.02 inches and less than or equal to 0.03 inches thick.

In further reference to FIGS. 123A through 123C, the carrier 7056a, 7056b can further include walls 7058 that extend laterally about the electrically conductive pad 7052 to further prevent lateral motion and/or deformation of the electrode. According to the non-limiting aspect of FIG. 123C, the carrier 7056b can include a forked stamping 7059 at the tip to afford the electrically conductive pad 7052 more thickness at a distal end, thereby enhancing the transfer of RF energy at a desired location. Such advantages are available to electrically conductive pads 7052 that are formed via the aforementioned overmolding process, although other means of forming the electrode to accomplish the same effect as contemplated by the present disclosure.

Referring now to FIGS. 124A through 124D, several top perspective views illustrating various components of a clamp arm assembly 7060 are depicted in accordance with at least one non-limiting aspect of the present disclosure.

Specifically, the non-limiting aspect of FIGS. 124A through 124D illustrate various means of mechanically securing and constraining an electrode stack—specifically, an electrically conductive pad 7062 and an electrically non-conductive pad 7064—within a clamp arm jaw 7061. The aspects can be used independently, or in conjunction with any of the previously-discussed means of assembling and securing the components of a clamp arm jaw 706, as described in other non-limiting aspects of the present disclosure.

According to the non-limiting aspect of FIGS. 124A through 124D, the clamp arm assembly 7060 can include an electrically conductive pad 7062, a clamp arm jaw 7061, and an electrically non-conductive pad 7064, which are configured to mechanically engage one another such that they collectively establish a clamp arm assembly 7060 configured to grasp tissue during an ultrasonic cutting operation and serve as an electrode for the delivery of RF energy during a sealing operation. The electrically conductive pad 7062 can first be secured to the clamp arm jaw 7061. According to the non-limiting aspect of FIG. 124A, the electrically conductive pad 7062 can include one or more geometric features configured to secure the electrically conductive pad 7062 to the clamp arm jaw 7061. For example, a plurality of holes 7063 can be defined within the electrically conductive pad 7062, each configured to engage a post 7065 from a plurality of posts 7065 positioned on the claim arm jaw 7061. As such, the electrically conductive pad 7062 can be lowered onto the clamp arm jaw 7061 such that each post 7065 traverses each hole 7063. Of course, geometric features of varying configurations can be dispositioned, assuming the provide the desired mechanical engagement between the electrically conductive pad 7062 and the clamp arm jaw 7061.

In further reference to FIGS. 124A through 124D, an electrically non-conductive pad 7064 can be configured to be mechanically engaged with the electrically conductive pad 7062 via another geometrical feature 7067. For example, the geometrical feature 7067 can be configured to be press fit into a T-slot of the clamp arm jaw 7061; however, alternate geometric features 7067 are contemplated by the present disclosure. As was previously discussed, the electrically conductive pad 7062 can be configured with a channel configured to accommodate the electrically non-conductive pad 7064. Thus, after the electrically conductive pad 7062 is mechanically engaged with the clamp arm jaw 7061, the electrically non-conductive jaw 7064 can be press-fit into the channel 7069 such that the feature 7067 in received by the T-slot of the clamp arm jaw 7061.

Referring now to FIGS. 125A and 125B, another clamp pad configuration 7070 is depicted in accordance with at least one aspect of the non-limiting disclosure. According to the non-limiting aspect of FIGS. 125A and 125B, the clamp pad configuration 7070 can include an electrically conductive pad 7072 and an electrically non-conductive pad 7074. The electrically non-conductive pad can include an "I-beam" shape featuring a geometric feature 7075—such as the symmetrical shelf and notch configuration of FIG. 125A—to be received by a channel 7076 of the electrically conductive pad 7072. Accordingly, the electrically conductive pad 7072 can be configured about the electrically non-conducive pad 7074 by pushing it up from a bottom B of the electrically conductive pad 7074, until the geometric feature 7075 is properly seated within the channel 7076 in a snap-fit configuration. As a result, the clamp pad configuration 7070, when viewed from above, constitutes a surface of the electrically conductive pad 7072 surrounding the electrically non-conductive pad 7074, as is depicted in FIG. 125B. As such, the electrically non-conductive pad 7074 can sit above the electrically conductive pad 7072, thereby preventing inadvertent contact and electrical shorting between the electrically conductive pad 7072—or first electrode of an RF energy circuit—and an ultrasonic blade—the return electrode of an RF energy circuit.

Referring now to FIGS. 126A and 126B, another clamp pad configuration 7080 is depicted in accordance with at least one aspect of the non-limiting disclosure. According to the non-limiting aspect of FIGS. 126A and 126B, the clamp pad configuration 7080 can include an electrically conductive pad 7082 and an electrically non-conductive pad 7084. The electrically non-conductive pad 7084 can include a similar "I-beam" configuration to the electrically non-conductive pad 7084 of FIGS. 125A and 125B. Each of the clamp arm jaw 7081 and electrically conductive pad 7084 include overhang features that, when coupled with the "I-beam" configured electrically non-conductive pad 7084, are sandwiched between a first crossbar 7083 and second crossbar 7085 of the electrically non-conductive pad 7084, as is depicted in FIG. 126A. As a result, the clamp pad configuration 7080, when viewed from above, constitutes a surface of the electrically conductive pad 7082 surrounding the electrically non-conductive pad 7084, as is depicted in FIG. 125B. As such, the electrically non-conductive pad 7084 can sit above the electrically conductive pad 7082, thereby preventing inadvertent contact and electrical shorting between the electrically conductive pad 7082—or first electrode of an RF energy circuit—and an ultrasonic blade—the return electrode of an RF energy circuit. Once installed, the electrically non-conductive pad 7084 can be secured to the electrically conductive pad 7082 at a proximal end via a staking 7087, as is depicted in FIG. 126B.

Referring now to FIGS. 127A through 127C, another clamp pad configuration 7090 is depicted in accordance with at least one aspect of the non-limiting disclosure. According to the non-limiting aspect of FIGS. 127A and 127B, the clamp pad configuration 7090 can include an electrically conductive pad 7092 and an electrically non-conductive pad 7094. Notably, the electrically conductive pad 7092 can include one or more geometric features 7097 configured to anchor the electrically conductive pad 7092 to the clamp arm jaw 7091. As is depicted in FIG. 127B, the anchors 7097 of the electrically conductive pad 7092 are configured to engage corresponding features defined within the clamp arm jaw 7091. Accordingly, the electrically conductive pad 7092 can be further secured within the ultimate electrode configuration, thereby mitigating its susceptibility to harmonic excitation due to ultrasonic activation and further enhancing its resistivity to wear and degradation. According to the non-limiting aspect of FIG. 127A, the anchors 7097 are cylindrically configured; however, other non-limiting aspects contemplate a variety of anchors 7097 located in a variety of positioned along the electrically conductive pad 7092. Otherwise the electrically non-conductive pad 7094 can include a "I-beam" configuration similar to those previously described. FIG. 127C depicts an assembly procedure for the clamp pad configuration 7090, wherein the electrically conductive pad 7092 and its anchors 7097 are installed into the clamp arm jaw 7091, after which the electrically non-conductive pad 7094 can be slid into place.

Referring now to FIG. 128, a top view of a clamp pad configuration 7100 is depicted in accordance with at least one aspect of the non-limiting disclosure. According to the non-limiting aspect of FIG. 128 the clamp pad configuration 7100 can include an electrically conductive pad 7102 and an electrically non-conductive pad 7104 coupled to a clamp arm jaw 7101. Notably, the clamp pad configuration 7100 of FIG. 128 can include heat staking 7106 (e.g., coin-like operation) on the portions of the electrically non-conductive pad 7104 that protrude from the electrode, or electrically conductive pad 7102. through the jaw. For example, the staking process can "mushroom" the portions of the electrically non-conductive pad 7104 to the electrically conductive pad 7102, which further constrains the electrically conductive pad 7102 within the assembly 7100, accordingly. Thus, the staking 7106 can further enhance the structural stability of the clamp pad configuration 7100, mitigate inadvertent reactions to harmonic excitations, and reduce susceptibility to wear and/or degradation.

Referring now to FIGS. 129A through 129C, side and top views of a configurable clamp arm assembly 7200 are depicted in accordance with at least one non-limiting aspect of the present disclosure. According to the non-limiting aspect of FIGS. 129A through 129D, the clamp arm assembly 7200 can include one or more flexible portions 7202 conjoined at one or more adjustable connections 7204. For example, the adjustable connections 7204 can include set screws configured to allow and disallow the flexible portions 7202 to move relative to one another, depending on user preference and/or intended application. Once tightened, the adjustable set screw 7204 can lock the relative position of the flexible portions 7202. Accordingly, the flexible portions can modify the overall shape and angle of the configurable clamp arm assembly 7200.

In further reference to 129B, a top view of the configurable clamp arm assembly 7200 of FIG. 129A is depicted. Accordingly, the segmented, flexible portions 7202 are evident, as are a plurality of tabs 7206, which can be welded in place to secure a particular arrangement of the flexible portions 7202. Additionally, any one portion 7202 can be removed from the assembly 7200 to allow for selective flexibility or a tunable pressure or tip profile. Once the desired profile is achieved, the set screws 7204 can be secured and the tabs 7206 welded, thereby fixing the clamp arm in a desired position and/or profile. The flexible portions 7202 can be generated using either additive and/or conventional manufacturing processes or techniques. It shall be appreciated that, by readjusting the arrangement of flexible portions 7202, a user can tune the clamp arm assembly 7200 to achieve a desired operational parameter, such as resonance, pressure profile, and/or tip profile, amongst others. Referring now to FIG. 129C, a top view of the configurable clamp arm assembly 7200 of FIG. 129A is depicted in a post-weld condition. Accordingly, the segmented, flexible portions 7202 are secured together, via a plurality of weld joints 7208 applied between each tab 7206 of the plurality of tabs 7206.

Referring now to FIG. 130, a side view of the configurable clamp arm assembly 7200 of FIGS. 129A through 129C positioned within a configuration block 7210 is depicted in accordance with at least one non-limiting aspect of the present disclosure. As previously described, the configurable clamp arm assembly 7200 can include a tunable device profile, which can be adjusted by clamping on a simulated blade 7208. Once the clamp arm conforms to the profile of the simulated blade 7208, the set screws 7204 can be tightened. Additionally and/or alternatively, the clamp arm assembly 7200 can be positioned against the simulated blade 7208 based on a desired pressure profile upon repeated clamping cycles. Once the set screws 7204 have been tightened, the tabs 7206 can be secured using any conventional bonding technique (e.g. welding, laser welding, fasteners, adhesives) to fix the clamp arm assembly 7200 profile in the desired position. According to the non-limiting aspect of FIG. 130, the assembly 7200 is depicted as being adjusted from an initial pitch $P_1$ to a desired pitch $P_2$. Additionally and/or alternatively, pressure profile sensors can be used to monitor the profile and ensure an accurate adjustment of the assembly 7200.

Additional fixtures and/or biasing are contemplated by the present disclosure to achieve the desired profile for a variety of clamp arms 7200 produced for a variety of intended applications. Alternatively, the clamping profile of the assembly 7200 can be achieved without clamping on a blade or blade surrogate, by using another fixture representative of either the ultrasonic blade and/or a desired profile and/or pitch of the assembly 7200. An example fixture is shown below that allows for the tip of the clamp arm to be adjusted until it is in the correct range.

Referring now to FIG. 131, a side view of the configurable clamp arm assembly 7200 of FIGS. 129A through 129C positioned within an alternate configuration fixture 7220 is depicted in accordance with at least one non-limiting aspect of the present disclosure. The alternate configuration fixture is similar to the configuration block 7210. However, the configuration fixture 7220 of FIG. 131 includes a plurality of adjustable set screws 7222, 7224, 7226 which are configured to interface with the clamp arm assembly 7200 when installed within the configuration fixture 7220. For example, proximal set screws 7222 can be tightened to secure a proximal end of the clamp arm assembly 7200. To adjust the pitch, a user might tighten or loosen the distal set screw 7224, which cantilevers the clamp arm assembly 7200 to achieve the desired profile. Side set screws 7226 can be used to adjust the lateral configuration of the clamp arm assembly 7200 in accordance with user preference and/or intended application. As such, the clamp arm assembly 7200 can be adjusted in an X, Y, and Z direction. Although the non-limiting aspect of FIG. 131 utilizes set screws 7222, 7224, 7226, the present disclosure contemplates other non-limiting aspects wherein alternate means of interfacing with and adjusting the clamp arm assembly 7200 through the configuration fixture 7220 are implemented. For example, any combination of springs, levers, and/or pistons will suffice. Additionally and/or alternatively, the adjustment mechanisms 7222, 7224, 7226 can be automated such that the clamp arm assembly 7200 can be adjusted without manual intervention.

EXAMPLES

Examples of various aspects of end-effectors and surgical instruments of the present disclosure are provided below. An aspect of the end-effector or surgical instrument may include any one or more than one, and any combination of, the examples described below:

Example 1. An end-effector configured to grasp tissue, wherein the end-effector includes: an ultrasonic blade configured to be coupled to an ultrasonic transducer, wherein the ultrasonic blade is configured to transfer ultrasonic energy to the tissue; a clamp arm, including a clamp arm pad, wherein the clamp arm pad includes: an electrically conductive material; and an electrically non-conductive material; wherein the clamp arm pad is configured as an electrode of a radiofrequency energy circuit, wherein the electrode is configured to transfer radiofrequency energy through the tissue to a return electrode of the radiofrequency energy circuit, and wherein the electrically non-conductive material is configured to reduce the possibility of an electrical short between the electrically conductive material and the ultrasonic blade as the clamp arm pad degrades throughout the usable life of the end effector.

Example 2. The end-effector of Example 1, wherein the clamp arm pad further includes an intermediate layer dispositioned between the non-conductive material and the electrically conductive material.

Example 3. The end-effector of any one of Examples 1-2, wherein the intermediate layer is an adhesive configured to bond the electrically non-conductive material to the electrically conductive material.

Example 4. The end-effector of any one of Examples 1-3, wherein the intermediate layer includes a perfluoroalkoxy alkane.

Example 5. The end-effector of any one of Examples 1-4, wherein the intermediate layer includes a thickness greater than or equal to 0.001 inches and less than or equal to 0.005 inches.

Example 6. The end-effector of any one of Examples 1-5, wherein the ultrasonic blade is configured as the return electrode of the radiofrequency energy circuit.

Example 7. The end-effector of any one of Examples 1-6, wherein the electrically non-conductive material and the electrically conductive material include polytetrafluoroethylene.

Example 8. The end-effector of any one of Examples 1-7, wherein the electrically conductive material further includes an electrically conductive fiber.

Example 9. The end-effector of any one of Examples 1-8, wherein the electrically conductive fiber includes at least one of carbon, stainless steel, and silver, or combinations thereof.

Example 10. The end-effector of any one of Examples 1-9, wherein the electrically conductive material is dispositioned about a portion of a top surface of the electrically non-conductive material.

Example 11. The end-effector of any one of Examples 1-10, wherein the electrically conductive material includes a predetermined pattern associated with a desired degradation of the electrically conductive material.

Example 12. The end-effector of any one of Examples 1-11, wherein the predetermined pattern is serpentine.

Example 13. The end-effector of any one of Examples 1-12, wherein the predetermined pattern is configured about a perimeter of the clamp arm pad.

Example 14. A clamp arm configured to grasp tissue in conjunction with an ultrasonic blade, wherein the clamp arm includes a clamp arm pad including: an electrically conductive layer defining a channel; and an electrically non-conductive layer, wherein the electrically non-conductive layer is positioned adjacent the electrically conductive layer such that at least a portion of the electrically non-conductive layer is positioned through the channel, wherein the clamp arm pad is configured as an electrode of a radiofrequency energy circuit, and wherein the electrically non-conductive material is configured to reduce the possibility of an electrical short between the electrically conductive material and the ultrasonic blade.

Example 15. The clamp arm of Example 14, wherein the clamp arm pad further includes an intermediate layer dispositioned between the electrically non-conductive layer and the electrically conductive layer.

Example 16. The clamp arm of any of Examples 14-15, wherein the intermediate layer is an adhesive configured to bond the electrically non-conductive layer to the electrically conductive layer.

Example 17. The clamp arm of any one of Examples 14-16, wherein the electrically non-conductive layer and the electrically conductive layer include polytetrafluoroethylene.

Example 18. The surgical instrument of any one of Examples 14-17, wherein the electrically conductive layer further includes an electrically conductive fiber doped throughout the polytetrafluoroethylene.

Example 19. An end-effector configured to grasp tissue, wherein the end-effector includes: an ultrasonic blade; a clamp arm, including a clamp arm pad, wherein the clamp arm pad includes: an electrically conductive material; and an electrically non-conductive material; wherein the electrically non-conductive material is configured to prevent the electrically conductive material from being positioned a predetermined distance away from the ultrasonic blade as the clamp arm pad degrades throughout the usable life of the end effector.

Example 20. The end-effector of Example 19, wherein the clamp arm pad further includes an adhesive layer dispositioned between the layer of non-conductive material and the layer of electrically conductive material, wherein the adhesive layer is configured to bond the electrically non-conductive material to the electrically conductive material.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. An end-effector configured to grasp tissue, wherein the end-effector comprises:
   an ultrasonic blade configured to be coupled to an ultrasonic transducer, wherein the ultrasonic blade is configured to transfer ultrasonic energy to the tissue;
   a clamp arm, comprising a clamp arm pad, wherein the clamp arm pad comprises:
      an electrically conductive material, wherein the electrically conductive material comprises a predetermined pattern associated with a desired degradation of the electrically conductive material; and
      an electrically non-conductive material;
      wherein the clamp arm pad is configured as an electrode of a radiofrequency energy circuit, wherein the electrode is configured to transfer radiofrequency energy through the tissue to a return electrode of the radiofrequency energy circuit, and wherein the electrically non-conductive material is a structural buffer disposed between the electrically conductive material and the ultrasonic blade.

2. The end-effector of claim 1, wherein the clamp arm pad further includes an intermediate layer dispositioned between the non-conductive material and the electrically conductive material.

3. The end-effector of claim 2, wherein the intermediate layer is an adhesive configured to bond the electrically non-conductive material to the electrically conductive material.

4. The end-effector of claim 2, wherein the intermediate layer comprises a perfluoroalkoxy alkane.

5. The end-effector of claim 2, wherein the intermediate layer comprises a thickness greater than or equal to 0.001 inches and less than or equal to 0.005 inches.

6. The end-effector of claim 1, wherein the ultrasonic blade is configured as the return electrode of the radiofrequency energy circuit.

7. The end-effector of claim 1, wherein the electrically non-conductive material and the electrically conductive material comprise polytetrafluoroethylene.

8. The end-effector of claim 7, wherein the electrically conductive material further comprises an electrically conductive fiber.

9. The end-effector of claim 8, wherein the electrically conductive fiber comprises at least one of carbon, stainless steel, and silver, or combinations thereof.

10. The end-effector of claim 1, wherein the electrically conductive material is dispositioned about a portion of a top surface of the electrically non-conductive material.

11. The end-effector of claim 1, wherein the predetermined pattern is serpentine.

12. The end-effector of claim 1, wherein the predetermined pattern is configured about a perimeter of the clamp arm pad.

13. An end-effector configured to grasp tissue, wherein the end-effector comprises:
an ultrasonic blade;
a clamp arm, comprising a clamp arm pad, wherein the clamp arm pad comprises:
an electrically conductive material, wherein the electrically conductive material comprises a predetermined pattern associated with a desired degradation of the electrically conductive material; and
an electrically non-conductive material;
wherein the electrically non-conductive material is configured to maintain a predetermined distance between the electrically conductive material and the ultrasonic blade.

14. The end-effector of claim 13, wherein the clamp arm pad further includes an adhesive layer dispositioned between a layer of the non-conductive material and a layer of the electrically conductive material, wherein the adhesive layer is configured to bond the electrically non-conductive material to the electrically conductive material.

15. The end-effector of claim 13, wherein the clamp arm pad further includes an intermediate layer dispositioned between the non-conductive material and the electrically conductive material.

16. The end-effector of claim 15, wherein the intermediate layer is an adhesive configured to bond the electrically non-conductive material to the electrically conductive material.

17. An end-effector configured to grasp tissue, wherein the end-effector comprises:
an ultrasonic blade;
a clamp arm comprising a clamp arm pad, the clamp arm pad comprising:
an electrically conductive layer, wherein the electrically conductive layer comprises a predetermined pattern associated with a desired degradation of the electrically conductive layer; and
an electrically non-conductive layer positioned adjacent the electrically conductive, wherein the clamp arm pad is configured as an electrode of a radiofrequency energy circuit, and wherein the electrically non-conductive layer is configured as a structural buffer between the electrically conductive layer and the ultrasonic blade.

18. The end-effector of claim 17, wherein the clamp arm pad further includes an intermediate layer dispositioned between the electrically non-conductive layer and the electrically conductive layer.

19. The end-effector of claim 18, wherein the intermediate layer is an adhesive configured to bond the electrically non-conductive layer to the electrically conductive layer.

20. The end-effector of claim 17, wherein the clamp arm pad further includes an adhesive layer dispositioned between the electrically non-conductive layer and the electrically conductive layer, wherein the adhesive layer is configured to bond the electrically non-conductive layer to the electrically conductive layer.

* * * * *